US007335689B2

(12) United States Patent
Dasseux et al.

(10) Patent No.: US 7,335,689 B2
(45) Date of Patent: Feb. 26, 2008

(54) DIHYDROXYL COMPOUNDS AND COMPOSITIONS FOR CHOLESTEROL MANAGEMENT AND RELATED USES

(75) Inventors: Jean-Louis Henri Dasseux, Brighton, MI (US); Carmen Daniela Oniciu, Ann Arbor, MI (US)

(73) Assignee: Esperion Therapeutics, Inc., Ann Arbor, MI (US)

( * ) Notice: Subject to any disclaimer, the term of this patent is extended or adjusted under 35 U.S.C. 154(b) by 567 days.

(21) Appl. No.: 10/743,109

(22) Filed: Dec. 23, 2003

(65) Prior Publication Data
US 2004/0214887 A1 Oct. 28, 2004

Related U.S. Application Data

(60) Provisional application No. 60/441,795, filed on Jan. 23, 2003.

(51) Int. Cl.
A61K 31/045 (2006.01)
A61K 31/00 (2006.01)
C07C 35/08 (2006.01)
C07C 31/18 (2006.01)

(52) U.S. Cl. ............... 514/729; 514/738; 568/822; 568/853

(58) Field of Classification Search ............... None
See application file for complete search history.

(56) References Cited

U.S. PATENT DOCUMENTS

| 3,152,148 A | 10/1964 | Easterly et al. |
| 3,441,605 A | 4/1969 | Blake et al. |
| 3,773,946 A | 11/1973 | Creger |
| 3,930,024 A | 12/1975 | Creger |
| 4,287,200 A | 9/1981 | Kawamatsu et al. |
| 4,584,321 A | 4/1986 | Manghisi et al. |
| 4,613,593 A | 9/1986 | Yamatsu et al. |
| 4,634,719 A | 1/1987 | Takaishi et al. |
| 4,689,344 A | 8/1987 | Bar-Tana |
| 4,711,896 A | 12/1987 | Bar-Tana et al. |
| 4,714,762 A | 12/1987 | Hoefle et al. |
| 5,166,174 A | 11/1992 | Ueno et al. |
| 5,225,439 A | 7/1993 | Ueno et al. |
| 5,284,858 A | 2/1994 | Ueno et al. |
| 5,380,709 A | 1/1995 | Ueno et al. |
| 5,428,062 A | 6/1995 | Ueno et al. |
| 5,502,198 A | 3/1996 | Picard et al. |
| 5,504,073 A | 4/1996 | Homan |
| 5,578,639 A | 11/1996 | Homan |
| 5,633,287 A | 5/1997 | Lee et al. |
| 5,648,387 A | 7/1997 | Bisgaier et al. |
| 5,750,569 A | 5/1998 | Bisgaier et al. |
| 5,756,344 A | 5/1998 | Onda et al. |
| 5,756,544 A | 5/1998 | Greger et al. |
| 5,783,600 A | 7/1998 | Bisgaier et al. |
| 5,834,596 A | 11/1998 | Ageland et al. |
| 5,886,034 A | 3/1999 | Ueno et al. |
| 5,968,963 A | 10/1999 | Homan |
| 5,981,595 A | 11/1999 | Picard et al. |
| 6,004,925 A | 12/1999 | Dasseux et al. |
| 6,017,905 A | 1/2000 | Roark et al. |
| 6,037,323 A | 3/2000 | Dasseux |
| 6,093,719 A | 7/2000 | Bocan |
| 6,093,744 A | 7/2000 | Lee et al. |
| 6,124,309 A | 9/2000 | Bocan |
| 6,143,755 A | 11/2000 | Bocan |
| 6,459,003 B1 | 10/2002 | Dasseux et al. |
| 6,646,170 B2 | 11/2003 | Dasseux et al. |
| 6,673,780 B2 | 1/2004 | Dasseux et al. |
| 6,699,910 B2 | 3/2004 | Dasseux et al. |
| 6,703,422 B2 | 3/2004 | Dasseux et al. |
| 6,713,507 B2 | 3/2004 | Dasseux et al. |
| 2004/0209847 A1 | 10/2004 | Dasseux et al. |
| 2005/0043278 A1 | 2/2005 | Dasseux et al. |

FOREIGN PATENT DOCUMENTS

EP    0 284 108    9/1987

(Continued)

OTHER PUBLICATIONS

Rychnovsky et al, Journal of Organic Chemistry, Optically Pure 1,3-Diols From (2R,4R)- and (2S,4S)-1,2:4,5-Diepoxypentane,1991, 56(17), pp. 5161-5169.*
Bicking, et al., "11,12-Secoprostaglandins. 1. Acylhydroxyalkanoic acids and related compounds", J. Med. Chem., 1977, pp. 35-43, vol. 20.
Nagano H, et al., "Stereoselectivity in the formation and radical reduction of cyclic bromoacetals, key intermediates for the sythesis of delta-hydroxy-and epsilon-hydroxy-alpha-methylcarboxylic acid esters", Tetrahedron Letters, 2003, pp. 6867-6870, vol. 44, No. 36.
Bobrova, et al., abstract, J. Org. Chem, 1983, pp. 259-261, vol. 19.
Narasaka, et al., abstract, Bull. Chem. Soc, 1987, pp. 1457-1464, vol. 60, No. 4.

(Continued)

Primary Examiner—Paul A. Zucker
(74) Attorney, Agent, or Firm—Michael J. Bruner; Charles W. Ashbrook; John H. Engelmann

(57) ABSTRACT

The prseent invention relates to novel dihydroxyl compounds, compositions comprising hydroxyl compounds, and methods useful for treating and preventing a variety of diseases and conditions such as, but not limited to aging, Alzheimer's Disease, cancer, cardiovascular disease, diabetic nephropathy, diabetic retinopathy, a disorder of glucose metabolism, dyslipidemia, dyslipoproteinemia, hypertension, impotence, inflammation, insulin resistance, lipid elimination in bile, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), thrombotic disorder. Compounds and methods of the invention can also be used to modulate C reactive protein or enhance bile production in a patient. In certain embodiments, the compounds, compositions, and methods of the invention are useful in combination therapy with other therapeutics, such as hypocholesterolemic and hypoglycemic agents.

31 Claims, No Drawings

FOREIGN PATENT DOCUMENTS

| | | |
|---|---|---|
| FR | 1 545 224 A | 11/1968 |
| GB | 1196594 | 7/1970 |
| GB | 1196595 | 7/1970 |
| GB | 1196596 | 7/1970 |
| GB | 1196597 | 7/1970 |
| GB | 1196598 | 7/1970 |
| WO | WO 96/30328 | 7/1998 |
| WO | WO 98/30530 A | 7/1998 |
| WO | WO 99/00116 | 1/1999 |

OTHER PUBLICATIONS

Rieke, et al., abstract, J. Org. Chem, 1996, pp. 2726-2730, vol. 61. No. 8.
Pechmann, abstract, Chem. Ber., 1904, p. 3819, vol. 37.
Lardelli, et al., abstract, Recl. Trav. Chim., 1967, pp. 481-503, vol. 86.
Crisan, abstract, Ann. Chim., 1956, pp. 436-459, vol. 13, No. 1.
Blatt, et al.; The reducing action of the Grignard reagent and the synthesis of tertiary aliphatic carbinols, J. Org. Chem., 1932, pp. 1495-1499, vol. 54.
Brown, et al., "Hydroboration. 67. Cyclic hydroboration of acyclic alpha, omega-dienes with 9-Borabicyclo '3.3.1 Inonane/borane-dimethyl sulfide", J. Org. Chem., pp. 1072-1078, vol. 49, No. 6.
Weber, et al., abstract, J. Med. Chem., 1992, pp. 3755-3773, vol. 35, No. 21.
Yamamoto, "Asymmetric synthesis of 5-and 6-memebered lactones from cyclic substrates bearing a c2-chiral auziliary", J. Org. Chem., 1991, pp. 1112-1119, vol. 35, No. 21.
Ooi T, et al., abstract, Angewandte Chemie., 2001, vol. 40, No. 19.
English, J. Am. Chem. Soc., 1941, p. 942, vol. 63.
Gleiter, et al., Synthesis of 5,510,10-tetramethyl-1-oxacyclotridecane-6,7,8,9-tetrone-on the mechanism of the Rubottom reaction, 1995, (9), pp. 1655-1661.
Gleiter, et al., Synthesis and properties of 4,4,9,9-tetramethyl-1-oxa-cycloundecane-5,6,7,8-tetrone and 9-tetramethyl-1-oxa-cyclotridecane-6,7,8,9-tetrone, 1996, 2(3), pp. 271-277.
Momenteau, et al., abstract, J. Chem Soc. Perkin Trans. 1985, pp. 221-232.
Corey et al., 1967, "A useful method for conversion of alcohols into iodides", J. Org. Chem, 32: 4160-4161.
Taravel et al, 1988, "Interglycosidic sup.13 C- sup 1 H Coupling Constants" Tetrahedeon Lett, 29:199-200.
Vamecq and Draye, 1989, "Pathophysiology of peroxisomal beta-oxidation", Essays Biochem, 24:115-225.
Silverman, The Organic Chemistry of Drug Design and Drug Interaction, 1992, pp. 15-22.
Bohme, V. and Lener, W., 1955, Annalen der Chemie, 595:169-178 (English language abstract).
Xu et al., 1989, "The retinoblastoma susceptibility gene product: a characteristic pattern in normal cells and abnormal expression in malignant cells", Oncogene 4: 807-812.
Ackerly, et al., 1995, "A novel approach to dual-acting thromboxane receptor antagonist/synthase inhibitors based on the link of 1,3-dioxane-thrombaxane receptor antagonists and -thromboxane synthase inhibitors", J. Med. Chem. 38:1608-1628.
Acton et al., 1996, "Identification of scavenger receptor SR-BI as a high density lipoprotein receptor", Science. 271(5248):518-20.
Ahrens et al., 1967, "A direct method for preparing pyridoxal and 4-pyridoxic acid (1)", J. Heterocycl. Chem. 4:625-26.
Alexander, K et al., 1948, "4,4'-Dichlorodibutyl ether and its derivatives from tetrahydrofuran", J. Am. Chem. Soc. 70:1839-42.
Badimon et al.,1992, "Role of High density lipoproteins in the regression of atherosclerosis", Circulation 86 (Suppl):III86-94.
Bailey, et al.,1990, "Convenient general method for the preparation ofprimary alkeyllithimus by lithium-iodine exchange", J. Org. Chem. 55:5404-06.
Barrans et al., 1996, "Pre-beta HDL; structure and metabolism", Biochim. Biophys. Acta. 1300(2):73-85.

Becker et al., 1982, "Intramolecular photoaddition of terminal allenes to conjugated cyclohexenones", J. Org. Chem. 47:3297-3310.
Bernady et al., 1979, "Prostaglandins and congeners. 20 . . . sup.1,2 Synthesis of prostaglandins via conjugate addition of lithiummm trans-1-alkenyltrialkylalanate reagents. A novel reagent for conjugate 1,4-additions", J. Org. Chem. 44:1438-47.
Bhanot et al.,1977, "Synthetic Studies on Terpenoids.5.Syntheses of .gamma.- and delta.-Lactones from .beta.-(2,7-Dimethyl-1,2-dihydroxycycloheptyl)propionic Acid", J. Org. Chem. 42:1623-1627.
Bisgaier et al.,1998, "A novel compound that elevates high density lipoprotein and activates the peroxisome proliferator activated receptor", J Lipid Res. 39(1):17-30.
Bisgaier et al.,1997, "Attenuation of plasma low density lipoprotein cholesterol by select 3-hydroxy-3-methylglutaryl coenzyme A reductase inhibitors in mice of low density lipoprotein receptors", J Lipid Res 38 (12):2502-2515.
Bongini et al., 1979 "A simple and practical method for tetrahydropyranylation of alcohols and phenols", Synthesis 618-620.
Brown et al.,1965, "Selective reductions. VII. Reaction of lithium trimethoxyluminohydride with selected organic compounds containing representative functional groups", J. Am. Chem. Soc. 87:5614-20.
Brown et al.,1980, "Selective reductions. 26 Lithium triethylborohydride as an exceptionally powerful and selective reducing agent in organic synthesis. Exploration of the reactions with selected organic compounds containing representative functional groups, .sup.1,2", J. Org. Chem 45:1-12.
Bruce et al.,1998, "Plasma lipid transfer proteins, high-density lipoproteins, and reverse cholesterol transport", Annu Rev Nutr. 1998;18:297-330.
Campagna et al., 1994, "Cyclic Amidine Analogues of Taurine and Homotaurine: Synthesis and Effects on Rat Skeletal Muscle", Farmaco, Ed. Sci 49:653-658.
Carothers, 1924, "Platinum oxide as a catalyst in the reduction of organic compounds. V. The preparation of primary alcohols by the catalytic hydrogenation of aldehydes.sup.1 ", J. Am. Chem. Soc. 46:1675-83.
Cerny et al., 1969, "Properties of Sodium Bis-(2-Methoxyethoxy_Aluminum Hydride", Collect Czech Chem Commn. 34:1025-33.
Chadwick et al., 1979, "Reaction between N-Alkylpyrroles and Alkyl-lithium Reagents" J. Chem Soc., Perkin Trans. I 2845.
Chaikin et al., 1949, "Lithium Borohydride as a Reducing Agent", J. Am. Chem. Soc. 71:3245-46.
Chen et al., 1998, "Asymetric total synthesis of phosphatidylinositol 3-phosphate and 4-phosphate derivatives", J. Org. Chem. 63:6511-22.
Comins et al., 1981, "A one pot synthesis of unsymmetrical secondary alcohols from two grignard reagents", Tetrahedron Lett. 22:1085-88.
Corbridge, 1985, "Phosphorus: An Outline of its Chemistry, Biochemistry and Technology", Studies In Inorganic Chemistry, 3.sup. rd ed, pp. 357-395.
Corey et al.,1979, "Useful procedures for the oxidation of alcohols involving pyridinum dichromate in aprotic media", Tetrahedron Lett. 5: 399-402.
Corey et al., 1967, "A useful method for the conversion of alcohols into iodides", J. Org. Chem. 32: 4160-4161.
Danheiser et al., 1991, "A Practical and Efficient Method for Synthesis of .beta.-Lactones", J. Org. Chem. 56:1176-85.
Dansky HM, Fisher EA, 1999, "High-density lipoprotein and plaque regression: the good cholesterol gets even better", Circulation 100(17):1762-3.
Decossin et al., 1997, "Subclasses of LpA-I in coronary artery disease: distribution and cholesterol efflux ability", Eur J Clin Invest. 27(4):299-307.
Desarlo et al., 1971, "Isoxazolin-5-one", J. Chem Soc.86-89.
Eaton et al., 1972, "Hydroxypropylation", J. Org. Chem. 37:1947-50.

Ehlinger, et al., 1980, "Silicon in Synthesis. 10. The (trimethylsilyl)allyl Anion: A .beta.-Acyl anion equivalent for the conversion of aldehydes and ketones into .lambda.-lactone", J. Am. Chem. Soc. 102:5004-11.

Fielding & Fielding, 1995, "Molecular physiology of reverse cholesterol transport", J Lipid Res. 36(2):211-28.

Fraser et al., 1985, "Acidity measurements in the THF. V . . . sup.1 Heteroaromatic compounds containing 5-membered rings", Can. J. Chem 63:3505-09.

Garegg et al., 1980, "Novel Reagent System for converting a Hydroxy-group into an Iodo-group in carbohydrates with Inversion of Configuration", J.C.S. Perkin I 2866-2868.

Gearing et al.; 1993, "Interaction of the peroxisome-proliferator-activated receptor and retinoid X receptor", Proc. Natl. Acad. Sci. USA 90(4):1440-1444.

Gigg et al., 1967, "The Preparation of Unsymmetrical Diglycerides", J. Chem. Soc., C, 431-434.

Green and Kehinde, 1975, "An established preadipose cell line and its differentiation in culture. II. Factors affecting the adipose conversion", Cell. 5(1):19-27.

Greene, T.W., 1999, "Protection for the Hydroxyl Group, Including 1,2- and 1,3-Diols", Protective Groups in O.

Harris and Kletzien, 1994, "Localization of a pioglitazone response element in the adipocyte fatty acid-binding protein gene", Mol Pharmacol. 45(3):439-45.

Hayden and Ma, 1992, "Molecular genetics of human lipoprotein lipase deficiency", Mol Cell Biochem. 113 (2):171-6.

Heyman, et al., 1992, "9-cis retinoic acid is a high affinity ligand for the retinoid X receptor", Cell 68(2):397-406.

Hidaka and Fidge, 1992, "Affinity purification of the hepatic high-density lipoprotein receptor identifies two acidic glycoproteins and enables further characterization of their binding properties", Biochem. J. 15(Pt1):161-7.

Hirano et al., 1997, "Genetic cholesteryl ester transfer deficiency is extremely frequent in the Omagari area of Japan. Marked hyperalphalipoproteinemia caused by CETP gene mutation is not associated with longevity", Arterioscler. Thromb. Vasc. Biol. 17(6):1053-1059.

Hoyer et al., 1986, "Catalysis by acidic clay of the protective tetrahydropyranylation of alcohols and phenols", Synthesis 655-57.

Hudlicky, M., 1996, "Reduction of esters and lactones of coraboxylic acids", Reductions in Organic Chemistry, 2.sup.nd Ed., pp. 212-217.

Hudlicky, M, 1996, "Reduction of aldehydes and their derivatives", Reductions in Organic Chemistry, 2.sup.nd ed. pp. 137-139.

Ishibashi, et al., 1994, "Massive xanthomatosis and atherosclerosis in cholesterol-fed low density lipoprotein receptor-negative mice", J Clin Invest. 93(5):1885-93.

Ishibashi et al., 1993, "Hypercholesterolemia in low density lipoprotein receptor knockout mice and its reversal by adenovirus-mediated gene delivery", J Clin Invest. 92(2):883-93.

Isseman and Green, 1990, "Activation of a member of the steroid hormone receptor superfamily by peroxisome proliferators", Nature 347(6294):645-650.

Iwai et al., 1966, "Studies on acetylenic compounds, XLIV. . . sup . . . 1 Synthesis of 3-aminoisoxazoles and 3-hydroxyisoxazoles (3-isoxazolones)", Chem. Pharm. Bull. 14:1277-86.

Johnston et al., 1988, "A new, mild heterogeneous catalyst for the tetrahydropyranylation of alcohols andphelos", Synthesis 393-4.

Katritzky et al., 1993, "Generation and Reactions of sp.sup.2 -Carbanionic Centers in the Vicinity of Heterocyclic Nitrogen Atoms", Adv. Het. Chem. 56:155-303.

Keller and Wahli, 1993, "Peroxisome proliferator-activated receptors—A link between endocrinology and Nutrition?", TEM, 4:291-296.

Keller et al., 1993, "Fatty acids and retinoids control lipid metabolism through activation of peroxisome proliferator-activated receptor-retinoid X receptor heterodimers", Proc. Natl. Acad. Sci. USA 90(6):2160-2164.

Kessar et al., 1997, "Lewis acid complextion of tertiary animes and related compounds: A strategy for a .alpha.-deprotonation and stereocontrol", Chem. Rev. 97:721-37.

Kurz et al., 1985, "Anomalous selectivities in methyl transfers to water: An explanation using free energy surfaces which model the effects of non-equilibrium solvation", Isr. J. Chem. 26:339-48.

Kletzein et al., 1991, "Enhancement of adipocyte differentiation by an insulin-sensitizing agent", Mol Pharmacol 41(2):393-398.

Kliewer et al., 1992, "Convergence of 9-cis retinoic acid and peroxisome proliferator signalling pathways through heterodimer formation of their receptors", Nature. 27;358(6389):771-4.

Kurata et al., 1998, "A candidate high density lipoprotein (HDL) receptor, HB2, with possible multiple functions shows sequence homology with adhesion molecules", J. Atherosclerosis and Thrombosis 4(3):112-7.

Kurz et al., 1986, "Evidence for a rate-determining solvation change in methyl transfer to water. Solvent dependence of H.sub.2 O/D.sub.2 O kinetic isotope effects", J. Am. Chem 108:2960-68.

Lagrost et al., 1996, "Opposite effects of cholesteryl ester transfer protein and phospholipid transfer protein on the size distribution of plasma high density lipoproteins. Physiological relevance in alcoholic patients", J Biol Chem. 271(32):19058-65.

Landshulz et al., 1996, "Regulation of scavenger receptor, class B, type I, a high density lipoprotein receptor, in liver and steroidogenic tissues of the rat", J. Clin. Invest. 98(4):984-995.

Larock, 1989, Comprehensive Organic Transformations; Ch. 6, VCH: New York, pp. 446-448.

Lazarow and Fujiki, 1985, "Biogenesis of peroxisomes", Annu Rev Cell Biol. 1:489-530.

Levin et al., 1992, "9-cis retinoic acid stereoisomer binds and activates the nuclear receptor RXR alpha", Nature 355(6358):359-61.

Ludwig et al., 1989, "Rapid and efficient synthesis of nucleoside 5'-O-(1-thiotriphosphates), 5'-Triphosphates and 2',3'-Cyclophosphorothioates using 2-Chloro-4H-1,3,2-benzodioxaphosphorin-4-one", J. Org. Chem. 54:631-35.

Maddaford et al., 1993, "A general asymmetric synthesis of (−)-.alpha.-Dimethylretrodendrin and its diastereomers", J. Org. Chem 58:4132-38.

March, J, 1992, Advanced Organic Chemistry; reactions Mechanisms, and Structure, 4.sup.th ed., pp. 248-272, 1196-98, 437-438, 920-929.

Masamune et al., 1976, "Tylonolide hemiacetal, the aglycone of tylosin, and its partial synthesis [letter]". J Am Chem Soc. 98(24):7874-5.

Masayuma et al., 2000, "Regio- and diastereocontrol in carbonyl allylation by 1-halobut-2-enes with Tin(II) halides", J Org Chem. 65(2):494-8.

Menger et al., 1981 "Synthetically useful oxidations at solid sodium permanganate surfaces", Tetrahedron Lett. 22:1655-56.

Miyashita et al., 1977, "Pyridinium .rho.-Toluenesulfonate. A mild and efficient catalyst for the tetrahydropyranylation of alcohols", J. Org. Chem 42:3772-74.

Moffet et al., 1963, "2-(1-Pyrrolidyl)Propanol", Org. Synth. Collect 4:834-5.

Myers et al., 1992, "Studies on the thermal generation and reactivity of a class of (.alpha., .pl.)-1,4-biradicals", J. Am. Chem. Soc. 114:9369-86.

Nemali et al., 1988, "Comparison of constitutive and inducible levels of expression of peroxisomal beta-oxidation and catalase genes in liver and extrahepatic tissues of rat", Cancer Res. 48(18):5316-24.

Nystrom et al., 1947, "Reduction of Organic Compounds by Lithium Aluminum Hydride", J. Am. Chem Soc. 69:1197-1199.

Nystrom et al., 1949, "Lithium borohydride as a reducing agent", J. Am. Chem. 71:3245-47.

Ogata et al., 1969, "Kinetics of the baeyer-Villiger reaction of benzaldehydes with perbenzoic acid in aquoorganic solvents", J. Org. Chem 34: 3985-91.

Okamoto et al., 1985, "Synthesis of Alkyl Dihydrogenphosphate by the Reaction of Alcohols and Silyl Polyphosphate", Bull Chem. Soc. Jpn. 58:3393-3394.

Olah et al., 1984, "N-Formylmorpholine: A New and Effective Formylating Agent for the Preparation of Aldehydes and Dialkyl(1-Formylalkyl)phosphonates from Grignard or Organolithium Reagents", J. Org. Chem 4.

Olah et al., 1987, "Formylating Agents", Chem Rec. 87:4, 671-686.

Olah et al., 1979, "Transformations with Chlorotrimethylsilane/Sodium Iodide, a Convenient in Situ Iodotrimethylsilane Reagent", J. Org. Chem 44:8, 1247-1251.

Oster et al., 1983, "Generation and Reactions of the Dianion of 3-Hydroxy-5-methylisoxazole, a convenient . beta.-Keto Amide Synthon", J. Org. Chem 48:4307-4311.

Parra et al., 1992, "A case-control study of lipoprotein particles in two populations at contrasting risk for coronary heart disease. The ECTIM Study", Arterioscler Thromb. 12:701-707.

Pop et al., 1997, "Allylic and Phenolic Phosphate Esters of Dexanabinol", Org. Prep. And Proc. Int. 29:341-347.

Ramirez et al., 1978, "Phosphorylation by means of cyclic enediol phosphates.sup.1 ", Acc. Chem. Res. 11:239.

Raunio et al., 1957, "Addition of Propargyl Acetal to Cyclohexanone in the Presence of Sodamide", J. Org. Chem 22:570.

Reaven, 1993, "Role of insulin resistance in human disease (syndrome X): an expanded.definition", Annu Rev Med. 44:121-31.

Reddy and Lalwani, 1983, "Carcinogenesis by hepatic peroxisome proliferators: evaluation of the risk of hypolipidemic drugs and industrial plasticizers to humans", Crit Rev Toxicol. 12(1):1-58.

Rigotti et al., 1996, Regulation by adrenocorticotropic hormone of the in vivo expression of scavenger receptor class B type I (SR-BI), a high density lipoprotein receptor, in steroidogenic cells of the murine adrenal.

Robins and Fasulo, 1997, "High density lipoproteins, but not other lipoproteins, provide a vehicle for sterol transport to bile", J Clin Invest. 99(3):380-4.

Sam et al., 1972, "Crown Polyether Chemistry. Potassium Permanganate Oxidations in Benzene", J. Am. Chem. Soc. 94:4024.

Saulnier et al., 1982, "Generation and Reactions of 3-Lithio-1-(phenylsulfonyl) indole", J. Org. Chem 47:757.

Shirley et al. 1995, "Metalation of pyrrole, 1-methylpyrrole, and 1-phenylpyrrole with n-Butyllithium", J. Org. Chem 20:225-31.

Sianesi et al., 1971, "2.4-dihydro-1H-2.1-, 3.4-Dihydro-2H-1.2-und 3.4-Dihydro-1H-2.3-benzothiazin-S.S-dioxid", Chem. Ber. 104:1880-91.

Skinner et al., 1995, "Benzoylcyanamide from ethyl benzoyltioncarbomate", J. Am. Chem. Soc. 77:5440-42.

Smith et al., 1957, "Nitrogen Compounds of thePhosphoric and Phosphonic Acids, III, Preparation andand Properties of Amides of Phenylphosphonic and Phenylphosphonothioic Acids", J. Org. Chem. 22:265-267.

Song et al., 1999, "Prapctical asymmetric synthesis of an endothelin receptor antagonist", J. Org. Chem. 64:9658-67.

Staels and Auwerx, 1998, "Regulation of apo A-I gene expression by fibrates", Atherosclerosis 137 Suppl:S19-23.

Stevens et al., 1982, "Further studies on the utility of sodium hypochlorite in organic synthesis. Selective oxidation of diols and direct conversion of aldehydes to esters", Tetrahedron Lett. 23:4647-4650.

Stowell et al., 1995, "A new method for the phosphorylation of alcohols and phenols", Tetrahedron Lett. 36(11):1825-26.

Sundararaman et al., 1978, "One step conversion of aldehydes to esters", Tetrahedron Lett. 19: 1627-1628.

Tomroka et al., 1995, "Catalytic Asymmetric Conjugate Addition of Grignard Reagents Mediated by Copper (I)-Chiral Bedentate Phosphine Complex", Tetrahedron Lett. 36:4275-4278.

Tontonoz et al., 1994, "Adipocyte-specific transcription factor ARF6 is a heterodimeric complex of two nuclear hormone receptors, PPAR gamma and RXR alpha", Nucleic Acids Res. 22(25):5626-34.

Uhlmann et al., 1986, "Chemical 5'-phosphorylation of oligonucleotides valuable in automated dna synthesis", Tetrahedron Lett. 27:1023-26.

Ulrich, et al., 1995, "Cultured hepatocytes as investigational models for hepatic toxicity: practical applications in drug discovery and development", Toxicol Lett 82/83:107-15.

Urata et al., 1991, "Transition metal complex catalyzed carbonylation od organic halides in the presence of molecular-sieves instead of base", Tetrahedron Lett. 32:36, 4733-36.

Vogtle et al., 1987, "Doubly Clamped Cope Systems", J. Org. Chem. 52:5560-5564.

Blatt ed., 1943, "Gilbert Sulfonation and Related Reactions"pp. 135-142, 160-165; Org. Synth. Coll. vol. II, Wiley, NY and Org. Synth. Coll. vol. IV, 1963, Wiley NY 529-531.

Williams et al., 1988, "Bromine as an oxidant for direct conversion of aldehydes to esters", Tetrahedron Lett. 29:5087-90.

Wilson et al., 1982, "A novel, nonoxidative method for the conversion of aldehydes to esters", J. Org. Chem. 47:1360-61.

Wroblewski and Ladue, 1995, "Lactic dehydrogenase activity in blood", Proc. Soc. Exp. Biol. Med. 90:210-213.

Yanagisawa et al., 1994, "Allylbarium Reagents: Unprecedented regio- and stereoselectiv eallylation reactions of carbonyl compounds", J. Am. Chem. Soc. 116:6130-6141.

Yoshikawa et al., 1986, "Ruthenium Complex Catalyzed Regioselective Dehydrogenation of Unsymmetrical . alpha.,.omega.-Diols", J. Org. Chem. 51:2034.

Yoshikawa et al., 1983, "Catalytic Regioselective Dehydrogenationof Unsymmetrical .alpha.,.omega.-Diols Using Ruthenium Complexes", Tetrahedron Lett. 26:2677-2680.

Yu et al., 1988, "A novel reagent for the synthesis of myo-inositol phosphates: n, n-diisopropyl dibenzyl phosphoramidite", Tetrahedron Lett. 29:979-82.

Nan F et al. "Dual Function Glutamate-Related Ligands: Discovery of A Novel, Potent Inhibitor of Glutamate Carboxypeptidase II Possessing mGluR3 Agonist Activity" Journal of Medicinal Chemistry 2000, 43:pp. 772-774.

Yunker et al., 1978, "Alpha-oxygenated fatty acids occurring as amides of 2-methylene-.beta.-alanine in a marine sponge", Tetrahedron Lett. 47:4651-52.

Mulzer, 1995, Comprehensive Organic Functional Group Transformations Oxford 5 pp161.

Sweeney, 1995, "Comprehensive Organic Functional Groups Transformations", Oxford, vol. 2, pp. 104-109.

* cited by examiner

DIHYDROXYL COMPOUNDS AND COMPOSITIONS FOR CHOLESTEROL MANAGEMENT AND RELATED USES

This application claims the benefit of U.S. Provisional Application No. 60/441,795, filed Jan. 23, 2003, which is incorporated herein by reference in its entirety.

1. FIELD OF THE INVENTION

The invention relates to hydroxyl compounds and pharmaceutically acceptable salts, hydrates, solvates, and mixtures thereof, compositions comprising a hydroxyl compound or a pharmaceutically acceptable salt, hydrate, solvate, or mixtures thereof; and methods for treating or preventing a disease or disorder such as, but not limited to, aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), and a thrombotic disorder, which method comprise administering a hydroxyl compound or composition of the invention. The compounds of the invention can also treat or prevent inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism.

2. BACKGROUND OF THE INVENTION

Obesity, hyperlipidemia, and diabetes have been shown to play a causal role in atherosclerotic cardiovascular diseases, which currently account for a considerable proportion of morbidity in Western society. Further, one human disease, termed "Syndrome X" or "Metabolic Syndrome", is manifested by defective glucose metabolism (insulin resistance), elevated blood pressure (hypertension), and a blood lipid imbalance (dyslipidemia). See e.g. Reaven, 1993, *Annu. Rev. Med.* 44:121-131.

The evidence linking elevated serum cholesterol to coronary heart disease is overwhelming. Circulating cholesterol is carried by plasma lipoproteins, which are particles of complex lipid and protein composition that transport lipids in the blood. Low density lipoprotein (LDL) and high density lipoprotein (HDL) are the major cholesterol-carrier proteins. LDL is believed to be responsible for the delivery of cholesterol from the liver, where it is synthesized or obtained from dietary sources, to extrahepatic tissues in the body. The term "reverse cholesterol transport" describes the transport of cholesterol from extrahepatic tissues to the liver, where it is catabolized and eliminated. It is believed that plasma HDL particles play a major role in the reverse transport process, acting as scavengers of tissue cholesterol. HDL is also responsible for the removal of non-cholesterol lipid, oxidized cholesterol and other oxidized products from the bloodstream.

Atherosclerosis, for example, is a slowly progressive disease characterized by the accumulation of cholesterol within the arterial wall. Compelling evidence supports the belief that lipids deposited in atherosclerotic lesions are derived primarily from plasma apolipoprotein B (apo B)-containing lipoproteins, which include chylomicrons, CLDL, intermediate-density lipoproteins (IDL), and LDL. The apo B-containing lipoprotein, and in particular LDL, has popularly become known as the "bad" cholesterol. In contrast, HDL serum levels correlate inversely with coronary heart disease. Indeed, high serum levels of HDL are regarded as a negative risk factor. It is hypothesized that high levels of plasma HDL are not only protective against coronary artery disease, but may actually induce regression of atherosclerotic plaque (e.g., see Badimon et al., 1992, *Circulation* 86:(Suppl. III)86-94; Dansky and Fisher, 1999, *Circulation* 100:1762 3.). Thus, HDL has popularly become known as the "good" cholesterol.

2.1 Cholesterol Transport

The fat-transport system can be divided into two pathways: an exogenous one for cholesterol and triglycerides absorbed from the intestine and an endogenous one for cholesterol and triglycerides entering the bloodstream from the liver and other non-hepatic tissue.

In the exogenous pathway, dietary fats are packaged into lipoprotein particles called chylomicrons, which enter the bloodstream and deliver their triglycerides to adipose tissue for storage and to muscle for oxidation to supply energy. The remnant of the chylomicron, which contains cholesteryl esters, is removed from the circulation by a specific receptor found only on liver cells. This cholesterol then becomes available again for cellular metabolism or for recycling to extrahepatic tissues as plasma lipoproteins.

In the endogenous pathway, the liver secretes a large, very-low-density lipoprotein particle (VLDL) into the bloodstream. The core of VLDL consists mostly of triglycerides synthesized in the liver, with a smaller amount of cholesteryl esters either synthesized in the liver or recycled from chylomicrons. Two predominant proteins are displayed on the surface of VLDL, apolipoprotein B-100 (apo B-100) and apolipoprotein E (apo E), although other apolipoproteins are present, such as apolipoprotein CIII (apo CIII) and apolipoprotein CII (apo CII). When VLDL reaches the capillaries of adipose tissue or of muscle, its triglyceride is extracted. This results in the formation of a new kind of particle called intermediate-density lipoprotein (IDL) or VLDL remnant, decreased in size and enriched in cholesteryl esters relative to a VLDL, but retaining its two apoproteins.

In human beings, about half of the IDL particles are removed from the circulation quickly, generally within two to six hours of their formation. This is because IDL particles bind tightly to liver cells, which extract IDL cholesterol to make new VLDL and bile acids. The IDL not taken up by the liver is catabolized by the hepatic lipase, an enzyme bound to the proteoglycan on liver cells. Apo E dissociates from IDL as it is transformed to LDL. Apo B-100 is the sole protein of LDL.

Primarily, the liver takes up and degrades circulating cholesterol to bile acids, which are the end products of cholesterol metabolism. The uptake of cholesterol-containing particles is mediated by LDL receptors, which are present in high concentrations on hepatocytes. The LDL receptor binds both apo E and apo B-100 and is responsible for binding and removing both IDL and LDL from the circulation. In addition, remnant receptors are responsible for clearing chylomicrons and VLDL remnants (i.e., IDL). However, the affinity of apo E for the LDL receptor is greater than that of apo B-100. As a result, the LDL particles have a much longer circulating life span than IDL particles; LDL circulates for an average of two and a half days before binding to the LDL receptors in the liver and other tissues. High serum levels of LDL, the "bad" cholesterol, are positively associated with coronary heart disease. For example, in atherosclerosis, cholesterol derived from circulating LDL accumulates in the walls of arteries. This accumulation forms bulky plaques that inhibit the flow of blood until a clot eventually forms, obstructing an artery and causing a heart attack or stroke.

Ultimately, the amount of intracellular cholesterol liberated from the LDL controls cellular cholesterol metabolism. The accumulation of cellular cholesterol derived from VLDL and LDL controls three processes. First, it reduces the ability of the cell to make its own cholesterol by turning off the synthesis of HMGCoA reductase, a key enzyme in the cholesterol biosynthetic pathway. Second, the incoming LDL-derived cholesterol promotes storage of cholesterol by the action of cholesterol acyltransferase ("ACAT"), the cellular enzyme that converts cholesterol into cholesteryl esters that are deposited in storage droplets. Third, the accumulation of cholesterol within the cell drives a feedback mechanism that inhibits cellular synthesis of new LDL receptors. Cells, therefore, adjust their complement of LDL receptors so that enough cholesterol is brought in to meet their metabolic needs, without overloading (for a review, see Brown & Goldstein, in *The Pharmacological Basis Of Therapeutics*, 8th Ed., Goodman & Gilman, Pergamon Press, New York, 1990, Ch. 36, pp. 874-896).

High levels of apo B-containing lipoproteins can be trapped in the subendothelial space of an artery and undergo oxidation. The oxidized lipoprotein is recognized by scavenger receptors on macrophages. Binding of oxidized lipoprotein to the scavenger receptors can enrich the macrophages with cholesterol and cholesteryl esters independently of the LDL receptor. Macrophages can also produce cholesteryl esters by the action of ACAT. LDL can also be complexed to a high molecular weight glycoprotein called apolipoprotein(a), also known as apo(a), through a disulfide bridge. The LDL-apo(a) complex is known as Lipoprotein(a) or Lp(a). Elevated levels of Lp(a) are detrimental, having been associated with atherosclerosis, coronary heart disease, myocardial infarction, stroke, cerebral infarction, and restenosis following angioplasty.

2.2 Reverse Cholesterol Transport

Peripheral (non-hepatic) cells predominantly obtain their cholesterol from a combination of local synthesis and uptake of preformed sterol from VLDL and LDL. Cells expressing scavenger receptors, such as macrophages and smooth muscle cells, can also obtain cholesterol from oxidized apo B-containing lipoproteins. In contrast, reverse cholesterol transport (RCT) is the pathway by which peripheral cell cholesterol can be returned to the liver for recycling to extrahepatic tissues, hepatic storage, or excretion into the intestine in bile. The RCT pathway represents the only means of eliminating cholesterol from most extrahepatic tissues and is crucial to the maintenance of the structure and function of most cells in the body.

The enzyme in blood involved in the RCT pathway, lecithin:cholesterol acyltransferase (LCAT), converts cell-derived cholesterol to cholesteryl esters, which are sequestered in HDL destined for removal. LCAT is produced mainly in the liver and circulates in plasma associated with the HDL fraction. Cholesterol ester transfer protein (CETP) and another lipid transfer protein, phospholipid transfer protein (PLTP), contribute to further remodeling the circulating HDL population (see for example Bruce et al., 1998, *Annu. Rev. Nutr.* 18:297 330). PLTP supplies lecithin to HDL, and CETP can move cholesteryl esters made by LCAT to other lipoproteins, particularly apoB-containing lipoproteins, such as VLDL. HDL triglycerides can be catabolized by the extracellular hepatic triglyceride lipase, and lipoprotein cholesterol is removed by the liver via several mechanisms.

Each HDL particle contains at least one molecule, and usually two to four molecules, of apolipoprotein A I (apo A I). Apo A I is synthesized by the liver and small intestine as preproapolipoprotein, which is secreted as a proprotein that is rapidly cleaved to generate a mature polypeptide having 243 amino acid residues. Apo A I consists mainly of a 22 amino acid repeating segment, spaced with helix-breaking proline residues. Apo A I forms three types of stable structures with lipids: small, lipid-poor complexes referred to as pre-beta-1 HDL; flattened discoidal particles, referred to as pre-beta-2 HDL, which contain only polar lipids (e.g., phospholipid and cholesterol); and spherical particles containing both polar and nonpolar lipids, referred to as spherical or mature HDL (HDL3 and HDL2). Most HDL in the circulating population contains both apo A I and apo A II, a second major HDL protein. This apo A I- and apo A II-containing fraction is referred to herein as the AI/AII-HDL fraction of HDL. But the fraction of HDL containing only apo A I, referred to herein as the AI HDL fraction, appears to be more effective in RCT. Certain epidemiologic studies support the hypothesis that the AI-HDL fraction is antiartherogenic (Parra et al., 1992, *Arterioscler. Thromb.* 12:701-707; Decossin et al., 1997, *Eur. J. Clin. Invest.* 27:299-307).

Although the mechanism for cholesterol transfer from the cell surface is unknown, it is believed that the lipid-poor complex, pre-beta-1 HDL, is the preferred acceptor for cholesterol transferred from peripheral tissue involved in RCT. Cholesterol newly transferred to pre-beta-1 HDL from the cell surface rapidly appears in the discoidal pre-beta-2 HDL. PLTP may increase the rate of disc formation (Lagrost et al., 1996, *J. Biol. Chem.* 271:19058-19065), but data indicating a role for PLTP in RCT is lacking. LCAT reacts preferentially with discoidal and spherical HDL, transferring the 2-acyl group of lecithin or phosphatidylethanolamine to the free hydroxyl residue of fatty alcohols, particularly cholesterol, to generate cholesteryl esters (retained in the HDL) and lysolecithin. The LCAT reaction requires an apolipoprotein such as apo A I or apo A-IV as an activator. ApoA-I is one of the natural cofactors for LCAT. The conversion of cholesterol to its HDL-sequestered ester prevents re-entry of cholesterol into the cell, resulting in the ultimate removal of cellular cholesterol. Cholesteryl esters in the mature HDL particles of the AI-HDL fraction are removed by the liver and processed into bile more effectively than those derived from the AI/AII-HDL fraction. This may be due, in part, to the more effective binding of AI-HDL to the hepatocyte membrane. Several HDL receptors have been identified, the most well characterized of which is the scavenger receptor class B, type I (SR BI) (Acton et al., 1996, *Science* 271:518-520). The SR-BI is expressed most abundantly in steroidogenic tissues (e.g., the adrenals), and in the liver (Landshulz et al., 1996, *J. Clin. Invest.* 98:984-995; Rigotti et al., 1996, *J. Biol. Chem.*

271:33545-33549). Other proposed HDL receptors include HB1 and HB2 (Hidaka and Fidge, 1992, *Biochem J.* 15:161 7; Kurata et al., 1998, *J. Atherosclerosis and Thrombosis* 4:112 7).

While there is a consensus that CETP is involved in the metabolism of VLDL- and LDL-derived lipids, its role in RCT remains controversial. However, changes in CETP activity or its acceptors, VLDL and LDL, play a role in "remodeling" the HDL population. For example, in the absence of CETP, the HDL becomes enlarged particles that are poorly removed from the circulation (for reviews on RCT and HDL, See Fielding & Fielding, 1995, *J. Lipid Res.* 36:211-228; Barrans et al., 1996, *Biochem. Biophys. Acta.* 1300:73-85; Hirano et al., 1997, *Arterioscler. Thromb. Vasc. Biol.* 17:1053-1059).

2.3 Reverse Transport of Other Lipids

HDL is not only involved in the reverse transport of cholesterol, but also plays a role in the reverse transport of other lipids, i.e., the transport of lipids from cells, organs, and tissues to the liver for catabolism and excretion. Such lipids include sphingomyelin, oxidized lipids, and lysophosphatidylcholine. For example, Robins and Fasulo (1997, *J. Clin. Invest.* 99:380 384) have shown that HDL stimulates the transport of plant sterol by the liver into bile secretions.

2.4 Peroxisome Proliferator Activated Receptor Pathway

Peroxisome proliferators are a structurally diverse group of compounds that, when administered to rodents, elicit dramatic increases in the size and number of hepatic and renal peroxisomes, as well as concomitant increases in the capacity of peroxisomes to metabolize fatty acids via increased expression of the enzymes required for the β-oxidation cycle (Lazarow and Fujiki, 1985, *Ann. Rev. Cell Biol.* 1:489 530; Vamecq and Draye, 1989, *Essays Biochem.* 24:1115 225; and Nelali et al., 1988, *Cancer Res.* 48:5316 5324). Chemicals included in this group are the fibrate class of hypolipidemic drugs, herbicides, and phthalate plasticizers (Reddy and Lalwani, 1983, *Crit. Rev. Toxicol.* 12:1 58). Peroxisome proliferation can also be elicited by dietary or physiological factors, such as a high fat diet and cold acclimatization.

Insight into the mechanism whereby peroxisome proliferators exert their pleiotropic effects was provided by the identification of a member of the nuclear hormone receptor superfamily activated by these chemicals (Isseman and Green, 1990, *Nature* 347:645 650). This receptor, termed peroxisome proliferator activated receptor α(PPARα), was subsequently shown to be activated by a variety of medium and long chain fatty acids. PPARα activates transcription by binding to DNA sequence elements, termed peroxisome proliferator response elements (PPRE), in the form of a heterodimer with the retinoid X receptor (RXR). RXR is activated by 9-cis retinoic acid (see Kliewer et al., 1992, *Nature* 358:771 774; Gearing et al., 1993, *Proc. Natl. Acad. Sci. USA* 90:1440 1444, Keller et al., 1993, *Proc. Natl. Acad. Sci. USA* 90:2160 2164; Heyman et al., 1992, *Cell* 68:397 406, and Levin et al., 1992, *Nature* 355:359 361). Since the discovery of PPARα, additional isoforms of PPAR have been identified, e.g., PPARβ, PPARγ and PPARδ, which have similar functions and are similarly regulated.

PPARs have been identified in the enhancers of a number of gene-encoding proteins that regulate lipid metabolism. These proteins include the three enzymes required for peroxisomal β-oxidation of fatty acids; apolipoprotein A-I; medium chain acyl-CoA dehydrogenase, a key enzyme in mitochondrial β-oxidation; and aP2, a lipid binding protein expressed exclusively in adipocytes (reviewed in Keller and Whali, 1993, *TEM,* 4:291 296; see also Staels and Auwerx, 1998, *Atherosclerosis* 137 Suppl:S 19 23). The nature of the PPAR target genes coupled with the activation of PPARs by fatty acids and hypolipidemic drugs suggests a physiological role for the PPARs in lipid homeostasis.

Pioglitazone, an antidiabetic compound of the thiazolidinedione class, was reported to stimulate expression of a chimeric gene containing the enhancer/promoter of the lipid binding protein aP2 upstream of the chloroamphenicol acetyl transferase reporter gene (Harris and Kletzien, 1994, *Mol. Pharmacol.* 45:439 445). Deletion analysis led to the identification of an approximately 30 bp region accounting for pioglitazone responsiveness. In an independent study, this 30 bp fragment was shown to contain a PPRE (Tontonoz et al., 1994, *Nucleic Acids Res.* 22:5628 5634). Taken together, these studies suggested the possibility that the thiazolidinediones modulate gene expression at the transcriptional level through interactions with a PPAR and reinforce the concept of the interrelatedness of glucose and lipid metabolism.

2.5 Current Cholesterol Management Therapies

In the past two decades or so, the segregation of cholesterolemic compounds into HDL and LDL regulators and recognition of the desirability of decreasing blood levels of the latter has led to the development of a number of drugs. However, many of these drugs have undesirable side effects and/or are contraindicated in certain patients, particularly when administered in combination with other drugs.

Bile-acid-binding resins are a class of drugs that interrupt the recycling of bile acids from the intestine to the liver. Examples of bile-acid-binding resins are cholestyramine (QUESTRAN LIGHT, Bristol-Myers Squibb), and colestipol hydrochloride (COLESTID, Pharmacia & Upjohn Company). When taken orally, these positively charged resins bind to negatively charged bile acids in the intestine. Because the resins cannot be absorbed from the intestine, they are excreted, carrying the bile acids with them. The use of such resins, however, at best only lowers serum cholesterol levels by about 20%. Moreover, their use is associated with gastrointestinal side-effects, including constipation and certain vitamin deficiencies. Moreover, since the resins bind to drugs, other oral medications must be taken at least one hour before or four to six hours subsequent to ingestion of the resin, complicating heart patients' drug regimens.

The statins are inhibitors of cholesterol synthesis. Sometimes, the statins are used in combination therapy with bile-acid-binding resins. Lovastatin (MEVACOR, Merck & Co., Inc.), a natural product derived from a strain of *Aspergillus*; pravastatin (PRAVACHOL, Bristol-Myers Squibb Co.); and atorvastatin (LIPITOR, Warner Lambert) block cholesterol synthesis by inhibiting HMGCoA reductase, the key enzyme involved in the cholesterol biosynthetic pathway. Lovastatin significantly reduces serum cholesterol and LDL-serum levels. However, serum HDL levels are only slightly increased following lovastatin administration. The mechanism of the LDL-lowering effect may involve both reduction of VLDL concentration and induction of cellular expression of LDL-receptor, leading to reduced production and/or increased catabolism of LDL. Side effects, including liver and kidney dysfunction are associated with the use of these drugs.

Nicotinic acid, also known as niacin, is a water-soluble vitamin B-complex used as a dietary supplement and antihyperlipidemic agent. Niacin diminishes the production of VLDL and is effective at lowering LDL. It is used in combination with bile-acid-binding resins. Niacin can increase HDL when administered at therapeutically effective doses; however, its usefulness is limited by serious side effects.

Fibrates are a class of lipid-lowering drugs used to treat various forms of hyperlipidemia, elevated serum triglycerides, which may also be associated with hypercholesterolemia. Fibrates appear to reduce the VLDL fraction and modestly increase HDL; however, the effects of these drugs on serum cholesterol is variable. In the United States, fibrates have been approved for use as antilipidemic drugs, but have not received approval as hypercholesterolemia agents. For example, clofibrate (ATROMID-S, Wyeth-Ayerst Laboratories) is an antilipidemic agent that acts to lower serum triglycerides by reducing the VLDL fraction. Although ATROMID-S may reduce serum cholesterol levels in certain patient subpopulations, the biochemical response to the drug is variable, and is not always possible to predict which patients will obtain favorable results. ATROMID-S has not been shown to be effective for prevention of coronary heart disease. The chemically and pharmacologically related drug, gemfibrozil (LOPID, Parke-Davis), is a lipid regulating agent which moderately decreases serum triglycerides and VLDL cholesterol. LOPID also increases HDL cholesterol, particularly the HDL2 and HDL3 subfractions, as well as both the AI/AII-HDL fractions. However, the lipid response to LOPID is heterogeneous, especially among different patient populations. Moreover, while prevention of coronary heart disease was observed in male patients between the ages of 40 and 55 without history or symptoms of existing coronary heart disease, it is not clear to what extent these findings can be extrapolated to other patient populations (e.g., women, older and younger males). Indeed, no efficacy was observed in patients with established coronary heart disease. Serious side-effects are associated with the use of fibrates, including toxicity; malignancy, particularly malignancy of gastrointestinal cancer; gallbladder disease; and an increased incidence in non-coronary mortality. These drugs are not indicated for the treatment of patients with high LDL or low HDL as their only lipid abnormality.

Oral estrogen replacement therapy may be considered for moderate hypercholesterolemia in post-menopausal women. However, increases in HDL may be accompanied with an increase in triglycerides. Estrogen treatment is, of course, limited to a specific patient population, postmenopausal women, and is associated with serious side effects, including induction of malignant neoplasms; gall bladder disease; thromboembolic disease; hepatic adenoma; elevated blood pressure; glucose intolerance; and hypercalcemia.

Long chain carboxylic acids, particularly long chain $\alpha,\omega$-dicarboxylic acids with distinctive substitution patterns, and their simple derivatives and salts, have been disclosed for treating atherosclerosis, obesity, and diabetes (See, e.g., Bisgaier et al., 1998, *J. Lipid Res.* 39:17-30, and references cited therein; International Patent Publication WO 98/30530; U.S. Pat. No. 4,689,344; International Patent Publication WO 99/00116; and U.S. Pat. No. 5,756,344). However, some of these compounds, for example the $\alpha,\omega$-dicarboxylic acids substituted at their $\alpha,\alpha'$-carbons (U.S. Pat. No. 3,773,946), while having serum triglyceride and serum cholesterol-lowering activities, have no value for treatment of obesity and hypercholesterolemia (U.S. Pat. No. 4,689,344).

U.S. Pat. No. 4,689,344 discloses $\beta,\beta,\beta',\beta'$-tetrasubstituted-$\alpha,\omega$-alkanedioic acids that are optionally substituted at their $\alpha,\alpha,\alpha',\alpha'$-positions, and alleges that they are useful for treating obesity, hyperlipidemia, and diabetes. According to this reference, both triglycerides and cholesterol are lowered significantly by compounds such as 3,3,14,14-tetramethyl-hexadecane-1,16-dioic acid. U.S. Pat. No. 4,689,344 further discloses that the $\beta,\beta,\beta',\beta'$-tetramethyl-alkanediols of U.S. Pat. No. 3,930,024 also are not useful for treating hypercholesterolemia or obesity.

Other compounds are disclosed in U.S. Pat. No. 4,711,896. In U.S. Pat. No. 5,756,544, $\alpha,\omega$-dicarboxylic acid-terminated dialkane ethers are disclosed to have activity in lowering certain plasma lipids, including Lp(a), triglycerides, VLDL-cholesterol, and LDL-cholesterol, in animals, and elevating others, such as HDL-cholesterol. The compounds are also stated to increase insulin sensitivity. In U.S. Pat. No. 4,613,593, phosphates of dolichol, a polyprenol isolated from swine liver, are stated to be useful in regenerating liver tissue, and in treating hyperuricuria, hyperlipemia, diabetes, and hepatic diseases in general.

U.S. Pat. No. 4,287,200 discloses azolidinedione derivatives with anti-diabetic, hypolipidemic, and anti-hypertensive properties. However, the administration of these compounds to patients can produce side effects such as bone marrow depression, and both liver and cardiac cytotoxicity. Further, the compounds disclosed by U.S. Pat. No. 4,287,200 stimulate weight gain in obese patients.

It is clear that none of the commercially available cholesterol management drugs has a general utility in regulating lipid, lipoprotein, insulin and glucose levels in the blood. Thus, compounds that have one or more of these utilities are clearly needed. Further, there is a clear need to develop safer drugs that are efficacious at lowering serum cholesterol, increasing HDL serum levels, preventing coronary heart disease, and/or treating existing disease such as atherosclerosis, obesity, diabetes, and other diseases that are affected by lipid metabolism and/or lipid levels. There is also a clear need to develop drugs that may be used with other lipid-altering treatment regimens in a synergistic manner. There is still a further need to provide useful therapeutic agents whose solubility and Hydrophile/Lipophile Balance (HLB) can be readily varied.

Citation or identification of any reference in Section 2 of this application is not an admission that such reference is available as prior art to the present invention.

3. SUMMARY OF THE INVENTION

The invention encompasses hydroxyl compounds useful in treating various disorders.

The invention further encompasses pharmaceutical compositions comprising one or more compounds of the invention and a pharmaceutically acceptable vehicle, excipient, or diluent. A pharmaceutically acceptable vehicle can comprise a carrier, excipient, diluent, or a mixture thereof.

The invention encompasses a method for treating or preventing aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), and a thrombotic disorder, comprising administering to a patient in need of such treatment or prevention a therapeutically effective amount of a compound of the invention or a pharmaceutical composition comprising a compound of the invention and a pharmaceutically acceptable vehicle, excipient, or diluent.

The invention also encompasses a method for inhibiting hepatic fatty acid and sterol synthesis comprising administering to a patient in need thereof a therapeutically effective amount of a compound of the invention or a pharmaceutical composition comprising a compound of the invention and a pharmaceutically acceptable vehicle, excipient, or diluent.

The invention also encompasses a method of treating or preventing a disease or disorder that is capable of being treated or prevented by increasing HDL levels, which comprises administering to a patient in need of such treatment or prevention a therapeutically effective amount of a compound of the invention and a pharmaceutically acceptable vehicle, excipient, or diluent.

The invention also encompasses a method of treating or preventing a disease or disorder that is capable of being treated or prevented by lowering LDL levels, which comprises administering to such patient in need of such treatment or prevention a therapeutically effective amount of a compound of the invention and a pharmaceutically acceptable vehicle, excipient, or diluent.

The compounds of the invention favorably alter lipid metabolism in animal models of dyslipidemia at least in part by enhancing oxidation of fatty acids through the ACC/malonyl-CoA/CPT-I regulatory axis and therefore the invention also encompasses methods of treatment or prevention of metabolic syndrome disorders.

The invention further encompasses a method for reducing the fat content of meat in livestock comprising administering to livestock in need of such fat-content reduction a therapeutically effective amount of a compound of the invention or a pharmaceutical composition comprising a compound of the invention and a pharmaceutically acceptable vehicle, excipient, or diluent.

The invention provides a method for reducing the cholesterol content of a fowl egg comprising administering to a fowl species a therapeutically effective amount of a compound of the invention or a pharmaceutical composition comprising a compound of the invention and a pharmaceutically acceptable vehicle, excipient, or diluent.

The present invention may be understood more fully by reference to the detailed description and examples, which are intended to exemplify non-limiting embodiments of the invention.

4. DEFINITIONS AND ABBREVIATIONS

Apo(a): apolipoprotein(a)
Apo A-I: apolipoprotein A-I
Apo B: apolipoprotein B
Apo E: apolipoprotein E
FH: Familial hypercholesterolemia
FCH: Familial combined hyperlipidemia
GDM: Gestational diabetes mellitus
HDL: High density lipoprotein
IDL: Intermediate density lipoprotein
IDDM: Insulin dependent diabetes mellitus
LDH: Lactate dehdyrogenase
LDL: Low density lipoprotein
Lp(a): Lipoprotein (a)
MODY: Maturity onset diabetes of the young
NIDDM: Non-insulin dependent diabetes mellitus
PPAR: Peroxisome proliferator activated receptor
RXR: Retinoid X receptor
VLDL: Very low density lipoprotein As used herein, the phrase "compounds of the invention" means compounds disclosed herein. Particular compounds of the invention are compounds of formulas I, II, III, IV, V, VI, and pharmaceutically acceptable salts, hydrates, enantiomers, diastereomer, racemates or mixtures of stereoisomers thereof. Thus, "compound of the invention" collectively means compound of formulas I, II, III, IV, V, VI, and pharmaceutically acceptable salts, hydrates, enantiomers, diastereomer, racemates or mixtures of stereoisomers thereof. The compounds of the invention are identified herein by their chemical structure and/or chemical name. Where a compound is referred to by both a chemical structure and a chemical name, and the chemical structure and chemical name conflict, the chemical structure is to be accorded more weight.

The compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compounds' enantiomers and stereoisomers, that is, both the stereomerically pure form (e.g., geometrically pure, enantiomerically pure, or diastereomerically pure) and enantiomeric and stereoisomeric mixtures.

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a reaction that is "substantially complete" means that the reaction contains more than about 80% by weight of the desired product, more preferably more than about 90% by weight of the desired product, even more preferably more than about 95% by weight of the desired product, and most preferably more than about 97% by weight of the desired product.

A compound of the invention is considered optically active or enantiomerically pure (i.e., substantially the R-form or substantially the S-form) with respect to a chiral center when the compound is about 90% ee (enantiomeric excess) or greater, preferably, equal to or greater than 95% ee with respect to a particular chiral center. A compound of the invention is considered to be in enantiomerically-enriched form when the compound has an enantiomeric excess of greater than about 1% ee, preferably greater than about 5% ee, more preferably, greater than about 10% ee with respect to a particular chiral center. A compound of the invention is considered diastereomerically pure with respect to multiple chiral centers when the compound is about 90% de (diastereomeric excess) or greater, preferably, equal to or greater than 95% de with respect to a particular chiral center. A compound of the invention is considered to be in diastereomerically-enriched form when the compound has an diastereomeric excess of greater than about 1% de, preferably greater than about 5% de, more preferably, greater than about 10% de with respect to a particular chiral center. As used herein, a racemic mixture means about 50% of one enantiomer and about 50% of is corresponding enantiomer relative to all chiral centers in the molecule. Thus, the invention encompasses all enantiomerically-pure, enantiomerically-enriched, diastereomerically pure, diastereomerically enriched, and racemic mixtures of compounds of Formulas I through VI.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

The compounds of the invention are defined herein by their chemical structures and/or chemical names. Where a compound is referred to by both a chemical structure and a chemical name, and the chemical structure and chemical name conflict, the chemical structure is determinative of the compound's identity.

When administered to a patient, e.g., to an animal for veterinary use or for improvement of livestock, or to a human for clinical use, the compounds of the invention are administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, of a single hydroxy compound of the invention by weight of the isolate.

The phrase "pharmaceutically acceptable salt(s)," as used herein includes, but is not limited to, salts of acidic or basic groups that may be present in the compounds of the invention. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds of the invention that include an amino moiety also can form pharmaceutically acceptable salts with various amino acids, in addition to the acids mentioned above. Compounds of the invention that are acidic in nature are capable of forming base salts with various pharmaceutically acceptable cations. Examples of such salts include alkali metal or alkaline earth metal salts and, particularly, calcium, magnesium, sodium lithium, zinc, potassium, and iron salts.

As used herein, the term "hydrate" means a compound of the invention or a salt thereof, that further includes a stoichiometric or non-stoichiometric amount of water bound by non-covalent intermolecular forces. The term hydrate includes solvates, which are stoichiometric or non-stoichiometric amounts of a solvent bound by non-covalent intermolecular forces. Preferred solvents are volatile, non-toxic, and/or acceptable for administration to humans in trace amounts.

As used herein, the term "altering lipid metabolism" indicates an observable (measurable) change in at least one aspect of lipid metabolism, including but not limited to total blood lipid content, blood HDL cholesterol, blood LDL cholesterol, blood VLDL cholesterol, blood triglyceride, blood Lp(a), blood apo A-I, blood apo E and blood non-esterified fatty acids.

As used herein, the term "altering glucose metabolism" indicates an observable (measurable) change in at least one aspect of glucose metabolism, including but not limited to total blood glucose content, blood insulin, the blood insulin to blood glucose ratio, insulin sensitivity, and oxygen consumption.

As used herein, the term "alkyl group" means a saturated, monovalent unbranched or branched hydrocarbon chain. Examples of alkyl groups include, but are not limited to, $(C_1-C_6)$alkyl groups, such as methyl, ethyl, propyl, isopropyl, 2-methyl-1-propyl, 2 methyl 2-propyl, 2-methyl-1-butyl, 3-methyl-1-butyl, 2 methyl-3-butyl, 2,2 dimethyl 1-propyl, 2-methyl-1-pentyl, 3 methyl-1-pentyl, 4 methyl-1-pentyl, 2-methyl-2-pentyl, 3-methyl-2-pentyl, 4 methyl 2 pentyl, 2,2 dimethyl 1 butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

As used herein, the term an "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to $(C_2-C_6)$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

As used herein, the term an "alkynyl group" means monovalent unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_6)$alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

As used herein, the term an "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. Preferably, the aryl group is a monocyclic ring, wherein the ring comprises 6 carbon atoms, referred to herein as "$(C_6)$aryl".

As used herein, the term an "heteroaryl group" means a monocyclic- or polycyclic aromatic ring comprising carbon atoms, hydrogen atoms, and one or more heteroatoms, preferably 1 to 3 heteroatoms, independently selected from nitrogen, oxygen, and sulfur. Illustrative examples of heteroaryl groups include, but are not limited to, pyridinyl, pyridazinyl, pyrimidinyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thiophenyl, isoxazolyl, thiazolyl, furyl, phenyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "($C_2$-$C_5$)heteroaryl".

As used herein, the term "cycloalkyl group" means a monocyclic or polycyclic saturated ring comprising carbon and hydrogen atoms and having no carbon-carbon multiple bonds. Examples of cycloalkyl groups include, but are not limited to, ($C_3$-$C_7$)cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or two suitable substituents. Preferably, the cycloalkyl group is a monocyclic ring or bicyclic ring.

As used herein, the term "heterocycloalkyl group" means a monocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 6 carbon atoms and form 1 to 3 heteroatoms, referred to herein as ($C_1$-$C_6$)heterocycloalkyl.

As used herein, the terms "heterocyclic radical" or "heterocyclic ring" mean a heterocycloalkyl group or a heteroaryl group.

As used herein, the term "alkoxy group" means an —O-alkyl group, wherein alkyl is as defined above. An alkoxy group can be unsubstituted or substituted with one or two suitable substituents. Preferably, the alkyl chain of an alkyloxy group is from 1 to 6 carbon atoms in length, referred to herein as "($C_1$-$C_6$)alkoxy".

As used herein, the term "aryloxy group" means an —O-aryl group, wherein aryl is as defined above. An aryloxy group can be unsubstituted or substituted with one or two suitable substituents. Preferably, the aryl ring of an aryloxy group is a monocyclic ring, wherein the ring comprises 6 carbon atoms, referred to herein as "($C_6$)aryloxy".

As used herein, the term "benzyl" means —$CH_2$-phenyl.

As used herein, the term "phenyl" means —$C_6H_5$. A phenyl group can be unsubstituted or substituted with one or two suitable substituents, wherein the subtituent replaces an H of the phenyl group. As used herein, "Ph," represents a phenyl group or a substituted phenyl group.

As used herein, the term "hydrocarbyl" group means a monovalent group selected from ($C_1$-$C_8$)alkyl, ($C_2$-$C_8$)alkenyl, and ($C_2$-$C_8$)alkynyl, optionally substituted with one or two suitable substituents. Preferably, the hydrocarbon chain of a hydrocarbyl group is from 1 to 6 carbon atoms in length, referred to herein as "($C_1$-$C_6$)hydrocarbyl".

As used herein, a "carbonyl" group is a divalent group of the formula C(O).

As used herein, the term "alkoxycarbonyl" group means a monovalent group of the formula —C(O)-alkoxy. Preferably, the hydrocarbon chain of an alkoxycarbonyl group is from 1 to 8 carbon atoms in length, referred to herein as a "lower alkoxycarbonyl" group.

As used herein, a "carbamoyl" group means the radical —C(O)N(R')$_2$, wherein R' is chosen from the group consisting of hydrogen, alkyl, and aryl.

As used herein, "halogen" means fluorine, chlorine, bromine, or iodine. Accordingly, the meaning of the terms "halo" and "Hal" encompass fluoro, chloro, bromo, and iodo.

As used herein, a "suitable substituent" means a group that does not nullify the synthetic or pharmaceutical utility of the compounds of the invention or the intermediates useful for preparing them. Examples of suitable substituents include, but are not limited to: ($C_1$-$C_8$)alkyl; ($C_1$-$C_8$)alkenyl; ($C_1$-$C_8$)alkynyl; ($C_6$)aryl; ($C_2$-$C_5$)heteroaryl; ($C_3$-$C_7$)cycloalkyl; ($C_1$-$C_8$)alkoxy; ($C_6$)aryloxy; —CN; —OH; oxo; halo, —$CO_2$H; —$NH_2$; —NH(($C_1$-$C_8$)alkyl); —N(($C_1$-$C_8$)alkyl)$_2$; —NH(($C_6$)aryl); —N(($C_6$)aryl)$_2$; —CHO; —CO(($C_1$-$C_8$)alkyl); —CO(($C_6$)aryl); —$CO_2$(($C_1$-$C_8$)alkyl); and —$CO_2$(($C_6$)aryl). One of skill in the art can readily choose a suitable substituent based on the stability and pharmacological and synthetic activity of the compound of the invention.

As used herein, a composition that is "substantially free" of a compound means that the composition contains less than about 20% by weight, more preferably less than about 10% by weight, even more preferably less than about 5% by weight, and most preferably less than about 3% by weight of the compound.

5. DETAILED DESCRIPTION OF THE INVENTION

The compounds of the invention are useful in medical applications for treating or preventing a variety of diseases and disorders such as, but not limited to, cardiovascular disease, stroke, and peripheral vascular disease; dyslipidemia; dyslipoproteinemia; a disorder of glucose metabolism; Alzheimer's Disease; Parkinson's Disease, diabetic nephropathy, diabetic retinopathy, insulin resistance, metabolic syndrome disorders (e.g., Syndrome X); a peroxisome proliferator activated receptor-associated disorder; septicemia; a thrombotic disorder; obesity; pancreatitis; hypertension; renal disease; cancer; inflammation; inflammatory muscle diseases, such as polymylagia rheumatica, polymyositis, and fibrositis; impotence; gastrointestinal disease; irritable bowel syndrome; inflammatory bowel disease; inflammatory disorders, such as asthma, vasculitis, ulcerative colitis, Crohn's disease, Kawasaki disease, Wegener's granulomatosis, (RA), systemic lupus erythematosus (SLE), multiple sclerosis (MS), and autoimmune chronic hepatitis; arthritis, such as rheumatoid arthritis, juvenile rheumatoid arthritis, and osteoarthritis; osteoporosis, soft tissue rheumatism, such as tendonitis; bursitis; autoimmune disease, such as systemic lupus and erythematosus; scleroderma; ankylosing spondylitis; gout; pseudogout; non-insulin dependent diabetes mellitus; polycystic ovarian disease; hyperlipidemias, such as familial hypercholesterolemia (FH), familial combined hyperlipidemia (FCH); lipoprotein lipase deficiencies, such as hypertriglyceridemia, hypoalphalipoproteinemia, and hypercholesterolemia; lipoprotein abnormalities associated with diabetes; lipoprotein abnormalities associated with obesity; and lipoprotein abnormalities associated with Alzheimer's Disease. The compounds and compositions of the invention are useful for treatment or prevention of high levels of blood triglycerides, high levels of low density lipoprotein cholesterol, high levels of apolipoprotein B, high levels of lipoprotein Lp(a) cholesterol, high levels of very low density lipoprotein cholesterol, high levels of fibrinogen, high levels of insulin, high levels of glucose, and low levels of high density lipoprotein cholesterol. The compounds and compositions of the invention also have utility for treatment of NIDDM without increasing weight gain. The compounds of the invention may also be used to reduce the fat content of meat in livestock and reduce the cholesterol content of eggs.

The invention provides novel compounds particularly useful for treating or preventing a variety of diseases and conditions, which include, but are not limited to aging, Alzheimer's Disease, cancer, cardiovascular disease, diabetic nephropathy, diabetic retinopathy, a disorder of glucose metabolism, dyslipidemia, dyslipoproteinemia, enhancing bile production, hypertension, impotence, inflammation, insulin resistance, lipid elimination in bile, modulating C reactive protein, obesity, oxysterol elimination in bile, pancreatitis, pancreatitius, Parkinson's disease, a peroxisome proliferator activated receptor-associated disorder, phospholipid elimination in bile, renal disease, septicemia, metabolic syndrome disorders (e.g., Syndrome X), and a thrombotic disorder.

In one embodiment, the invention encompasses compounds of formula I:

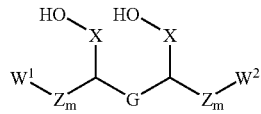

or a pharmaceutically acceptable salt, hydrate, solvate, or a mixture thereof, wherein (a) each occurrence of Z is independently $CH_2$, $CH=CH$, or phenyl, where each occurrence of m is independently an integer ranging from 1 to 9, but when Z is phenyl then m is 1;

(b) G is $(CH_2)_x$, where x is 1-7, $CH_2CH=CHCH_2$, $CH=CH$, $CH_2$-phenyl-$CH_2$, or phenyl;

(c) $W^1$ and $W^2$ are independently L, V, $C(R^1)(R^2)$—$(CH_2)_c$-$C(R^3)(R^4)$—$(CH_2)_n$-Y or $C(R^1)(R^2)$—$(CH_2)_c$-V where c is 1 or 2 and n is an integer ranging from 0 to 7;

(d) each occurrence of $R^1$ or $R^2$ is independently ($C_1$-$C_6$) alkyl, ($C_2$-$C_6$)alkenyl, ($C_2$-$C_6$)alkynyl, phenyl, or benzyl or when one or both of $W^1$ and $W^2$ is $C(R^1)(R^2)$—$(CH_2)_c$-$C(R^3)(R^4)$—$(CH_2)_n$-Y, then $R^1$ and $R^2$ can both be H to form a methylene group; or $R^1$ and $R^2$ and the carbon to which they are both attached are taken together to form a ($C_3$-$C_7$)cycloakyl group;

(e) $R^3$ is H, ($C_1$-$C_6$)alkyl, ($C_2$-$C_6$)alkenyl, ($C_2$-$C_6$)alkynyl, ($C_1$-$C_6$)alkoxy, phenyl, benzyl, Cl, Br, CN, $NO_2$, or $CF_3$;

(f) $R^4$ is OH, ($C_1$-$C_6$)alkyl, ($C_2$-$C_6$)alkenyl, ($C_2$-$C_6$)alkynyl, ($C_1$-$C_6$)alkoxy, phenyl, benzyl, Cl, Br, CN, $NO_2$, or $CF_3$;

(g) L is $C(R^1)(R^2)$—$(CH_2)_n$-Y, wherein n is an integer from 0 to 5;

(h) V is:

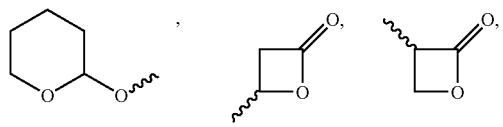

-continued

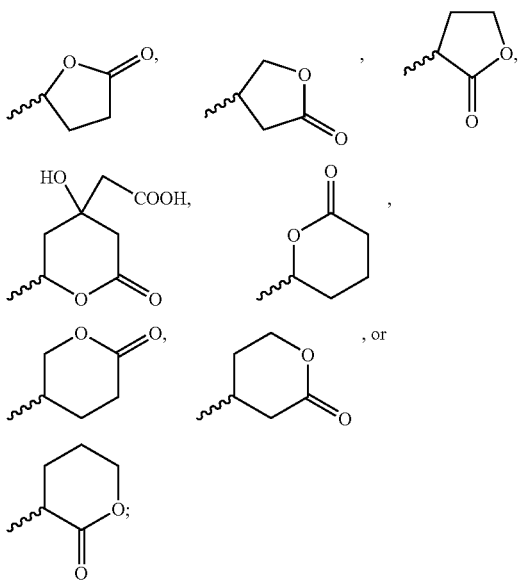

(i) each occurrence of Y is independently ($C_1$-$C_6$)alkyl, OH, COOH, $COOR^5$, $SO_3H$,

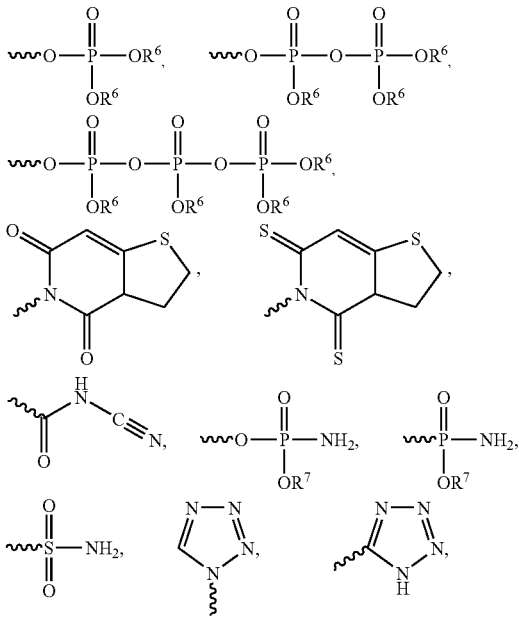

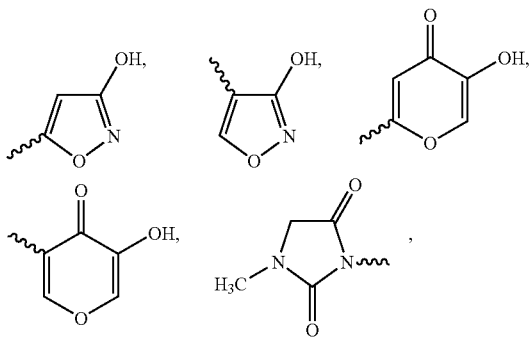

-continued

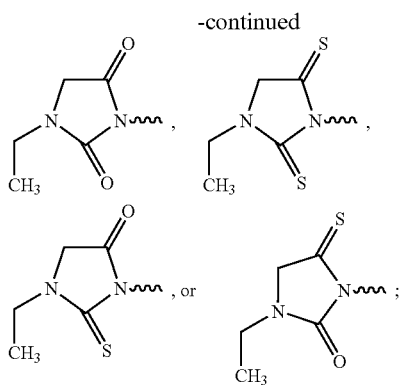

wherein:
(i) $R^5$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of $R^6$ is independently H, $(C_1-C_6)$alkyl, $(C_2-C_6)$alkenyl, or $(C_2-C_6)$alkynyl and is unsubstituted or substituted with one or two halo, OH, $(C_1-C_6)$alkoxy, or phenyl groups;
(iii) each occurrence of $R^7$ is independently H, $(C_1-C_6)$alkyl, $(C_2-C_6)$alkenyl, or $(C_2-C_6)$alkynyl; and
(j) X is $(CH_2)_z$ or Ph, wherein z is an integer from 0 to 4.

In another embodiment, the invention encompasses compounds of formula II:

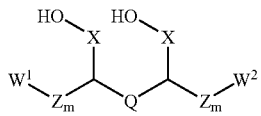

II or a pharmaceutically acceptable salt, hydrate, solvate, or a mixture thereof, wherein:
(a) each occurrence of Z is independently $CH_2$ or $CH=CH$, wherein each occurrence of m is independently an integer ranging from 1 to 9;
(b) Q is $(CH_2)_x$, $CH_2CH=CHCH_2$, or $CH=CH$, where x is 2, 3, or 4;
(c) $W^1$ and $W^2$ are independently L, V, or $C(R^1)(R^2)$—$(CH_2)_c$-V, where c is 1 or 2;
(d) each occurrence of $R^1$ and $R^2$ is independently $(C_1-C_6)$alkyl, $(C_2-C_6)$alkenyl, $(C_2-C_6)$alkynyl, phenyl, benzyl, or $R^1$ and $R^2$ and the carbon to which they are both attached are taken together to form a $(C_3-C_7)$cycloakyl group;
(e) L is $C(R^1)(R^2)$—$(CH_2)_n$-Y, where n is an integer ranging from 0 to 5;
(f) V is:

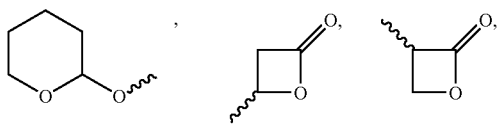

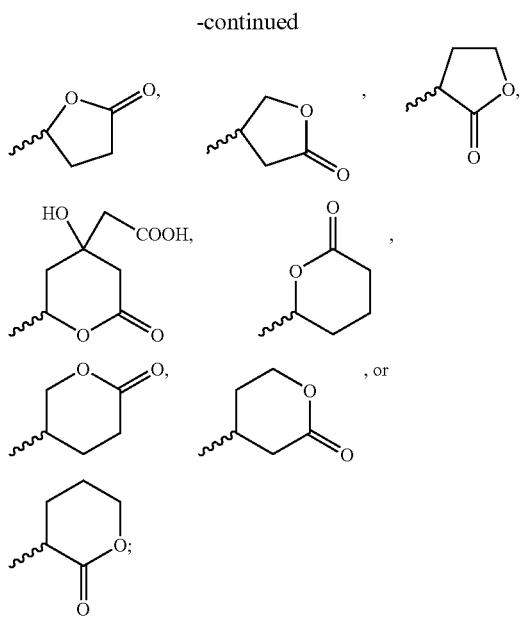

(g) each occurrence of Y is independently $(C_1-C_6)$alkyl, OH, COOH, $COOR^3$, $SO_3H$,

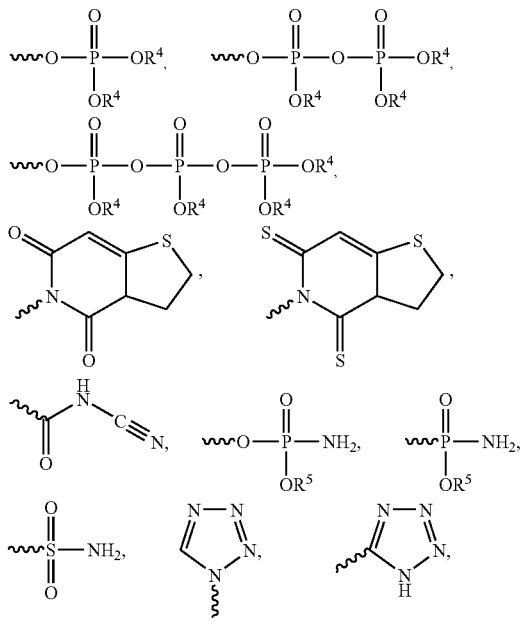

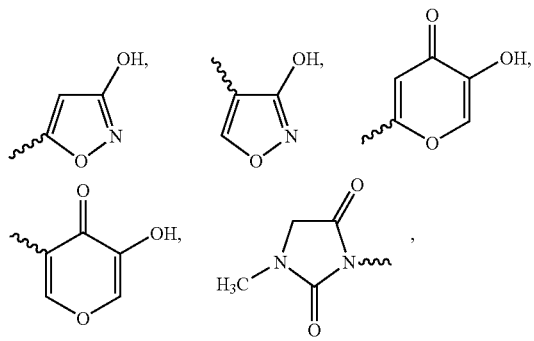

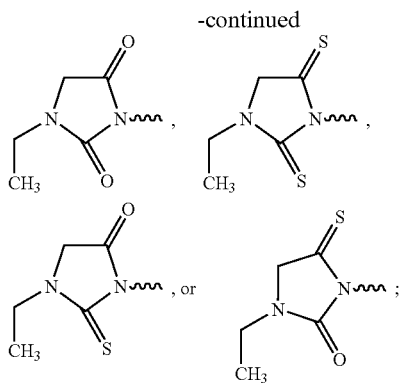

wherein:
(i) R³ is (C₁-C₆)alkyl, (C₂-C₆)alkenyl, (C₂-C₆)alkynyl, phenyl, or benzyl and is unsubstituted or substituted with one or more halo, OH, (C₁-C₆)alkoxy, or phenyl groups,
(ii) each occurrence of R⁴ is independently H, (C₁-C₆)alkyl, (C₂-C₆)alkenyl, or (C₂-C₆)alkynyl and is unsubstituted or substituted with one or two halo, OH, (C₁-C₆)alkoxy, or phenyl groups; and
(iii) each occurrence of R⁵ is independently H, (C₁-C₆)alkyl, (C₂-C₆)alkenyl, or (C₂-C₆)alkyny; and (h) X is (CH₂)$_z$ or Ph, wherein z is an integer from 0 to 4.

Preferably, in formula II each occurrence of Y is independently OH, COOR³, or COOH.

In yet another embodiment, the invention encompasses compounds of formula III

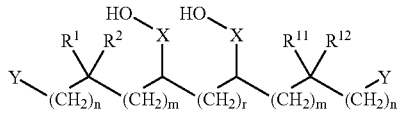

III or a pharmaceutically acceptable salt, hydrate, solvate, or a mixture thereof, wherein:
(a) each occurrence of m is independently an integer ranging from 1 to 9;
(b) r is 2, 3, or 4;
(c) each occurrence of n is independently an integer ranging from 0 to 7;
(d) each occurrence of R¹, R², R¹¹, and R¹² is independently (C₁-C₆)alkyl, (C₂-C₆)alkenyl, (C₂-C₆)alkynyl, phenyl, benzyl, or R¹ and R² and the carbon to which they are both attached are taken together to form a (C₃-C₇)cycloakyl group, or R¹¹ and R¹² and the carbon to which they are both attached are taken together to form a (C₃-C₇)cycloakyl group; and
(e) each occurrence of Y is independently (C₁-C₆)alkyl, OH, COOH, COOR³, SO₃H,

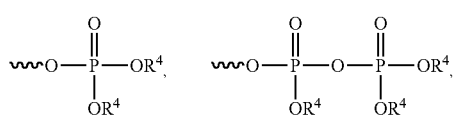

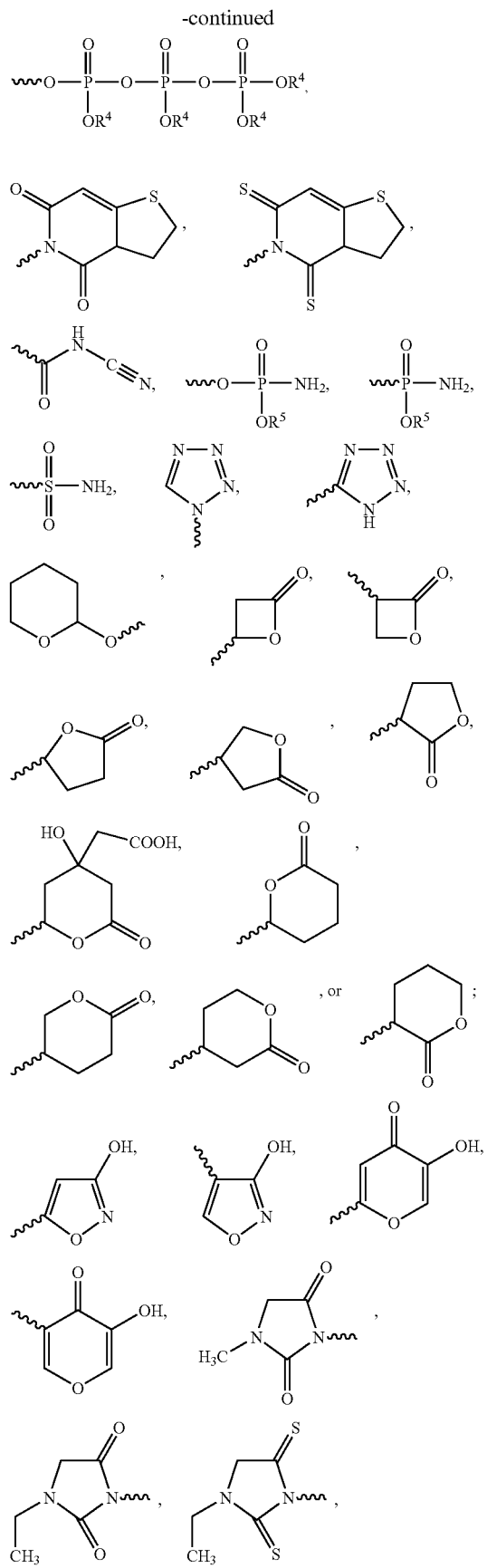

-continued

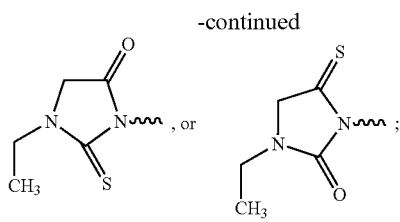, or 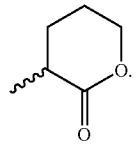;

wherein:
(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of $R^4$ is independently H, $(C_1-C_6)$alkyl, $(C_2-C_6)$alkenyl, or $(C_2-C_6)$alkynyl and is unsubstituted or substituted with one or two halo, OH, $C_1-C_6$ alkoxy, or phenyl groups;
(iii) each occurrence of $R^5$ is independently H, $(C_1-C_6)$alkyl, $(C_2-C_6)$alkenyl, or $(C_2-C_6)$alkynyl; and (f) X is $(CH_2)_z$ or Ph, wherein z is an integer from 0 to 4;

Preferably in formula III, each occurrence of Y is independently OH, $COOR^3$, or COOH.

In still another embodiment, the invention encompasses compounds of formula IV

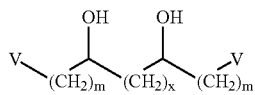

IV or a pharmaceutically acceptable salt, hydrate, solvate, or a mixture thereof, wherein:
(a) each occurrence of m is an independent integer ranging from 1 to 9;
(b) x is 2, 3, or 4;
(c) V is:

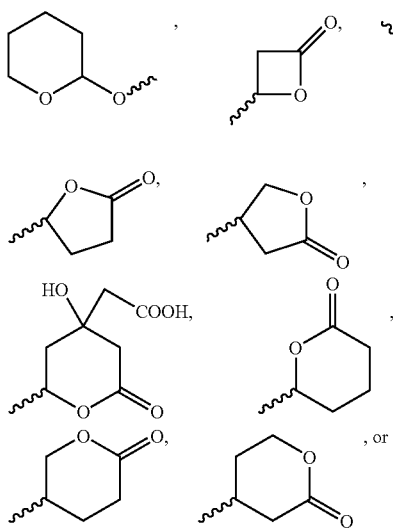

, or

-continued

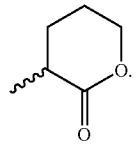

In yet another embodiment, the invention encompasses compounds of formula V:

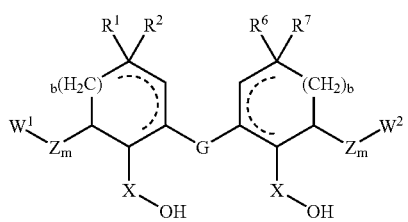

V or a pharmaceutically acceptable salt, hydrate, solvate, or a mixture thereof, wherein:
(a) each occurrence of Z is independently $CH_2$, CH=CH, or phenyl, where each occurrence of m is independently an integer ranging from 1 to 5, but when Z is phenyl then its associated m is 1;
(b) G is $(CH_2)_x$, $CH_2CH=CHCH_2$, CH=CH, $CH_2$-phenyl-$CH_2$, or phenyl, where x is an integer ranging from 1 to 7;
(c) $W^1$ and $W^2$ are independently $C(R^8)(R^9)$—$(CH_2)_n$-Y, where n is an integer ranging from 0 to 7;

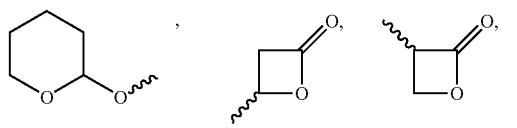

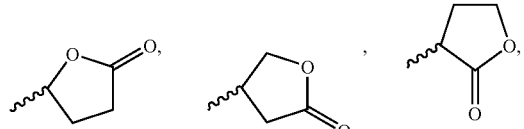

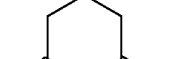

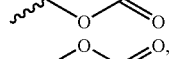

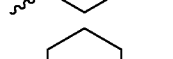

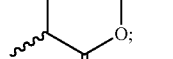

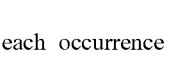, or (d) each occurrence of $R^8$ and $R^9$ is independently H, $(C_1-C_6)$alkyl, $(C_2-C_6)$alkenyl, $(C_2-C_6)$alkynyl, phenyl, or benzyl or $R^8$ and $R^9$ can be taken together to form a carbonyl group;

(e) each occurrence of $R^1$ and $R^2$ is independently H, $(C_1-C_6)$alkyl, $(C_2-C_6)$alkenyl, $(C_2-C_6)$alkynyl, phenyl, or benzyl or $R^1$ and $R^2$ can be taken together to form a carbonyl group or $R^1$ and $R^2$ and the carbon to which they are both attached are taken together to form a $(C_3-C_7)$cycloakyl group;

(f) each occurrence of $R^6$ and $R^7$ is independently H, $(C_1-C_6)$alkyl, or $R^6$ and $R^7$ can be taken together to form a carbonyl group or $R^6$ and $R^7$ and the carbon to which they are both attached are taken together to form a $(C_3-C_7)$cycloakyl group;

(g) Y is $(C_1-C_6)$alkyl, OH, COOH, $COOR^3$, $SO_3H$,

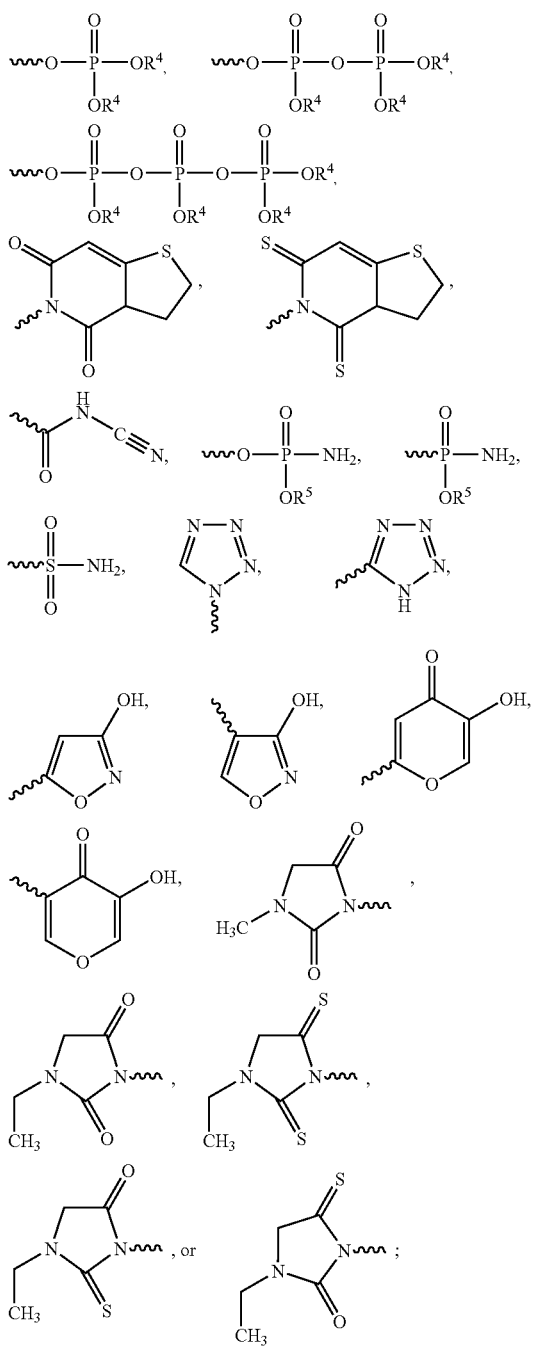

wherein:
(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of $R^4$ is independently H, $(C_1-C_6)$alkyl, $(C_2-C_6)$alkenyl, or $(C_2-C_6)$alkynyl and is unsubstituted or substituted with one or two halo, OH, $C_1-C_6$ alkoxy, or phenyl groups;
(iii) each occurrence of $R^5$ is independently H, $(C_1-C_6)$alkyl, $(C_2-C_6)$alkenyl, or $(C_2-C_6)$alkynyl;

(h) each occurrence of b is independently 0 or 1 or optionally the presence of one or more additional carbon-carbon bonds that when present complete one or more carbon-carbon double bonds; and (i) X is $(CH_2)_z$ or Ph, wherein z is an integer from 0 to 4.

Preferably in formula V, each occurrence of $W^1$ and $W^2$ is an independent $C(R^1)(R^2)$—$(CH_2)_n$-Y group and each occurrence of Y is independently OH, $COOR^3$, or COOH.

In yet another embodiment, the invention encompasses compounds of formula VI:

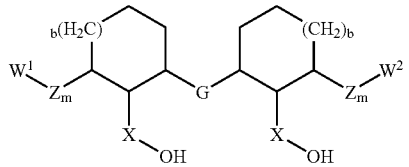

or a pharmaceutically acceptable salt, hydrate, solvate, or a mixture thereof, wherein
(a) each occurrence of m is independently an integer ranging from 1 to 5;
(b) X is $(CH_2)_z$ or Ph, wherein z is an integer from 0 to 4;
(c) $W^1$ and $W^2$ are independently $C(R^1)(R^2)$—$(CH_2)_n$-Y, where n is an integer ranging from 0 to 7;

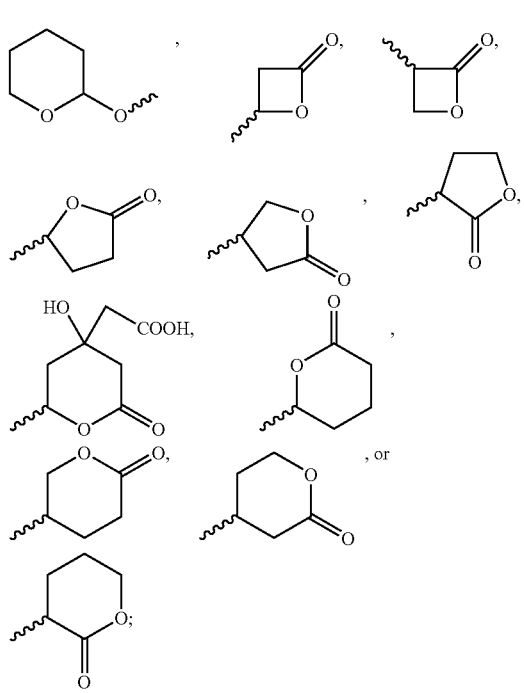

(d) each occurrence of $R^1$ or $R^2$ is independently $(C_1-C_6)$ alkyl, $(C_2-C_6)$alkenyl, $(C_2-C_6)$alkynyl, or $R^1$ and $R^2$ and the carbon to which they are both attached are taken together to form a $(C_3-C_7)$cycloakyl group;

(e) Y is $(C_1-C_6)$alkyl, $(CH_2)_nOH$, $(CH_2)_nCOOH$, $(CH_2)_nCOOR^3$, $SO_3H$,

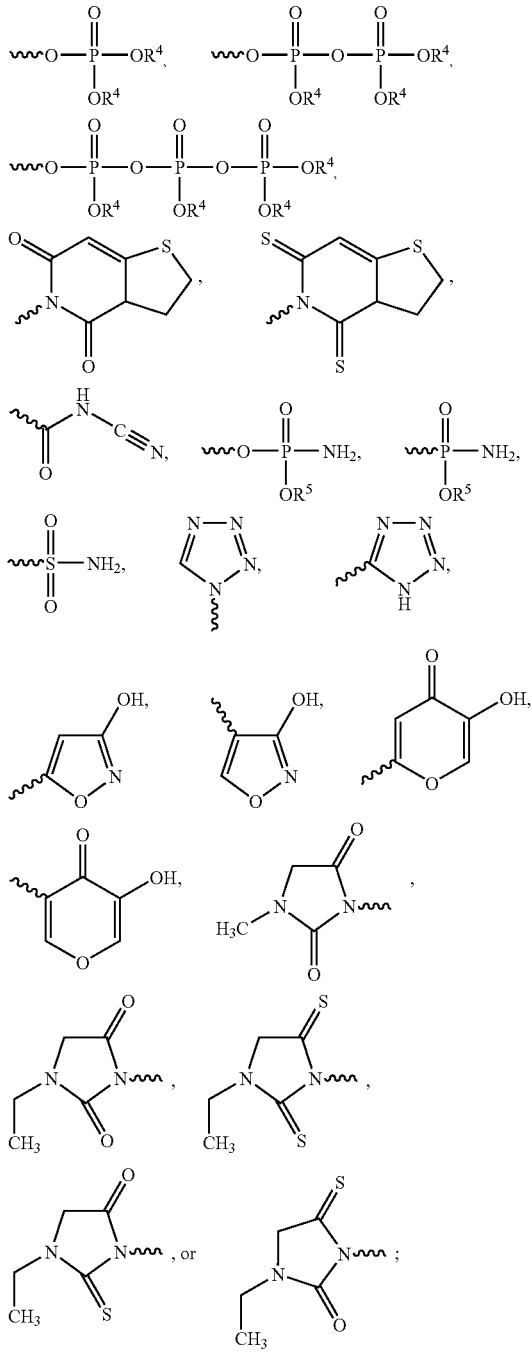

wherein:

(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups, (ii) each occurrence of $R^4$ is independently H, $(C_1-C_6)$ alkyl, $(C_2-C_6)$alkenyl, or $(C_2-C_6)$alkynyl and is unsubstituted or substituted with one or two halo, OH, $C_1$-$C_6$ alkoxy, or phenyl groups, (iii) each occurrence of $R^5$ is independently H, $(C_1-C_6)$ alkyl, $(C_2-C_6)$alkenyl, or $(C_2-C_6)$alkynyl;

(f) each occurrence of b is independently 0 or 1; and (g) X is $(CH_2)_z$ or Ph, wherein z is an integer from 0 to 4.

Preferably in compound VI, $W^1$ and $W^2$ are independent $C(R^1)(R^2)$—$(CH_2)_n$Y, groups and each occurrence of Y is independently OH, $COOR^3$, or COOH.

The present invention further provides pharmaceutical compositions comprising one or more compounds of the invention. Particular pharmaceutical compositions further comprise pharmaceutically acceptable vehicle, which can comprise a carrier, excipient, diluent, or a mixture thereof.

The present invention provides a method for treating or preventing aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, pancreatitius, Parkinson's disease, a peroxisome proliferator activated receptor-associated disorder, phospholipid elimination in bile, renal disease, septicemia, metabolic syndrome disorders (e.g., Syndrome X), and a thrombotic disorder, comprising administering to a patient in need of such treatment or prevention a therapeutically effective amount of a compound of the invention.

The present invention further provides a method for reducing the fat content of meat in livestock comprising administering to livestock in need of such fat-content reduction a therapeutically effective amount of a compound of the invention or a pharmaceutical composition.

The present invention provides a method for reducing the cholesterol content of a fowl egg comprising administering to a fowl species a therapeutically effective amount of a compound of the invention.

The compounds of the invention are particularly useful when incorporated in a pharmaceutical composition comprising a carrier, excipient, diluent, or a mixture thereof. However, a compound of the invention need not be administered with excipients or diluents and can be delivered in a gel cap or drug delivery device.

In certain embodiments of the invention, a compound of the invention is administered in combination with another therapeutic agent. The other therapeutic agent provides additive or synergistic value relative to the administration of a compound of the invention alone. Examples of other therapeutic agents include, but are not limited to, a lovastatin; a thiazolidinedione or fibrate; a bile-acid-binding-resin; a niacin; an anti-obesity drug; a hormone; a tyrophostine; a sulfonylurea-based drug; a biguanide; an a-glucosidase inhibitor; an apolipoprotein A-I agonist; apolipoprotein E; a cardiovascular drug; an HDL-raising drug; an HDL enhancer; or a regulator of the apolipoprotein A-I, apolipoprotein A-IV and/or apolipoprotein genes.

Illustrative examples of compounds of the invention include those shown below, and pharmaceutically acceptable salts, hydrates, enantiomers, diastereomers, and geometric isomers thereof:

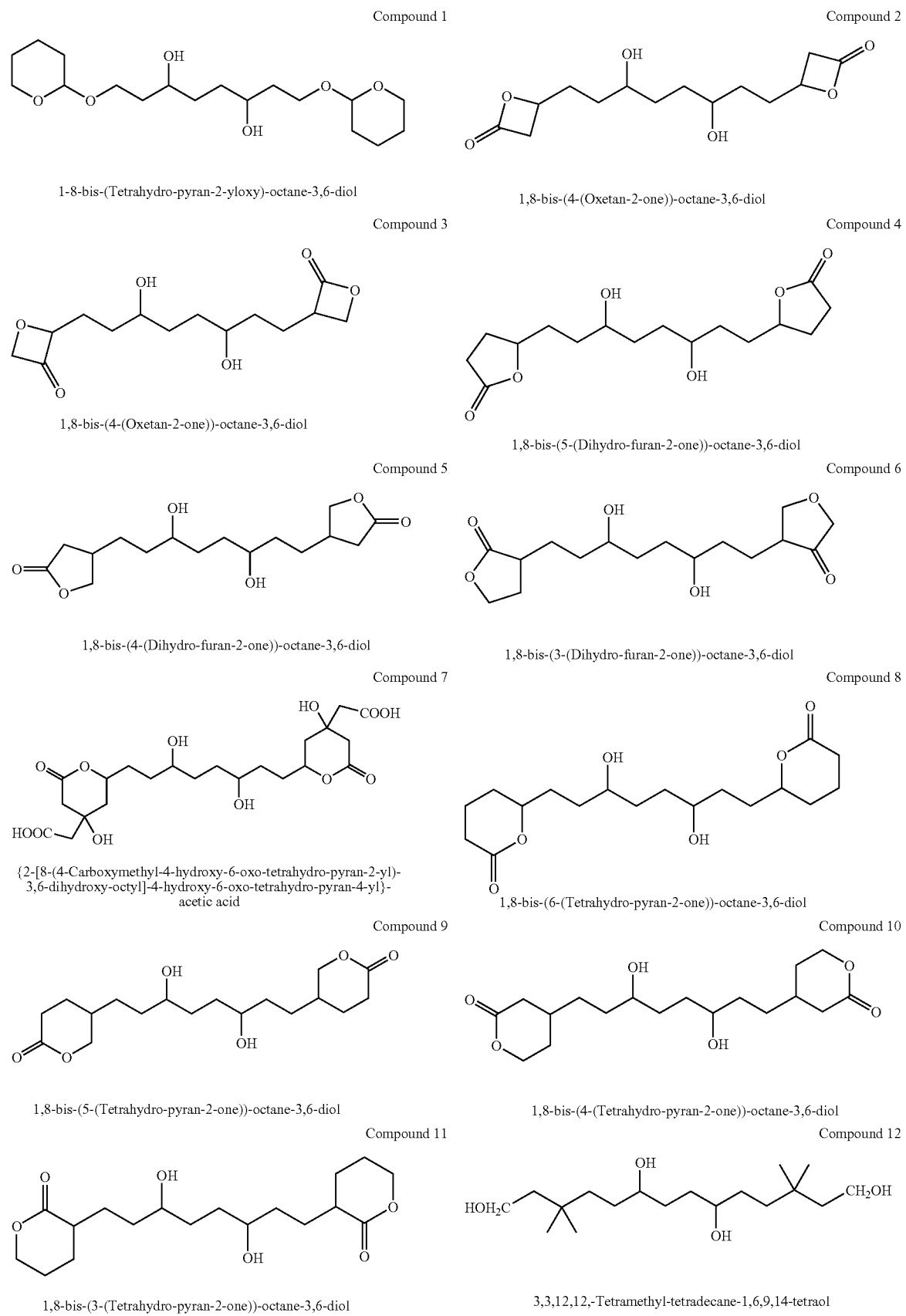

-continued

Compound 13

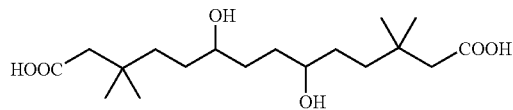

6,9-Dihydroxy-3,3,12,12-tetramethyl-tetradec anedioic acid

Compound 14

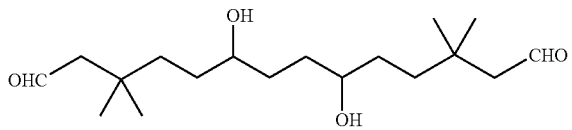

6,9-Dihydroxy-3,3,12,12-tetramethyl-tetradecanedial

Compound 15

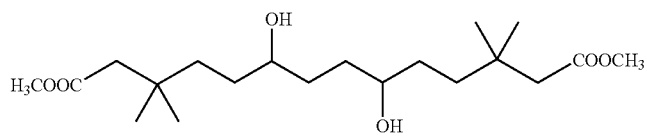

6,9-Dihydroxy-3,3,12,12-tetramethyl-tetradec anedioic acid
dimethyl ester

Compound 16

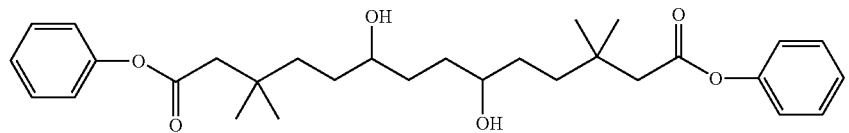

6,9-Dihydroxy-3,3,12,12-tetramethyl-tetradec anedioic acid
diphenyl ester

Compound 17

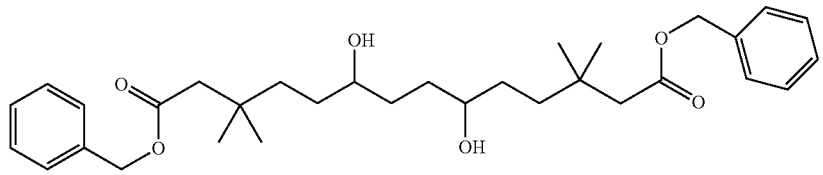

6,9-Dihydroxy-3,3,12,12-tetramethyl-tetradec anedioic acid
dibenzyl ester

Compound 18

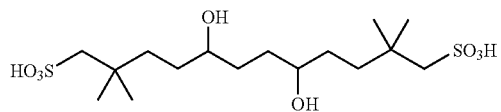

5,8-Dihydroxy-2,2,11,11,-tetramethyl-dodecan e-1,12-disulfonic acid

Compound 19

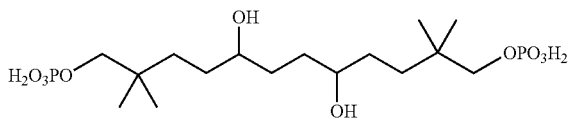

Phosphoric acid
mono-(5,8-dihydroxy-2,2,11,11-tetramethyl-1
2-phosphonooxy-dodecyl) ester Compound 20

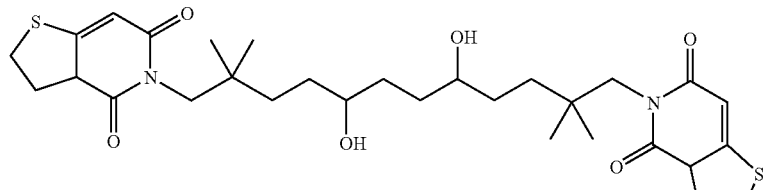

1,12-bis-(N-(3,3a-dihydro-2H-
thieno[3,2,c]pyridine-4,6-dione))-5,8-dihydroxy-2,2,11,11-
tetramethyl-dodecane Compound 21

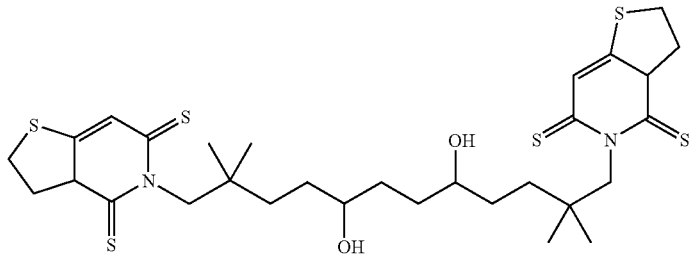

1,12-bis-(N-3,3a-dihydro-2H-
thieno[3,2,c]pyridine-4,6-dithioxo))-5,8-dihydroxy-2,2,11,11-
tetramethyl-dodecane Compound 22

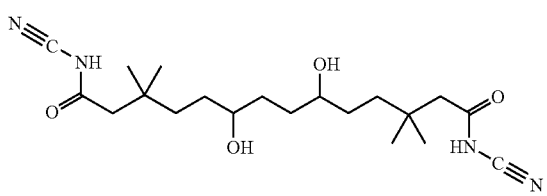

1,14-bis-(N-Cyanoamido)-6,9-dihydroxy-3,3,12,12-tetramethyl-
tetradecane

Compound 23

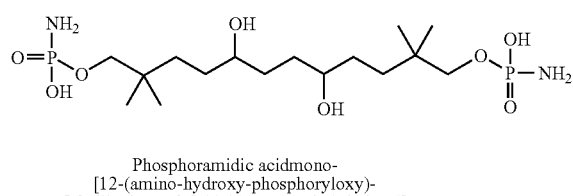

Phosphoramidic acidmono-
[12-(amino-hydroxy-phosphoryloxy)-
5,8-dihydroxy-2,2,11,11-tetramethyl-dodecyl]

Compound 24

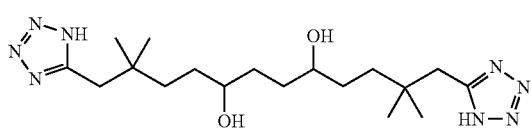

2,2,11,11-Tetramethyl-1,12-bis-(1H-tetrazol-5-yl)-dodecane-5,8-
diol

Compound 25

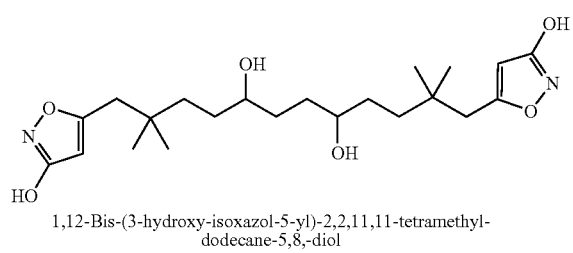

1,12-Bis-(3-hydroxy-isoxazol-5-yl)-2,2,11,11-tetramethyl-
dodecane-5,8,-diol

Compound 26

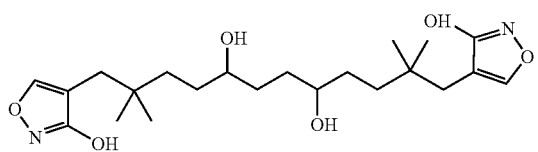

1,12-Bis-(3-hydroxy-isoxazol-4-yl)-2,2,11,11-
tetramethyl-dodecane-5,8,-diol

Compound 27

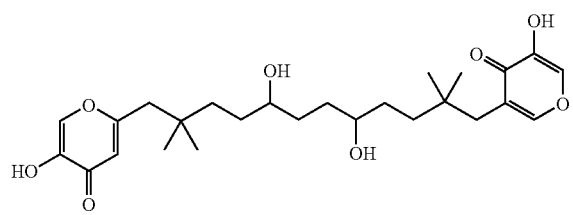

1-(6-(3-hydroxy-pyran-4-one)-12-(5-
(3-hydroxy-pyran-4-one)-2,2,11,11-tetramethyl-dodecane-5,8-diol Compound 28

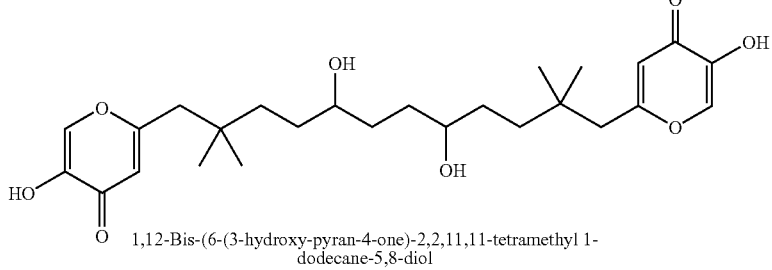

1,12-Bis-(6-(3-hydroxy-pyran-4-one)-2,2,11,11-tetramethyl 1-
dodecane-5,8-diol

Compound 29

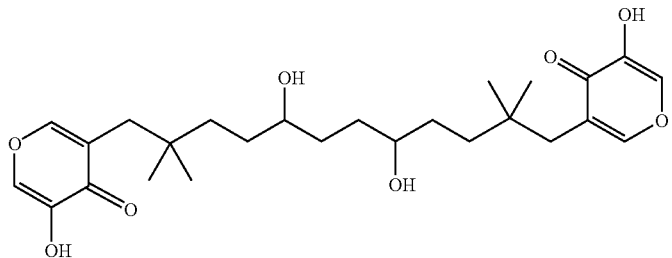

1,12-Bis-(5-(3-hydroxy-pyran-4-one)-2,2,11,11-tetramethyl 1-dodecane-5,8-diol

Compound 30

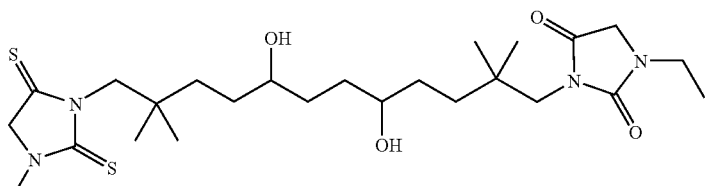

1-Ethyl-3-[12-(3-ethyl-2,5-dithioxo-imidazolidin-1-yl)-5,8,-dihydroxy-2,2,11,11-tetramethyl-dodecyl]-imidazolidine-2,4-dione Compound 31

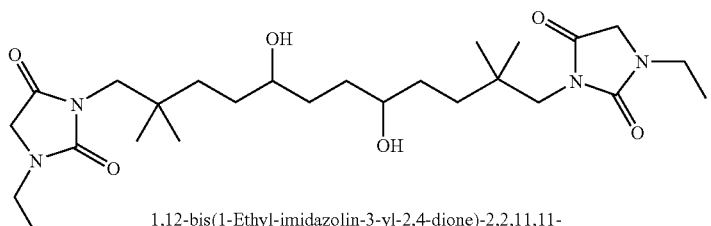

1,12-bis(1-Ethyl-imidazolin-3-yl-2,4-dione)-2,2,11,11-tetramethyl-dodecane-5,8-diol Compound 32

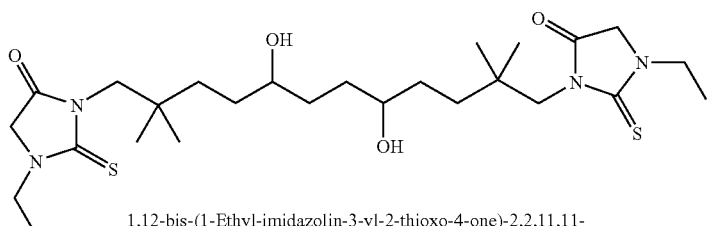

1,12-bis-(1-Ethyl-imidazolin-3-yl-2-thioxo-4-one)-2,2,11,11-tetramethyl-dodecane-5,8-diol Compound 33

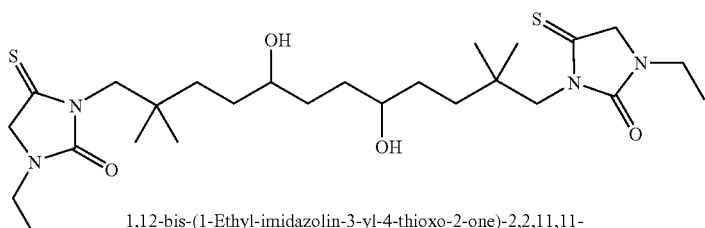

1,12-bis-(1-Ethyl-imidazolin-3-yl-4-thioxo-2-one)-2,2,11,11-tetramethyl-dodecane-5,8-diol Compound 34

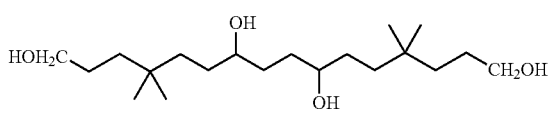

4,4,13,13-Tetramethyl-hexadecane-1,7,1016-5 etraol

Compound 35

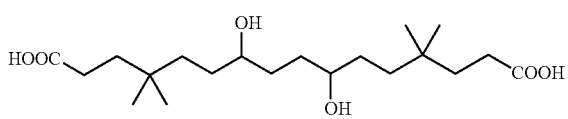

7,10-Dihydroxy-4,4,13,13-tetramethyl-hexadecanedioic acid

Compound 36

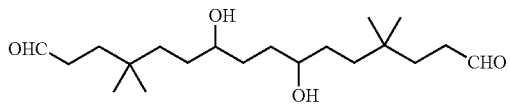

7,10-Dihydroxy-4,4,13,13-tetramethyl-hexadecanedial

Compound 37

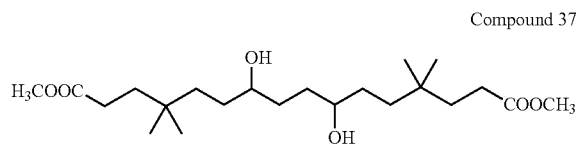

7,10-Dihydroxy-4,4,13,13-tetramethyl-hexadecanedioic acid dimethyl ester

Compound 38

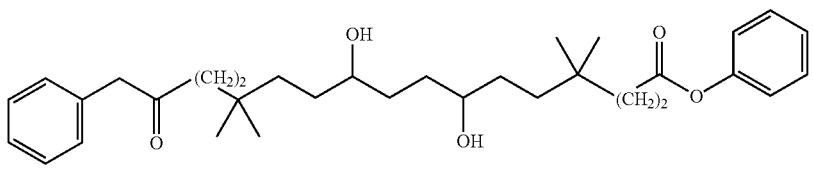

7,10-Dihydroxy-4,4,13,13-tetramethyl-hexadecanedioic acid diphenyl ester

Compound 39

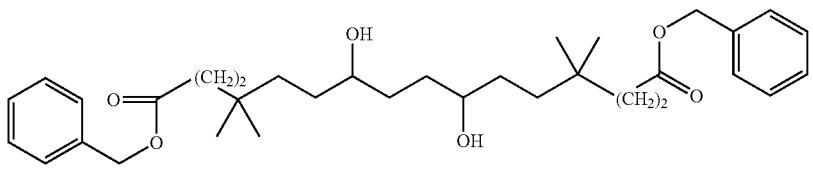

7,10-Dihydroxy-4,4,13,13-tetramethyl-hexadecanedioic acid dibenzyl ester

Compound 40

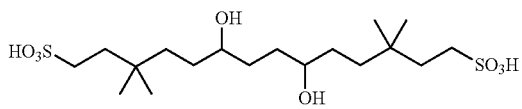

6,9-Dihydroxy-3,3,12,12-tetramethyl-tetradecane-1,14-disulfonic acid

Compound 41

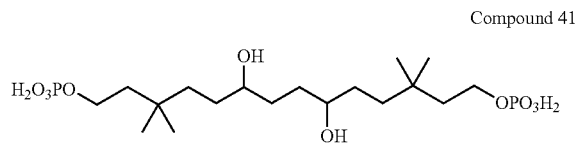

Phosphoric acid mono-(6,9-dihydroxy-3,3,12,12-tetramethyl-1 4-phosphonooxy-tetradecyl) ester Compound 42

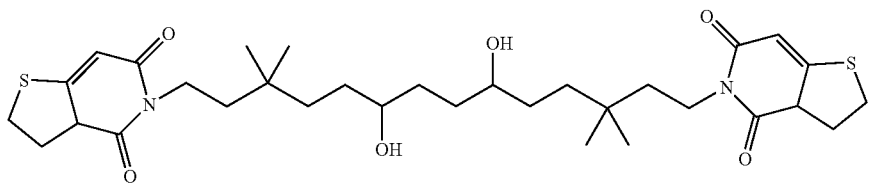

1,14-bis-(3,3a-Dihydro-2H-thieno[3,2,c]pyridine-4,6-dione)-3,3,12,12-tetramethyl-tetradecane-6,9-

Compound 43

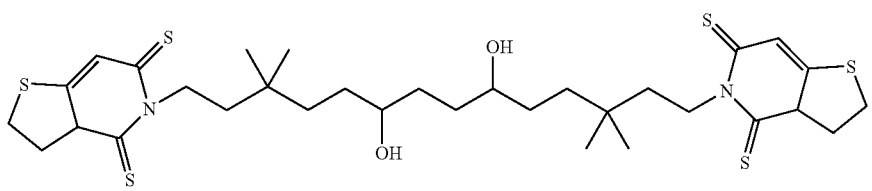

1,14-bis-(3,3a-Dihydro-2H-thieno[3,2,c]pyridine-4,6-dithioxo)-3,3,12,12-tetramethyl-tetradecane-6,9-diol Compound 44

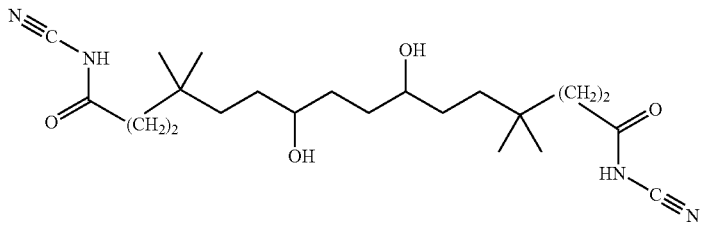

1,14-bis-(3,3a-Dihydro-2H-thieno[3,2,c]pyridine-4,6-dithioxo)-
3,3,12,12-tetramethyl-tetradecane-6,9-diol Compound 45

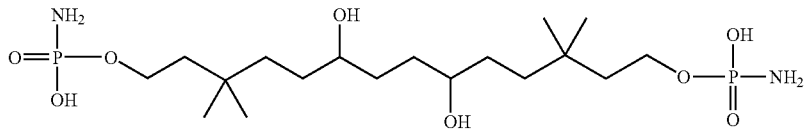

Phosphoramidic acid mono-[14-amino-hydroxy-phosphoryloxy)-
6,9-dihydroxy-3,3,12,12-tetramethyl-tetradecyl]ester Compound 46

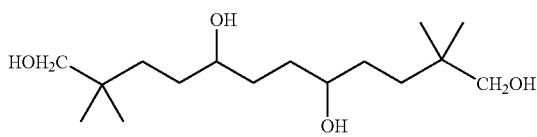

2,2,11,11-Tetramethyl-dodecane-1,5,8,12-tetraol

Compound 47

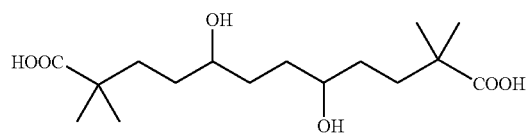

5,8-Dihydroxy-2,2,11,11-tetramethyl-dodecanedioic acid

Compound 48

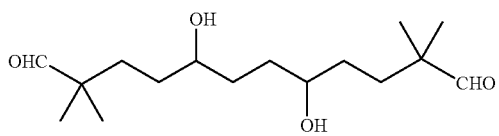

5,8-Dihydroxy-2,2,11,11-tetramethyl-dodecanedial

Compound 49

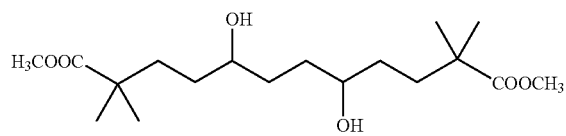

5,8-Dihydroxy-2,2,11,11-tetramethyl-dodecanedioic acid dimethyl
ester

Compound 50

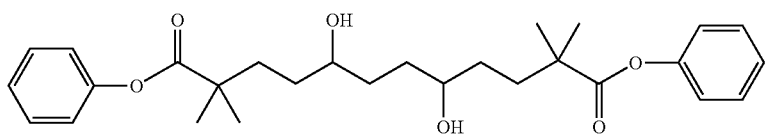

5,8-Dihydroxy-2,2,11,11-tetramethyl-dodecanedioic acid diphenyl
ester

Compound 51

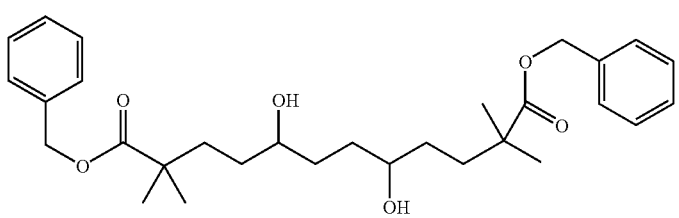

5,8-Dihydroxy-2,2,11,11-tetramethyl-dodecanedioic acid dibenzyl
ester

Compound 52

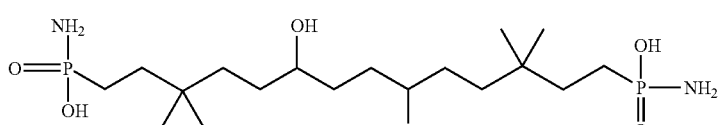

Phosphoramic acid mono-[14-(amino-hydroxy-phosphoryloxy)-
6,9-dihydroxy-3,3,12,12-tetramethyl-tetradecyl] ester -continued Compound 53

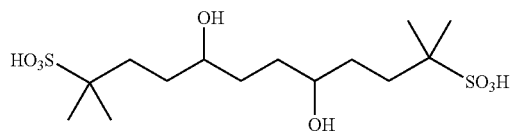

5,8-Dihydroxy-2,11-dimethyl-dodecane-2,11-disulfonic acid

Compound 54

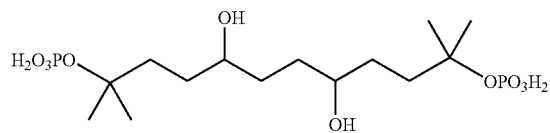

Phosphoric acid
mono-(4,7-dihydroxy-1,1,10-trimethyl-10-phosphonooxy-
undecyl)ester Compound 55

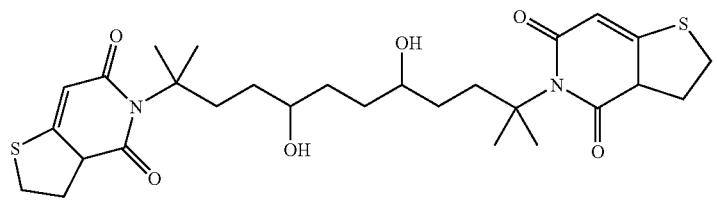

2,11-bix-(N-3,3a-dihydro-2H-thieno[3,2,c]pyridine-4,6-dione))-
5,8-dihydroxy-1,12-dimethyl-dodecane Compound 56

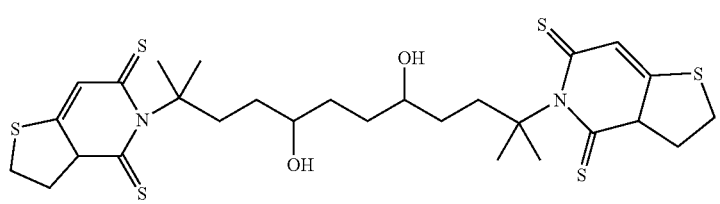

2,11-bis-(N-3,3a-dihydro-2H-thieno[3,2,c]pyridine-4,6-
dithioxo))-5,8-dihydroxy-1,12-dimethyl-dodecane Compound 57

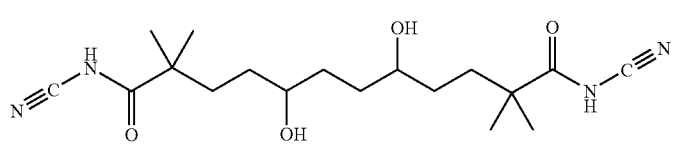

1,12-bis(N-Cyanoamido)-5,8-dihydroxy-2,2,11,11-tetramethyl-dodecane

Compound 58

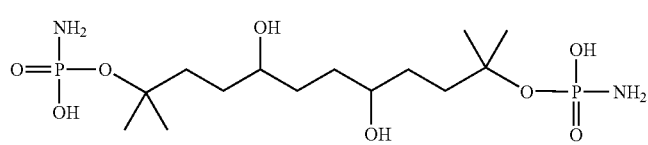

Phosphoramidic acid mono-[10-(amino-hydroxy phosphoryloxy)-
4,7-dihydroxy-1,1,10-trimethyl-undecyl]ester Compound 59

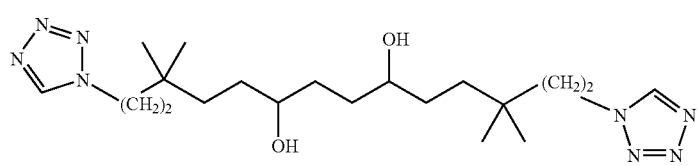

3,3,12,12-Tetramethyl-1,14-bis-tetrazol-1-yl tetradecane-6,9-diol

Compound 60

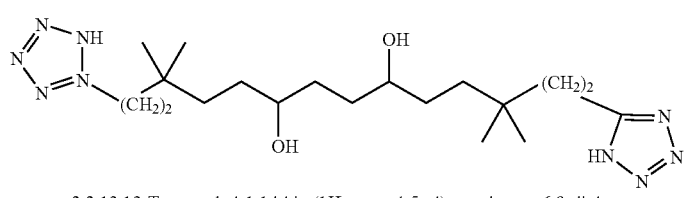

3,3,12,12-Tetramethyl-1,14-bis-(1H-tetrazol-5-yl) tetradecane-6,9-diol

Compound 61
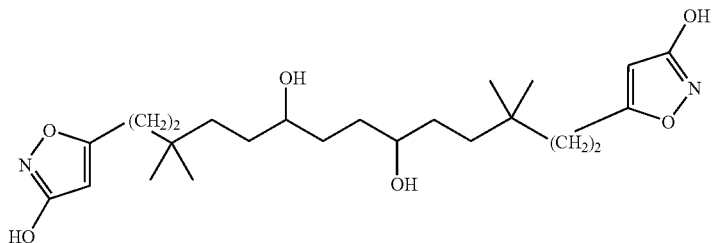
1,14-Bis-(3-hydroxy-isoxazol-5-yl)-3,3,12,12-tetramethyl-tetradecane-6,9-diol
Compound 62
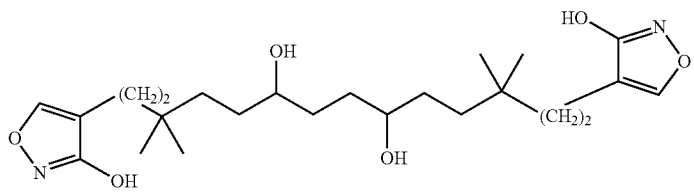
1,14-Bis-(3-hydroxy-isoxazol-4-yl)-3,3,12,12-tetramethyl-tetradecane-6,9-diol
Compound 63
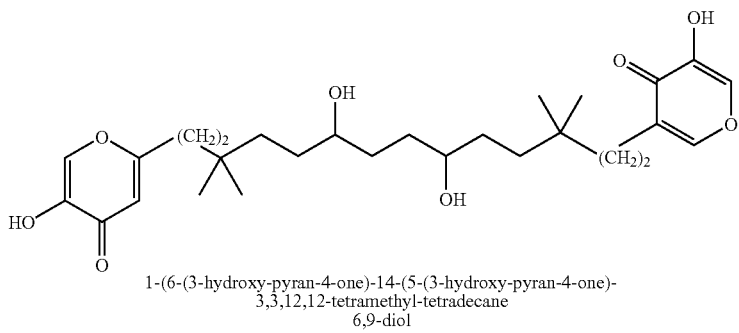
1-(6-(3-hydroxy-pyran-4-one)-14-(5-(3-hydroxy-pyran-4-one)-3,3,12,12-tetramethyl-tetradecane 6,9-diol
Compound 64
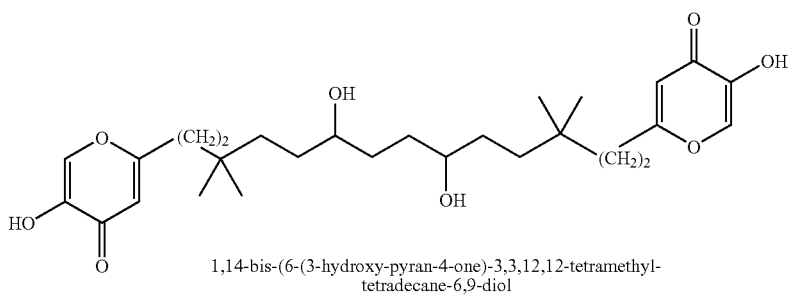
1,14-bis-(6-(3-hydroxy-pyran-4-one)-3,3,12,12-tetramethyl-tetradecane-6,9-diol
Compound 65
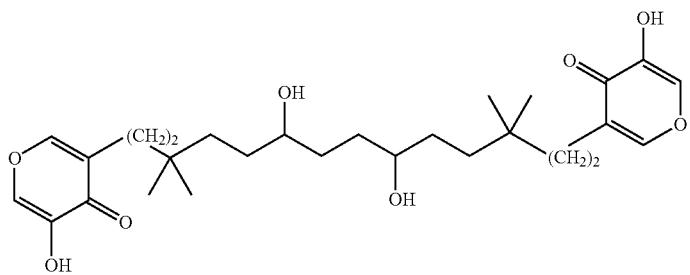
1,14-bis-(5-(3-hydroxy-pyran-4-one)-3,3,12,12-tetramethyl-tetradecane-6,9-diol -continued

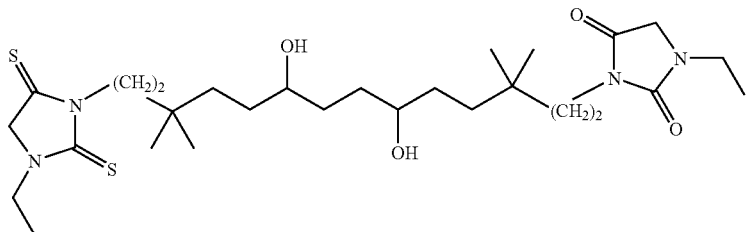

1-Ethyl-3-[14-(3-ethyl-2,5-dithioxo-imidazoli-din-1 yl)-6,9-dihydroxy-3,3,12,12-tetramethyl-tetradecyl] imidazolidine-2,4-dione Compound 66

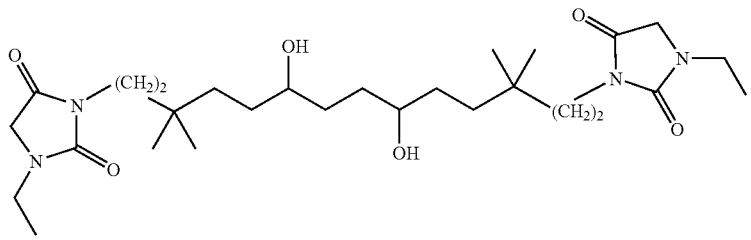

1,14-Bis-(1-Ethyl-imidazolin-3-yl-2,4-dione)-3,3,12,12-tetramethyl tetradecane-6,9-diol Compound 67

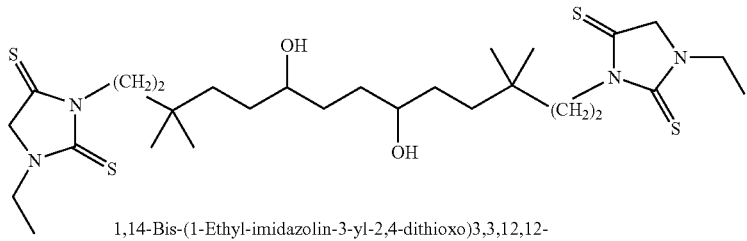

1,14-Bis-(1-Ethyl-imidazolin-3-yl-2,4-dithioxo)3,3,12,12-tetramethyl-tetradecane-6,9-diol Compound 68

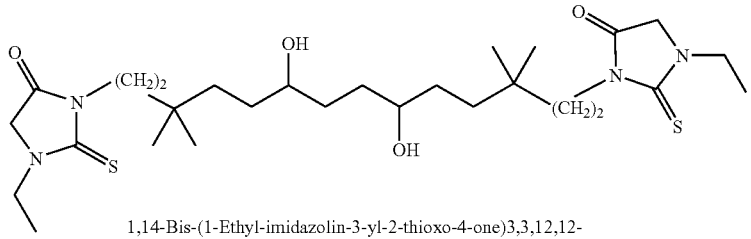

1,14-Bis-(1-Ethyl-imidazolin-3-yl-2-thioxo-4-one)3,3,12,12-tetramethyl-tetradecane-6,9-diol Compound 69

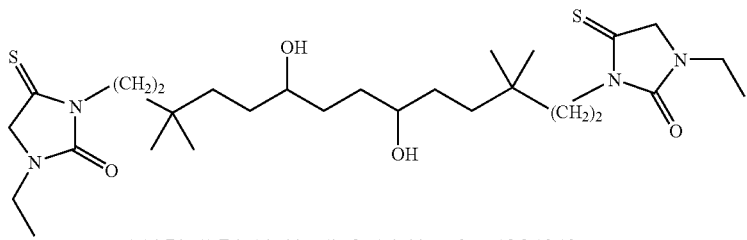

1,14-Bis-(1-Ethyl-imidazolin-3-yl-4-thioxo-2-one)3,3,12,12-tetramethyl-tetradecane-6,9-diol Compound 70

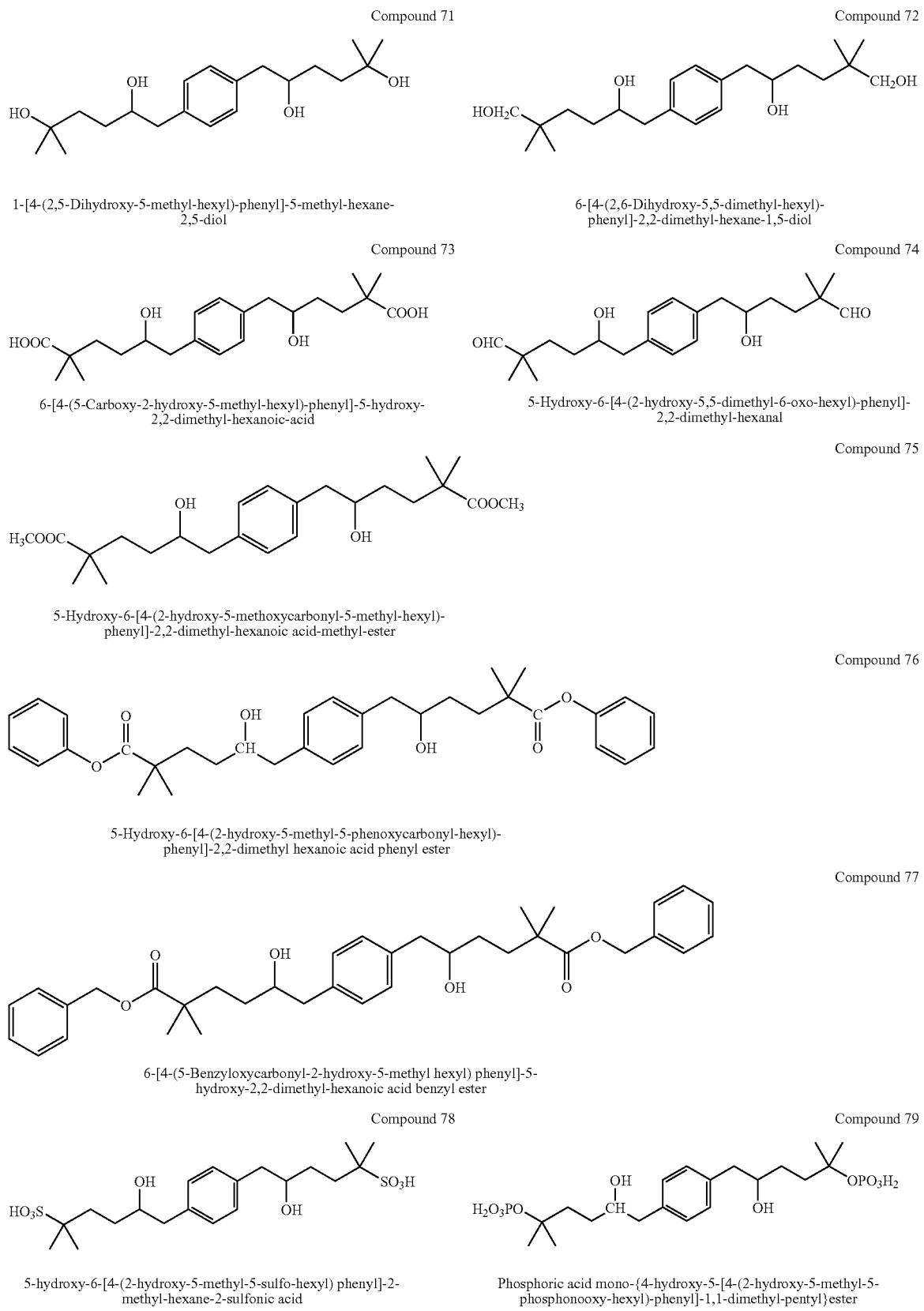

-continued

Compound 80

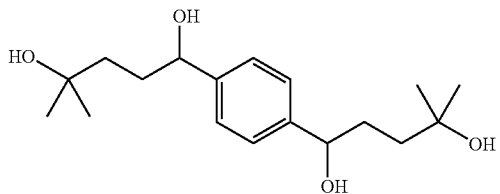

1-[4-(1,4-Dihydroxy-4-methyl-pentyl)-phenyl]-4- methyl-pentane-1,4-diol

Compound 81

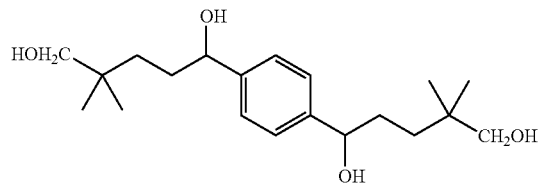

1-[4-(1,5 Dihydroxy-4,4-dimethyl-pentyl)-phenyl] 4,4-dimethyl-pentane-1,5-diol

Compound 82

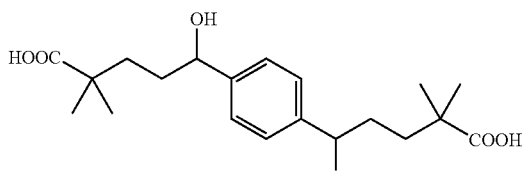

5-[4-(4-Carboxy-1-hydroxy-4-methyl-pentyl)-phenyl]-5-hydroxy-2,2-dimethyl-pentanoic acid Compound 83

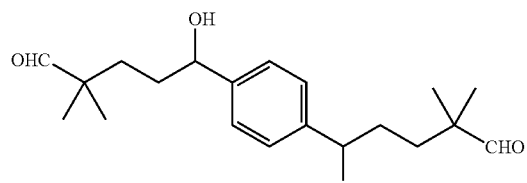

5-hydroxy-5-[4-(1-hydroxy-4,4-dimethyl-5-oxo pentyl)-phenyl]-2,2-dimethyl-pentanal Compound 84

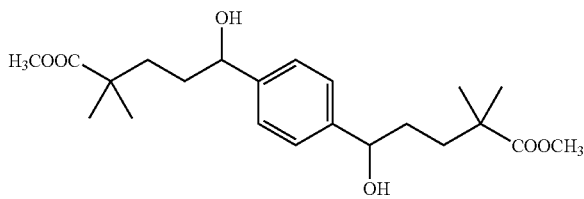

5-hydroxy-5-[4-(1-hydroxy-4-methoxycarbonyl-4-methyl-pentyl)-phenyl]-2,2-dimethyl-pentanoic acid methyl ester Compound 85

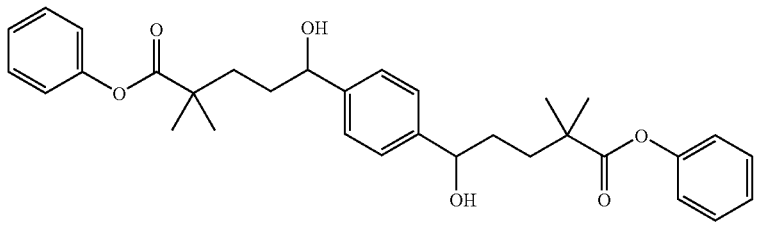

5-hydroxy-5-[4-(1-hydroxy-4-methyl-4-phenoxycarbonyl-pentyl)-phenyl]-2,2-dimethyl-pentanoic acid phenyl ester Compound 86

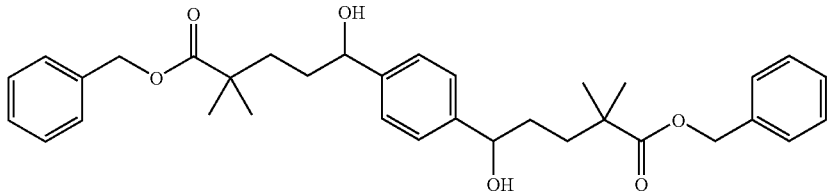

5-[4-(4-Benzyloxycarbonyl-1-hydroxy-4-methyl pentyl)-phenyl]-5-hydroxy-2,2-dimethyl-pentanoic acid benzyl ester -continued Compound 87

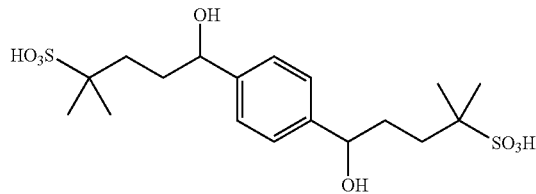

5-Hydroxy-5-[4-(1-hydroxy-4-methyl-4-sulfo-pentyl)-phenyl]-2-methyl-pentane-2-sulfonic acid Compound 88

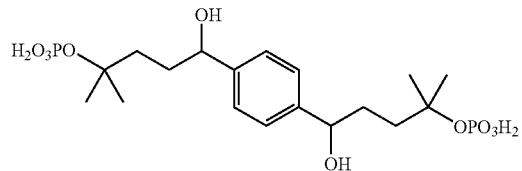

Phosphoric acid mono-{4-hydroxy-4-[4-(1-hydroxy 4-methyl-4-phosphonooxy-pentyl)-phenyl]-1,1-dimethyl-butyl}ester Compound 89

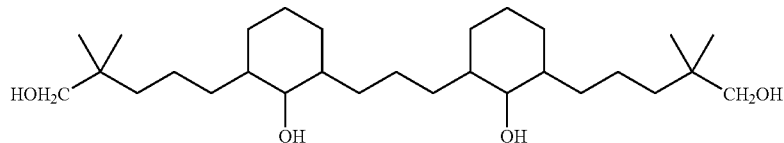

5-(2-hydroxy-3-{3-[2-hydroxy-3 (5-hydroxy-4,4-dimethyl-pentyl)-cyclohexyl]-propyl}-cyclohexyl)-2,2-dimethyl-pentanol Compound 90

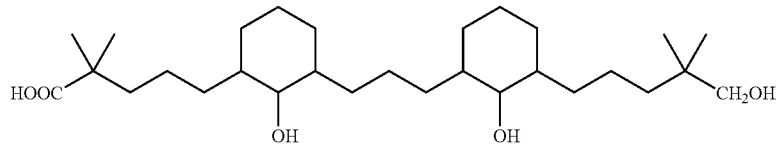

5-(2-Hydroxy-3-{3-[2-hydroxy-3-(5-hydroxy-4,4-dimethyl-pentyl)-cyclohexyl]-propyl}-cyclohexyl)-2,2-dimethyl-pentanoic acid Compound 91

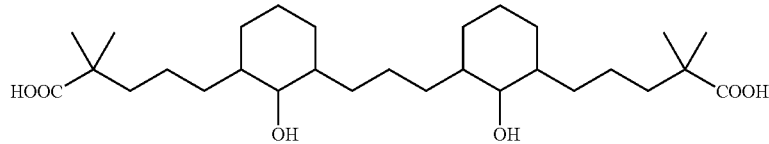

5-(3-{3-[3-(4-Carboxy-4-methyl-pentyl)-2-hydroxy-cyclohexyl]-propyl}-2-hydroxy-cyclohexyl)-2,2-dimethyl-pentanoic acid Compound 92

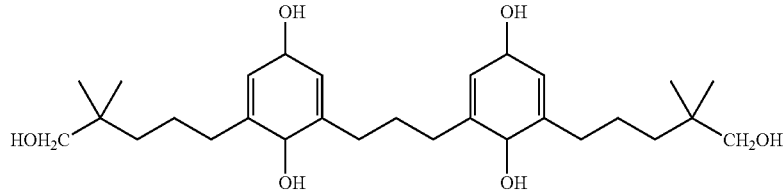

5-(5-3-[3,6-Dihydroxy-5-(5-hydroxy-4,4-dimethyl-pentyl)-cyclohexa-1,4-dienyl]-propyl}-3,6,-dihydroxy-cyclohexa-1,4-dienyl)-2,2-dimethyl-pentanol Compound 93

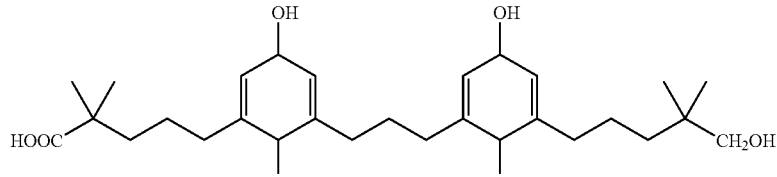

5-(5-{3-[3,6-Dihydroxy-5-(5-hydroxy-4,4-dimethyl-pentyl)-cyclohexa-1,4-dienyl]-propyl}-3,6-dihydroxy-cyclohexa-1,4-dienyl)-2,2-dimethyl-pentanoic acid -continued

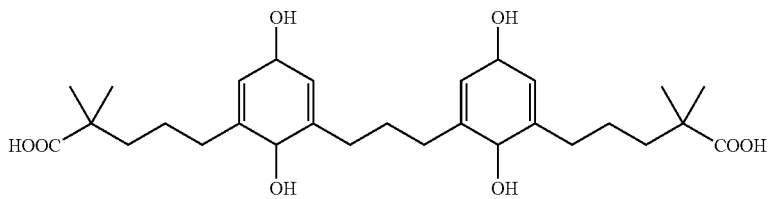

5-(5-{3-[5-(4-Carboxy-4-methyl-pentyl)-3,6-dihydroxy-cyclohexa-1,4-dienyl]-propyl}-3,6-hydroxy-cyclohexa-1,4-dienyl)-2,2-dimethyl-pentanoic acid Compound 94

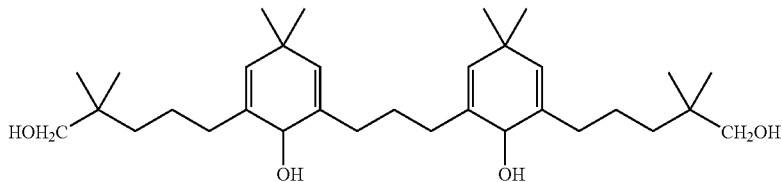

5-(6-Hydroxy-5-{3-[6-hydroxy-5-(5-hydroxy-4,4-dimethyl-pentyl)-3,3-dimethyl-cyclohexa-1,4-dienyl]-propyl}-3,3-dimethyl-cyclohexa-1,4-dienyl)-2,2-dimethyl-pentanol Compound 95

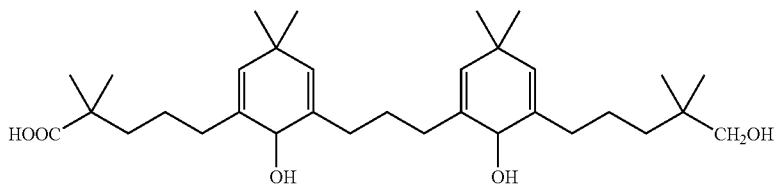

5-(6-Hydroxy-5-{3-[6-hydroxy-5-(5-hydroxy-4,4-dimethyl-pentyl)-3,3-dimethyl-cyclohexa-1,4-dienyl]-propyl}-3,3-dimethyl-cyclohexa-1,4-dienyl)-2,2-dimethyl-pentanoic acid Compound 96

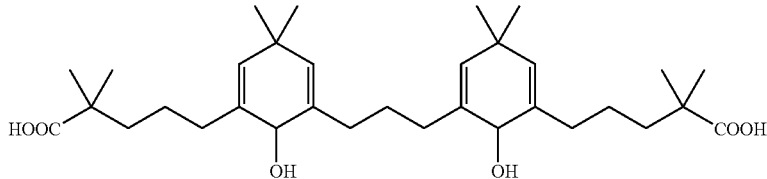

5-(5-{3-[5-(4-Carboxy-4-methyl-pentyl)-6-hydroxy-3,3-dimethyl-cyclohexa-1,4-dienyl]-propyl}-6-hydroxy-3,3-dimethyl-cyclohexa-1,4-dienyl)-2,2-dimethyl-pentanoic acid Compound 97

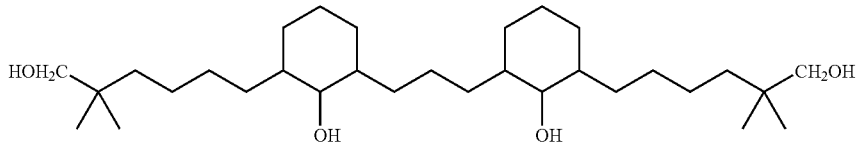

6-(2-Hydroxy-3-{3-[2-hydroxy-3-(6-hydroxy-5,5-dimethyl-hexyl)-cyclohexyl]-propyl}-cyclohexyl)-2,2-dimethyl-hexanol Compound 98

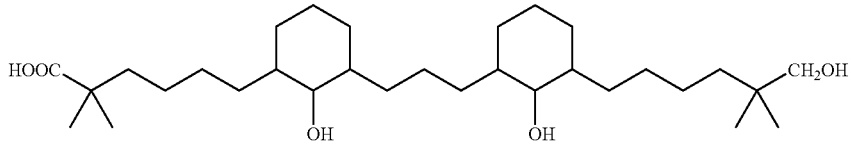

6-(2-Hydroxy-3-{3-[2-hydroxy-3-(6-hydroxy-5,5-dimethyl-hexyl)-cyclohexyl]-propyl}-cyclohexyl)-2,2-dimethyl-hexanoic acid Compound 99

-continued

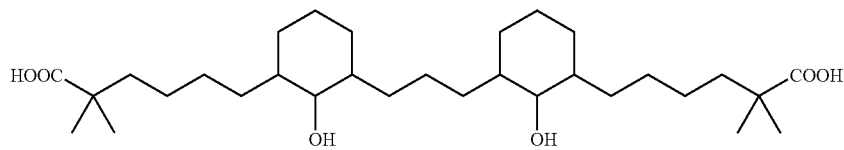

6-(3-{3-[3-(5-Carboxy-5-methyl-hexyl)-2-hydroxy-cyclohexyl]-propyl}-2-hydroxy-cyclohexyl-2,2-dimethyl-hexanoic acid Compound 100

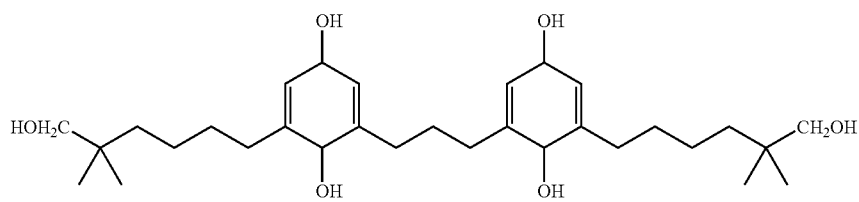

6-(5-{3-[3,6-Dihydroxy-5-(6-hydroxy-5,5-dimethyl-hexyl)-cyclohexa-1,4-dienyl]-propyl}-3,6-dihydroxy-cyclohexa-1,4-dienyl)-2,2-dimethyl-hexanol Compound 101

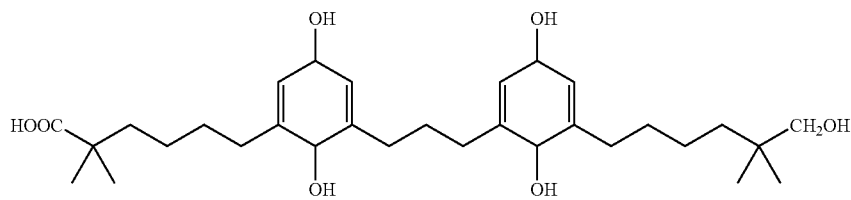

6-(5-{3-[3,6-Dihydroxy-5-(6-hydroxy-5,5-dimethyl-hexyl)-cyclohexa-1,4-dienyl]-propyl}-3,6-dihydroxy-cyclohexa-1,4-dienyl)-2,2-dimethyl-hexanoic acid Compound 102

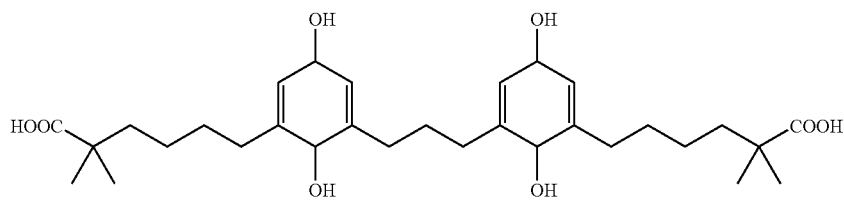

6-(5-{3-[5-(5-Carboxy-5-methyl-hexyl)-3,6-dihydroxy-cyclohexa-1,4-dienyl]-propyl}-3,6-dihydroxy-cyclohexa-1,4-dienyl)-2,2-dimethyl-hexanoic acid Compound 103

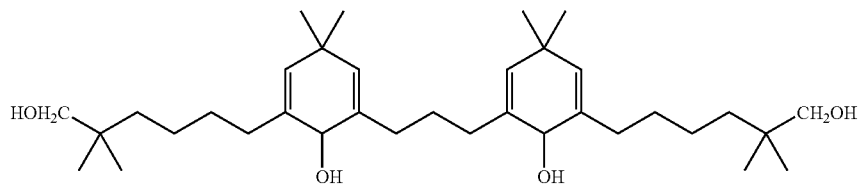

6-(6-Hydroxy-5-{3-[6-hydroxy-5-(6-hydroxy-5,5-dimethyl-hexyl)-3,3-dimethyl-cyclohexa-1,4-dienyl]-propyl}-3,3-dimethyl-cyclohexa-1,4-dienyl)-2,2-dimethyl-hexanol Compound 104

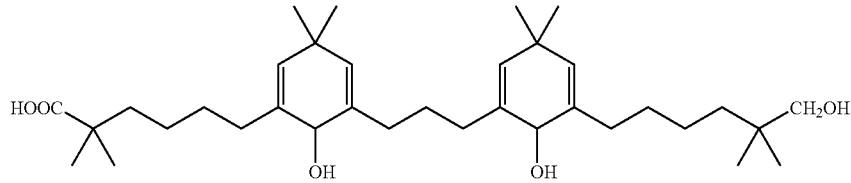

6-(6-Hydroxy-{3-[6-hydroxy-5-(6-hydroxy-5,5-dimethyl-hexyl)-3,3-dimethyl-cyclohexa-1,4-dienyl]propyl}-3,3-dimethyl-cyclohexa-1,4-dienyl)-2,2-dimethyl-hexanoic acid Compound 105

-continued

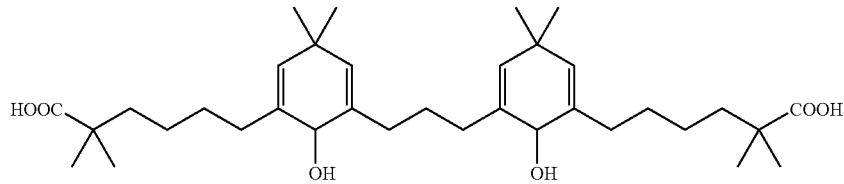

6-(5-{3-[5-(5-Carboxy-5-methyl-hexyl)-6-hydroxy-3,3-dimethyl-
cyclohexa-1,4-dienyl]-propyl}-6-hydroxy-3,3-dimethyl-cyclohexa-
1,4-dienyl)-2,2-dimethyl-hexanoic acid Compound 106

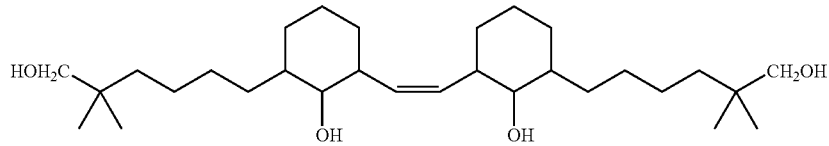

6-(2-Hydroxy-3-{2-[2-hydroxy-3-(6-hydroxy-5,5-dimethyl-hexyl)-
cyclohexyl]-vinyl}-cyclohexyl)-2,2-dimethyl-hexanol Compound 107

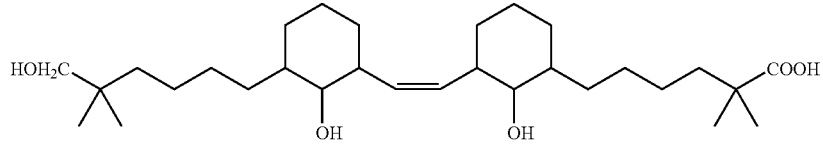

6-(2-Hydroxy-3-{2-[2-hydroxy-3-(6-hydroxy-5,5-dimethyl-hexyl)-
cyclohexyl]-vinyl}-cyclohexyl)-2,2-dimethyl-hexanoic acid Compound 108

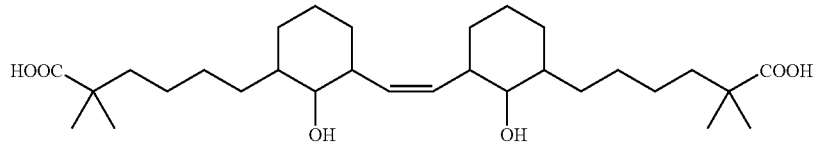

6-(3-{2-[3-(5-Carboxy-5-methyl-hexyl)-2-hydroxy-cyclohexyl]-
vinyl}-2-hydroxy-cyclohexyl)-2,2-dimethyl-hexanoic acid Compound 109

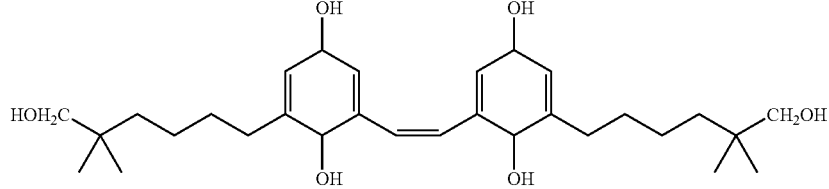

6-(5-{2-[3,6-Dihydroxy-5-(6-hydroxy-5,5-dimethyl-hexyl)-
cyclohexa-1,4-dienyl]-vinyl}-3,6,-dihydroxy-cyclohexa-1,4-
dienyl)-2,2-dimethyl-hexanol Compound 110

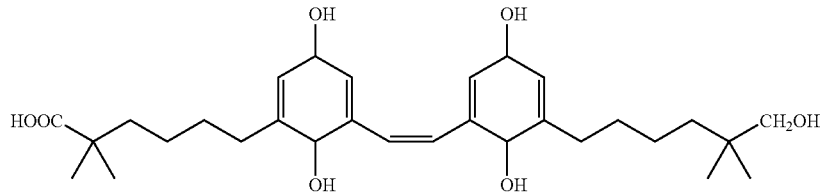

6-(5-{2-[3,6-Dihydroxy-5-(6-hydroxy-5,5-dimethyl-hexyl)-
cyclohexa-1,4-dienyl]-vinyl}-3,6,-dihydroxy-cyclohexa-1,4-
dienyl)-2,2-dimethyl-hexanoic acid Compound 111

-continued

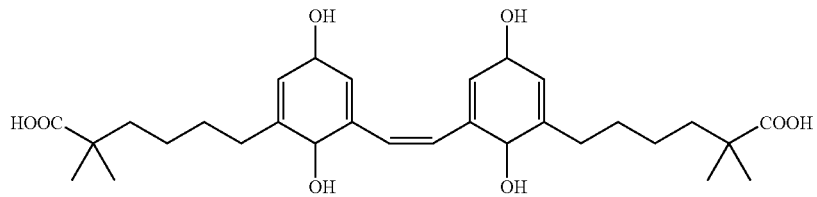

6-(5-{2-[5-(5-Carboxy-5-methyl-hexyl)-3,6-dihydroxy-cyclohexa-1,4-dienyl]-vinyl}-3,6-dihydroxy-cyclohexa-1,4-dienyl)-2,2-dimethyl-hexanoic acid Compound 112

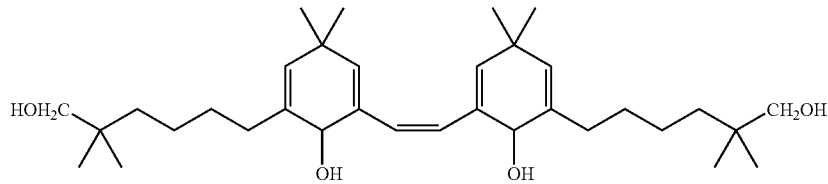

6-(6-Hydroxy-5-{2-[6-hydroxy-5-(6-hydroxy-5,5-dimethyl-hexyl)-3,3-dimethyl-cyclohexa-1,4-dienyl]-vinyl}-3,3-dimethyl-cyclohexa-1,4-dienyl)-2,2-dimethyl-hexanol Compound 113

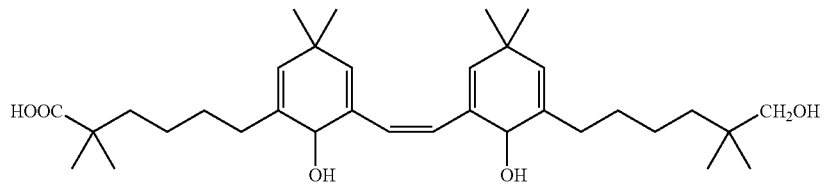

6-(6-Hydroxy-5-{2-[6-hydroxy-5-(6-hydroxy-5,5-dimethyl-hexyl)-3,3-dimethyl-cyclohexa-1,4-dienyl-]vinyl}-3,3-dimethyl-cyclohexa-1,4-dienyl)-2,2-dimethyl-hexanoic acid Compound 114

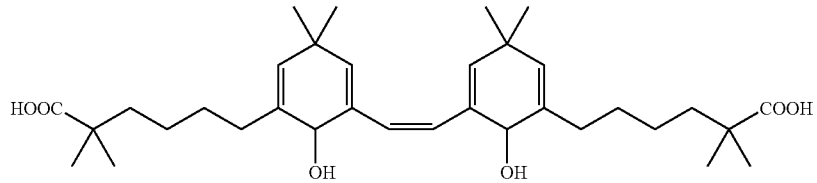

6-(5-{2-[5-(5-Carboxy-5-methyl-hexyl)-6-hydroxy-3,3-dimethyl-cyclohexa-1,4-dienyl]-vinyl}-6-hydroxy-3,3-dimethyl-cyclohexa-1,4-dienyl)-2,2-dimethyl-hexanoic acid Compound 115

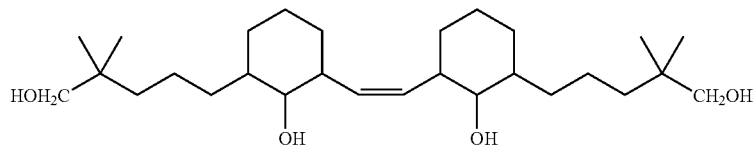

5-(2-Hydroxy-3-{2-[2-hydroxy-3-(5-hydroxy-4,4-dimethyl-penthyl)-cyclohexyl]-vinyl}-cyclohexyl)-2,2-dimethyl-pentanol Compound 116

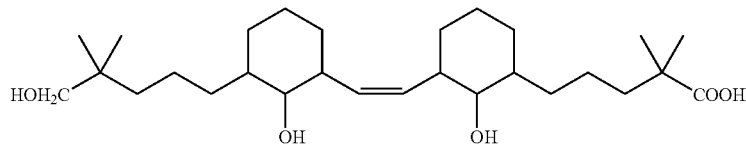

5-(2-Hydroxy-3-{2-[2-hydroxy-3-(5-hydroxy-4,4-dimethyl-penthyl)-cyclohexyl]-vinyl}-cyclohexyl)-2,2-dimethyl-pentanoic acid Compound 117

-continued

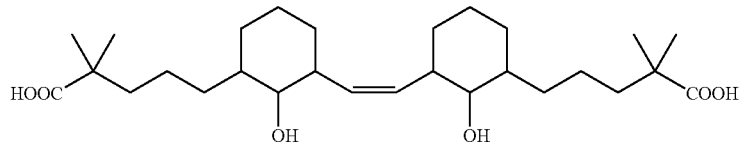

5-(3-{2-[3-(4-Carboxy-4-methyl-pentyl)-2-hydroxy-cyclohexyl]-
vinyl}-2-hydroxy-cyclohexyl)-2,2-dimethyl-pentanoic acid Compound 118

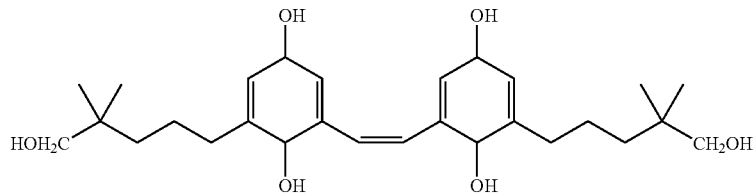

5-(5-{2-[3,6-Dihydroxy-5-(5-hydroxy-4,4-dimethyl-pentyl)-
cyclohexa-1,4-dienyl]-vinyl}-3,6,-dihydroxy-cyclohexa-1,4-
dienyl)-2,2-dimethyl-pentanol Compound 119

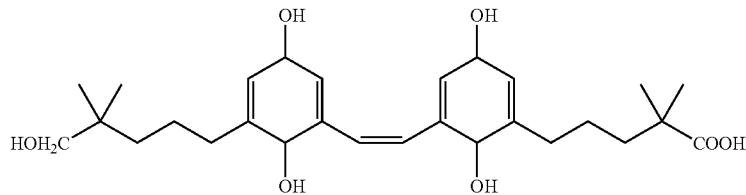

5-(5-{2-[3,6-Dihydroxy-5-(5-hydroxy-4,4-dimethyl-pentyl)-
cyclohexa-1,4-dienyl]-vinyl}-3,6-dihydroxy-cyclohexa-1,4-
dienyl)-2,2-dimethyl-pentanoic acid Compound 120

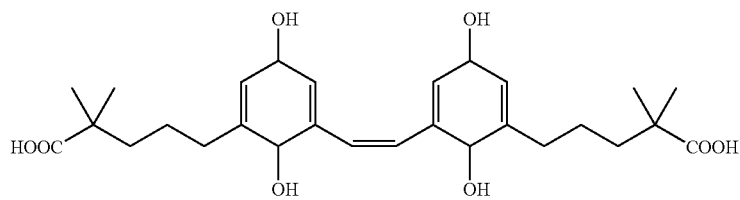

5-(5-{2-[5-(4-Carboxy-4-methyl-pentyl)-3,6-dihydroxy-cyclohexa-
1,4-dienyl]-vinyl}-3,6-dihydroxy-cyclohexa-1,4-dienyl)-2,2-
dimethyl-pentanoic acid Compound 121

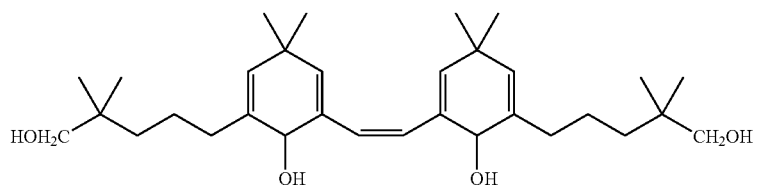

5-(6-Hydroxy-5-{2-[6-hydroxy-5-(5-hydroxy-4,4-dimethyl-
pentyl)-3,3-dimethyl-cyclohexa-1,4-dienyl]-vinyl}-3,3-dimethyl-
cyclohexa-1,4-dienyl)-2,2-dimethyl-pentanol Compound 122

-continued

Compound 123

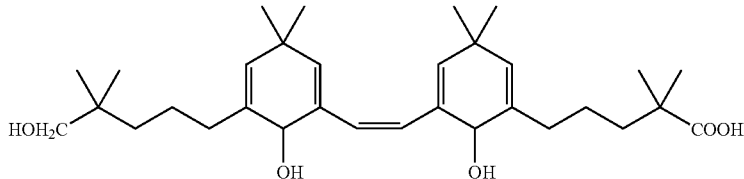

5-(6-Hydroxy-5-{2-[6-hydroxy-5-(5-hydroxy-4,4-dimethyl-
pentyl)-3,3-dimethyl-cyclohexa-1,4-dienyl]-vinyl}-3,3-dimethyl-
cyclohexa-1,4-dienyl)-2,2-dimethyl-pentanoic acid Compound 124

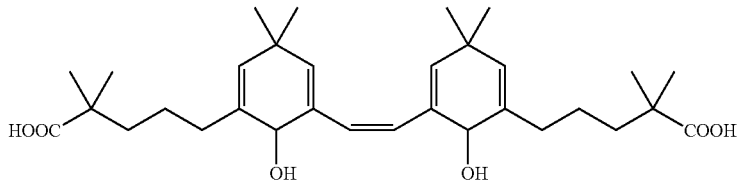

5-(5-{2-[5-(4-Carboxy-4-methyl-pentyl)-6-hydroxy-3,3-dimethyl-
cyclohexa-1,4-dienyl]-vinyl}-6-hydroxy-3,3-dimethyl-cyclohexa-
1,4-dienyl)-2,2-dimethyl-pentanoic acid Compound 125

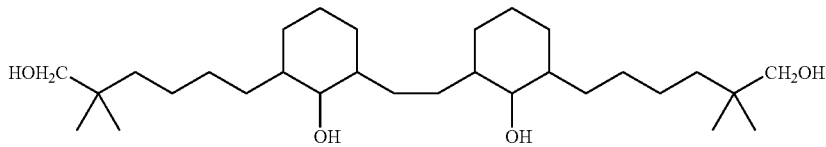

6-(2-Hydroxy-3-{3-[2-hydroxy-3-(6-hydroxy-5,5-dimethyl-hexyl)-
cyclohexyl]-ethyl}-cyclohexyl)-2,2-dimethyl-hexanol Compound 126

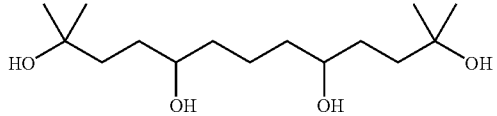

1) 2,12-Dimethyl-tridecane-2,5,9,12-tetraol

Compound 127

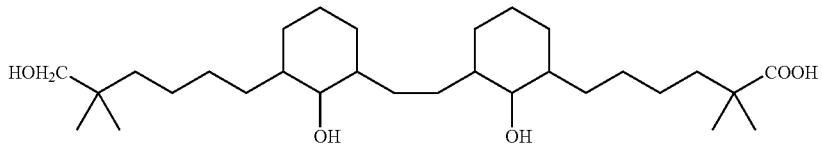

6-(2-Hydroxy-3-{2-[2-hydroxy-3-(6-hydroxy-5,5-dimethyl-hexyl)-
cyclohexyl]-ethyl}-cyclohexyl)-2,2-dimethyl-hexanoic acid Compound 128

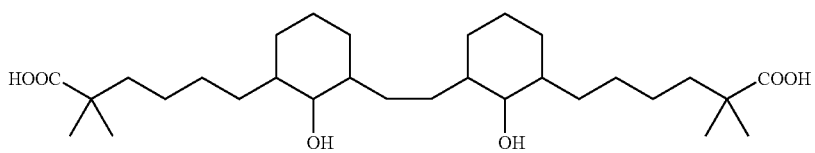

6-(3-{2-[3-(5-Carboxy-5-methyl-hexyl)-2-hydroxy-cyclohexyl]-
ethyl}-2-hydroxy-cyclohexyl)-2,2-dimethyl-hexanoic acid

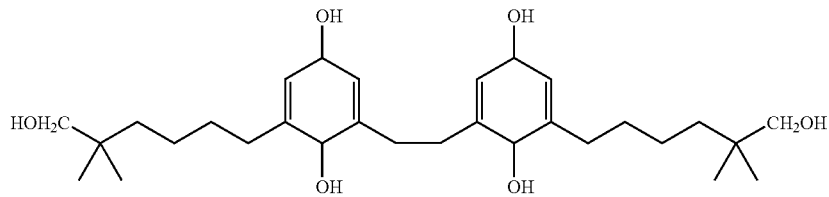

6-(5-{2-[3,6-Dihydroxy-5-(6-hydroxy-5,5-dimethyl-hexyl)-cyclohexa-1,4-dienyl]-ethyl}-3,6-dihydroxy-cyclohexa-1,4-dienyl)-2,2-dimethyl-hexanol Compound 129

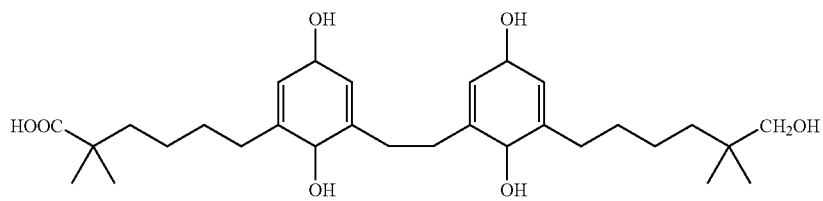

6-(5-{2-[3,6-Dihydroxy-5-(6-hydroxy-5,5-dimethyl-hexyl)-cyclohexa-1,4-dienyl]-ethyl}-3,6,-dihydroxy-cyclohexa-1,4-dienyl)-2,2-dimethyl-hexanoic acid Compound 130

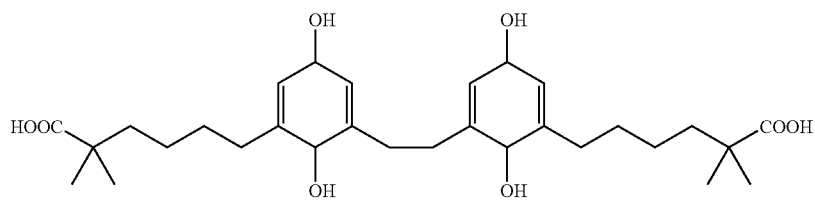

6-(5-{2-[5-(5-Carboxy-5-methyl-hexyl)-3,6-dihydroxy-cyclohexa-1,4-dienyl]-ethyl}-3,6-hydroxy-cyclohexa-1,4-dienyl)-2,2-dimethyl-hexanoic acid Compound 131

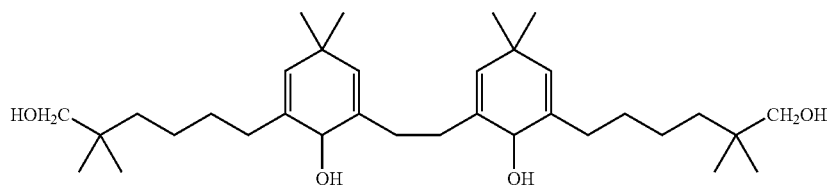

6-(6-Hydroxy-5-{2-[6-hydroxy-5-(6-hydroxy-5,5-dimethyl-hexyl)-3,3-dimethyl-cyclohexa-1,4-dienyl]-ethyl}-3,3-dimethyl-cyclohexa-1,4-dienyl)-2,2-dimethyl-hexanol Compound 132

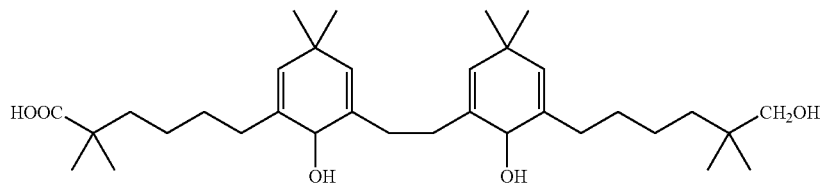

6-(6-Hydroxy-5-{2-[6-hydroxy-5-(6-hydroxy-5,5-dimethyl-hexyl)-3,3-dimethyl-cyclohexa-1,4-dienyl]-ethyl}-3,3-dimethyl-cyclohexa-1,4-dienyl)-2,2-dimethyl-hexanoic acid Compound 133

-continued

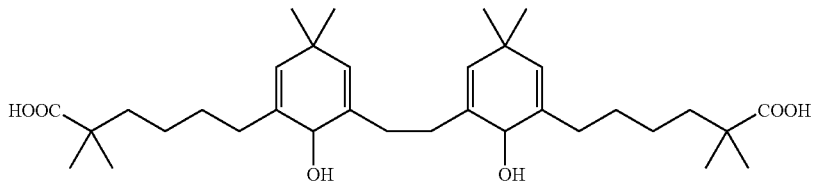

6-(5-{2-[5-(5-Carboxy-5-methyl-hexyl)-6-hydroxy-3,3-dimethyl-
cyclohexa-1,4-dienyl]-ethyl}-6-hydroxy-3,3-dimethyl-cyclohexa-
1,4-dienyl)-2,2-dimethyl-hexanoic acid Compound 134

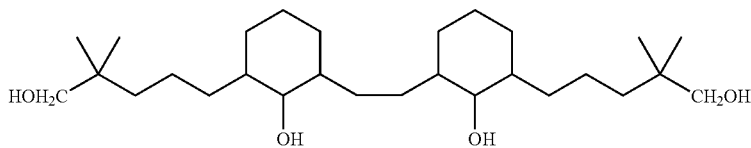

5-(2-Hydroxy-3-{2-[2-hydroxy-3-(5-hydroxy-4,4-dimethyl-
pentyl)-cyclohexyl]-ethyl}-cyclohexyl)-2,2-dimethyl-pentanol Compound 135

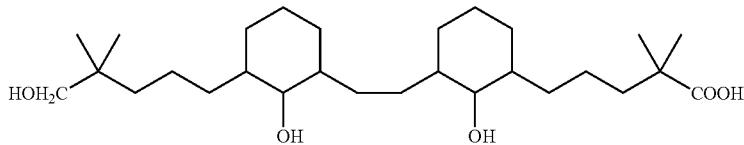

5-(2-Hydroxy-3-{2-[2-hydroxy-3-(5-hydroxy-4,4-dimethyl-
pentyl)-cyclohexyl]-ethyl}-cyclohexyl)-2,2-dimethyl-pentanoic acid Compound 136

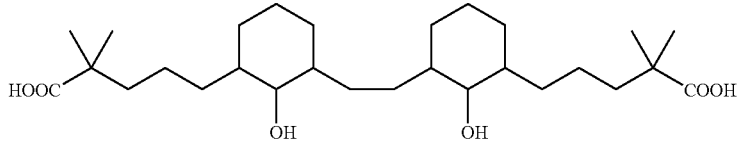

5-(3-{2-[3-(4-Carboxy-4-methyl-pentyl)-2-hydroxy-cyclohexyl]-
ethyl}-2-hydroxy-cyclohexyl)-2,2-dimethyl-pentanoic acid Compound 137

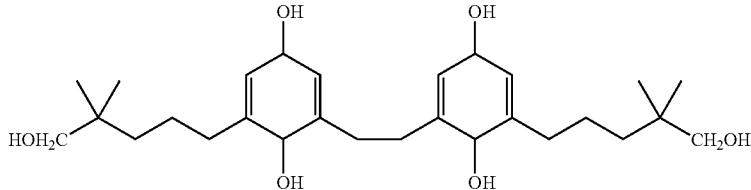

5-(5-{2-[3,6-Dihydroxy-5-(5-hydroxy-4,4-dimethyl-pentyl)-
cyclohexa-1,4-dienyl]-ethyl}-3,6-dihydroxy-cyclohexa-1,4-
dienyl)-2,2-dimethyl-pentanol Compound 138

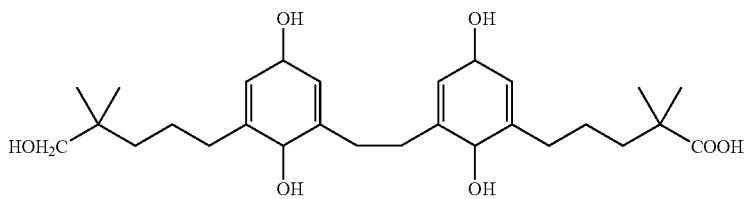

5-(5-{2-[3,6-Dihydroxy-5-(5-hydroxy-4,4-dimethyl-pentyl)-
cyclohexa-1,4-dienyl]-ethyl}-3,6-dihydroxy-cyclohexa-1,4-
dienyl)-2,2-dimethyl-pentanoic acid Compound 139

-continued

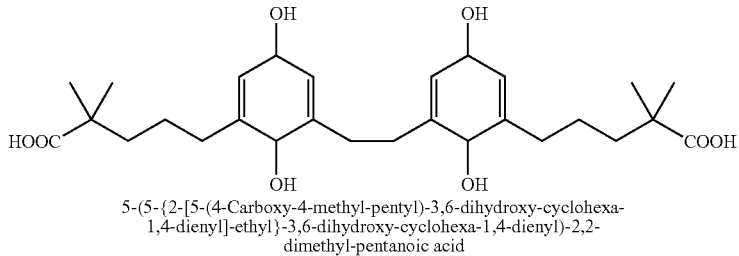

5-(5-{2-[5-(4-Carboxy-4-methyl-pentyl)-3,6-dihydroxy-cyclohexa-1,4-dienyl]-ethyl}-3,6-dihydroxy-cyclohexa-1,4-dienyl)-2,2-dimethyl-pentanoic acid Compound 140

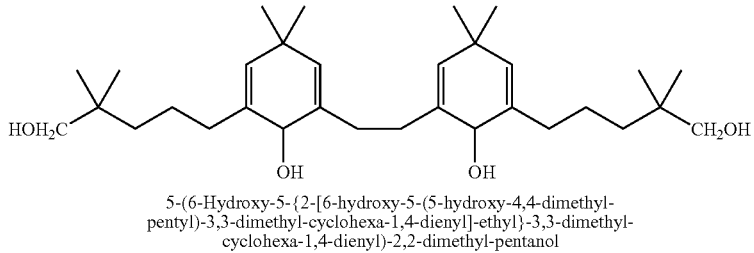

5-(6-Hydroxy-5-{2-[6-hydroxy-5-(5-hydroxy-4,4-dimethyl-pentyl)-3,3-dimethyl-cyclohexa-1,4-dienyl]-ethyl}-3,3-dimethyl-cyclohexa-1,4-dienyl)-2,2-dimethyl-pentanol Compound 141

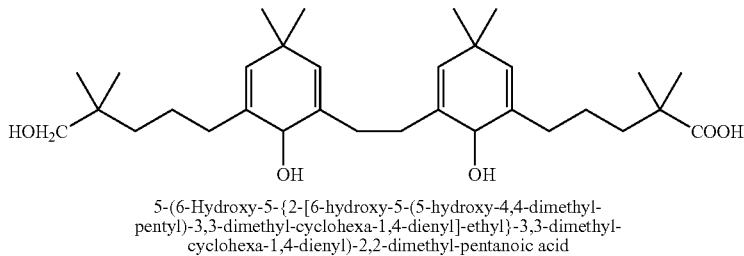

5-(6-Hydroxy-5-{2-[6-hydroxy-5-(5-hydroxy-4,4-dimethyl-pentyl)-3,3-dimethyl-cyclohexa-1,4-dienyl]-ethyl}-3,3-dimethyl-cyclohexa-1,4-dienyl)-2,2-dimethyl-pentanoic acid Compound 142

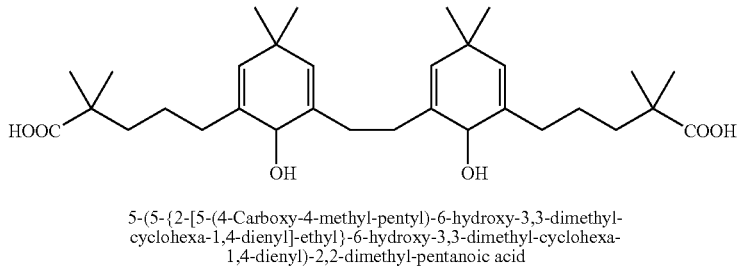

5-(5-{2-[5-(4-Carboxy-4-methyl-pentyl)-6-hydroxy-3,3-dimethyl-cyclohexa-1,4-dienyl]-ethyl}-6-hydroxy-3,3-dimethyl-cyclohexa-1,4-dienyl)-2,2-dimethyl-pentanoic acid Compound 143

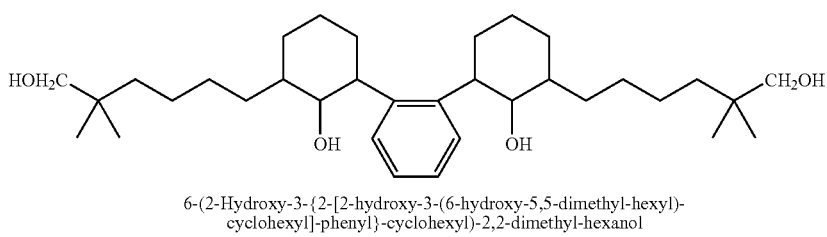

6-(2-Hydroxy-3-{2-[2-hydroxy-3-(6-hydroxy-5,5-dimethyl-hexyl)-cyclohexyl]-phenyl}-cyclohexyl)-2,2-dimethyl-hexanol Compound 144

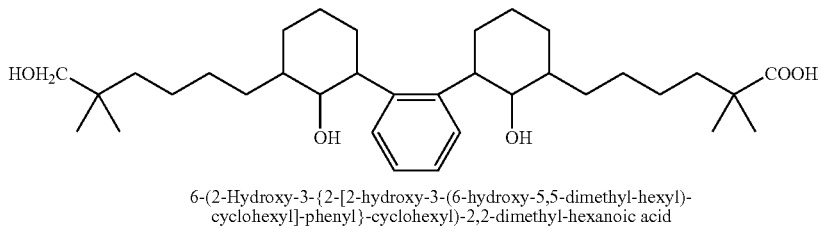

6-(2-Hydroxy-3-{2-[2-hydroxy-3-(6-hydroxy-5,5-dimethyl-hexyl)-cyclohexyl]-phenyl}-cyclohexyl)-2,2-dimethyl-hexanoic acid Compound 145

-continued

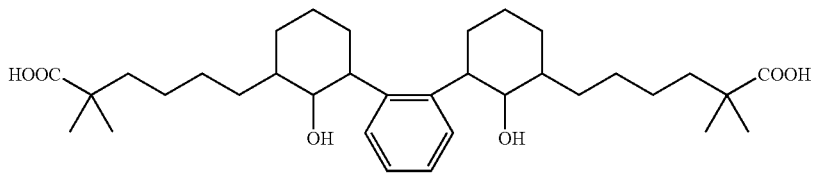

Compound 146

6-(3-{2-[3-(5-Carboxy-5-methyl-hexyl)-2-hydroxy-cyclohexyl]-
phenyl}-2-hydroxy-cyclohexyl)-2,2-dimethyl-hexanoic acid

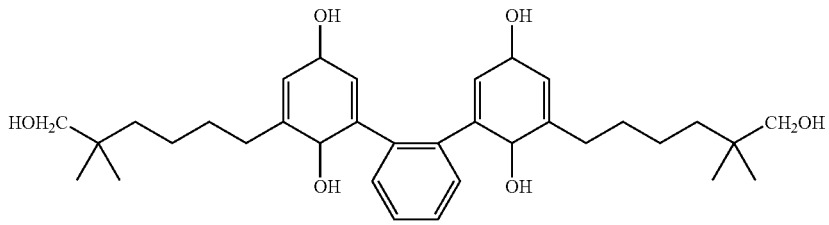

Compound 147

6-(5-{2-[3,6-Dihydroxy-5-(6-hydroxy-5,5-dimethyl-hexyl)-
cyclohexa-1,4-dienyl]-phenyl}-3,6,-dihydroxy-cyclohexa-1,4-
dienyl)-2,2-dimethyl-hexanol

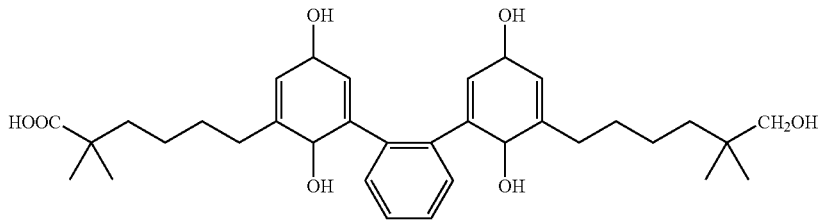

Compound 148

6-(5-{2-[3,6-Dihydroxy-5-(6-hydroxy-5,5-dimethyl-hexyl)-
cyclohexa-1,4-dienyl]-phenyl}-3,6,-dihydroxy-cyclohexa-1,4-
dienyl)-2,2-dimethyl-hexanoic acid

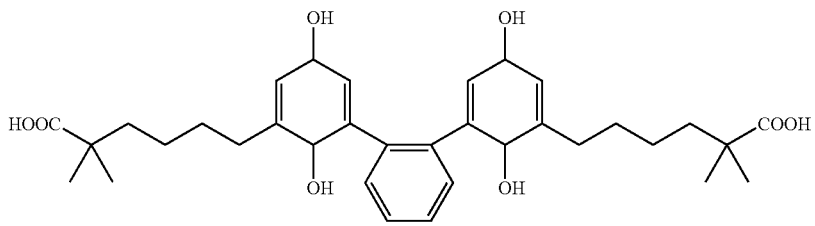

Compound 149

6-(5-{2-[5-(5-Carboxy-5-methyl-hexyl)-3,6-dihydroxy-cyclohexa-
1,4-dienyl]-phenyl}-3,6-dihydroxy-cyclohexa-1,4-dienyl)-2,2-
dimethyl-hexanoic acid

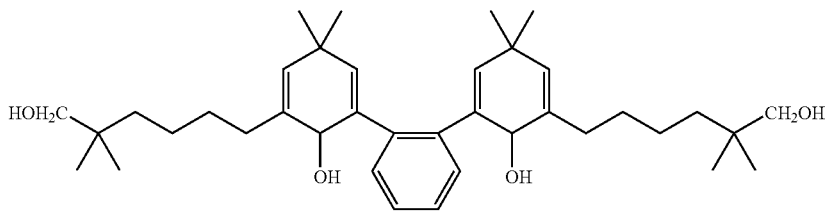

Compound 150

6-(6-Hydroxy-5-{2-[6-hydroxy-5-(6-hydroxy-5,5-dimethyl-hexyl)-
3,3-dimethyl-cyclohexa-1,4-dienyl]-phenyl}-3,3-dimethyl-
cyclohexa-1,4-dienyl)-2,2-dimethyl-hexanol -continued

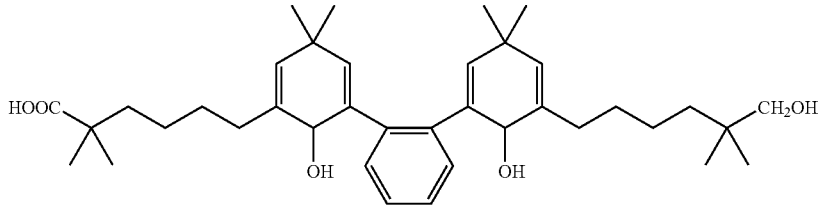

Compound 151

6-(6-Hydroxy-5-{2-[6-hydroxy-5-(6-hydroxy-5,5-dimethyl-hexyl)-
3,3-dimethyl-cyclohexa-1,4-dienyl]-phenyl}-3,3-dimethyl-
cyclohexa-1,4-dienyl)-2,2-dimethyl-hexanoic acid

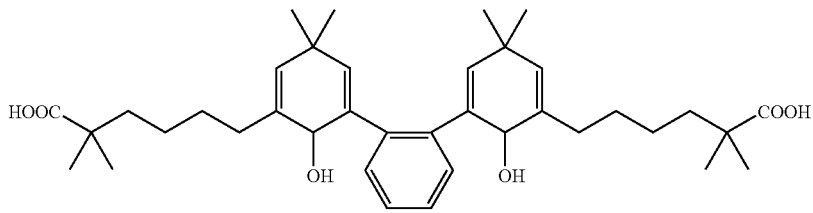

Compound 152

6-(5-{2-[5-(5-Carboxy-5-methyl-hexyl)-6-hydroxy-3,3-dimethyl-
cyclohexa-1,4-dienyl]-phenyl}-6-hydroxy-3,3-dimethyl-
cyclohexa-1,4-dienyl)-2,2-dimethyl-hexanoic acid

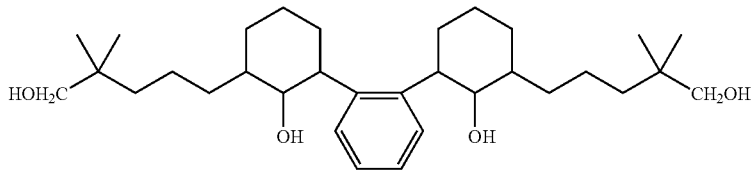

Compound 153

5-(2-Hydroxy-3-{2-[2-hydroxy-3-(5-hydroxy-4,4-dimethyl-
pentyl)-cyclohexyl]-phenyl}-cyclohexyl)-2,2-dimethyl-pentanol

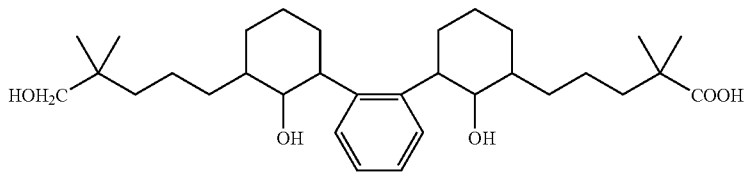

Compound 154

5-(2-Hydroxy-3-{2-[2-hydroxy-3-(5-hydroxy-4,4-dimethyl-
penthyl)-cyclohexyl]-phenyl}-cyclohexyl)-2,2-dimethyl-pentanoic acid

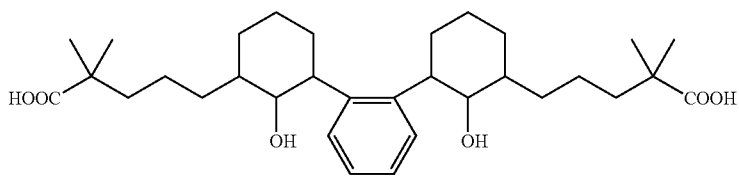

Compound 155

5-(3-{2-[3-(4-Carboxy-4-methyl-pentyl)-2-hydroxy-cyclohexyl]-
phenyl}-2-hydroxy-cyclohexyl)-2,2-dimethyl-pentanoic acid -continued

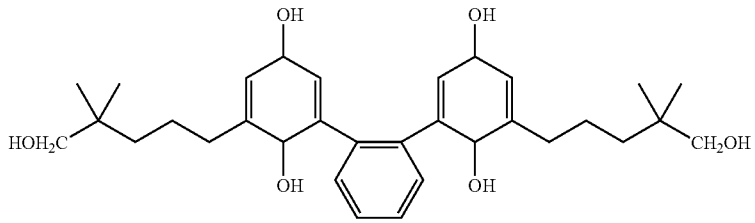

5-(5-{2-[3,6-Dihydroxy-5-(5-hydroxy-4,4-dimethyl-pentyl)-cyclohexa-1,4-dienyl]-phenyl}-3,6,-dihydroxy-cyclohexa-1,4-dienyl)-2,2-dimethyl-pentanol Compound 156

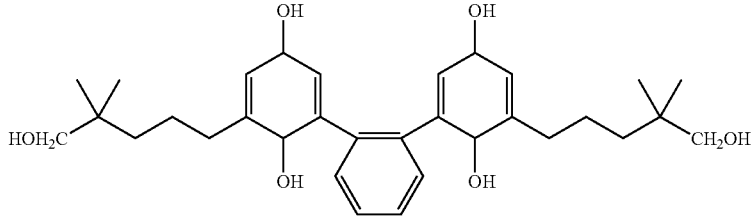

5-(5-{2-[3,6-Dihydroxy-5-(5-hydroxy-4,4-dimethyl-pentyl)-cyclohexa-1,4-dienyl]-phenyl}-3,6-dihydroxy-cyclohexa-1,4-dienyl)-2,2-dimethyl-pentanoic acid Compound 157

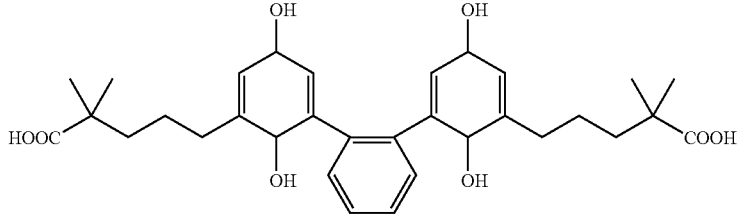

5-(5-{2-[5-(4-Carboxy-4-methyl-pentyl)-3,6-dihydroxy-cyclohexa-1,4-dienyl]-phenyl}-3,6-dihydroxy-cyclohexa-1,4-dienyl)-2,2-dimethyl-pentanoic acid Compound 158

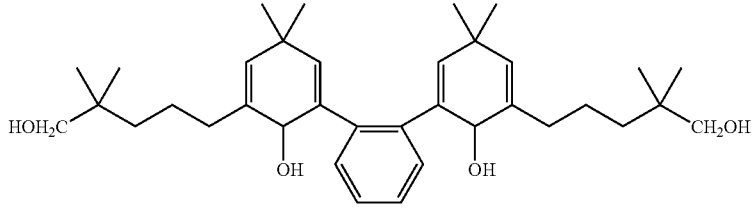

5-(6-Hydroxy-5-{2-[6-hydroxy-5-(5-hydroxy-4,4-dimethyl-pentyl)-3,3-dimethyl-cyclohexa-1,4-dienyl]phenyl}-3,3-dimethyl-cyclohexa-1,4-dienyl)-2,2-dimethyl-pentanol Compound 159

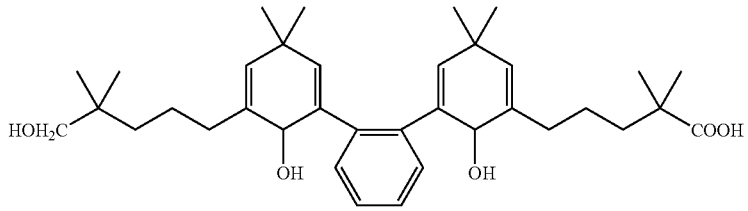

5-(6-Hydroxy-5-{2-[6-hydroxy-5-(5-hydroxy-4,4-dimethyl-pentyl)-3,3-dimethyl-cyclohexa-1,4-dienyl]phenyl}-3,3-dimethyl-cyclohexa-1,4-dienyl)-2,2-dimethyl-pentanoic acid Compound 160

-continued

Compound 161

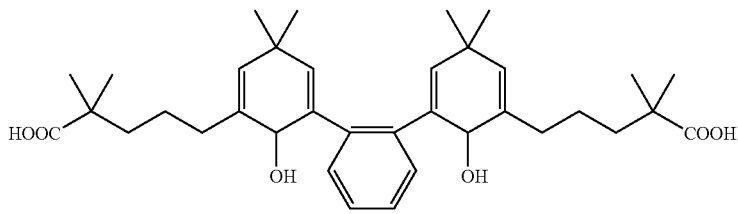

5-(5-{2-[5-(4-Carboxy-4-methyl-pentyl)-6-hydroxy-3,3-dimethyl-
cyclohexa-1,4-dienyl]-phenyl}-6-hydroxy-3,3-dimethyl-
cyclohexa-1,4-dienyl)-2,2-dimethyl-pentanoic acid Compound 162

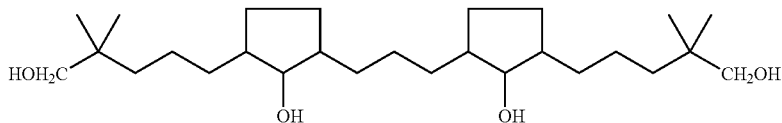

5-(2-Hydroxy-3-{3-[2-hydroxy-3-(5-hydroxy-4,4-dimethyl-
pentyl)-cyclopentyl]-propyl}-cyclopentyl)-2,2-dimethyl-pentanol Compound 163

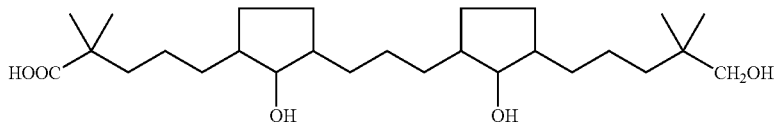

5-(2-Hydroxy-3-{3-[2-hydroxy-3-(5-hydroxy-4,4-dimethyl-
pentyl)-cyclopentyl]-propyl}-cyclopentyl)-2,2-dimethyl-pentanoic acid Compound 164

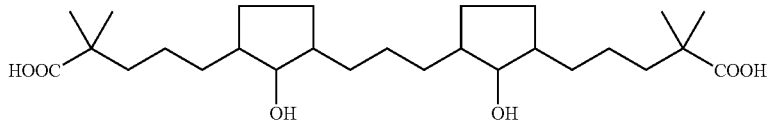

5-(3-{3-[3-(4-Carboxy-4-methyl-pentyl)-2-hydroxy-cyclopentyl]-
propyl}-2-hydroxy-cyclopentyl)-2,2-dimethyl-pentanoic acid Compound 165

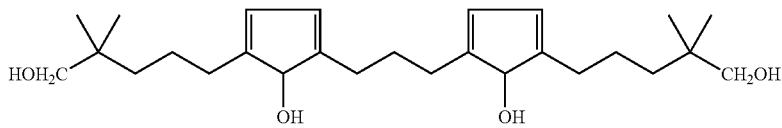

5-(5-Hydroxy-4-{3-[5-hydroxy-4-(5-hydroxy-4,4-dimethyl-
pentyl)-cyclopenta-1,3-dienyl]-propyl}-cyclopenta-1,3-dienyl)-
2,2-dimethyl-pentanol Compound 166

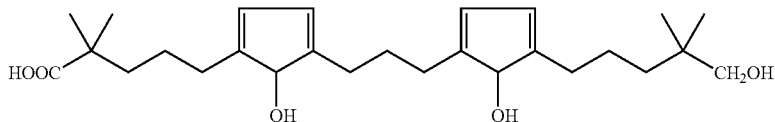

5-(5-Hydroxy-4-{3-[5-hydroxy-4-(5-hydroxy-4,4-dimethyl-
pentyl)-cyclopenta-1,3-dienyl]-propyl}-cyclopenta-1,3-dienyl)-
2,2-dimethyl-pentanoic acid Compound 167

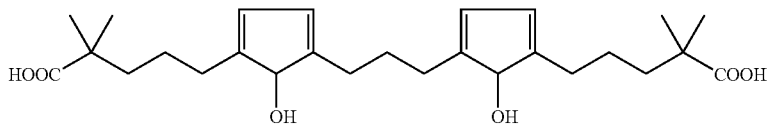

5-(4-{3-[4-(4-Carboxy-4-methyl-pentyl)-5-hydroxy-cyclopenta-
1,3-dienyl]-propyl}-5-hydroxy-cyclopenta-1,3-dienyl)-2,2-
dimethyl-pentanoic acid -continued

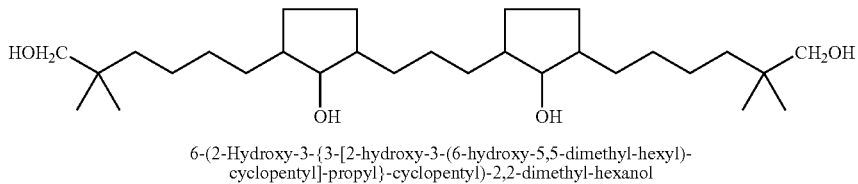

6-(2-Hydroxy-3-{3-[2-hydroxy-3-(6-hydroxy-5,5-dimethyl-hexyl)-
cyclopentyl]-propyl}-cyclopentyl)-2,2-dimethyl-hexanol Compound 168

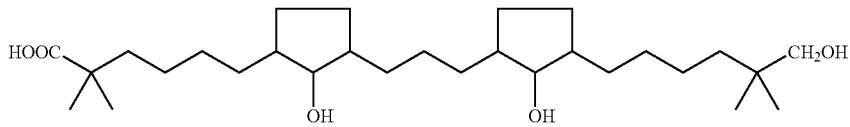

6-(2-Hydroxy-3-{3-[2-hydroxy-3-(6-hydroxy-5,5-dimethyl-hexyl)-
cyclopentyl]-propyl}-cyclopentyl)-2,2-dimethyl-hexanoic acid Compound 169

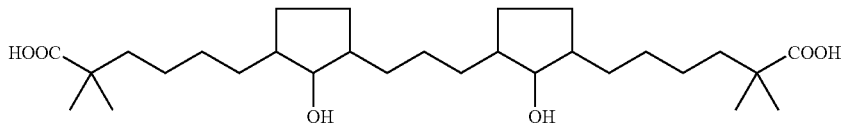

6-(3-{3-[3-(5-Carboxy-5-methyl-hexyl)-2-hydroxy-cyclopentyl]-
propyl}-2-hydroxy-cyclopentyl)-2,2-dimethyl-hexanoic acid Compound 170

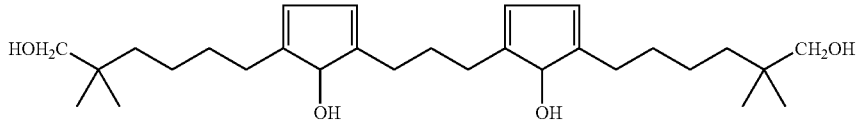

6-(5-Hydroxy-4-{3-[5-hydroxy-4-(6-hydroxy-5,5-dimethyl-hexyl)-
cyclopenta-1,3-dienyl]-propyl}-cyclopenta-1,3-dienyl)-2,2-
dimethyl-hexanol Compound 171

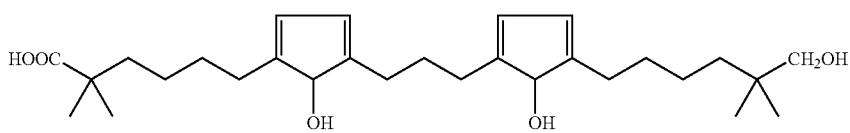

6-(5-Hydroxy-4-{3-[5-hydroxy-4-(6-hydroxy-5,5-dimethyl-hexyl)-
cyclopenta-1,3-dienyl]-propyl}-cyclopenta-1,3-dienyl)-2,2-
dimethyl-hexanoic acid Compound 172

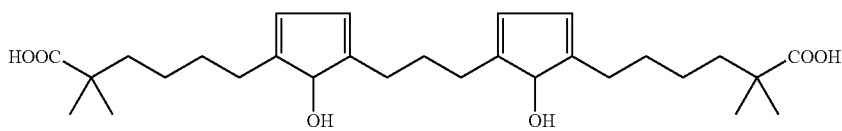

6-(4-{3-[4-(5-Carboxy-5-methyl-hexyl)-5-hydroxy-cyclopenta-
1,3-dienyl]-propyl}-5-hydroxy-cyclopenta-1,3-dienyl)-2,2-
dimethyl-hexanoic acid Compound 173

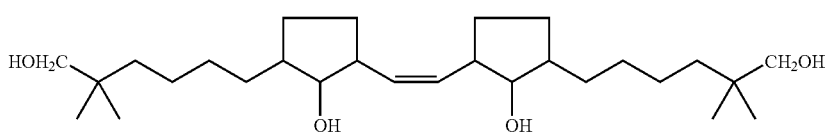

6-(2-Hydroxy-3-{2-[2-hydroxy-3-(6-hydroxy-5,5-dimethyl-hexyl)-
cyclopentyl]-vinyl}-cyclopentyl)-2,2-dimethyl-hexanol Compound 174

-continued

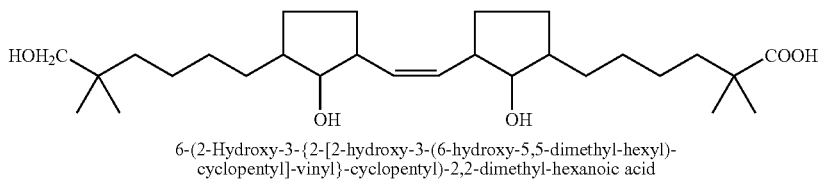

6-(2-Hydroxy-3-{2-[2-hydroxy-3-(6-hydroxy-5,5-dimethyl-hexyl)-
cyclopentyl]-vinyl}-cyclopentyl)-2,2-dimethyl-hexanoic acid Compound 175

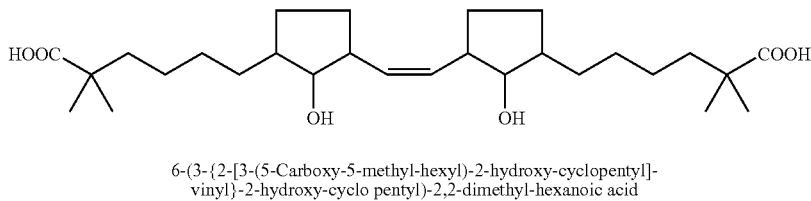

6-(3-{2-[3-(5-Carboxy-5-methyl-hexyl)-2-hydroxy-cyclopentyl]-
vinyl}-2-hydroxy-cyclo pentyl)-2,2-dimethyl-hexanoic acid Compound 176

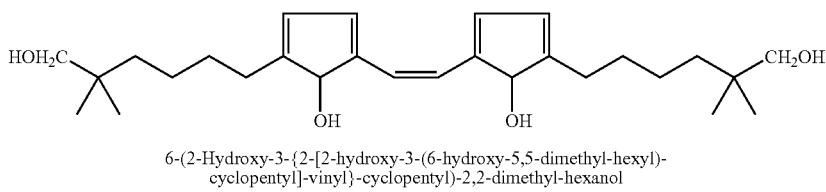

6-(2-Hydroxy-3-{2-[2-hydroxy-3-(6-hydroxy-5,5-dimethyl-hexyl)-
cyclopentyl]-vinyl}-cyclopentyl)-2,2-dimethyl-hexanol Compound 177

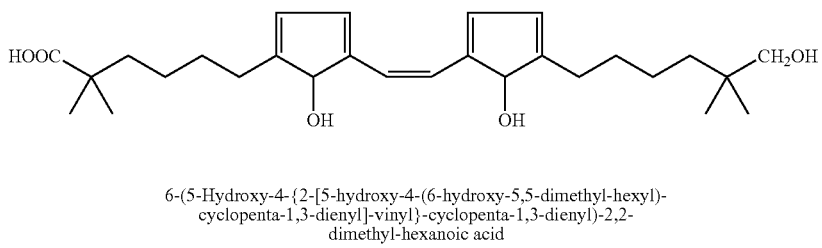

6-(5-Hydroxy-4-{2-[5-hydroxy-4-(6-hydroxy-5,5-dimethyl-hexyl)-
cyclopenta-1,3-dienyl]-vinyl}-cyclopenta-1,3-dienyl)-2,2-
dimethyl-hexanoic acid Compound 178

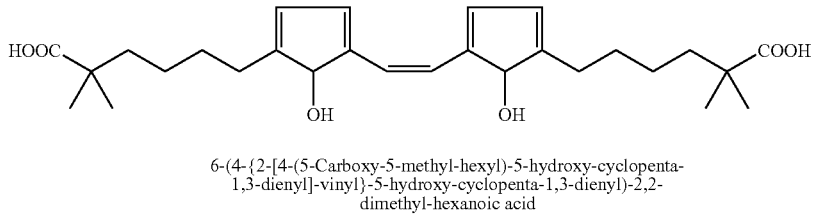

6-(4-{2-[4-(5-Carboxy-5-methyl-hexyl)-5-hydroxy-cyclopenta-
1,3-dienyl]-vinyl}-5-hydroxy-cyclopenta-1,3-dienyl)-2,2-
dimethyl-hexanoic acid Compound 179

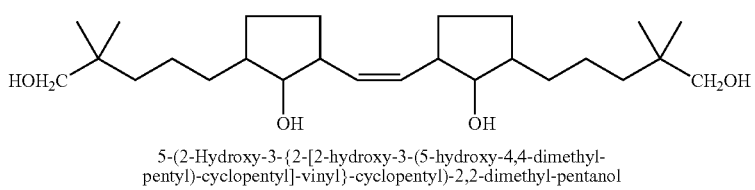

5-(2-Hydroxy-3-{2-[2-hydroxy-3-(5-hydroxy-4,4-dimethyl-
pentyl)-cyclopentyl]-vinyl}-cyclopentyl)-2,2-dimethyl-pentanol Compound 180

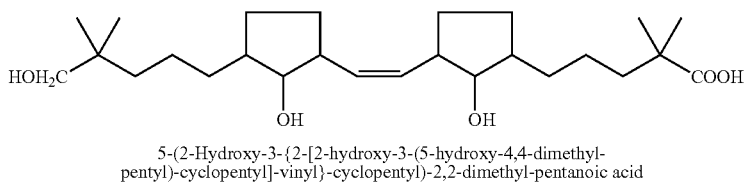

5-(2-Hydroxy-3-{2-[2-hydroxy-3-(5-hydroxy-4,4-dimethyl-
pentyl)-cyclopentyl]-vinyl}-cyclopentyl)-2,2-dimethyl-pentanoic acid Compound 181

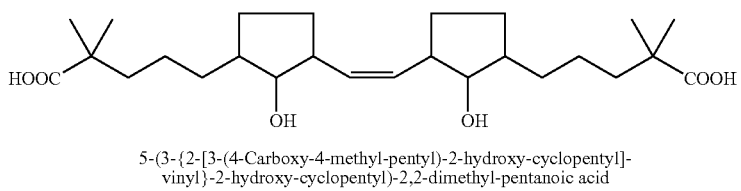

5-(3-{2-[3-(4-Carboxy-4-methyl-pentyl)-2-hydroxy-cyclopentyl]-
vinyl}-2-hydroxy-cyclopentyl)-2,2-dimethyl-pentanoic acid Compound 182

-continued

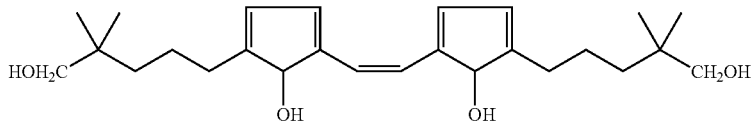

5-(5-Hydroxy-4-{2-[5-hydroxy-4-(5-hydroxy-4,4-dimethyl-pentyl)-cyclopenta-1,3-dienyl]-vinyl}-cyclopenta-1,3-dienyl)-2,2-dimethyl-pentanol Compound 183

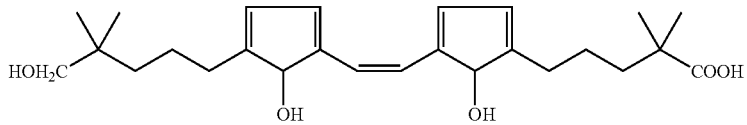

5-(5-Hydroxy-4-{2-[5-hydroxy-4-(5-hydroxy-4,4-dimethyl-pentyl)-cyclopenta-1,3-dienyl]-vinyl}-cyclopenta-1,3-dienyl)-2,2-dimethyl-pentanoic acid Compound 184

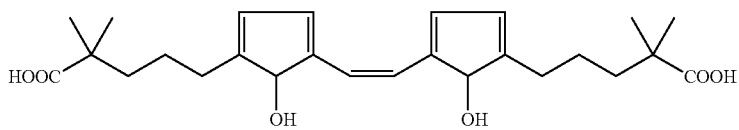

5-(4-{2-[4-(4-Carboxy-4-methyl-pentyl)-5-hydroxy-cyclopenta-1,3-dienyl]-vinyl}-5-hydroxy-cyclopenta-1,3-dienyl)-2,2-dimethyl-pentanoic acid Compound 185

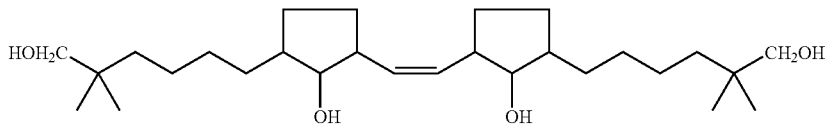

6-(2-Hydroxy-3-{2-[2-hydroxy-3-(6-hydroxy-5,5-dimethyl-hexyl)-cyclopentyl]-vinyl}-cyclopentyl)-2,2-dimethyl-hexanol Compound 186

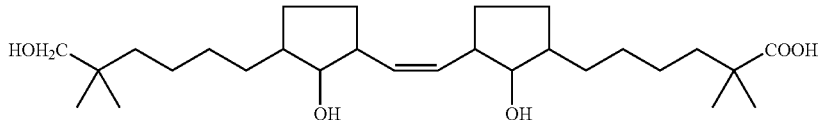

6-(2-Hydroxy-3-{2-[2-hydroxy-3-(6-hydroxy-5,5-dimethyl-hexyl)-cyclopentyl]-vinyl}-cyclopentyl)-2,2-dimethyl-hexanoic acid Compound 187

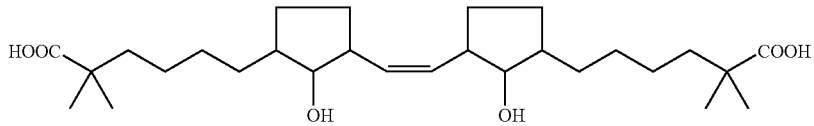

6-(3-{2-[3-(5-Carboxy-5-methyl-hexyl)-2-hydroxy-cyclopentyl]-vinyl}-2-hydroxy-cyclopentyl)-2,2-dimethyl-hexanoic acid Compound 188

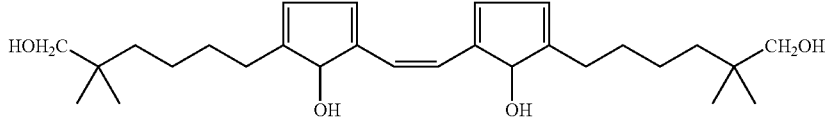

6-(5-Hydroxy-4-{2-[5-hydroxy-4-(6-hydroxy-5,5-dimethyl-hexyl)-cyclopenta-1,3-dienyl]-vinyl}-cyclopenta-1,3-dienyl)-2,2-dimethyl-hexanol Compound 189

-continued

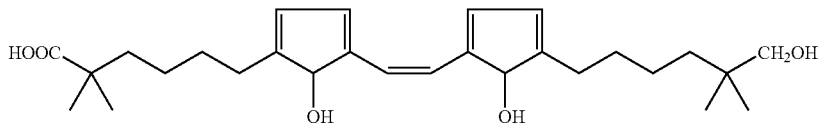

Compound 190

6-(5-Hydroxy-4-{2-[5-hydroxy-4-(6-hydroxy-5,5-dimethyl-hexyl)-
cyclopenta-1,3-dienyl]-vinyl}-cyclopenta-1,3-dienyl)-2,2-
dimethyl-hexanoic acid

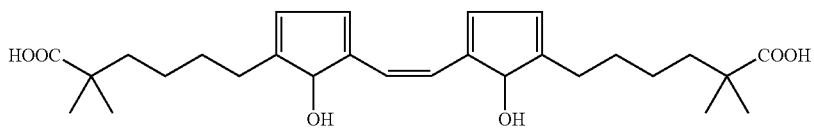

Compound 191

6-(4-{2-[4-(5-Carboxy-5-methyl-hexyl)-5-hydroxy-cyclopenta-
1,3-dienyl]-vinyl}-5-hydroxy-cyclopenta-1,3-dienyl)-2,2-
dimethyl-hexanoic acid

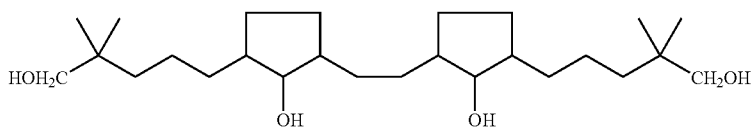

Compound 192

5-(2-Hydroxy-3-{2-[2-hydroxy-3-(5-hydroxy-4,4-dimethyl-
pentyl)-cyclopentyl]-ethyl}-cyclopentyl)-2,2-dimethyl-pentanol

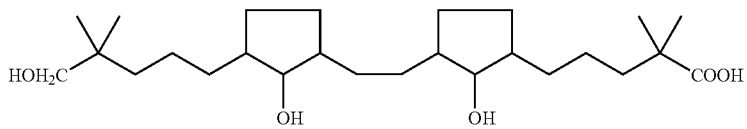

Compound 193

5-(2-Hydroxy-3-{2-[2-hydroxy-3-(5-hydroxy-4,4-dimethyl-
pentyl)-cyclopentyl]-ethyl}-cyclopentyl)-2,2-dimethyl-pentanoic acid

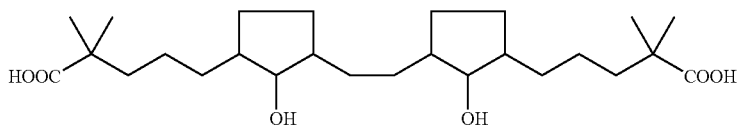

Compound 194

5-(3-{2-[3-(4-Carboxy-4-methyl-pentyl)-2-hydroxy-cyclopentyl]-
ethyl}-2-hydroxy-cyclopentyl)-2,2-dimethyl-pentanoic acid

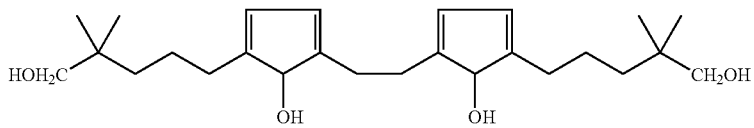

Compound 195

5-(5-Hydroxy-4-{2-[5-hydroxy-4-(5-hydroxy-4,4-dimethyl-
pentyl)-cyclopenta-1,3-dienyl]-ethyl}-cyclopenta-1,3-dienyl)-2,2-
dimethyl-pentanol

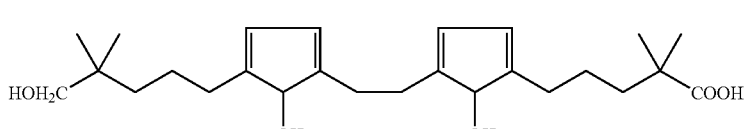

Compound 196

5-(5-Hydroxy-4-{2-[5-hydroxy-4-(5-hydroxy-4,4-dimethyl-
pentyl)-cyclopenta-1,3-dienyl]-ethyl}-cyclopenta-1,3-dienyl)-2,2-
dimethyl-pentanoic acid Compound 197

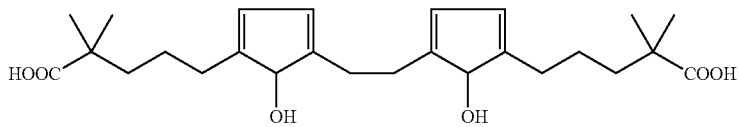

5-(4-{2-[4-(4-Carboxy-4-methyl-pentyl)-2-hydroxy-cyclopenta-
1,3-dienyl]-ethyl}-5-hydroxy-cyclopena-1,3-dienyl)-2,2-dimethyl-pentanoic acid Compound 198

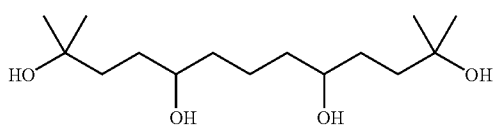

2,12-Dimethyl-tridecane-2,5,9,12-tetraol

Compound 199

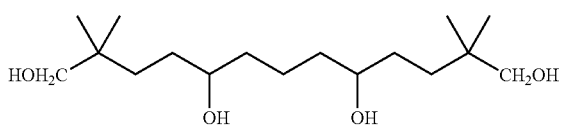

2,2,12,12-Tetramethyl-tridecane-1,5,9,13-tetraol

Compound 200

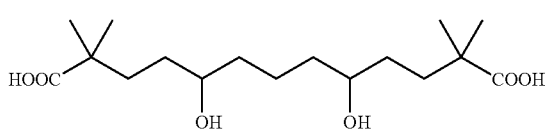

5,9-Dihydroxy-2,2,12,12-tetramethyl-tridecanedioic acid

Compound 201

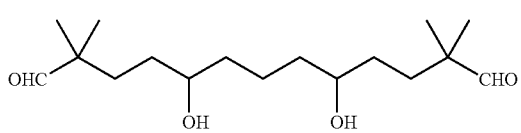

5,9-Dihydroxy-2,2,12,12-tetramethyl-tridecanedial

Compound 202

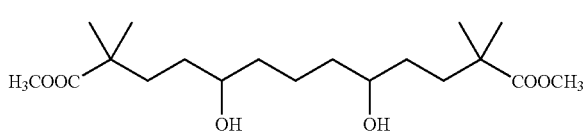

5,9-Dihydroxy-2,2,12,12-tetramethyl-tridecanedioic acid dimethyl
ester

Compound 203

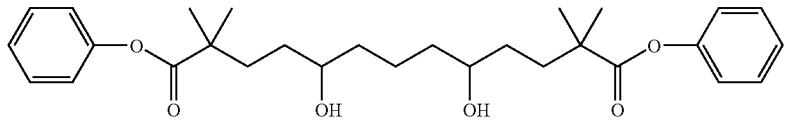

5,9-Dihydroxy-2,2,12,12-tetramethyl-tridecanedioic acid diphenyl ester

Compound 204

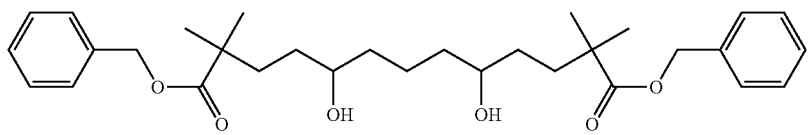

5,9-Dihydroxy-2,2,12,12-tetramethyl-tridecanedioic acid dibenzyl ester

Compound 205

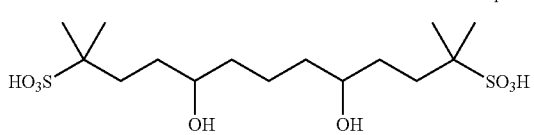

5,9-Dihydroxy-2,12-dimethyl-tridecane-2,12-disulfonic acid

Compound 206

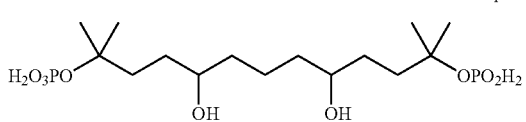

Phosphoric acid mono-(4,8-dihydroxy-1,1,11-trimethyl-11-
phosphonooxy-dodecyl)ester Compound 207

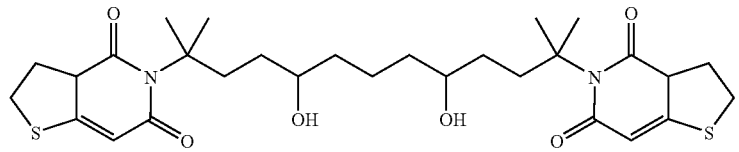

2,12-bis-(N-(3,3a-dihydro-2H-thieno[3,2,c]pyridine-4,6-dione))-
5,9-dihydroxy-2,12-dimethyl-tridecane Compound 208

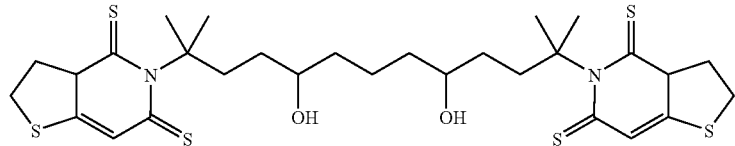

2,12-bis-(N-(3,3a-dihydro-2H-thieno[3,2,c]pyridine-4,6-
dithioxo))-5,9-dihydroxy-2,12-dimethyl-tridecane Compound 209

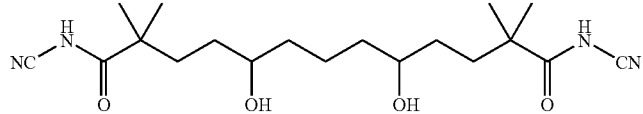

1,14-bis-(N-Cyanoamido)-5,9-dihydroxy-2,2,12,12-tetramethyl-tridecane

Compound 210

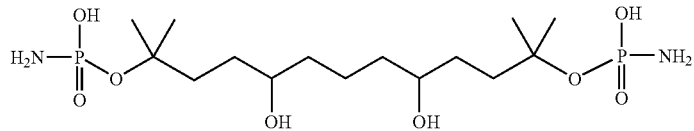

Phosphoramidic acid mono-[11-(amino-hydroxy-phosphoryloxy)-
4,8-dihydroxy-1,1,11-trimethyl-dodecyl] ester Compound 211

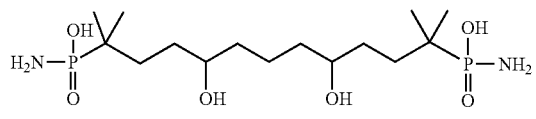

Phosphoramic acid mono-[11-(amino-hydroxy-phosphoryloxy)-
4,8-dihydroxy-1,1,11-trimethyl-dodecyl] ester Compound 212

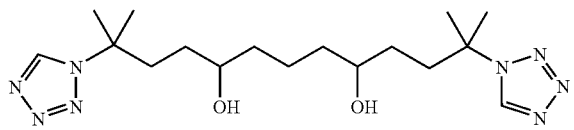

2,12-Dimethyl-2,12-bis-tetrazol-1-yl-tridecane-5,9-diol

Compound 213

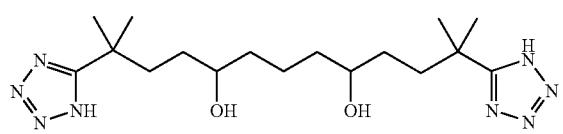

2,12-Dimethyl-2,12-bis-(1H-tetrazol-5-yl)-tridecane-5,9-diol

Compound 214

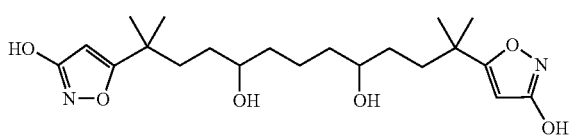

2,12-Bis-(3-hydroxy-isoxazol-5-yl)-2,12-dimethyl-tridecane-5,9-
diol

Compound 215

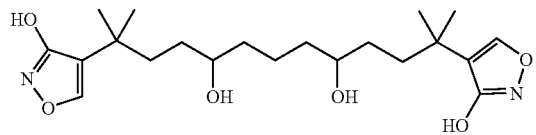

2,12-Bis-(3-hydroxy-isoxazol-4-yl)-2,12-dimethyl-tridecane-5,9-
diol

Compound 216

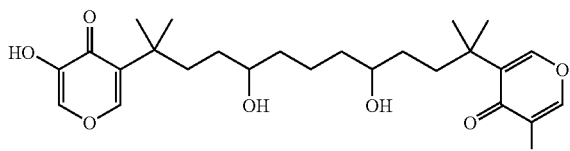

1,12-Bis-(5-(3-hydroxy-pyran-4-one)-2,12-dimethyl-tridecane-5,9-
diol

-continued

Compound 217

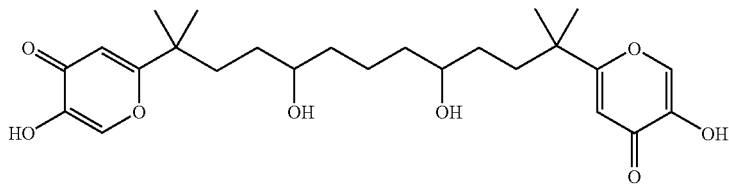

1,12-Bis-(6-(3-hydroxy-pyran-4-one)-2,12-dimethyl-tridecane-5,9-diol

Compound 218

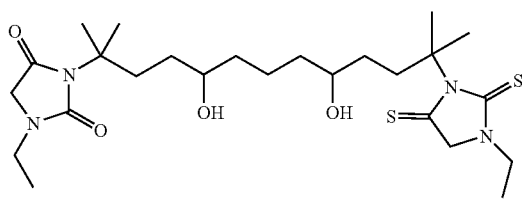

1-Ethyl-3-[11-(3-ethyl-2,5-dithioxo-imidazolin-1-yl)-4,8,-dihydroxy-1,1,11-trimethyl-dodecyl]-imidazolidine-2,4-dione Compound 219

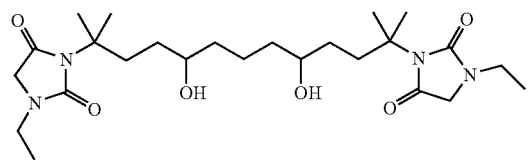

1,12-Bis-(1-Ethyl-imidazolin-3-yl-2,4-dione)-2,12-tetramethyl-tridecane-5,9-diol Compound 220

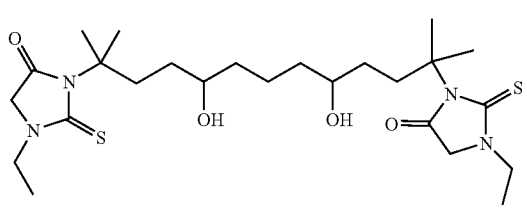

1,12-Bis-(1-Ethyl-imidazolin-3-yl-2-thioxo-4-one)-2,12-tetramethyl-tridecane-5,9-diol Compound 221

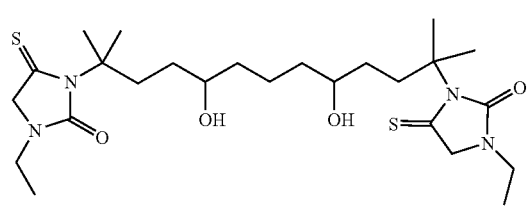

1,12-Bis-(1-Ethyl-imidazolin-3-yl-5-thioxo-4-one)-2,12-tetramethyl-tridecane-5,9-diol Compound 222

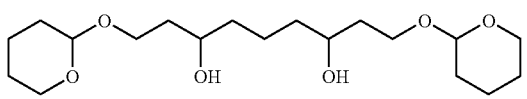

1,9-Bis-(tetrahydro-pyran-2-yloxy)-nonane-3,7-diol

Compound 223

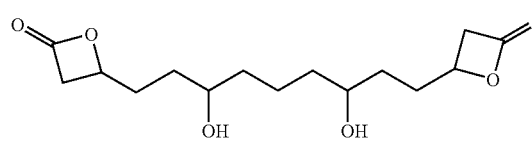

1,9-bis-(4-(Oxetan-2-one))-nonane-3,7-diol

Compound 224

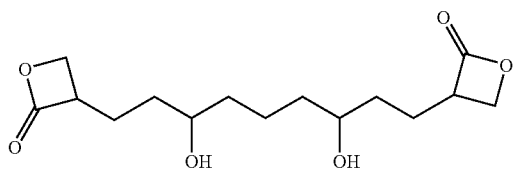

1,9-bis-(3-(Oxetan-2-one))-nonane-3,7-diol

Compound 225

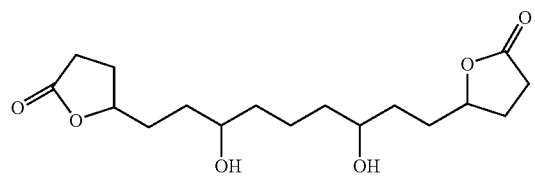

1,9-bis-(5-(Dihydro-furan-2-one))-nonane-3,7-diol

Compound 226

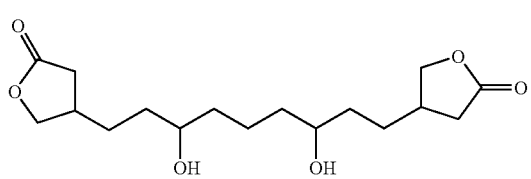

1,9-bis-(4-(Dihydro-furan-2-one))-nonane-3,7-diol

Compound 227

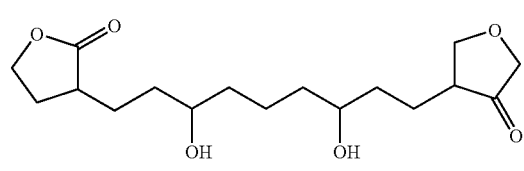

1,9-bis-(3-(Dihydro-furan-2-one))-nonane-3,7-diol

Compound 228

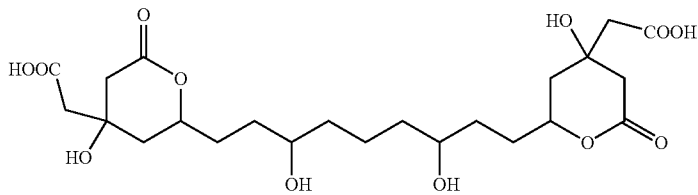

{2-[9-(4-Carboxymethyl-4-hydroxy-6-oxo-tetrahydro-pyran-2-yl)-
3,7-dihydroxy-nonyl]-4-hydroxy-6-oxo-tetrahydro-pyran-4-yl}-
acetic acid Compound 229

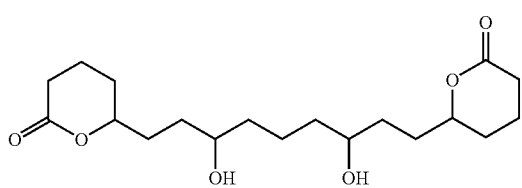

1,9-bis-(6-(Tetrahydro-pyran-2-one))-nonane-3,7-dio

Compound 230

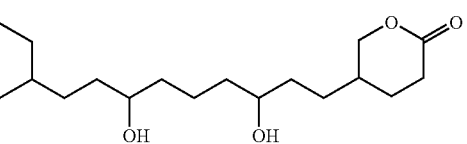

1,9-bis-(5-(Tetrahydro-pyran-2-one))-nonane-3,7-diol

Compound 231

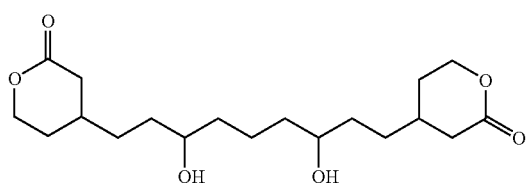

1,9-bis-(4-(Tetrahydro-pyran-2-one))-nonane-3,7-diol

Compound 232

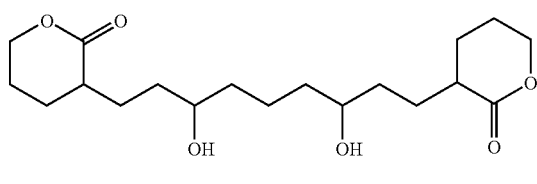

1,9-bis-(6-(Tetrahydro-pyran-2-one))-nonane-3,7-diol

Compound 233

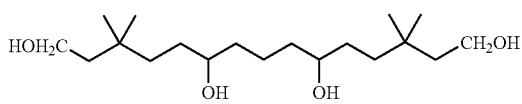

3,3,13,13,-Tetramethyl-pentadecane-1,6,10,15-tetraol

Compound 234

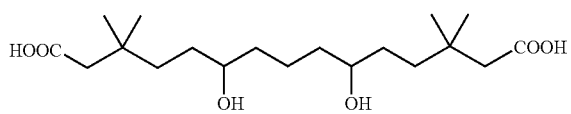

6,10-Dihydroxy-3,3,13,13,-tetramethyl-pentadecanedioic acid

Compound 235

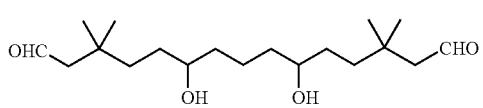

6,10-Dihydroxy-3,3,13,13-tetramethyl-pentadecanedial

Compound 236

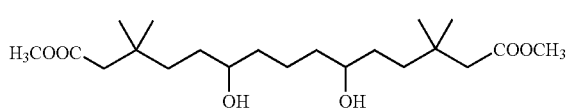

6,10-Dihydroxy-3,3,13,13-tetramethyl-pentadecanedioic acid
dimethyl ester

Compound 237

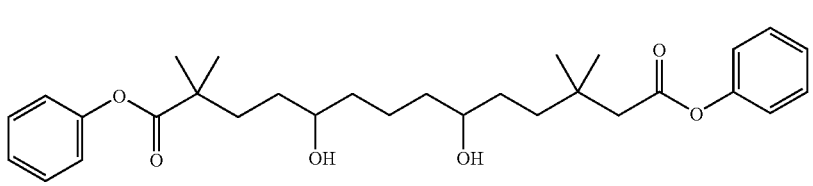

5,9-Dihydroxy-2,2,12,12-tetramethyl-tetradecanedioic acid
diphenyl ester

Compound 238

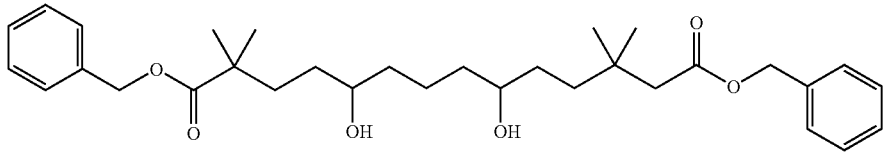

5,9-Dihydroxy-2,2,12,12-tetramethyl-tetradecanedioic acid
dibenzyl ester

Compound 239

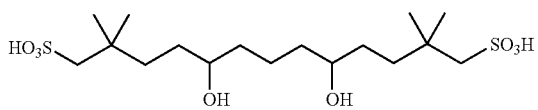

5,9-Dihydroxy-2,2,12,12-tetramethyl-tridecane-1,13-disulfonic
acid

Compound 240

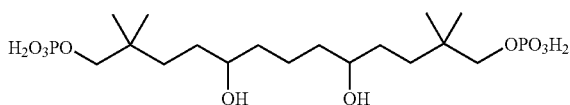

Phosphoric acid mono-(5,9-dihydroxy-2,2,12,12-tetramethyl-13-
phosphonooxy-tridecyl) ester Compound 241

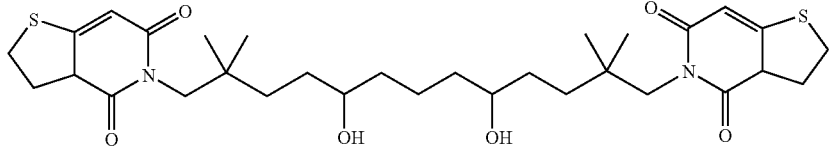

1,13-bis-(N-(3,3a-dihydro-2H-thieno[3,2,c]pyridine-4,6-dione))-
5,9-dihydroxy-2,2,12,12-tetramethyl-tridecane Compound 242

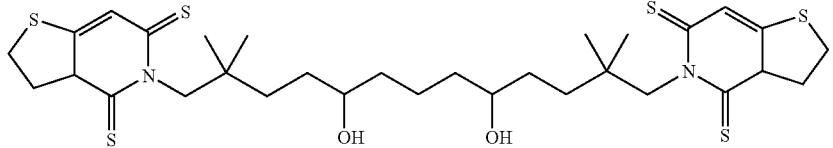

1,13-bis-(N-(3,3a-dihydro-2H-thieno[3,2,c]pyridine-4,6-
dithioxo))-5,9-dihydroxy-2,2,12,12-tetramethyl-tridecane Compound 243

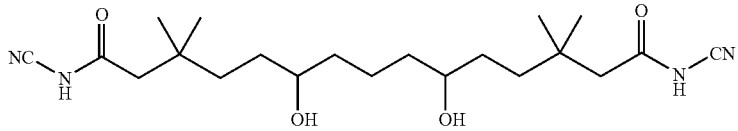

1,15-bis-(N-Cyanoamido)-6,10-dihydroxy-3,3,13,13-tetramethyl-
pentadecane

Compound 244

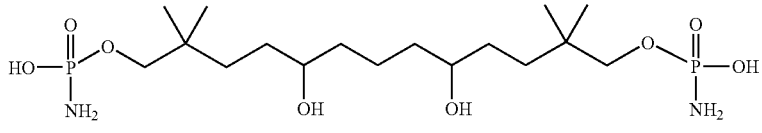

Phosphoramidic acid mono-[13-(amino-hydroxy-phosphoryloxy)-
5,9-dihydroxy-2,2,12,12-tetramethyl-tridecyl] ester Compound 245

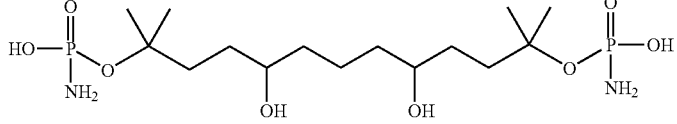

Phosphoramidic acid mono-[11-(amino-hydroxy-phosphoryloxy)-
4,8-dihydroxy-1,1,11-trimethyl-dodecyl] ester -continued Compound 246

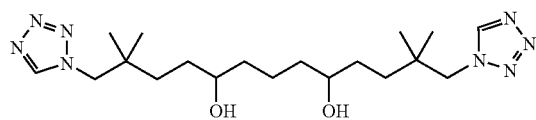

2,2,12,12-Tetramethyl-1,13-bis-tetrazol-1-yl-tridecane-5,9-diol

Compound 247

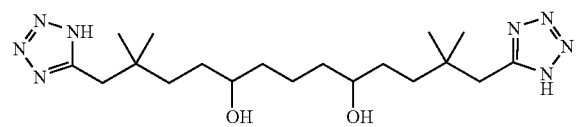

2,2,12,12-Tetramethyl-1,13-bis-(1H-tetrazol-5-yl)-tridecane-5,9-diol

Compound 248

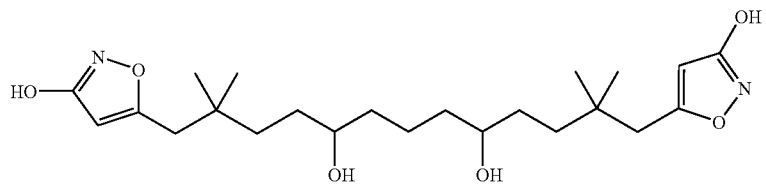

1,13-Bis-(3-hydroxy-isoxazol-5-yl)-2,2,12,12-tetramethyl-tridecane-5,9-diol

Compound 249

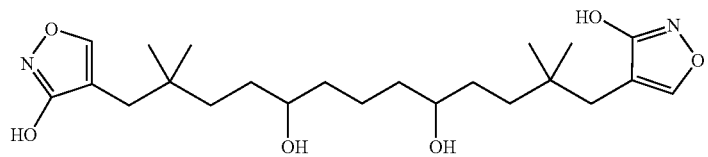

1,13-Bis-(3-hydroxy-isoxazol-4-yl)-2,2,12,12-tetramethyl-tridecane-5,9-diol

Compound 250

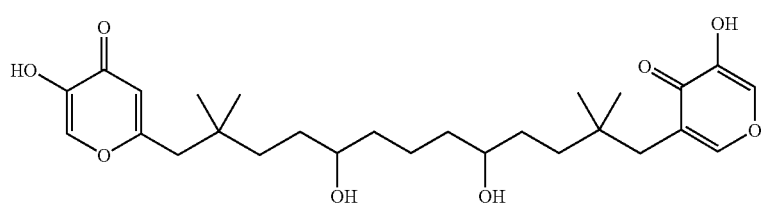

1-(6-(3-hydroxy-pyran-4-one)-13-(5-(3-hydroxy-pyran-4-one)-2,2,12,12-tetramethyl-tridecane-5,9-diol Compound 251

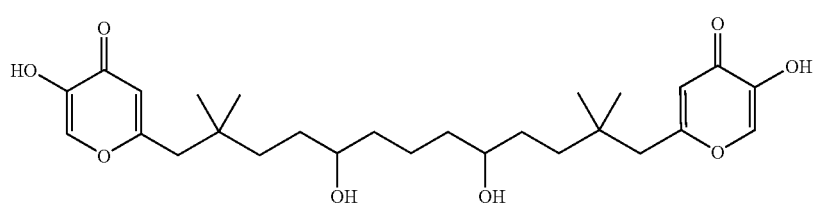

1,13-bis-(6-(3-hydroxy-pyran-4-one)-2,2,12,12-tetramethyl-tridecane-5,9-diol

Compound 252

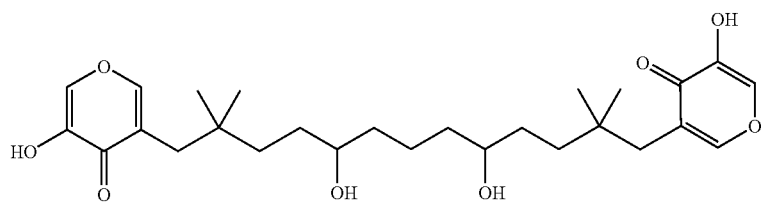

1,13-bis-(5-(3-hydroxy-pyran-4-one)-2,2,12,12-tetramethyl-tridecane-5,9-diol

Compound 253

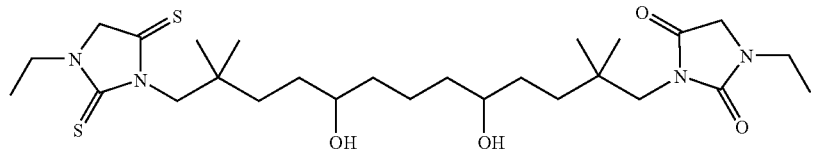

1-Ethyl-3-[13-(3-ethyl-2,5-dithioxo-imidazolin-1-yl)-5,9-dihydroxy-2,2,12,12-tetramethyl-tridecyl]-imidazolidine-2,4-dione Compound 254

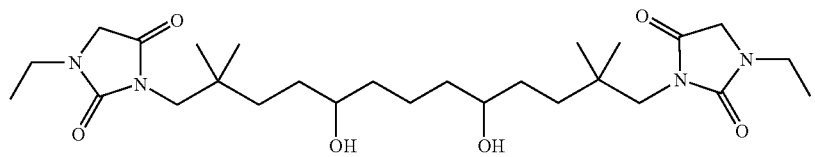

1,13-bis-(1-Ethyl-imidazolin-3-yl-2,4-dione)-2,2,12,12-tetramethyl-dodecane-5,9-diol Compound 255

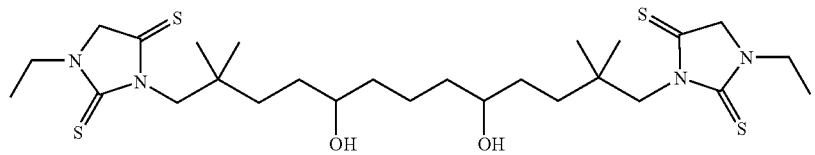

1,13-bis-(1-Ethyl-imidazolin-3-yl-2,4-dithioxo)-2,2,12,12-tetramethyl-dodecane-5,9-diol Compound 256

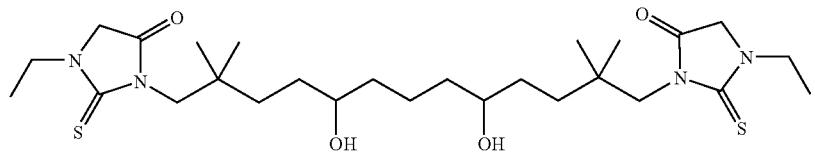

1,13-bis-(1-Ethyl-imidazolin-3-yl-2-thioxo-4-one)-2,2,12,12-tetramethyl-dodecane-5,9-diol Compound 257

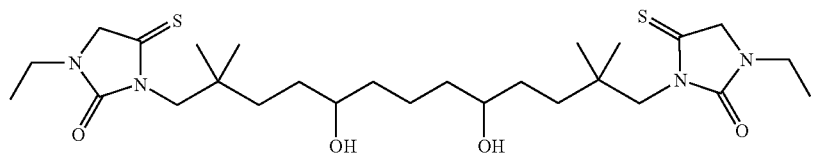

1,13-bis-(1-Ethyl-imidazolin-3-yl-4-thioxo-2-one)-2,2,12,12-tetramethyl-dodecane-5,9-diol Compound 258

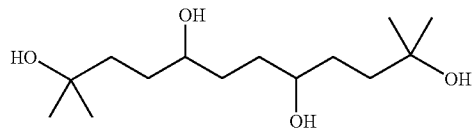

2,11-Dimethyl-dodecane-2,5,8,11-tetraol

Compound 259

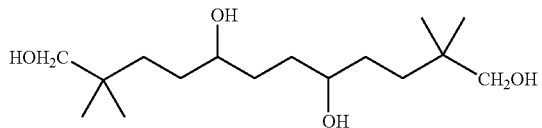

2,2,11,11-Tetramethyl-dodecane-1,5,8,12-tetraol

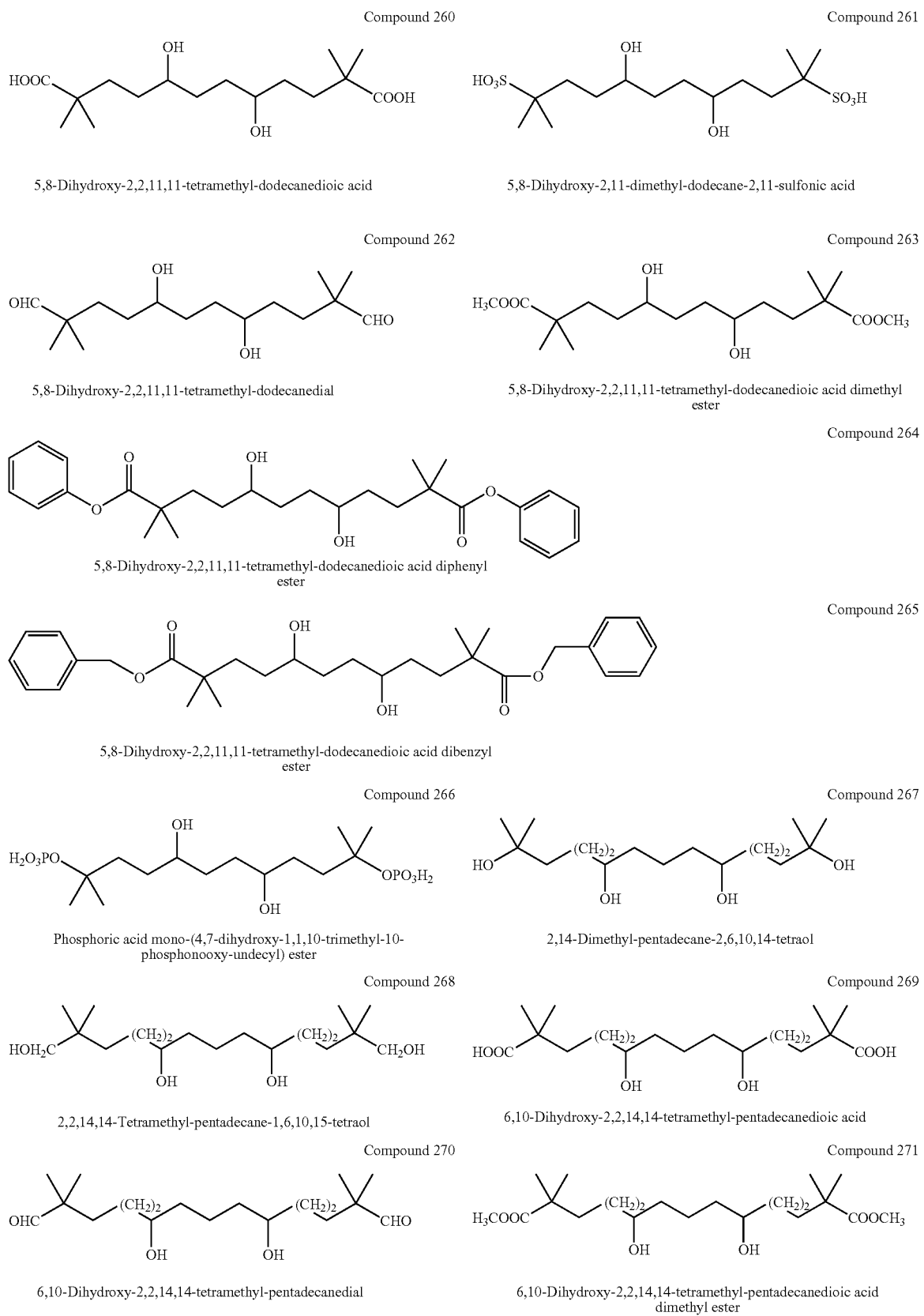

-continued

Compound 272

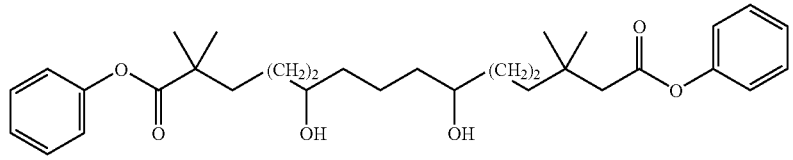

6,10-Dihydroxy-2,2,14,14-tetramethyl-hexadecanedioic acid diphenyl ester

Compound 273

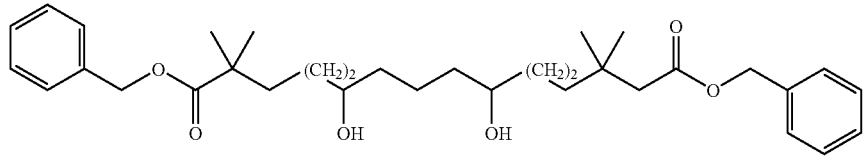

6,10-Dihydroxy-2,2,14,14-tetramethyl-hexadecanedioic acid dibenzyl ester

Compound 274

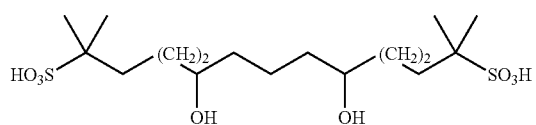

6,10-Dihydroxy-2,14-dimethyl-pentadecane-2,14-disulfonic acid

Compound 275

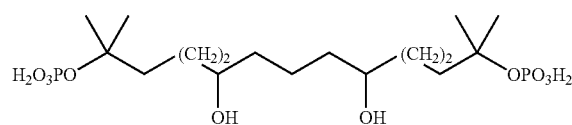

Phosphoric acid mono-(5,9-dihydroxy-1,1,13-trimethyl-13-phosphonooxy-tetradecyl) ester Compound 276

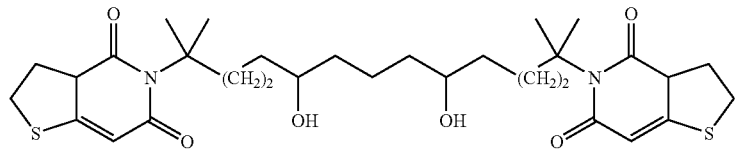

2,14-bis-(N-(3,3a-dihydro-2H-thieno[3,2,c]pyridine-4,6-dione))-6,10-dihydoxy-2,14-dimethyl-pentadecane Compound 277

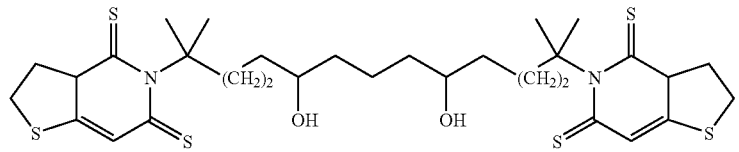

2,14-bis-(N-(3,3a-dihydro-2H-thieno[3,2,c]pyridine-4,6-dithioxo))-6,10-dihydoxy-2,14-dimethyl-pentadecane Compound 278

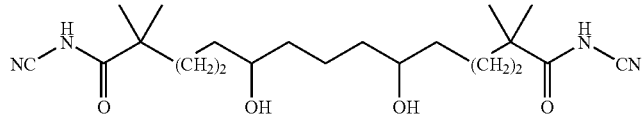

1,15-bis-(N-Cyanoamido)-6,10-dihydroxy-2,14-dimethyl-pentadecane

Compound 279

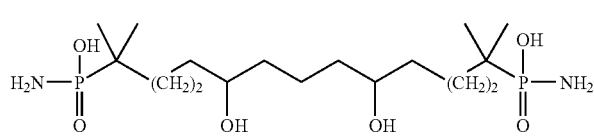

Phosphoramic acid mono-[13-(amino-hydroxy-phosphoryloxy)-1,1,13-trimethyl-5,9-dioxo-tetradecyl] ester Compound 280

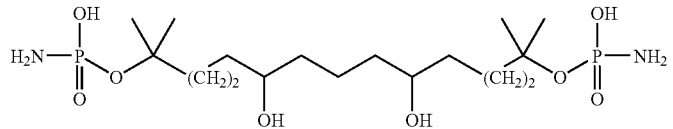

Phosphoramidic acid mono-[13-(amino-hydroxy-phosphoryloxy)-
1,1,13-trimethyl-5,9-dioxo-tetradecyl] ester Compound 281

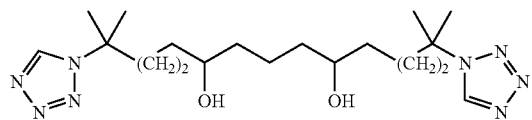

2,14-Dimethyl-2,14-bis-tetrazol-1-yl-pentadecane-6,10-diol

Compound 282

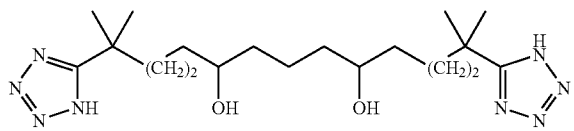

2,14-Dimethyl-2,14-bis-(1H-tetrazol-5-yl)-pentadecane-6,10-diol

Compound 283

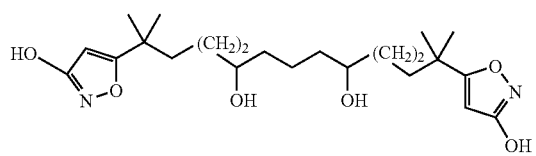

2,14-Bis-(3-hydroxy-isoxazol-5-yl)-2,14-dimethyl-pentadecane-
6,10-diol

Compound 284

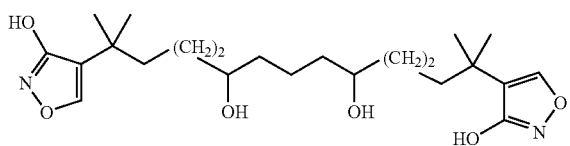

2,14-Bis-(3-hydroxy-isoxazol-4-yl)-2,14-dimethyl-pentadecane-
6,10-diol

Compound 285

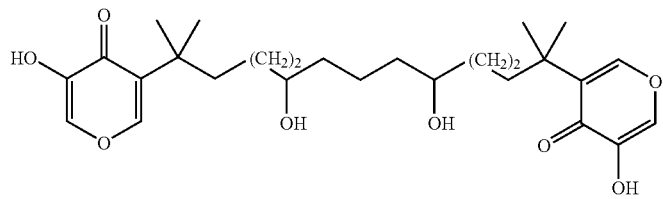

2,14-bis-(5-(3-Hydroxy-pyran-4-one)-2,14-dimethyl-pentadecane-
6,10-diol

Compound 286

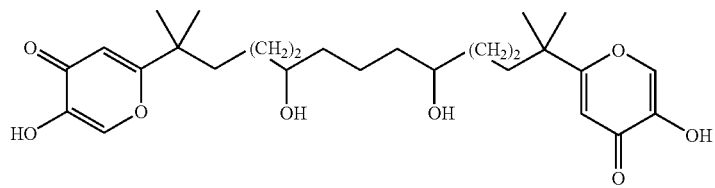

2,14-bis-(6-(3-Hydroxy-pyran-4-one)-2,14-dimethyl-pentadecane-
6,10-diol

Compound 287

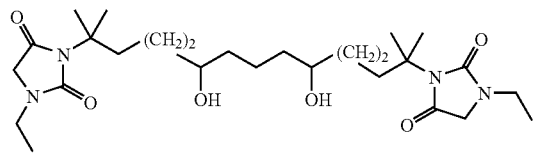

1,15-bis-(1-Ethyl-imidazolin-3-yl-2,4-dione)-2,14-dimethyl-
pentadecane-6,10-diol Compound 288

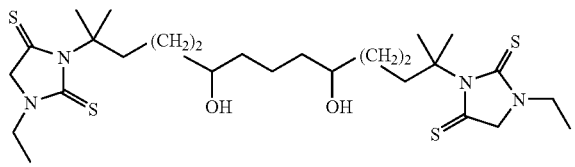

2,14-bis-(1-Ethyl-imidazolin-3-yl-2,4-dithioxo)-2,14-dimethyl-
pentadecane-6,10-diol Compound 289

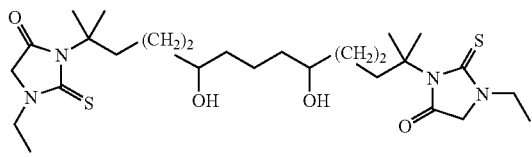

2,14-bis-(1-Ethyl-imidazolin-3-yl-2-thioxo-4-one)-2,14-dimethyl-pentadecane-6,10-diol Compound 290

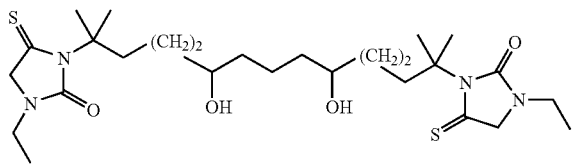

2,14-bis-(1-Ethyl-imidazolin-3-yl-4-thioxo-2-one)-2,14-dimethyl-pentadecane-6,10-diol Compound 291

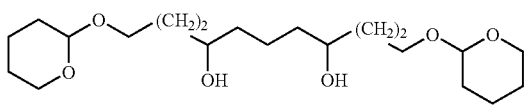

1,11-Bis-(tetrahydro-pyran-2-yloxy)-undecane-4,8-diol

Compound 292

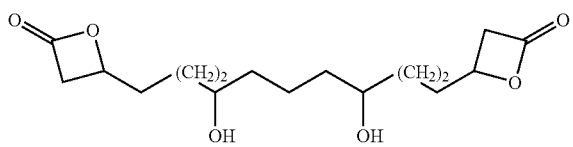

1,11-bis-(4-(Oxetan-2-one))-undecane-4,8-diol

Compound 293

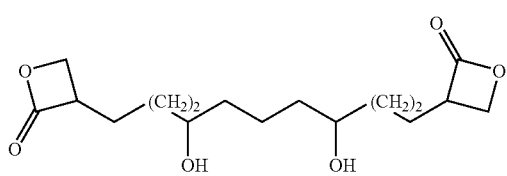

1,11-bis-(3-(Oxetan-2-one))-undecane-4,8-diol

Compound 294

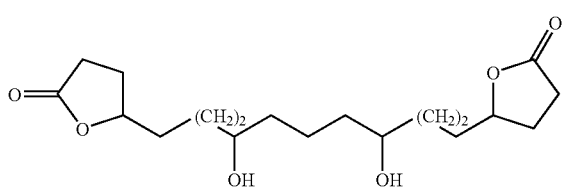

1,11-bis-(5-(Dihydro-furan-2-one))-undecane-4,8-diol

Compound 295

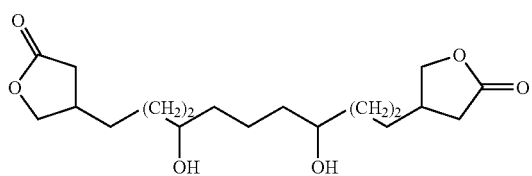

1,11-bis-(4-(Dihydro-furan-2-one))-undecane-4,8-diol

Compound 296

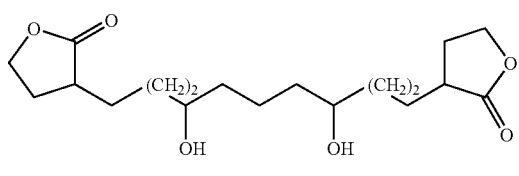

1,11-bis-(5-(Dihydro-furan-2-one))-undecane-4,8-diol

Compound 297

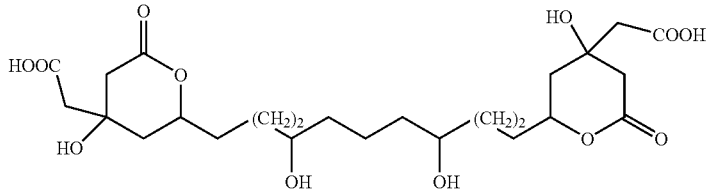

{2-[11-(4-Carboxymethyl-4-hydroxy-6-oxo-tetrahydro-pyran-2-yl)-4,8-dihydroxy-undecyl]-4-hydroxy-6-oxo-tetrahydro-pyran-4-yl}-acetic acid Compound 298

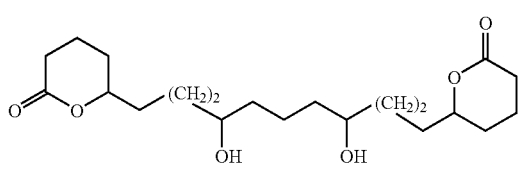

1,11-bis-(6-(Tetrahydro-pyran-2-one))-undecane-4,8-diol

Compound 299

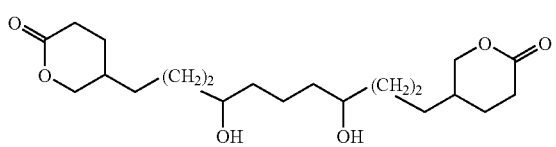

1,11-bis-(5-(Tetrahydro-pyran-2-one))-undecane-4,8-diol

Compound 300

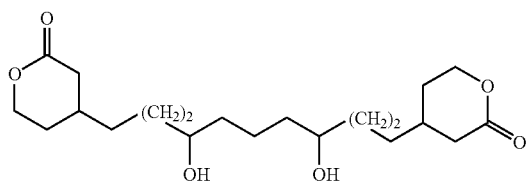

1,11-bis-(4-(Tetrahydro-pyran-2-one))-undecane-4,8-diol

Compound 301

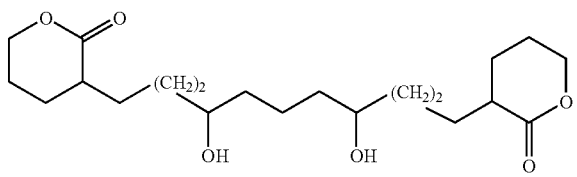

1,11-bis-(3-(Tetrahydro-pyran-2-one))-undecane-4,8-diol

Compound 302

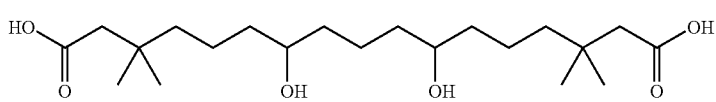

7,11-Dihydroxy-3,3,15,15-tetramethyl-heptadecanedioic acid

Compound 303

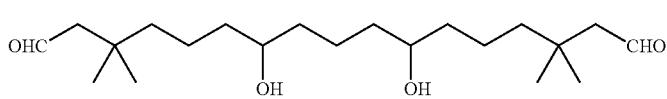

7,11-Dihydroxy-3,315,15-tetramethyl-heptad

Compound 304

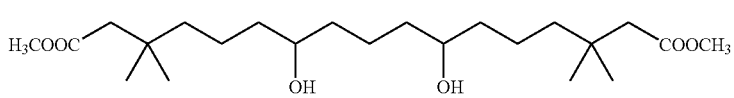

7,11-Dihydroxy-3,3,15,15-tetramethyl-heptadecanedioic acid dimethyl ester

Compound 305

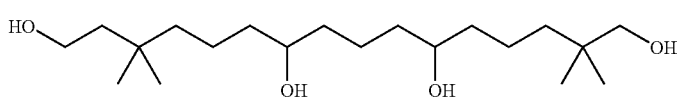

3,3,15,15-Tetramethyl-heptadecane-1,7,11,17-tetraol

Compound 306

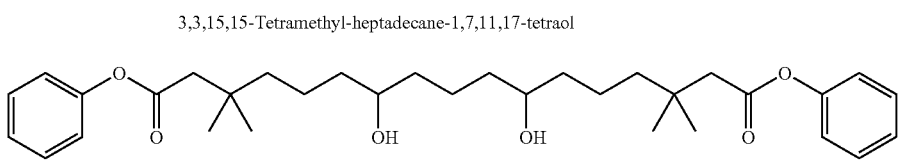

7,11-Dihydroxy-3,3,15,15-tetramethyl-heptadecanedioic acid diphenyl ester

Compound 307

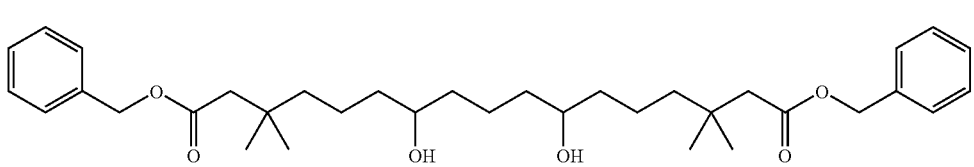

7,11-Dihydroxy-3,3,15,15-tetramethyl-heptadecanedioic acid dibenzyl ester

Compound 308

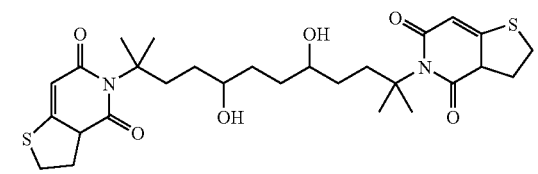

1,11-bis-(N-(3,3a-dihydro-2H-thieno[3,2,c]pyridine-4,6-dione))-5,8-dihydroxy-2-11-dimethyl-dodecane Compound 309

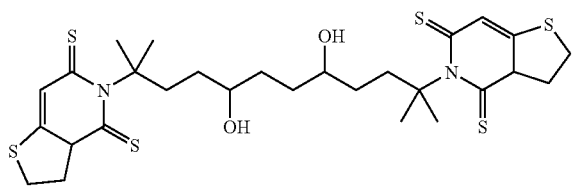

1,11-bis-(N-(3,3a-dihydro-2H-thieno[3,2,c]pyridine-4,6-dithioxo))-5,8-dihydroxy-2-11-dimethyl-dodecane -continued Compound 310

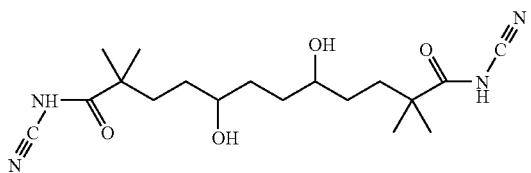

2,11-bis-(N-Cyanoamido)-5,8-dihydroxy-2,11-dimethyl-dodecane

Compound 311

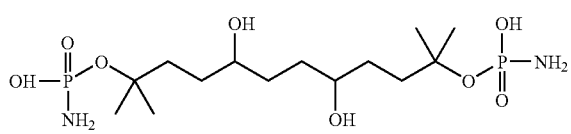

2-Phosporamidic acid mono-[11-(amino-hydroxy-phosphoryloxy)-2,11,11-trimethyl-5,8-dioxo-dodecyl] ester Compound 312

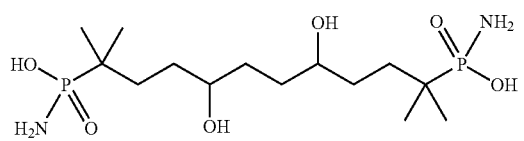

Phosphoramic acid mono-[11-(amino-hydroxy-phosphoryloxy)-1,1,11-trimethyl-5,8,-dioxo-dodecyl]ester Compound 313

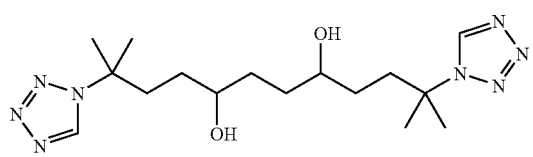

Phosphoramic acid mono-[11-(amino-hydroxy-phosphoryloxy)-1,1,11-trimethyl-5,8,-dioxo-dodecyl]ester Compound 314

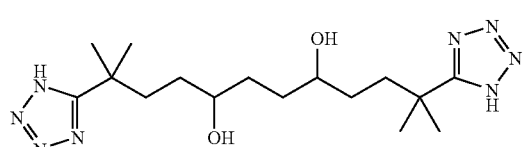

2,11-Dimethyl-2,11-bis-(1H-tetrazol-5-yl)-dodecane-5,8-diol

Compound 315

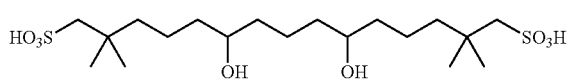

6,10-Dihydroxy-2,2,14,14-tertramethyl-pentadecane-1,15-disulfonic acid

Compound 316

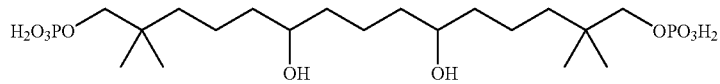

Phosphoric acid mono-(6,10-dihydroxy-2,2,14,14-tetramethyl-15-phosphonooxy-pentadecyl) ester Compound 317

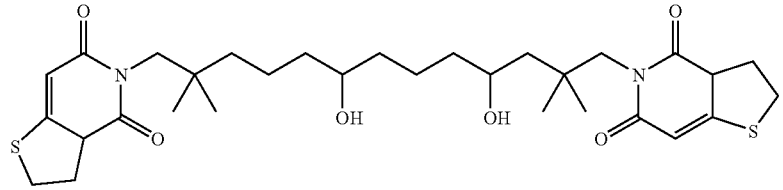

1,15-bis-(N-(3,3a-dihydro-2H-thieno[3,2,c]pyridine-4,6-dione))-6,10-dihydroxy-2,2,14,14-tetramethyl-pentadecane Compound 318

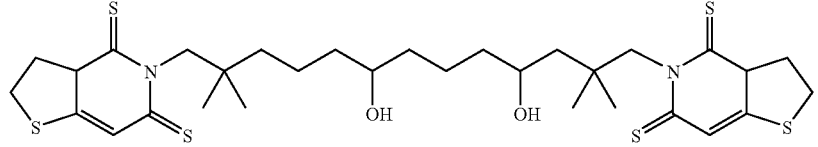

1,15-bis-(N-(3,3a-dihydro-2H-thieno[3,2,c]pyridine-4,6-dithioxo))-6,10-dihydroxy-2,2,14,14-tetramethyl-pentadecane Compound 319

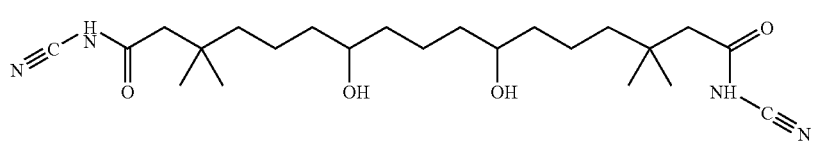

1,15-bis-(N-Cyanoamido)-6,10-dihydroxy-2,14-tetramethyl-pentadecane

-continued

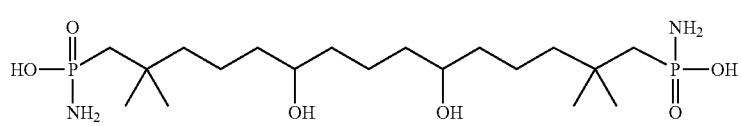

Phosphoramidic acid mono-15-(amino-hydroxy-phosphoryloxy)-
(2,2,14,14-tetramethyl-6,10-dioxo)-pentadecane Compound 320

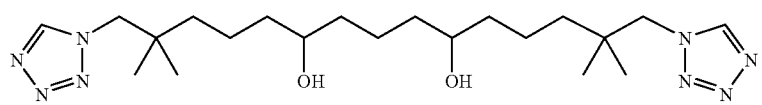

2,2,14,14-Tetramethyl-1,15-bis-tetrazol-1-yl-pentadecane-6,10-diol

Compound 321

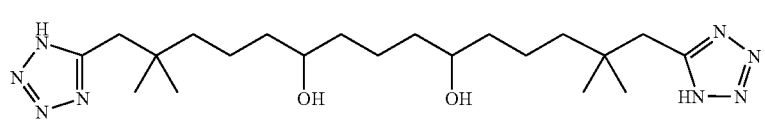

2,2,14,14-Tetramethyl-1,15-bis-(1H-tetrazol-5-yl)-pentadecane-
6,10-diol

Compound 322

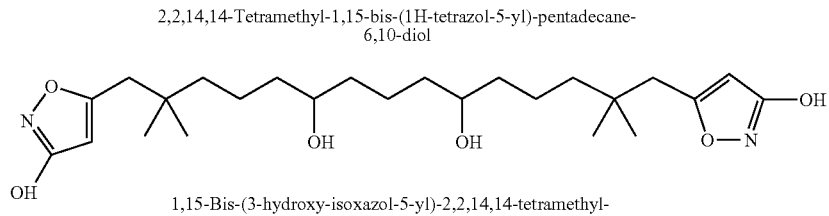

1,15-Bis-(3-hydroxy-isoxazol-5-yl)-2,2,14,14-tetramethyl-
pentadecane-6,10-diol

Compound 323

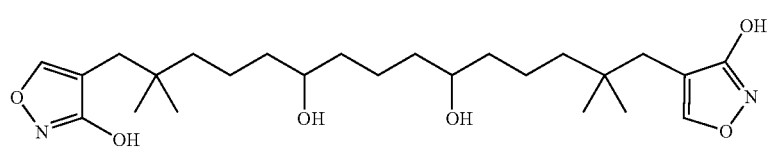

1,15-Bis-(3-hydroxy-isoxazol-4-yl)-2,2,14,14-tetramethyl-
pentadecane-6,10-diol

Compound 324

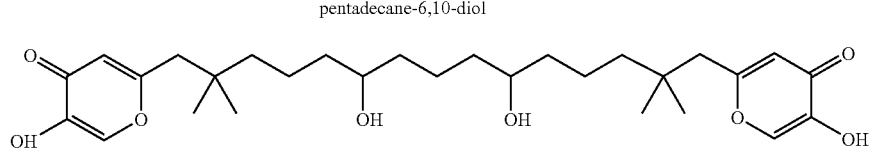

1,15-Bis-(6-(3-hydroxy-pyran-4-one)-2,2,14,14-tetramethyl-
pentadecane-6,10-diol Compound 325

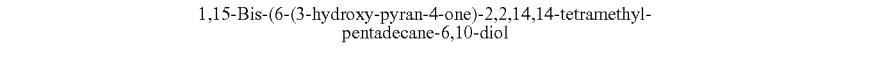

1,15-Bis-(5-(3-hydroxy-pyran-4-one)-2,2,14,14-tetramethyl-
pentadecane-6,10-diol Compound 326

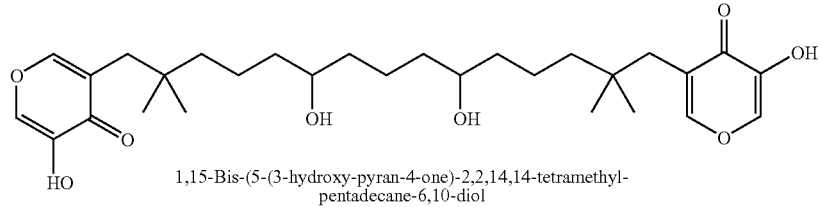

1-Ethyl-3-[15-(3-ethyl-2,5-dithioxo-imidazolidin-1-yl)-6,10-
dihydroxy-2,2,14,14-tetramethyl-pentadecyl]-imidazolidine-2,4-
dione Compound 327

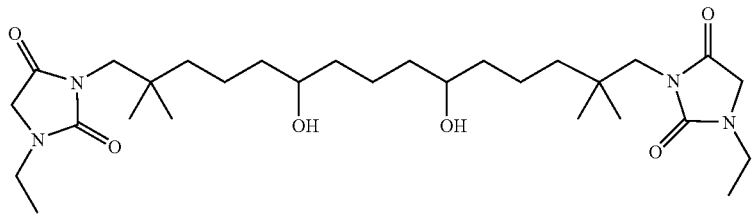

Compound 328

1,15-bis-(1-Ethyl-imidazolin-3-yl-2,4-dithioxo)-2,2,14,14-dimethyl-pentadecane-6,10-diol

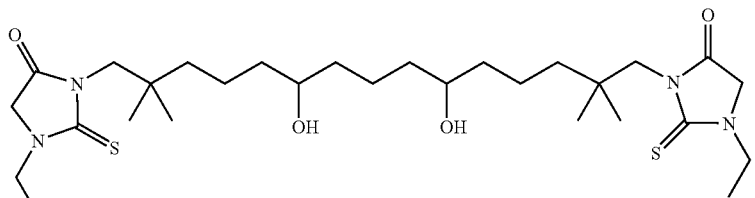

Compound 329

1,15-bis-(1-Ethyl-imidazolin-3-yl-2-thioxo-4-one)-2,2,14,14-tetramethyl-pentadecane-6,10-diol

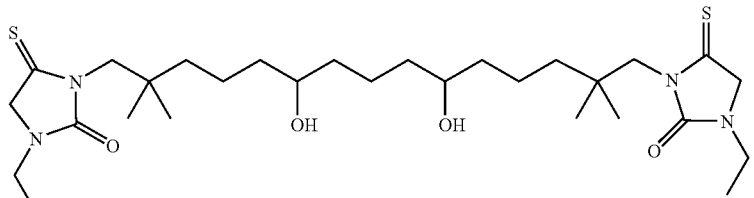

Compound 330

1,15-bis-(1-Ethyl-imidazolin-3-yl-4-thioxo-2-one)-2,2,14,14-tetramethyl-pentadecane-6,10-diol

5.1 Synthesis of the Compounds of the Invention

The compounds of the invention can be obtained via the synthetic methodology illustrated in Schemes 1-16. Starting materials useful for preparing the compounds of the invention and intermediates thereof, are commercially available or can be prepared from commercially available materials using known synthetic methods and reagents.

Scheme 1: Synthesis of Compounds of Formula X

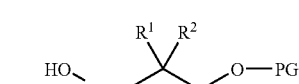

4

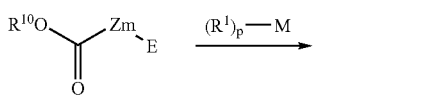

5

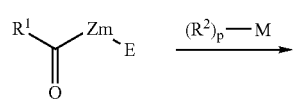

6

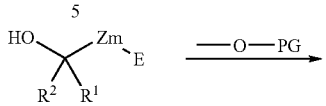

X: n = 0

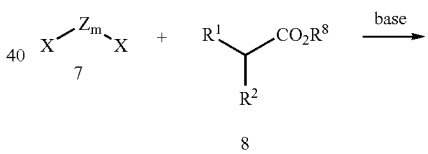

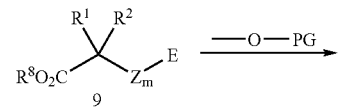

9

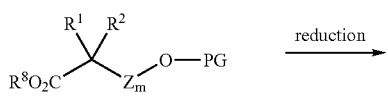

10

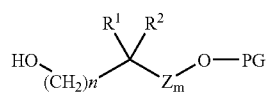

X: n = 1

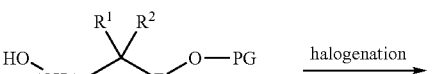

X

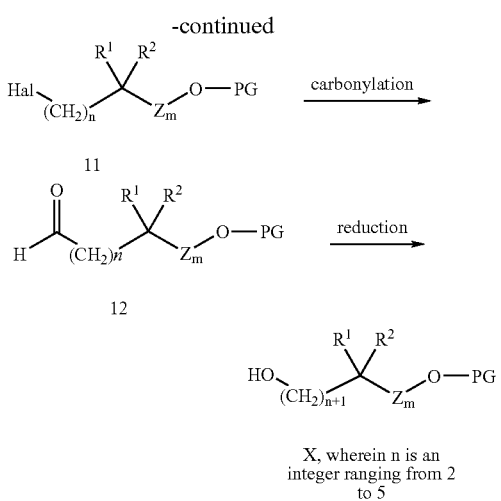

X, wherein n is an integer ranging from 2 to 5

Scheme 1 illustrates the synthesis of mono-protected diols of the formula X, wherein n is an integer ranging from 0 to 4 and $R^1$ and $R^2$ are as defined herein, and E is a leaving group as defined herein. Scheme 1 first outlines the synthesis of mono-protected diols X, wherein n is 0, where esters 4 are successively reacted with a first $((R^1)_p\text{-M})$ then a second $((R^2)_p\text{-M})$ organometallic reagent providing hydroxys 5 and alcohols 6, respectively. M is a metal group and p is the metal's valency value (e.g., the valency of Li is 1 and that of Zn is 2). Suitable metals include, but are not limited to, Zn, Na, Li, and —Mg-Hal, wherein Hal is a halide selected from iodo, bromo, or chloro. Preferably, M is —Mg-Hal, in which case the organometallic reagents, $(R^1)_p$-Mg-Hal and $(R^2)_p$-Mg-Hal, are known in the art as a Grignard reagents. Esters 4 are available commercially (e.g., Aldrich Chemical Co., Milwaukee, Wis.) or can be prepared by well-known synthetic methods, for example, via esterification of the appropriate 5-halovaleric acid (commercially available, e.g., Aldrich Chemical Co., Milwaukee, Wis.). Both $(R^1)_p$-M and $(R^2)_p$-M are available commercially (e.g., Aldrich Chemical Co., Milwaukee, Wis.) or can be prepared by well-known methods (see e.g., Kharasch et al., *Grignard Reactions of Non-Metallic Substances*; Prentice-Hall, Englewood Cliffs, N.J., pp. 138-528 (1954) and Hartley; Patai, *The Chemistry of the Metal-Carbon Bond*, Vol. 4, Wiley: New York, pp. 159-306 and pp. 162-175 (1989), both citations are hereby expressly incorporated herein by reference). The reaction of a first $((R^1)_p\text{-M})$ then a second $((R^2)_p\text{-M})$ organometallic reagent with esters 4 can be performed using the general procedures referenced in March, J. *Advanced Organic Chemistry; Reactions Mechanisms, and Structure*, 4th ed., 1992, pp. 920-929 and Eicher, Patai, *The Chemistry of the Carbonyl Group*, pt. 1, pp. 621-693; Wiley: New York, (1966), hereby expressly incorporated herein by reference. For example, the synthetic procedure described in Comins et al., 1981, *Tetrahedron Lett.* 22:1085, hereby expressly incorporated herein by reference, can be used. As one example, the reaction can be performed by adding an organic solution of $(R^1)_p$-M (about 0.5 to about 1 equivalents) to a stirred, cooled (about 0° C. to about −80° C.) solution comprising esters 4, under an inert atmosphere (e.g., nitrogen) to give a reaction mixture comprising ketones 5. Preferably, $(R^1)_p$-M is added at a rate such that the reaction-mixture temperature remains within about one to two degrees of the initial reaction-mixture temperature. The progress of the reaction can be followed by using an appropriate analytical method, such as thin-layer chromatography or high-performance-liquid chromatography. Next, an organic solution of $(R^2)_p$-M (about 0.5 to about 1 equivalent) is added to the reaction mixture comprising ketones 5 in the same manner used to add $(R^1)_p$-M. After the reaction providing alcohols 6 is substantially complete, the reaction mixture can be quenched and the product can be isolated by workup. Suitable solvents for obtaining alcohols 6 include, but are not limited to, dichloromethane, diethyl ether, tetrahydrofuran, benzene, toluene, xylene, hydrocarbon solvents (e.g., pentane, hexane, and heptane), and mixtures thereof. Preferably, the organic solvent is diethyl ether or tetrahydrofuran. Next, alcohols 6 are converted to mono-protected diols X, wherein n is 0, using the well-known Williamson ether synthesis. This involves reacting alcohols 6 with —O—PG, wherein —PG is a hydroxy-protecting group. For a general discussion of the Williamson ether synthesis, See March, J. *Advanced Organic Chemistry; Reactions Mechanisms, and Structure*, 4th ed., 1992, pp. 386-387, and for a list of procedures and reagents useful in the Williamson ether synthesis, See, for example, Larock *Comprehensive Organic Transformations*; VCH: New York, 1989, pp. 446-448, both of which references are incorporated herein by reference. As used herein, the term "hydroxy-protecting group" means a group that is reversibly attached to a hydroxy moiety that renders the hydroxy moiety unreactive during a subsequent reaction(s) and that can be selectively cleaved to regenerate the hydroxy moiety once its protecting purpose has been served. Examples of hydroxy-protecting groups are found in Greene, T. W., *Protective Groups in Organic Synthesis*, 3rd edition 17-237 (1999), hereby expressly incorporated herein by reference. Preferably, the hydroxy-protecting group is stable in a basic reaction medium, but can be cleaved by acid. Examples of suitable base-stable acid-labile hydroxy-protecting groups suitable for use with the invention include, but are not limited to, ethers, such as methyl, methoxy methyl, methylthiomethyl, methoxyethoxymethyl, bis(2-chloroethoxy)methyl, tetrahydropyranyl, tetrahydrothiopyranyl, tetrahyrofuranyl, tetrahydrothiofuranyl, 1-ethoxy-ethyl, 1-methyl-1-methoxyethyl, t-butyl, allyl, benzyl, o-nitrobenzyl, triphenylmethyl, a-naphthyldiphenylmethyl, p-methoxyphenyldiphenylmethyl, 9-(9-phenyl-10-oxo)an-thranyl, trimethylsilyl, isopropyldimethylsilyl, t-butyldim-ethylsilyl, t-butyldiphenylsilyl, tribenzylsilyl, and triisopropylsilyl; and esters, such as pivaloate, adamantoate, and 2,4,6-trimethylbenzoate. Ethers are preferred, particularly straight chain ethers, such as methyl ether, methoxymethyl ether, methylthiomethyl ether, methoxyethoxymethyl ether, bis(2-chloroethoxy)methyl ether. Preferably —PG is methoxymethyl ($CH_3OCH_2$-). Reaction of alcohols 6 with —O—PG under the conditions of the Williamson ether synthesis involves adding a base to a stirred organic solution comprising HO—PG (e.g., methoxymethanol), maintained at a constant temperature within the range of about 0° C. to about 80° C., preferably at about room temperature. Preferably, the base is added at a rate such that the reaction-mixture temperature remains within about one to two degrees of the initial reaction-mixture temperature. The base can be added as an organic solution or in undiluted form. Preferably, the base will have a base strength sufficient to deprotonate a proton, wherein the proton has a $pK_a$ of greater than about 15, preferably greater than about 20. As is well known in the art, the $pK_a$ is a measure of the acidity of an acid H—A, according to the equation $pK_a = -\log K_a$, wherein $K_a$ is the equilibrium constant for the proton transfer. The acidity of an acid H—A is proportional to the stability of its conjugate base —A. For tables listing pK$_a$ values for various organic acids and a discussion on pK$_a$ measurement, see March, J. *Advanced Organic Chemistry; Reactions Mechanisms, and Structure,* 4th ed., 1992, pp. 248-272, incorporated herein by reference. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. The preferred base is lithium diisopropylamide. Solvents suitable for reacting alcohols 6 with —OPG include, but are not limited, to dimethyl sulfoxide, dichloromethane, ethers, and mixtures thereof, preferably tetrahydrofuran. After addition of the base, the reaction mixture can be adjusted to within a temperature range of about 0° C. to about room temperature and alcohols 6 can be added, preferably at a rate such that the reaction-mixture temperature remains within about one to two degrees of the initial reaction-mixture temperature. Alcohols 6 can be diluted in an organic solvent or added in their undiluted form. The resulting reaction mixture is stirred until the reaction is substantially complete as determined by using an appropriate analytical method, preferably by gas chromatography, then the mono-protected diols X can be isolated by workup and purification.

Next, Scheme 1 outlines a method useful for synthesizing mono-protected diols X, wherein n is 1. First, compounds 7, wherein E is a suitable leaving group, are reacted with compounds 8, wherein R$^1$ and R$^2$ are as defined above and R$^8$ is H, (C$_1$-C$_6$)alkyl or (C$_6$)aryl, providing compounds 9. Suitable leaving groups are well known in the art, for example, but not limited to halides, such as chloride, bromide, and iodide; aryl- or alkylsulfonyloxy, substituted arylsulfonyloxy (e.g., tosyloxy or mesyloxy); substituted alkylsulfonyloxy (e.g., haloalkylsulfonyloxy); (C$_6$)aryloxy or subsituted (C$_6$)aryloxy; and acyloxy groups. Compounds 7 are available commercially (e.g., Aldrich Chemical Co., Milwaukee, Wis.) or can be prepared by well-known methods such as halogenation or sulfonation of butanediol. Compounds 8 are also available commercially (e.g., Aldrich Chemical Co., Milwaukee, Wis.) or by well-known methods, such as those listed in Larock *Comprehensive Organic Transformations*; Wiley-VCH: New York, 1999, pp. 1754-1755 and 1765. A review on alkylation of esters of type 8 is given by J. Mulzer in *Comprehensive Organic Functional Transformations*, Pergamon, Oxford 1995, pp. 148-151 and exemplary synthetic procedures for reacting compounds 7 with compounds 8 are described in U.S. Pat. No. 5,648,387, column 6 and Ackerly, et al., *J. Med. Chem.* 1995, pp. 1608, all of which citations are hereby expressly incorporated herein by reference. The reaction requires the presence of a suitable base. Preferably, a suitable base will have a pK$_a$ of greater than about 25, more preferably greater than about 30. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; hydride bases such as sodium hydride and potassium hydride. Metal amide bases, such as lithium diisopropylamide are preferred. Preferably, to react compounds 7 with compounds 8, a solution of about 1 to about 2 equivalents of a suitable base is added to a stirred solution comprising esters 8 and a suitable organic solvent, under an inert atmosphere, the solution maintained at a constant temperature within the range of about –95° C. to about room temperature, preferably at about –78° C. to about –20° C. Preferably, the base is diluted in a suitable organic solvent before addition. Preferably, the base is added at a rate of about 1.5 moles per hour. Organic solvents suitable for the reaction of compounds 7 with the compounds 8 include, but are not limited to, dichloromethane, diethyl ether, tetrahydrofuran, dimethylformamide, dimethyl sulfoxide, benzene, toluene, xylene, hydrocarbon solvents (e.g., pentane, hexane, and heptane), and mixtures thereof. After addition of the base, the reaction mixture is allowed to stir for about 1 to about 2 hours, and a compound 7, preferably dissolved in a suitable organic solvent, is added, preferably at a rate such that the reaction-mixture temperature remains within about one to two degrees of the initial reaction-mixture temperature. After addition of compounds 7, the reaction-mixture temperature can be adjusted to within a temperature range of about –20° C. to about room temperature, preferably to about room temperature, and the reaction mixture is allowed to stir until the reaction is substantially complete as determined by using an appropriated analytical method, preferably thin-layer chromatography or high-performance liquid chromatography. Then the reaction mixture is quenched and compounds 9, wherein n is 1 can be isolated by workup. Compounds 10 are then synthesized by reacting compounds 9 with —O—PG according to the protocol described above for reacting alcohols 6 with —O—PG. Next, compounds 10 can be converted to mono-protected diols X, wherein n is 1, by reduction of the ester group of compounds 10 to an alcohol group with a suitable reducing agent. A wide variety of reagents are available for reduction of such esters to alcohols, e.g., see M. Hudlicky, *Reductions in Organic Chemistry,* 2nd ed., 1996 pp. 212-217, hereby expressly incorporated herein by reference. Preferably, the reduction is effected with a hydride type reducing agent, for example, lithium aluminum hydride, lithium borohydride, lithium triethyl borohydride, diisobutylaluminum hydride, lithium trimethoxyaluminum hydride, or sodium bis(2-methoxy) aluminum hydride. For exemplary procedures for reducing esters to alcohols, see Nystrom et al., 1947, *J. Am. Chem. Soc.* 69:1197; and Moffet et al., 1963, *Org. Synth., Collect.* 834(4), lithium aluminum hydride; Brown et al., 1965, *J. Am. Chem. Soc.* 87:5614, lithium trimethoxyaluminum hydride; Cemy et al., 1969, *Collect. Czech. Chem. Commun.* 34:1025, sodium bis(2-methoxy)aluminum hydride; Nystrom et al., 1949, *J. Am. Chem.* 71:245, lithium borohydride; and Brown et al., 1980, *J. Org. Chem.* 45: 1, lithium triethyl borohydride, all of which citations are hereby expressly incorporated herein by reference. Preferably, the reduction is conducted by adding an organic solution of compounds 10 to a stirred mixture comprising a reducing agent, preferably lithium aluminum hydride, and an organic solvent. During the addition, the reaction mixture is maintained at a constant temperature within the range of about –20° C. to about 80° C., preferably at about room temperature. Organic solvents suitable for reacting 9 with —OPG include, but are not limited to, dichloromethane, diethyl ether, tetrahydrofuran or mixtures thereof, preferably tetrahydrofuran. After the addition, the reaction mixture is stirred at a constant temperature within the range of about room temperature to about 60° C., until the reaction is substantially complete as determined by using an appropriate analytical method, preferably thin-layer chromatography or high-performance-liquid chromatography. Then the reaction mixture can be quenched and mono-protected diols X, wherein n is 1, can be isolated by workup and purification.

Scheme 1 next illustrates a three step synthetic sequence for homologating mono-protected diols X comprising: (a) halogenation (converting —$CH_2OH$ to —$CH_2$Hal); (b) carbonylation (replacing -Hal with —CHO); and (c) reduction (converting —CHO to —$CH_2OH$), wherein a reaction sequence of (a), (b), and (c) increases the value of n by 1. In step (a) protected halo-alcohols 11, wherein Hal is a halide selected from the group of chloro, bromo, or iodo, preferably iodo, can be prepared by halogenating mono-protected diols X, by using well-known methods (for a discussion of various methods for conversion of alcohols to halides see March, J. *Advanced Organic Chemistry; Reactions Mechanisms, and Structure*, 4th ed., 1992, pp. 431-433, hereby expressly incorporated herein by reference). For example, protected iodo-alcohols 11 can be synthesized starting from mono-protected diols X by treatment with $Ph_3/I_2$/imidazole (Garegg et al., 1980, *J.C.S Perkin I* 2866); 1,2-dipheneylene phosphorochloridite/$I_2$ (Corey et al., 1967, *J. Org. Chem.* 82:4160); or preferably with $Me_3SiCl$/NaI (Olah et al., 1979, *J. Org. Chem.* 44:8, 1247), all of which citations are hereby expressly incorporated herein by reference. Step (b); carbonylation of alkyl halides, such as protected halo-alcohols 11, is reviewed in Olah et al., 1987, *Chem Rev.* 87:4, 671; and March, J., *Advanced Organic Chemistry; Reactions Mechanisms, and Structure*, 4th ed., 1992, pp. 483-484, both of which are hereby expressly incorporated herein by reference). Protected halo-alcohols 11 can be carbonylated with $Li(BF_3.Et_2O)$/$HCONMe_2$ using the procedure described in Maddaford et al., 1993, *J. Org. Chem.* 58:4132; Becker et al., 1982, *J. Org. Chem.* 3297; or Myers et al., 1992, *J. Am. Chem. Soc.* 114:9369 or, alternatively, with an organometallic/N-formylmorpholine using the procedure described in Olah et al., 1984, *J. Org. Chem.* 49:3856 or Vogtle et al., 1987, *J. Org. Chem.* 52:5560, all of which citations are hereby expressly incorporated herein by reference. The method described in Olah et al., 1984, *J. Org. Chem.* 49:3856 is preferred. Reduction step (c) useful for synthesizing mono-protected diols X from aldehydes 12, can be accomplished by well-known methods in the art for reduction of aldehydes to the corresponding alcohols (for a discussion see M. Hudlicky, *Reductions in Organic Chemistry*, 2nd ed., 1996 pp 137-139), for example, by catalytic hydrogenation (see e.g., Carothers, 1949, *J. Am. Chem. Soc.* 46:1675) or, preferably by reacting aldehydes 12 with a hydride reducing agent, such as lithium aluminum hydride, lithium borohydride, sodium borohydride (see e.g., the procedures described in Chaikin et al., 1949, *J. Am. Chem. Soc.* 71:3245; Nystrom et al., 1947, *J. Am. Chem. Soc.* 69:1197; and Nystrom et al., 1949, *J. Am. Chem.* 71:3245, all of which are hereby expressly incorporated herein by reference). Reduction with lithium aluminum hydride is preferred.

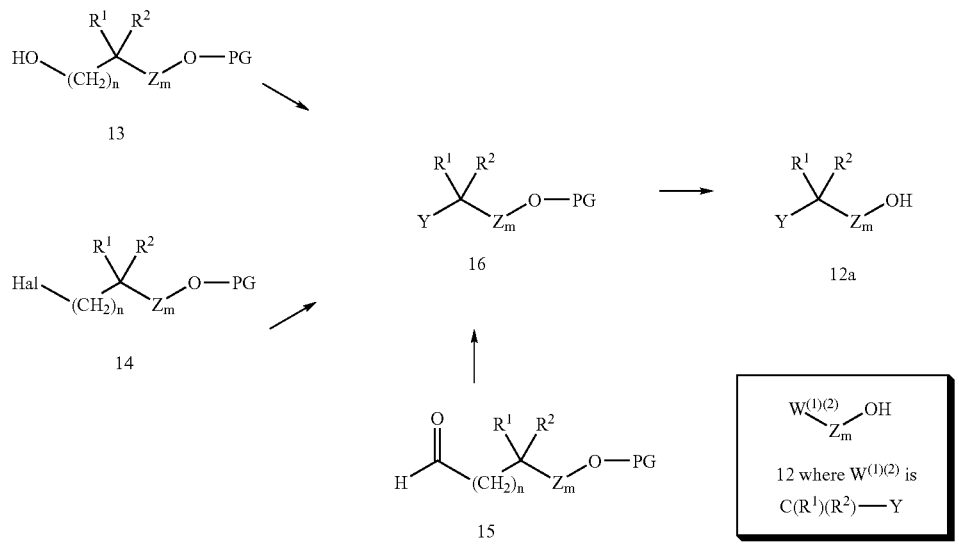

Scheme 2 outlines the method for the synthesis of protected alcohols 12a wherein Y, $R^1$, $R^2$, Z, and m are defined as above. Protected alcohols 12a correspond to compounds of the formula $W^{(1)(2)}$-Zm-OPG, wherein $W^{(1)(2)}$ is $C(R^1)(R^2$—Y.

Protected alcohols 16, wherein Y comprises a —C(O)OH group, can be synthesized by oxidizing mono-protected diols X with an agent suitable for oxidizing a primary alcohol to a carboxylic acid (for a discussion see M. Hudlicky, *Oxidations in Organic Chemistry*, ACS Monograph 186, 1990, pp. 127-130, hereby expressly incorporated herein by reference). Suitable oxidizing agents include, but are not limited to, pyridinium dichromate (Corey et al., 1979, *Tetrahedron Lett.* 399); manganese dioxide (Ahrens et al., 1967, *J. Heterocycl. Chem.* 4:625); sodium permanganate monohydrate (Menger et al., 1981, *Tetrahedron Lett.* 22:1655); and potassium permanganate (Sam et al., 1972, *J. Am. Chem. Soc.* 94:4024), all of which citations are hereby expressly incorporated herein by reference. The preferred oxidizing reagent is pyridinium dichromate. In an alternative synthetic procedure, protected alcohols 16, wherein Y comprises a —C(O)OH group, can be synthesized by treatment of protected halo-alcohols 15, wherein X is iodo, with CO or $CO_2$, as described in Bailey et al., 1990, *J. Org. Chem.* 55:5404 and Yanagisawa et al., 1994, *J. Am. Chem. Soc.* 116:6130, the two of which citations are hereby expressly incorporated herein by reference. Protected alcohols 16, wherein Y comprises —C(O)OR$^5$, wherein R$^5$ is as defined above, can be synthesized by oxidation of mono-protected diols X in the presence of R$^5$OH (see generally, March, J. *Advanced Organic Chemistry; Reactions Mechanisms, and Structure,* 4th ed., 1992, p. 1196). An exemplary procedure for such an oxidation is described in Stevens et al., 1982, *Tetrahedron Lett.* 23:4647 (HOCl); Sundararaman et al., 1978, *Tetrahedron Lett.* 1627 ($O_3$/KOH); Wilson et al., 1982, *J. Org. Chem.* 47:1360 (t-BuOOH/Et$_3$N); and Williams et al., 1988, *Tetrahedron Lett.* 29:5087 (Br$_2$), the four of which citations are hereby expressly incorporated herein by reference. Preferably, protected alcohols 16, wherein Y comprises a —C(O)OR$^5$ group are synthesized from the corresponding carboxylic acid (i.e., 16, wherein Y comprises —C(O)OH) by esterification with R$^5$OH (e.g., see March, J., *Advanced Organic Chemistry; Reactions Mechanisms, and Structure,* 4th ed., 1992, p. 393-394, hereby expressly incorporated herein by reference). In another alternative synthesis, protected alcohols 16, wherein Y comprises —C(O)OR$^5$, can be prepared from protected halo-alcohols 14 by carbonylation with transition metal complexes (see e.g., March, J. *Advanced Organic Chemistry; Reactions Mechanisms, and Structure,* 4th ed., 1992, p. 484-486; Urata et al., 1991, *Tetrahedron Lett.* 32:36, 4733); and Ogata et al., 1969, *J. Org. Chem.* 3985, the three of which citations are hereby expressly incorporated herein by reference).

Protected alcohols 16, wherein Y comprises —OC(O)R$^5$, wherein R$^5$ is as defined above, can be prepared by acylation of mono-protected diols X with a carboxylate equivalent such as an acyl halide (i.e., R$^5$C(O)-Hal, wherein Hal is iodo, bromo, or chloro, see e.g., March, J. *Advanced Organic Chemistry; Reactions Mechanisms, and Structure,* 4th ed., 1992, p. 392 and *Org. Synth. Coll.* Vol. III, Wiley, N.Y., pp. 142, 144, 167, and 187 (1955)) or an anhydride (i.e., R$^5$C(O)—O—(O)CR$^5$, see e.g., March, J. *Advanced Organic Chemistry; Reactions Mechanisms, and Structure,* 4th ed., 1992, p. 392-393 and *Org. Synth. Coll.* Vol. III, Wiley, N.Y., pp. 11, 127, 141, 169, 237, 281, 428, 432, 690, and 833 (1955), all of which citations are hereby expressly incorporated herein by reference). Preferably, the reaction is conducted by adding a base to a solution comprising mono-protected diols X, a carboxylate equivalent, and an organic solvent, which solution is preferably maintained at a constant temperature within the range of 0° C. to about room temperature. Solvents suitable for reacting mono-protected diols X with a carboxylate equivalent include, but are not limited to, dichloromethane, toluene, and ether, preferably dichloromethane. Suitable bases include, but are not limited to, hydroxide sources, such as sodium hydroxide, potassium hydroxide, sodium carbonate, or potassium carbonate; or an amine such as triethylamine, pyridine, or dimethylaminopyridine, amines are preferred. The progress of the reaction can be followed by using an appropriate analytical technique, such as thin layer chromatography or high performance liquid chromatography and when substantially complete, the product can be isolated by workup and purified if desired.

Protected alcohols 16, wherein Y comprises one of the following phosphate ester groups

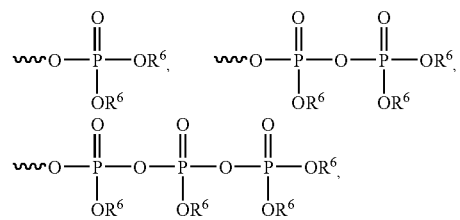

wherein R$^6$ is defined as above, can be prepared by phosphorylation of mono-protected diols X according to well-known methods (for a general reviews, see Corbridge *Phosphorus: An Outline of its Chemistry, Biochemistry, and Uses,* Studies in Inorganic Chemistry, 3rd ed., pp. 357-395 (1985); Ramirez et al., 1978, *Acc. Chem. Res.* 11:239; and Kalckare *Biological Phosphorylations,* Prentice-Hall, New York (1969); J. B. Sweeny in *Comprehensive Organic Functional Group Transformations,* A. R. Katritzky, O. Meth-Cohn and C. W. Rees, Eds. Pergamon: Oxford, 1995, vol 2, pp. 104-109, the four of which are hereby expressly incorporated herein by reference). Protected alcohols 16 wherein Y comprises a monophosphate group of the formula:

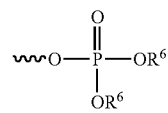

wherein R$^6$ is defined as above, can be prepared by treatment of mono-protected diol X with phosphorous oxychloride in a suitable solvent, such as xylene or toluene, at a constant temperature within the range of about 100° C. to about 150° C. for about 2 hours to about 24 hours. After the reaction is deemed substantially complete, by using an appropriate analytical method, the reaction mixture is hydrolyzed with R$^6$-OH. Suitable procedures are referenced in Houben-Weyl, Methoden der Organische Chemie, Georg Thieme Verlag Stuttgart 1964, vol. XII/2, pp. 143-210 and 872-879, hereby expressly incorporated herein by reference. Alternatively, when both R$^6$ are hydrogen, can be synthesized by reacting mono-protected diols X with silyl polyphosphate (Okamoto et al., 1985, *Bull Chem. Soc. Jpn.* 58:3393, hereby expressly incorporated herein by reference) or by hydrogenolysis of their benzyl or phenyl esters (Chen et al., 1998, *J. Org. Chem.* 63:6511, hereby expressly incorporated herein by reference). In another alternative procedure, when R$^6$ is ($C_1$-$C_6$)alkyl, ($C_2$-$C_6$)alkenyl, or ($C_2$-$C_6$)alkynyl, the mono-phosphate esters can be prepared by reacting mono-protected diols X with appropriately substituted phophoramidites followed by oxidation of the intermediate with m-chloroperbenzoic acid (Yu et al., 1988, *Tetrahedron Lett.* 29:979, hereby expressly incorporated herein by reference) or by reacting mono-protected diols X with dialkyl or diaryl substituted phosphorochloridates (Pop, et al, 1997, *Org. Prep. and Proc. Int.* 29:341, hereby expressly incorporated herein by reference). The phosphoramidites are commercially available (e.g., Aldrich Chemical Co., Milwaukee, Wis.) or readily prepared according to literature procedures (see e.g., Uhlmann et al. 1986, *Tetrahedron Lett.* 27:1023 and Tanaka et al., 1988, *Tetrahedron Lett.* 29:199, both of which are hereby expressly incorporated herein by reference). The phosphorochloridates are also commercially available (e.g., Aldrich Chemical Co., Milwaukee, Wis.) or prepared according to literature methods (e.g., Gajda et al, 1995, *Synthesis* 25:4099. In still another alternative synthesis, protected alcohols 16, wherein Y comprises a monophosphate group and $R^6$ is alkyl or aryl, can be prepared by reacting $IP^+(OR^6)_3$ with mono-protected diols X according to the procedure described in Stowell et al., 1995, *Tetrahedron Lett.* 36:11, 1825 or by alkylation of protected halo alcohols 14 with the appropriate dialkyl or diaryl phosphates (see e.g., Okamoto, 1985, *Bull Chem. Soc. Jpn.* 58:3393, hereby expressly incorporated herein by reference).

Protected alcohols 16 wherein Y comprises a diphosphate group of the formula

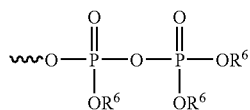

wherein $R^6$ is defined as above, can be synthesized by reacting the above-discussed monophosphates of the formula:

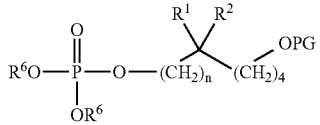

with a phosphate of the formula

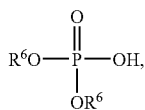

(commercially available, e.g., Aldrich Chemical Co., Milwaukee, Wis.), in the presence of carbodiimide such as dicyclohexylcarbodiimide, as described in Houben-Weyl, *Methoden der Organische Chemie*, Georg Thieme Verlag Stuttgart 1964, vol. XII/2, pp. 881-885. In the same fashion, protected alcohols 16, wherein Y comprises a triphosphate group of the formula:

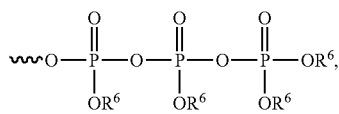

can be synthesized by reacting the above-discussed diphosphate protected alcohols, of the formula:

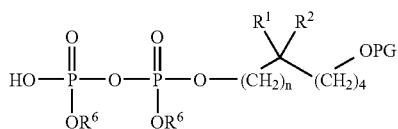

with a phosphate of the formula:

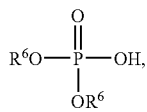

as described above. Alternatively, when $R^6$ is H, protected alcohols 16 wherein Y comprises the triphosphate group, can be prepared by reacting mono-protected diols X with salicyl phosphorochloridite and then pyrophosphate and subsequent cleavage of the adduct thus obtained with iodine in pyridine as described in Ludwig et al., 1989, *J. Org. Chem.* 54:631, hereby expressly incorporated herein by reference.

Protected alcohols 16, wherein Y is —$SO_3H$ or a heterocyclic group selected from the group consisting of:

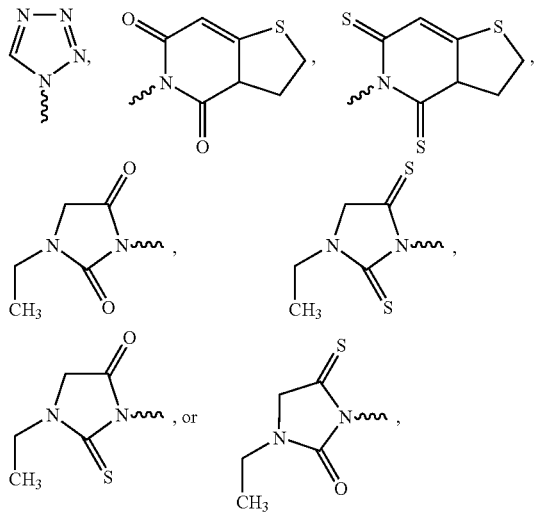

can be prepared by halide displacement from protected halo-alcohols 14. Thus, when Y is —$SO_3H$, protected alcohols 16 can by synthesized by reacting protected halo-alcohols 14 with sodium sulfite as described in Gilbert *Sulfonation and Related Reactions*; Wiley: New York, 1965, pp. 136-148 and pp. 161-163; *Org. Synth. Coll.* Vol. II, Wiley, N.Y., 558, 564 (1943); and *Org. Synth. Coll.* Vol. IV, Wiley, N.Y., 529 (1963), all three of which are hereby expressly incorporated herein by reference. When Y is one of the above-mentioned heterocycles, protected alcohols 16 can be prepared by reacting protected halo-alcohols 14 with the corresponding heterocycle in the presence of a base. The heterocycles are available commercially (e.g., Aldrich Chemical Co., Milwaukee, Wis.) or prepared by well-known synthetic methods (see the procedures described in Ware, 1950, *Chem. Rev.* 46:403-470, hereby expressly incorporated herein by reference). Preferably, the reaction is conducted by stirring a mixture comprising 14, the heterocycle, and a solvent at a constant temperature within the range of about room temperature to about 100° C., preferably within the range of about 50° C. to about 70° C. for about 10 to about 48 hours. Suitable bases include hydroxide bases such as sodium hydroxide, potassium hydroxide, sodium carbonate, or potassium carbonate. Preferably, the solvent used in forming protected alcohols 16 is selected from dimethylformamide; formamide; dimethyl sulfoxide; alcohols, such as methanol or ethanol; and mixtures thereof. The progress of the reaction can be followed by using an appropriate analytical technique, such as thin layer chromatography or high performance liquid chromatography and when substantially complete, the product can be isolated by workup and purified if desired.

Protected alcohols 16, wherein Y is a heteroaryl ring selected from

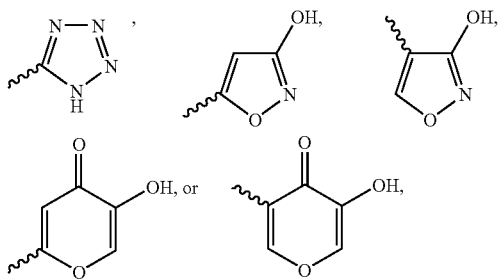

can be prepared by metallating the suitable heteroaryl ring then reacting the resulting metallated heteroaryl ring with protected halo-alcohols 14 (for a review, see Katritzky *Handbook of Heterocyclic Chemistry*, Pergamon Press: Oxford 1985). The heteroaryl rings are available commercially or prepared by well-known synthetic methods (see e.g., Joule et al., *Heterocyclic Chemistry*, 3rd ed., 1995; De Sarlo et al., 1971, *J. Chem. Soc.* (*C*) 86; Oster et al., 1983, *J. Org. Chem.* 48:4307; Iwai et al., 1966, *Chem. Pharm. Bull.* 14:1277; and U.S. Pat. No. 3,152,148, all of which citations are hereby expressly incorporated herein by reference). As used herein, the term "metallating" means the forming of a carbon-metal bond, which bond may be substantially ionic in character. Metallation can be accomplished by adding about 2 equivalents of strong organometallic base, preferably with a p$K_a$ of about 25 or more, more preferably with a p$K_a$ of greater than about 35, to a mixture comprising a suitable organic solvent and the heterocycle. Two equivalents of base are required: one equivalent of the base deprotonates the —OH group or the —NH group, and the second equivalent metallates the heteroaryl ring. Alternatively, the hydroxy group of the heteroaryl ring can be protected with a base-stable, acid-labile protecting group as described in Greene, T. W., *Protective Groups in Organic Synthesis*, 3rd edition 17-237 (1999), hereby expressly incorporated herein by reference. Where the hydroxy group is protected, only one equivalent of base is required. Examples of suitable base-stable, acid-labile hydroxyl-protecting groups, include but are not limited to, ethers, such as methyl, methoxy methyl, methylthiomethyl, methoxyethoxymethyl, bis(2-chloroethoxy)methyl, tetrahydropyranyl, tetrahydrothiopyranyl, tetrahyrofuranyl, tetrahydrothiofuranyl, 1-ethoxyethyl, 1-methyl-1-methoxyethyl, t-butyl, allyl, benzyl, o-nitrobenzyl, triphenylmethyl, α-naphthyldiphenylmethyl, p-methoxyphenyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, triisopropylsilyl; and esters, such as pivaloate, adamantoate, and 2,4,6-trimethylbenzoate. Ethers are preferred, particularly straight chain ethers, such as methyl ether, methoxymethyl ether, methylthiomethyl ether, methoxyethoxymethyl ether, bis(2-chloroethoxy)methyl ether. Preferably, the p$K_a$ of the base is higher than the p$K_a$ of the proton of the heterocycle to be deprotonated. For a listing of p$K_a$s for various heteroaryl rings, see Fraser et al., 1985, *Can. J. Chem.* 63:3505, hereby expressly incorporated herein by reference. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. If desired, the organometallic base can be activated with a complexing agent, such as N,N,N',N'-tetramethylethylenediamine or hexamethylphosphoramide (1970, *J. Am. Chem. Soc.* 92:4664, hereby expressly incorporated herein by reference). Solvents suitable for synthesizing protected alcohols 16, wherein Y is a heteroaryl ring include, but are not limited to, diethyl ether; tetrahydrofuran; and hydrocarbons, such as pentane. Generally, metallation occurs alpha to the heteroatom due to the inductive effect of the heteroatom, however, modification of conditions, such as the identity of the base and solvents, order of reagent addition, reagent addition times, and reaction and addition temperatures can be modified by one of skill in the art to achieve the desired metallation position (see e.g., Joule et al., *Heterocyclic Chemistry*, 3rd ed., 1995, pp. 30-42, hereby expressly incorporated herein by reference) Alternatively, the position of metallation can be controlled by use of a halogenated heteroaryl group, wherein the halogen is located on the position of the heteroaryl ring where metallation is desired (see e.g., Joule et al., *Heterocyclic Chemistry*, 3rd ed., 1995, p. 33 and Saulnier et al., 1982, *J. Org. Chem.* 47:757, the two of which citations are hereby expressly incorporated herein by reference). Halogenated heteroaryl groups are available commercially (e.g., Aldrich Chemical Co., Milwaukee, Wis.) or can be prepared by well-known synthetic methods (see e.g., Joule et al., *Heterocyclic Chemistry*, 3rd ed., 1995, pp. 78, 85, 122, 193, 234, 261, 280, 308, hereby expressly incorporated herein by reference). After metallation, the reaction mixture comprising the metallated heteroaryl ring is adjusted to within a temperature range of about 0° C. to about room temperature and protected halo-alcohols 14 (diluted with a solvent or in undiluted form) are added, preferably at a rate such that the reaction-mixture temperature remains within about one to two degrees of the initial reaction-mixture temperature. After addition of protected halo-alcohols 14, the reaction mixture is stirred at a constant temperature within the range of about room temperature and about the solvent's boiling temperature and the reaction's progress can be monitored by the appropriate analytical technique, preferably thin-layer chromatography or high-performance liquid chromatography. After the reaction is substantially complete, protected alcohols 16 can be isolated by workup and purification. It is to be understood that conditions, such as the identity of protected halo-alcohol 14, the base, solvents, orders of reagent addition, times, and temperatures, can be modified by one of skill in the art to optimize the yield and selectivity. Exemplary procedures that can be used in such a transformation are described in Shirley et al., 1995, *J. Org. Chem.* 20:225; Chadwick et al., 1979, *J. Chem. Soc., Perkin Trans.* 1 2845; Rewcastle, 1993, *Adv. Het. Chem.* 56:208; Katritzky et al., 1993, *Adv. Het. Chem.* 56:155; and Kessar et al., 1997, *Chem. Rev.* 97:721. When Y is

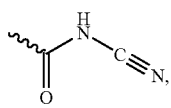

protected alcohols 16 can be prepared from their corresponding carboxylic acid derivatives (16, wherein Y is —CO$_2$H) as described in Belletire et al, 1988, *Synthetic Commun.* 18:2063 or from the corresponding acylchlorides (16, wherein Y is —O-halo) as described in Skinner et al., 1995, *J. Am. Chem. Soc.* 77:5440, both citations are hereby expressly incorporated herein by reference. The acylhalides can be prepared from the carboxylic acids by well known procedures such as those described in March, J., *Advanced Organic Chemistry; Reactions Mechanisms, and Structure*, 4th ed., 1992, pp. 437-438, hereby expressly incorporated herein by reference. When Y is

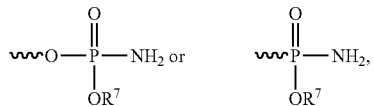

wherein R$^7$ is as defined above, protected alcohols 16 can be prepared by first reacting protected halo-alcohols 15 with a trialkyl phosphite according to the procedure described in Kosolapoff, 1951, *Org. React.* 6:273 followed by reacting the derived phosphonic diester with ammonia according to the procedure described in Smith et al., 1957, *J. Org. Chem.* 22:265, hereby expressly incorporated herein by reference.

When Y is

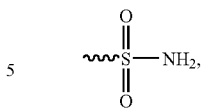

protected alcohols 16 can be prepared by reacting their sulphonic acid derivatives (i.e., 16, wherein Y is —SO$_3$H) with ammonia as described in Sianesi et al., 1971, *Chem. Ber.* 104:1880 and Campagna et al., 1994, *Farmaco, Ed. Sci.* 49:653, both of which citations are hereby expressly incorporated herein by reference).

As further illustrated in Scheme 2, protected alcohols 16 can be deprotected providing alcohols 20a. The deprotection method depends on the identity of the alcohol-protecting group, see e.g., the procedures listed in Greene, T. W., *Protective Groups in Organic Synthesis*, 3rd edition 17-237 (1999), particularly see pages 48-49, hereby expressly incorporated herein by reference. One of skill in the art will readily be able to choose the appropriate deprotection procedure. When the alcohol is protected as an ether function (e.g., methoxymethyl ether), the alcohol is preferably deprotected with aqueous or alcoholic acid. Suitable deprotection reagents include, but are not limited to, aqueous hydrochloric acid, p-toluenesulfonic acid in methanol, pyridinium-p-toluenesulfonate in ethanol, Amberlyst H-15 in methanol, boric acid in ethylene-glycol-monoethylether, acetic acid in a water-tetrahydrofuran mixture, aqueous hydrochloric acid is preferred. Examples of such procedures are described, respectively, in Bemady et al., 1979, *J. Org. Chem.* 44:1438; Miyashita et al., 1977, *J. Org. Chem.* 42:3772; Johnston et al., 1988, *Synthesis* 393; Bongini et al., 1979, *Synthesis* 618; and Hoyer et al., 1986, *Synthesis* 655; Gigg et al., 1967, *J. Chem. Soc. C*, 431; and Corey et al., 1978, *J. Am. Chem. Soc.* 100:1942, all of which are hereby expressly incorporated herein by reference.

Scheme 3: Synthesis of Compounds of Formula 13a, which correspond to W$^{(1)(2)}$—Z$_m$—OH, Wherein W$^{(1)(2)}$ is a Lactone Group

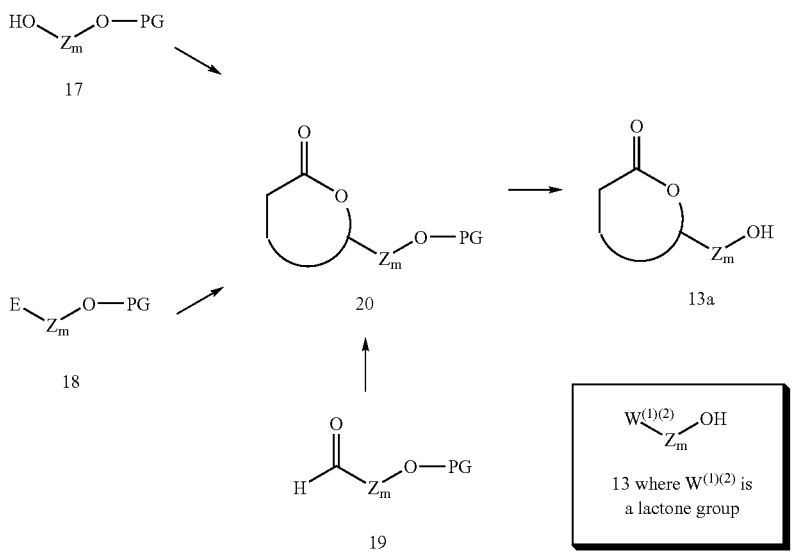

Scheme 3 depicts the synthesis of protected lactone alcohols 20 and lactone alcohols 13a. Compounds 20 and 13a correspond to compounds of the formula $W^{(1)(2)}$-$Z_m$-OPG and $W^{(1)(2)}$-$Z_m$-OH respectively, wherein $W^{(1)(2)}$ is a lactone group selected from:

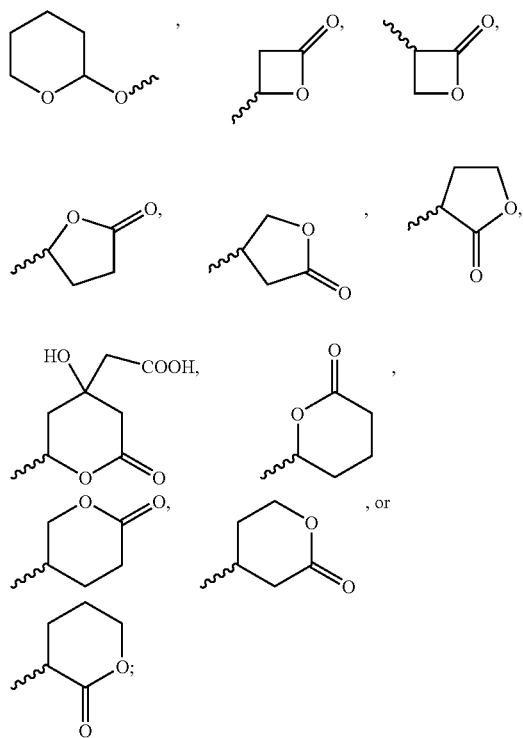

Protected lactone alcohols 20 can be prepared from compounds of the formula 17, 18, or 19 by using well-known condensation reactions and variations of the Michael reaction. Methods for the synthesis of lactones are disclosed in Multzer in *Comprehensive Organic Functional Group Transformations*, A. R. Katritzky, O. Meth-Cohn and C. W. Rees, Eds. Pergamon: Oxford, 1995, vol 5, pp. 161-173, hereby expressly incorporated herein by reference. Monoprotected diols 19, electrophilic protected alcohols 18, and aldehydes 19 are readily available ether commercially (e.g., Aldrich Chemical Co., Milwaukee, Wis.) or by well known synthetic procedures.

When $W^{(1)(2)}$ is a beta-lactone group of the formula:

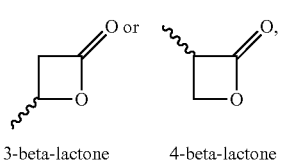

3-beta-lactone    4-beta-lactone protected lactone alcohols 20 can be prepared from aldehydes 19 and electrophilic protected alcohols 18, respectively, by a one-pot-addition-lactonization according to the procedure of Masamune et al., 1976, *J. Am. Chem. Soc.* 98:7874 and Danheiser et al., 1991, *J. Org. Chem.* 56:1176, both of which are hereby expressly incorporated herein by reference. This one-pot-addition-lactonization methodology has been reviewed by Multzer in *Comprehensive Organic Functional Group Transformations*, A. R. Katritzky, O. Meth-Cohn and C. W. Rees, Eds. Pergamon: Oxford, 1995, vol 5, pp. 161, hereby expressly incorporated herein by reference When $W^{(1)(2)}$ is a gamma- or delta-lactone group of the formula:

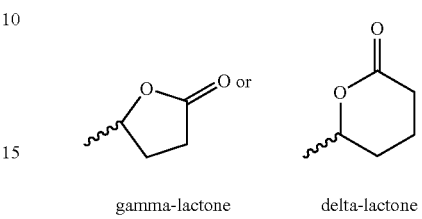

gamma-lactone    delta-lactone protected lactone alcohols 20 can be prepared from aldehydes 19 according to well known synthetic methodology. For example, the methodology described in Masuyama et al., 2000, *J. Org. Chem.* 65:494; Eisch et al., 1978, *J. Organo. Met. Chem.* C8 160; Eaton et al., 1947, *J. Org. Chem.* 37:1947; Yunker et al., 1978, *Tetrahedron Lett.* 4651; Bhanot et al., 1977, *J. Org. Chem.* 42:1623; Ehlinger et al., 1980, *J. Am. Chem. Soc.* 102:5004; and Raunio et al., 1957, *J. Org. Chem.* 22:570, all of which citations are hereby expressly incorporated herein by reference. For instance, as described in Masuyama et al., 2000, *J. Org. Chem.* 65:494, aldehydes 19 can be treated with about 1 equivalent of a strong organometallic base, preferably with a $pK_a$ of about 25 or more, more preferably with a $pK_a$ of greater than about 35, in a suitable organic solvent to give a reaction mixture. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. The reaction-mixture temperature is adjusted to within the range of about 0° C. to about 100° C., preferably about room temperature to about 50° C., and a halide of the formula:

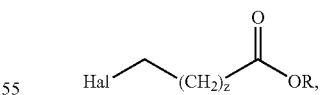

wherein z is 1 or 2 (diluted with a solvent or in undiluted form) is added. The reaction mixture is stirred for a period of about 2 hours to about 48 hours, preferably about 5 to about 10 hours, during which time the reaction's progress can be followed by using an appropriate analytical technique, such as thin layer chromatography or high performance liquid chromatography. When the reaction is deemed substantially complete, protected lactone alcohols 20 can be isolated by workup and purified if desired. When $W^{(1)(2)}$ is a gamma- or delta-lactone group of the formula:

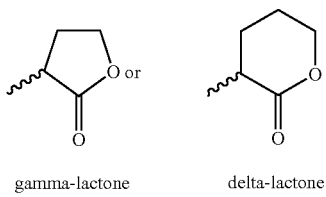

gamma-lactone        delta-lactone protected lactone alcohols 20 can be synthesized by deprotonating the corresponding lactone with a strong base providing the lactone enolate and reacting the enolate with electrophilic protected alcohols 20 (for a detailed discussion of enolate formation of active methylene compounds such as lactones, see House *Modern Synthetic Reactions*; W. A. Benjamin, Inc. Philippines 1972 pp. 492-570, and for a discussion of reaction of lactone enolates with electrophiles such as carbonyl compounds, see March, J. *Advanced Organic Chemistry; Reactions Mechanisms, and Structure,* 4th ed., 1992, pp. 944-945, both of which are hereby expressly incorporated herein by reference). Lactone-enolate formation can be accomplished by adding about 1 equivalent of a strong organometallic base, preferably with a $pK_a$ of about 25 or more, more preferably with a $pK_a$ of greater than about 35, to a mixture comprising a suitable organic solvent and the lactone. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Solvents suitable for lactone-enolate formation include, but are not limited to, diethyl ether and tetrahydrofuran. After enolate formation, the reaction-mixture temperature is adjusted to within the range of about −78° C. to about room temperature, preferably about −50° C. to about 0° C., and electrophilic protected alcohols 18 (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, protected lactone alcohols 20 can be isolated by workup and purified if desired. When $W^{(1)(2)}$ is a lactone group of the formula:

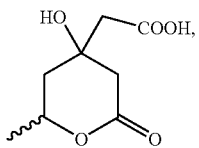

protected lactone alcohols 20 can be prepared from aldehydes 19 according to the procedure described in U.S. Pat. No. 4,622,338, hereby expressly incorporated herein by reference.

When $W^{(1)(2)}$ is a gamma- or delta-lactone group of the formula:

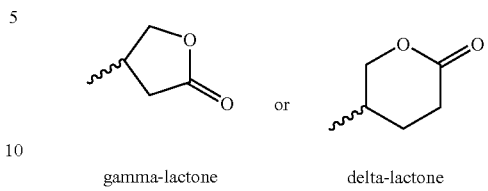

gamma-lactone        delta-lactone protected lactone alcohols 20 can be prepared according to a three step sequence. The first step comprises base-mediated reaction of electrophilic protected alcohols 18 with succinic acid esters (i.e., $R^9O_2CCH_2CH_2CO_2R^9$, wherein $R^9$ is alkyl) or glutaric acid esters (i.e., $R^9O_2CCH_2CH_2CH_2CO_2R^9$, wherein $R^9$ is alkyl) providing a diester intermediate of the formula 21:

21

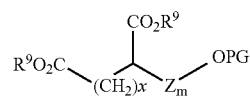

wherein x is 1 or 2 depending on whether the gamma or delta lactone group is desired. The reaction can be performed by adding about 1 equivalent of a strong organometallic base, preferably with a $pK_a$ of about 25 or more, more preferably with a $pK_a$ of greater than about 35, to a mixture comprising a suitable organic solvent and the succinic or glutaric acid ester. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. After enolate formation, the reaction-mixture temperature is adjusted to within the range of about −78° C. to about room temperature, preferably about −50° C. to about 0° C., and electrophilic protected alcohols 18 (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, the diester intermediate be isolated by workup and purified if desired. In the second step, the intermediate diester can be reduced, with a hydride reducing agent, to yield a diol of the formula 22:

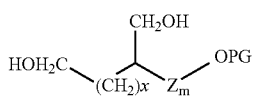

22

The reduction can be performed according to the procedures referenced in March, J. *Advanced Organic Chemistry; Reactions Mechanisms, and Structure,* 4th ed., 1992, p. 1214, hereby expressly incorporated herein by reference). Suitable reducing agents include, but are not limited to, lithium aluminum hydride, diisobutylaluminum hydride, sodium borohydride, and lithium borohydride). In the third step, the diol can be oxidatively cyclized with $RuH_2(PPh_3)_4$ to the product protected lactone alcohols 20 according to the procedure of Yoshikawa et al., 1986, *J. Org. Chem.* 51:2034 and Yoshikawa et al., 1983, *Tetrahedron Lett.* 26:2677, both of which citations are hereby expressly incorporated herein by reference. When $W^{(1)(2)}$ is a lactone group of the formula:

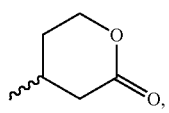

protected lactone alcohols 20 can be synthesized by reacting the Grignard salts of electrophilic protected alcohols 18, where E is a halide, with 5,6-dihydro-2H-pyran-2-one, commercially available (e.g., Aldrich Chemical Co., Milwaukee, Wis.), in the presence of catalytic amounts of a 1-dimethylaminoacetyl)pyrolidine-2yl)methyl-diarylphosphine-copper(I) iodide complex as described in Tomioka et al., 1995, *Tetrahedron Lett.* 36:4275, hereby expressly incorporated herein by reference.

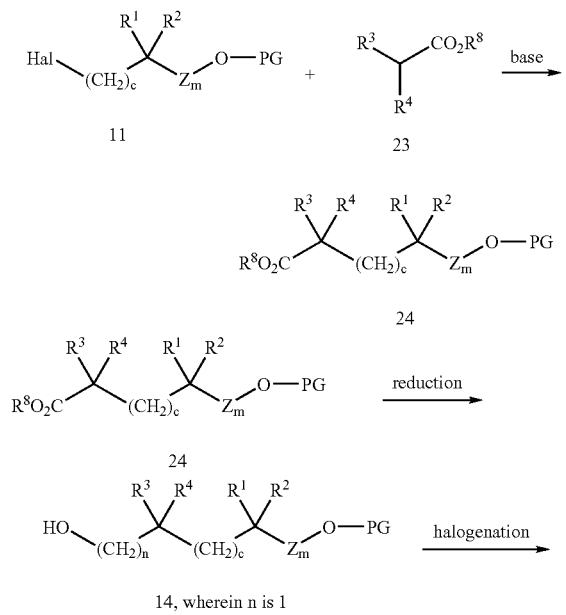

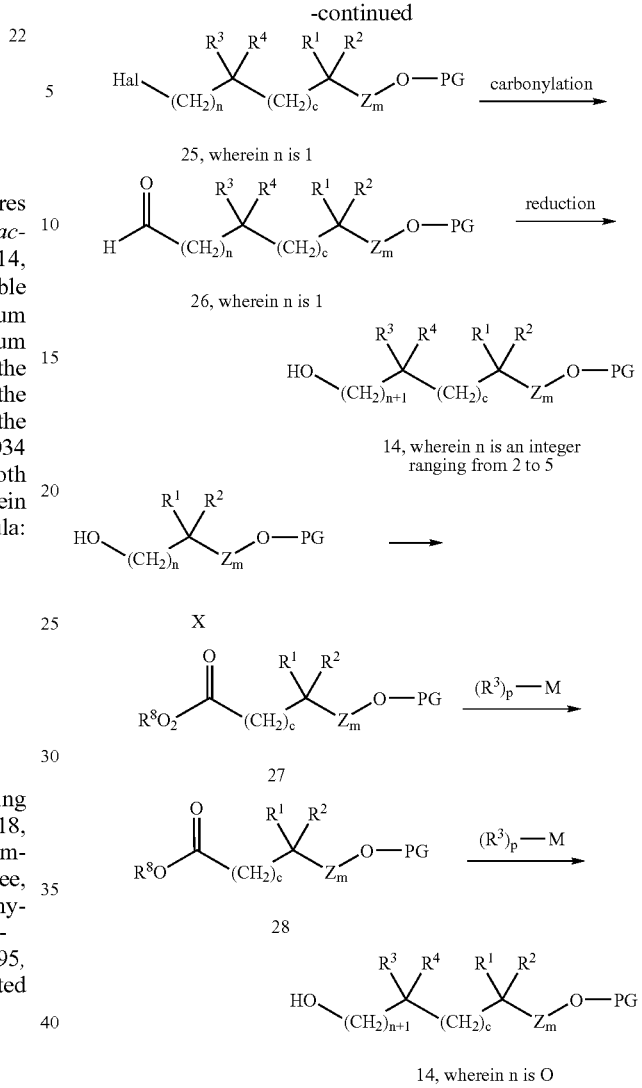

Scheme 4 outlines methodology for the synthesis of protected alcohols 14. Compounds 14, wherein n is an integer ranging from 1 to 5, can be prepared from compounds 11 using general synthetic strategy depicted and adapting the synthetic protocols from those discussed for Scheme 1.

Next, Scheme 4 depicts the general strategy for the synthesis of compounds 14 wherein n is 0. First, Esters 27, wherein $R^8$ is as defined above, are synthesized by oxidation of mono-protected diols X in the presence of $R^8OH$ (see generally, March, J. *Advanced Organic Chemistry; Reactions Mechanisms, and Structure,* 4th ed., 1992, p. 1196). An exemplary procedure for such an oxidation is described in Stevens et al., 1982, *Tetrahedron Lett.* 23:4647 (HOCl); Sundararaman et al., 1978, *Tetrahedron Lett.* 1627 ($O_3$/KOH); Wilson et al., 1982, *J. Org. Chem.* 47:1360 (t-BuOOH/$Et_3N$); and Williams et al., 1988, *Tetrahedron Lett.* 29:5087 ($Br_2$), the four of which citations are hereby expressly incorporated herein by reference. Compounds 28 are converted to compounds 14 wherein n is 0 by adapting the synthetic procedures depicted in Scheme 1.

Scheme 5: Synthesis of Compounds of Formula 15a, which correspond to compounds $W^{(1)(2)}$—$Z_m$—OH, Where $W^{(1)(2)}$ is $C(R^1)(R^2)$—$(CH_2)_c C(R^3)(R^4)$—Y

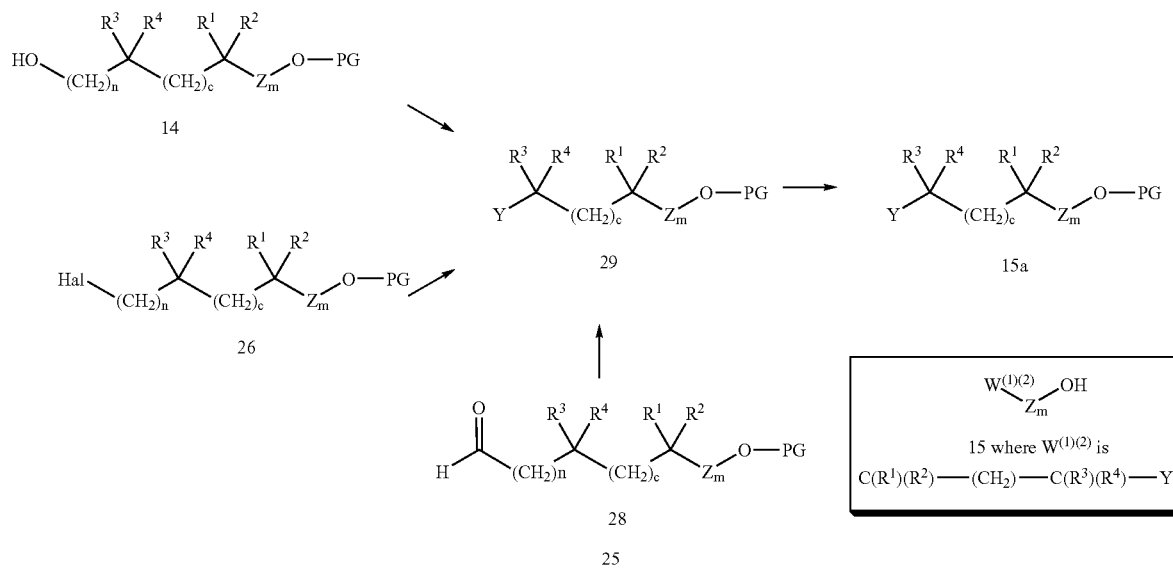

Scheme 5 outlines methodology for the synthesis of protected alcohols 29 and alcohols 15a, which correspond to $W^{(1)(2)}$-$Z_m$-OPG and $W^{(1)(2)}$-$Z_m$-OH, respectively, wherein $W^{(1)(2)}$ is $C(R^1)(R^2)$—$(CH_2)_c C(R^3)(R^4)$—Y.

The synthesis of starting materials 14, 26, and 28 are depicted in Scheme 4 and the synthetic methods and procedures can be adapted from those described for Scheme 2.

Scheme 6: Synthesis of Compounds of Formula 16, which correspond to compounds $W^{(1)(2)}$—$Z_m$—OH, Wherein $W^{(1)(2)}$ is $C(R^1)(R^2)$—$(CH_2)_c$—V and V is a Lactone Group

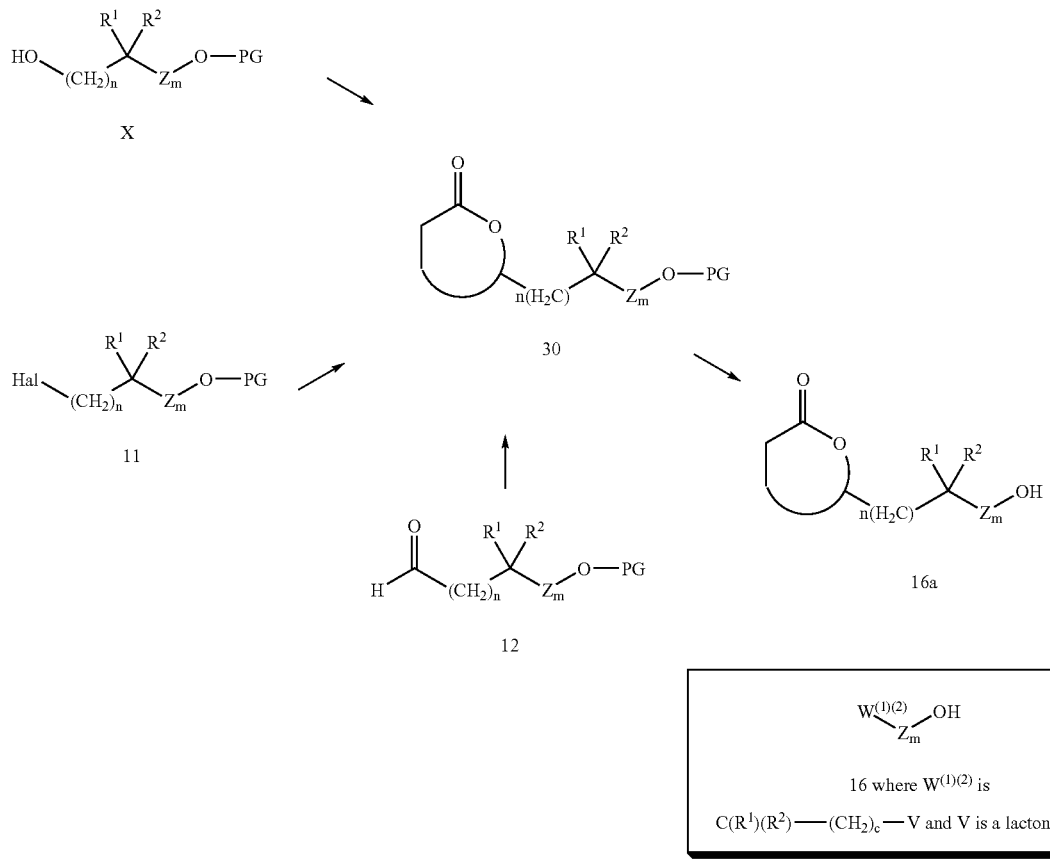

Scheme 6 depicts the synthesis of protected lactone alcohols 30 and lactone alcohols 16a. Compounds 30 and 16a correspond to compounds of the formula, which correspond to compounds $W^{(1)(2)}$-$Z_m$-OH, wherein $W^{(1)(2)}$ is $C(R^1)(R^2)(CH_2)_c$-V and V is a Group selected from:

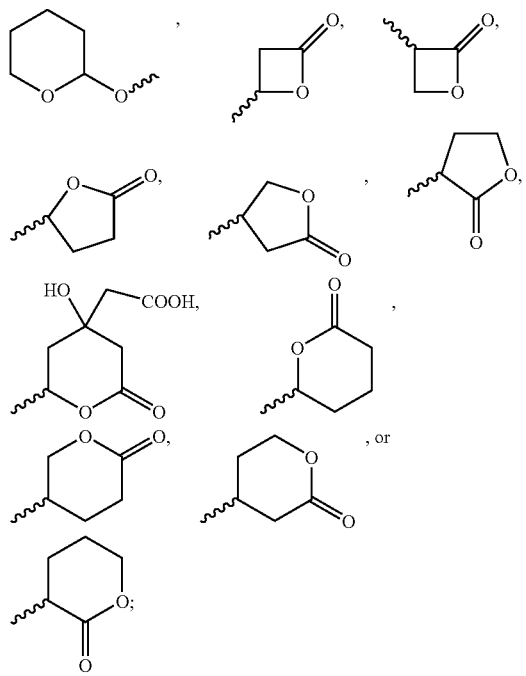

As shown in Scheme 6, protected lactone alcohols 30 and lactone alcohols 16a can be synthesized from compounds of the formula X, 11, or 12 by adaptation of the methods and procedures discussed above for Scheme 3.

Scheme 7: Conversion of Alcohols 18 to Halides 18e

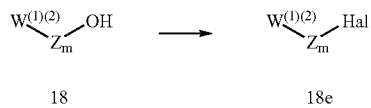

18           18e

Scheme 7 depicts the synthesis of halides 18e. Halides 18 can be synthesized by a variety of methods. One method involves conversion of the alcohol to a leaving group such as a sulfonic ester, such as, for example, tosylate, brosylate, mesylate, or nosylate. This intermediate is then treated with a source of $X^-$, wherein $X^-$ is $I^-$, $Br^-$, or $Cl^-$ in a solvent such as THF or ether. A general method for converting vinyl and phenyl alcohols to thiols involves initially converting the alcohol to a leaving group (e.g., a tosylate) then treating with a halide nucleophile.

Scheme 8: Synthesis of Compounds of Formula I

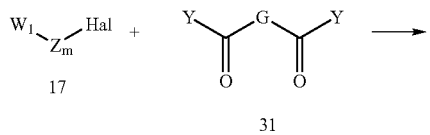

17         31

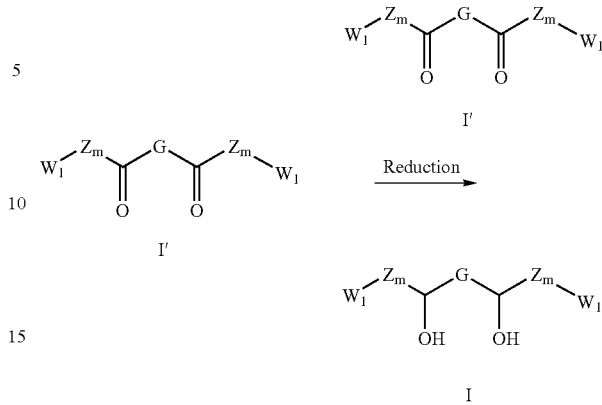

Scheme 8 outlines the synthesis of compounds I. In the first step, compounds I are synthesized by reacting compounds 17 (compounds X, 11, 12, 13, 14, 15, and 16 are encompassed by 17) with compounds 31 under the conditions suitable for the formation of compounds I'. The conditions and methods discussed in Scheme 1 above for the synthesis of mono-protected diols X from alcohols 6 can be adapted for the synthesis of compounds 17. Compounds 31, wherein Y is a suitable leaving group as defined above, preferably an anhydride, an ester, or an amide group, are readily obtained commercially (e.g., Aldrich Chemical Co. Milwaukee Wis.) or by well known synthetic methods. Compounds I' are obtained by reacting compounds 31 with compounds 17 under the conditions suitable for alkyl-deacyloxy substitution. Compounds I' can also be prepared as described in U.S. patent application Ser. No. 09/976,938, filed Oct. 11, 2001, which is incorporated herein by reference in it entirety. (For a review, See Kharasch; Reinmuth, *Grignard Reactions of Nonmetallic Substances*; Prentice Hall: Englewood Cliffs, N.J., 1954, pp. 561-562 and 846-908). In a preferred procedure, the conversion of anhydrides, carboxylic esters, or amides to ketones can be accomplished with organometallic compounds. In a particular procedure, anhydrides and carboxylic esters give ketones when treated using inverse addition of Grignard reagents at low temperature with a solvent in the presence of HMPA. See Newman, *J. Org. Chem.* 1948, 13, 592; Huet; Empotz; Jubier *Tetrahedron* 1973, 29, 479; and Larock, *Comprehensive Organic Transformations*; VCH: New York, 1989, pp. 685-686, 693-700. Ketones can also be prepare by the treatment of thioamides with organolithium compounds (alkyl or aryl). See Tominaga; Kohra; Hosomi *Tetrahedron Lett.* 1987, 28, 1529. Moreover, alkyllithium compounds have been used to give ketones from carboxylic esters. See Petrov; Kaplan; Tsir *J. Gen. Chem. USSR* 1962, 32, 691. The reaction must be carried out in a high-boiling solvent such as toluene. Di-substituted amides also can be used to synthesize ketones. See Evans J. Chem. Soc. 1956, 4691; and Wakefield *Organolithium Methods*; Academic Press: New York, 1988, pp. 82-88. Finally, compounds I' are reduced using methods known to those of ordinary skill in the art to afford diol I. See *Comprehensive Organic Transformations*; VCH: New York, 1989. It is readily recognized that the diol compound I are stereoisomeric and can therefore exist as enantiomers and diastereomers. Separation of the stereoisomers (i.e., enantiomers or diastereomers) can be achieved by methods known in the art, for example, conversion to a chiral salt and crystallization, chiral chromatography, or chiral HPLC.

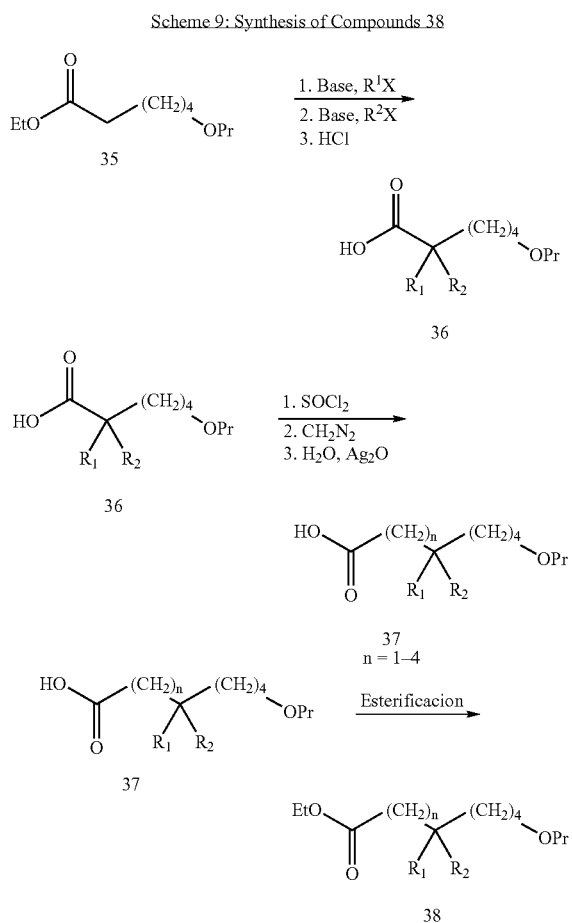

Scheme 9 illustrates the a-disubstitution of an ester containing a terminal protected hydroxyl moiety. Compounds that contain strong electron withdrawing groups are easily converted to the corresponding enolates. These enolate ions can readily attack an electrophile resulting in alpha substitution. For a review see *Some Modern Methods of Organic Synthesis*, $3^{rd}$ Ed.; Cambridge University Press: Cambridge, 1986, pp. 1-26, incorporated herein by reference. Typical procedures are described in Juaristi et al., *J. Org. Chem.*, 56, 1623 (1991) and Julia et al., *Tetrahedron*, 41, 3717 (1985). The reaction is successful for primary and secondary alkyl, allylic, and benzylic. The use of polar aprotic solvents, e.g., dimethylformamide or dimethylsulfoxide, are preferred. Phase transfer catalysts can also be used. See Tundo et al. *J. Chem. Soc., Perkin Trans.* 1, 1987, 2159, which is hereby expressly incorporated herein by reference.

The conversion to a carboxylic acid with an additional carbon is achieved by treating an acyl halide with diazomethane to generate an intermediate diazo ketone, which in the presence of water and silver oxide rearranges through a ketene intermediate to a carboxylic acid with an additional carbon aton 37. If the reaction is done in an alcohol instead of water an ester is recovered. *See Vogel's Textbook of Practical Chemistry*, Longman: London, 1978, pp. 483; Meier et al. *Angew. Chem. Int. Ed. Eng.* 1975, 14, 32-43, which are incorporated herein by reference. Alternatively, the carboxylic acid can be esterified by known techniques. The reaction can be repeated to generate methylene groups adjacent to the carboxylic acid.

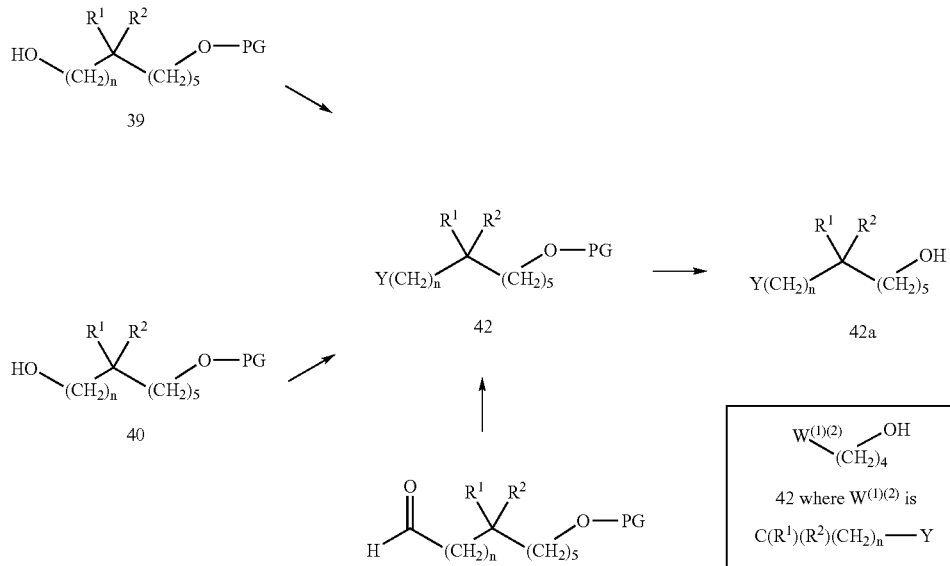

Scheme 10 outlines methodology for the synthesis of protected alcohols 42a wherein Y, $R^1$, $R^2$, Z, and m are defined as above. Protected alcohols 42a correspond to compounds of the formula $W^{(1)(2)}$-Zm-OPG, wherein $W^{(1)(2)}$ is $C(R^1)(R^2)$—Y.

Protected alcohols 42, wherein Y comprises a —C(O)OH group, can be synthesized by oxidizing mono-protected diols 39 with an agent suitable for oxidizing a primary alcohol to a carboxylic acid. (M. Hudlicky, *Oxidations in Organic Chemistry*, ACS Monograph 186, 1990, pp. 127-130, incorporated herein by reference). Suitable oxidizing agents include, but are not limited to, pyridinium dichromate (Corey et al, 1979, *Tetrahedron Lett.* 399); manganese dioxide (Ahrens et al., 1967, *J. Heterocycl. Chem.* 4:625); sodium permanganate monohydrate (Menger et al., 1981, *Tetrahedron Lett.* 22:1655); and potassium permanganate (Sam et al, 1972, *J. Am. Chem. Soc.* 94:4024), all of which citations are hereby expressly incorporated herein by reference. The preferred oxidizing reagent is pyridinium dichromate. In an alternative synthetic procedure, protected alcohols 42, wherein Y comprises a —C(O)OH group, can be synthesized by treatment of protected halo-alcohols 40, wherein X is iodo, with CO or $CO_2$, as described in Bailey et al., 1990, *J. Org. Chem.* 55:5404 and Yanagisawa et al., 1994, *J. Am. Chem. Soc.* 116:6130, the two of which citations are hereby expressly incorporated herein by reference. Protected alcohols 42, wherein Y comprises —C(O)$OR^5$, wherein $R^5$ is as defined above, can be synthesized by oxidation of mono-protected diols 39 in the presence of $R^5$OH (see generally, March, J. *Advanced Organic Chemistry; Reactions Mechanisms, and Structure*, 4th ed., 1992, p. 1196). An exemplary procedure for such an oxidation is described in Stevens et al., 1982, *Tetrahedron Lett.* 23:4647 (HOCl); Sundararaman et al., 1978, *Tetrahedron Lett.* 1627 ($O_3$/KOH); Wilson et al., 1982, *J. Org. Chem.* 47:1360 (t-BuOOH/$Et_3N$); and Williams et al., 1988, *Tetrahedron Lett.* 29:5087 ($Br_2$), the four of which citations are incorporated herein by reference. Preferably, protected alcohols 42, wherein Y comprises a —C(O)$OR^5$ group are synthesized from the corresponding carboxylic acid (i.e., 42, wherein Y comprises —C(O)OH by esterification with $R^5$OH (e.g., see March, J., *Advanced Organic Chemistry; Reactions Mechanisms, and Structure*, 4th ed., Wiley, New York, 1992, p. 393-394, incorporated herein by reference). In another alternative synthesis, protected alcohols 42, wherein Y comprises —C(O)$OR^5$, can be prepared from protected halo-alcohols 40 by carbonylation with transition metal complexes (see e.g., March, J. *Advanced Organic Chemistry; Reactions Mechanisms, and Structure*, 4th ed., Wiley, New York, 1992, p. 484-486; Urata et al., 1991, *Tetrahedron Lett.* 32:36, 4733); and Ogata et al., 1969, *J. Org. Chem.* 3985, the three of which citations are hereby expressly incorporated herein by reference).

Protected alcohols 42, wherein Y comprises —OC(O)$R^5$, wherein $R^5$ is as defined above, can be prepared by acylation of mono-protected diols 39 with a carboxylate equivalent such as an acyl halide (i.e., $R^5$C(O)-Hal, wherein Hal is iodo, bromo, or chloro, see e.g., March, J. *Advanced Organic Chemistry; Reactions Mechanisms, and Structure*, 4th ed., Wiley, New York, 1992, p. 392 and *Org. Synth. Coll.* Vol. III, Wiley, N.Y., pp. 142, 144, 167, and 187 (1955)) or an anhydride (i.e., $R^5$C(O)—O—(O)$CR^5$, see e.g., March, J. *Advanced Organic Chemistry; Reactions Mechanisms, and Structure*, 4th ed., 1992, p. 392-393 and *Org. Synth. Coll.* Vol. III, Wiley, N.Y., pp. 11, 127, 141, 169, 237, 281, 428, 432, 690, and 833 (1955), all of which citations are incorporated herein by reference). Preferably, the reaction is conducted by adding a base to a solution comprising mono-protected diols 39, a carboxylate equivalent, and an organic solvent, which solution is preferably maintained at a constant temperature within the range of 0° C. to about room temperature. Solvents suitable for reacting mono-protected diols 39 with a carboxylate equivalent include, but are not limited to, dichloromethane, toluene, and ether, preferably dichloromethane. Suitable bases include, but are not limited to, hydroxide sources, such as sodium hydroxide, potassium hydroxide, sodium carbonate, or potassium carbonate; or an amine such as triethylamine, pyridine, or dimethylaminopyridine. The progress of the reaction can be followed by using an appropriate analytical technique, such as thin layer chromatography or high performance liquid chromatography and when substantially complete, the product can be isolated by workup and purified if desired.

Protected alcohols 42, wherein Y comprises one of the following phosphate ester groups

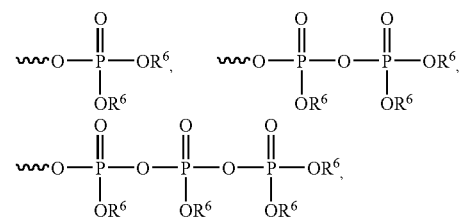

wherein $R^6$ is defined as above, can be prepared by phosphorylation of mono-protected diols X according to well-known methods (for general reviews, see Corbridge *Phosphorus: An Outline of its Chemistry, Biochemistry, and Uses*, Studies in Inorganic Chemistry, 3rd ed., pp. 357-395 (1985); Ramirez et al., 1978, *Acc. Chem. Res.* 11:239; and Kalckare *Biological Phosphorylations*, Prentice-Hall, New York (1969); J. B. Sweeny in *Comprehensive Organic Functional Group Transformations*, A. R. Katritzky, O. Meth-Cohn and C. W. Rees, Eds. Pergamon: Oxford, 1995, vol 2, pp. 104-109, the four of which are hereby expressly incorporated herein by reference). Protected alcohols 42 wherein Y comprises a monophosphate group of the formula:

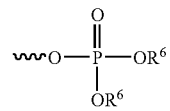

wherein $R^6$ is defined as above, can be prepared by treatment of mono-protected diol 39 with phosphorous oxychloride in a suitable solvent, such as xylene or toluene, at a constant temperature within the range of about 100° C. to about 150° C. for about 2 hours to about 24 hours. After the reaction is deemed substantially complete, by using an appropriate analytical method, the reaction mixture is hydrolyzed with $R^6$-OH. Suitable procedures are referenced in Houben-Weyl, Methoden der Organische Chemie, Georg Thieme Verlag Stuttgart: 1964, vol. XII/2, pp. 143-210 and 872-879, incorporated herein by reference. Alternatively, when both $R^6$ are hydrogen, can be synthesized by reacting mono-protected diols X with silyl polyphosphate (Okamoto et al., 1985, *Bull Chem. Soc. Jpn.* 58:3393, hereby expressly incorporated herein by reference) or by hydrogenolysis of their benzyl or phenyl esters (Chen et al., 1998, *J. Org. Chem.* 63:6511, incorporated herein by reference). In another alternative procedure, when $R^6$ is $(C_1-C_6)$alkyl, $(C_2-C_6)$alkenyl, or $(C_2-C_6)$alkynyl, the monophosphate esters can be prepared by reacting mono-protected diols 39 with appropriately substituted phophoramidites followed by oxidation of the intermediate with m-chloroperbenzoic acid (Yu et al., 1988, *Tetrahedron Lett.* 29:979, incorporated herein by reference) or by reacting mono-protected diols 39 with dialkyl or diaryl substituted phosphorochloridates (Pop, et al, 1997, *Org. Prep. and Proc. Int.* 29:341, incorporated herein by reference). The phosphoramidites are commercially available (e.g., Aldrich Chemical Co., Milwaukee, Wis.) or readily prepared according to literature procedures (see e.g., Uhlmann et al. 1986, *Tetrahedron Lett.* 27:1023 and Tanaka et al., 1988, *Tetrahedron Lett.* 29:199, both of which are incorporated herein by reference). The phosphorochloridates are also commercially available (e.g., Aldrich Chemical Co., Milwaukee, Wis.) or prepared according to literature methods (e.g., Gajda et al, 1995, Synthesis 25:4099. In still another alternative synthesis, protected alcohols 42, wherein Y comprises a monophosphate group and $R^6$ is alkyl or aryl, can be prepared by reacting $IP^+(OR^6)_3$ with mono-protected diols 39 according to the procedure described in Stowell et al., 1995, *Tetrahedron Lett.* 36:11, 1825 or by alkylation of protected halo alcohols 40 with the appropriate dialkyl or diaryl phosphates (see e.g., Okamoto, 1985, *Bull Chem. Soc. Jpn.* 58:3393, incorporated herein by reference).

Protected alcohols 42 wherein Y comprises a diphosphate group of the formula

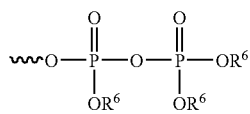

wherein $R^6$ is defined as above, can be synthesized by reacting the above-discussed monophosphates of the formula:

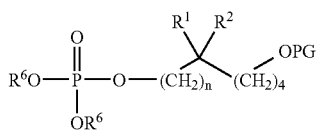

with a phosphate of the formula

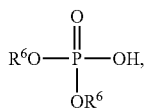

(commercially available, e.g., Aldrich Chemical Co., Milwaukee, Wis.), in the presence of carbodiimide such as dicyclohexylcarbodiimide, as described in Houben-Weyl, *Methoden der Organische Chemie*, Georg Thieme Verlag Stuttgart 1964, vol. XII/2, pp. 881-885. In the same fashion, protected alcohols 42, wherein Y comprises a triphosphate group of the formula:

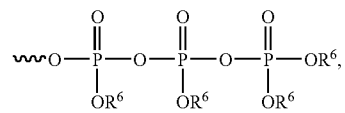

can be synthesized by reacting the above-discussed diphosphate-protected alcohols, of the formula:

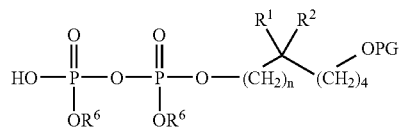

with a phosphate of the formula:

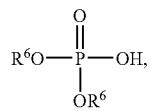

as described above. Alternatively, when $R^6$ is H, protected alcohols 42 wherein Y comprises the triphosphate group, can be prepared by reacting mono-protected diols 39 with salicyl phosphorochloridite and then pyrophosphate and subsequent cleavage of the adduct thus obtained with iodine in pyridine as described in Ludwig et al., 1989, *J. Org. Chem.* 54:63 1, incorporated herein by reference.

Protected alcohols 42, wherein Y is —$SO_3H$ or a heterocyclic group selected from the group consisting of:

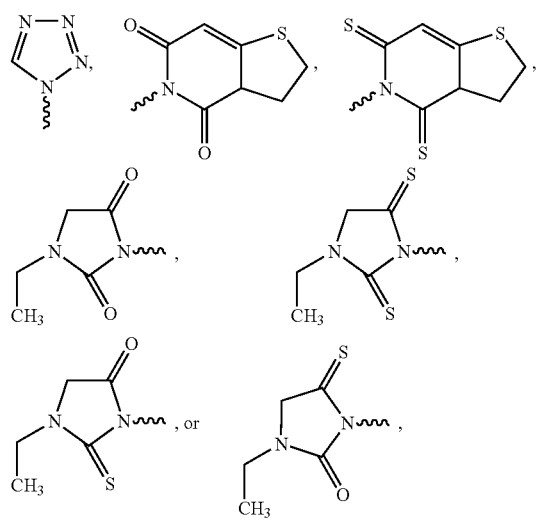

can be prepared by halide displacement from protected halo-alcohols 40. Thus, when Y is —$SO_3H$, protected alcohols 42 can by synthesized by reacting protected haloalcohols 40 with sodium sulfite as described in Gilbert *Sulfonation and Related Reactions*; Wiley: New York, 1965, pp. 136-148 and pp. 161-163; *Org. Synth. Coll.* Vol. 11, Wiley, N.Y., 558, 564 (1943); and *Org. Synth. Coll.* Vol. IV, Wiley, N.Y., 529 (1963), all three of which are incorporated herein by reference. When Y is one of the above-mentioned heterocycles, protected alcohols 42 can be prepared by reacting protected halo-alcohols 40 with the corresponding heterocycle in the presence of a base. The heterocycles are available commercially (e.g., Aldrich Chemical Co., Milwaukee, Wis.) or prepared by well-known synthetic methods (see the procedures described in Ware, 1950, Chem. Rev. 46:403-470, incorporated herein by reference). Preferably, the reaction is conducted by stirring a mixture comprising 40, the heterocycle, and a solvent at a constant temperature within the range of about room temperature to about 100° C., preferably within the range of about 50° C. to about 70° C. for about 10 to about 48 hours. Suitable bases include hydroxide bases such as sodium hydroxide, potassium hydroxide, sodium carbonate, or potassium carbonate. Preferably, the solvent used in forming protected alcohols 42 is selected from dimethylformamide; formamide; dimethyl sulfoxide; alcohols, such as methanol or ethanol; and mixtures thereof. The progress of the reaction can be followed by using an appropriate analytical technique, such as thin layer chromatography or high performance liquid chromatography and when substantially complete, the product can be isolated by workup and purified if desired.

Protected alcohols 42, wherein Y is a heteroaryl ring selected from

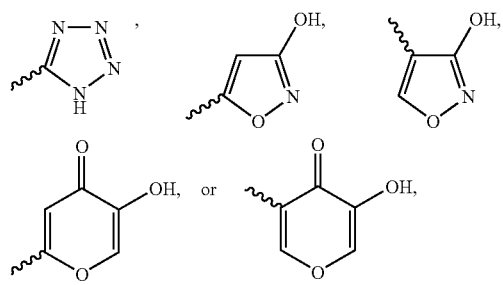

can be prepared by metallating the suitable heteroaryl ring then reacting the resulting metallated heteroaryl ring with protected halo-alcohols 40 (for a review, see Katritzky *Handbook of Heterocyclic Chemistry*, Pergamon Press: Oxford 1985). The heteroaryl rings are available commercially or prepared by well-known synthetic methods (see e.g., Joule et al., *Heterocyclic Chemistry*, 3rd ed., 1995; De Sarlo et al., 1971, *J. Chem. Soc.* (C) 86; Oster et al., 1983, *J. Org. Chem.* 48:4307; Iwai et al., 1966, *Chem. Pharm. Bull.* 14:1277; and U.S. Pat. No. 3,152,148, all of which citations are incorporated herein by reference). As used herein, the term "metallating" means the forming of a carbon-metal bond, which bond may be substantially ionic in character. Metallation can be accomplished by adding about 2 equivalents of strong organometallic base, preferably with a $pK_a$ of about 25 or more, more preferably with a $pK_a$ of greater than about 35, to a mixture comprising a suitable organic solvent and the heterocycle. Two equivalents of base are required: one equivalent of the base deprotonates the —OH group or the —NH group, and the second equivalent metallates the heteroaryl ring. Alternatively, the hydroxy group of the heteroaryl ring can be protected with a base-stable, acid-labile protecting group as described in Greene, T. W., *Protective Groups in Organic Synthesis*, 3rd edition 17-237 (1999), hereby expressly incorporated herein by reference. Where the hydroxy group is protected, only one equivalent of base is required. Examples of suitable base-stable, acid-labile hydroxyl-protecting groups, include but are not limited to, ethers, such as methyl, methoxy methyl, methylthiomethyl, methoxyethoxymethyl, bis(2-chloroethoxy)methyl, tetrahydropyranyl, tetrahydrothiopyranyl, tetrahyrofuranyl, tetrahydrothiofuranyl, 1-ethoxyethyl, 1-methyl-1-methoxyethyl, t-butyl, allyl, benzyl, o-nitrobenzyl, triphenylmethyl, α-naphthyldiphenylmethyl, p-methoxyphenyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, triisopropylsilyl; and esters, such as pivaloate, adamantoate, and 2,4,6-trimethylbenzoate. Ethers are preferred, particularly straight chain ethers, such as methyl ether, methoxymethyl ether, methylthiomethyl ether, methoxyethoxymethyl ether, bis(2-chloroethoxy)methyl ether. Preferably, the $pK_a$ of the base is higher than the $pK_a$ of the proton of the heterocycle to be deprotonated. For a listing of $pK_a$s for various heteroaryl rings, see Fraser et al., 1985, *Can. J. Chem.* 63:3505, incorporated herein by reference. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. If desired, the organometallic base can be activated with a complexing agent, such as N,N,N',N'-tetramethylethylenediamine or hexamethylphosphoramide (1970, *J. Am. Chem. Soc.* 92:4664, hereby expressly incorporated herein by reference). Solvents suitable for synthesizing protected alcohols 42, wherein Y is a heteroaryl ring include, but are not limited to, diethyl ether; tetrahydrofuran; and hydrocarbons, such as pentane. Generally, metallation occurs alpha to the heteroatom due to the inductive effect of the heteroatom, however, modification of conditions, such as the identity of the base and solvents, order of reagent addition, reagent addition times, and reaction and addition temperatures can be modified by one of skill in the art to achieve the desired metallation position (see e.g., Joule et al., *Heterocyclic Chemistry*, 3rd ed., 1995, pp. 30-42, hereby expressly incorporated herein by reference) Alternatively, the position of metallation can be controlled by use of a halogenated heteroaryl group, wherein the halogen is located on the position of the heteroaryl ring where metallation is desired (see e.g., Joule et al., *Heterocyclic Chemistry*, 3rd ed., 1995, p. 33 and Saulnier et al., 1982, *J. Org. Chem.* 47:757, the two of which citations are hereby expressly incorporated herein by reference). Halogenated heteroaryl groups are available commercially (e.g., Aldrich Chemical Co., Milwaukee, Wis.) or can be prepared by well-known synthetic methods (see e.g., Joule et al., *Heterocyclic Chemistry*, 3rd ed., 1995, pp. 78, 85, 122, 193, 234, 261, 280, 308, hereby expressly incorporated herein by reference). After metallation, the reaction mixture comprising the metallated heteroaryl ring is adjusted to within a temperature range of about 0° C. to about room temperature and protected halo-alcohols 40 (diluted with a solvent or in undiluted form) are added, preferably at a rate such that the reaction-mixture temperature remains within about one to two degrees of the initial reaction-mixture temperature. After addition of protected halo-alcohols 40, the reaction mixture is stirred at a constant temperature within the range of about room temperature and about the solvent's boiling temperature and the reaction's progress can be monitored by the appropriate analytical technique, preferably thin-layer chromatography or high-performance liquid chromatography. After the reaction is substantially complete, protected alcohols 42 can be isolated by workup and purification. It is to be understood that conditions, such as the identity of protected halo-alcohol 40, the base, solvents, orders of reagent addition, times, and temperatures, can be modified by one of skill in the art to optimize the yield and selectivity. Exemplary procedures that can be used in such a transformation are described in Shirley et al., 1995, *J. Org. Chem.* 20:225; Chadwick et al., 1979, *J. Chem. Soc.*, Perkin Trans. 1 2845; Rewcastle, 1993, *Adv. Het. Chem.* 56:208; Katritzky et al., 1993, *Adv. Het. Chem.* 56:155; and Kessar et al., 1997, *Chem. Rev.* 97:721.

When Y is

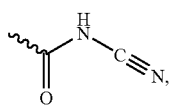

protected alcohols 42 can be prepared from their corresponding carboxylic acid derivatives (42, wherein Y is —CO$_2$H) as described in Belletire et al, 1988, *Synthetic Commun.* 18:2063 or from the corresponding acylchlorides (42, wherein Y is —CO-halo) as described in Skinner et al., 1995, *J. Am. Chem. Soc.* 77:5440, both citations are incorporated herein by reference. The acylhalides can be prepared from the carboxylic acids by well known procedures such as those described in March, J., *Advanced Organic Chemistry; Reactions Mechanisms, and Structure,* 4th ed., 1992, pp. 437-438, hereby expressly incorporated herein by reference.

When Y is

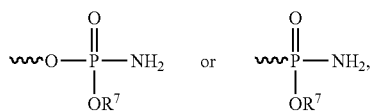

wherein R$^7$ is as defined above, protected alcohols 42 can be prepared by first reacting protected halo-alcohols 40 with a trialkyl phosphite according to the procedure described in Kosolapoff, 1951, *Org. React.* 6:273 followed by reacting the derived phosphonic diester with ammonia according to the procedure described in Smith et al., 1957, *J. Org. Chem.* 22:265, incorporated herein by reference. When Y is

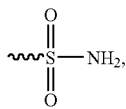

protected alcohols 42 can be prepared by reacting their sulphonic acid derivatives (i.e., 42, wherein Y is —SO$_3$H) with ammonia as described in Sianesi et al., 1971, *Chem. Ber.* 104:1880 and Campagna et al., 1994, *Farmaco, Ed. Sci.* 49:653, both of which citations are incorporated herein by reference).

As further illustrated in Scheme 10, protected alcohols 42 can be deprotected providing alcohols 42a. The deprotection method depends on the identity of the alcohol-protecting group, see e.g., the procedures listed in Greene, T. W., *Protective Groups in Organic Synthesis,* 3rd edition 17-237 (1999), particularly see pages 48-49, incorporated herein by reference. One of skill in the art will readily be able to choose the appropriate deprotection procedure. When the alcohol is protected as an ether function (e.g., methoxymethyl ether), the alcohol is preferably deprotected with aqueous or alcoholic acid. Suitable deprotection reagents include, but are not limited to, aqueous hydrochloric acid, p-toluenesulfonic acid in methanol, pyridinium-p-toluenesulfonate in ethanol, Amberlyst H-15 in methanol, boric acid in ethylene-glycol-monoethylether, acetic acid in a water-tetrahydrofuran mixture, aqueous hydrochloric acid is preferred. Examples of such procedures are described, respectively, in Bemady et al., 1979, *J. Org. Chem.* 44:1438; Miyashita et al., 1977, *J. Org. Chem.* 42:3772; Johnston et al., 1988, *Synthesis* 393; Bongini et al., 1979, *Synthesis* 618; and Hoyer et al., 1986, *Synthesis* 655; Gigg et al., 1967, *J. Chem. Soc. C,* 431; and Corey et al., 1978, *J. Am. Chem. Soc.* 100:1942, all of which are incorporated herein by reference.

Scheme 11: Synthesis of Compounds of Formula 46 which correspond to Compounds
W$^{(1)(2)}$—(CH$_2$)$_4$—OH, wherein W$^{(1)(2)}$ is C(R$^1$)(R$^2$)(CH$_2$)$_4$-Lactone

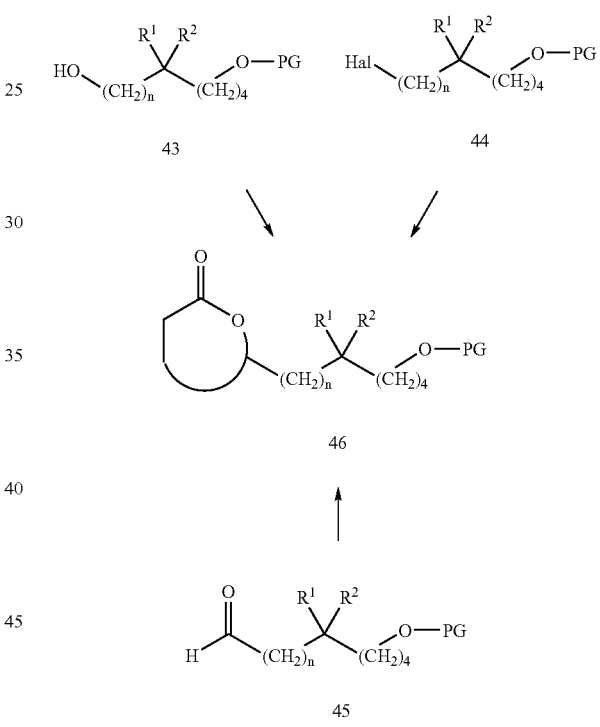

Scheme 11 depicts the synthesis of protected lactone alcohols 46 and lactone. Compound 46 corresponds to compounds of the formula W$^{(1)(2)}$-Zm-OPG and, wherein W$^{(1)(2)}$ is a lactone group selected from:

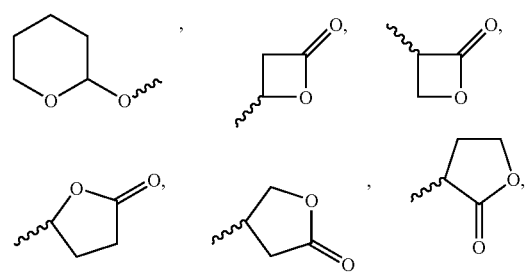

-continued

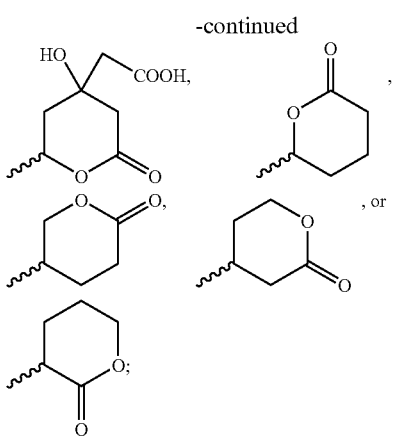

Protected lactone alcohols 46 can be prepared from compounds of the formula 43, 44, or 45 by using well-known condensation reactions and variations of the Michael reaction. Methods for the synthesis of lactones are disclosed in Multzer in *Comprehensive Organic Functional Group Transformations*, A. R. Katritzky, O. Meth-Cohn and C. W. Rees, Eds. Pergamon: Oxford, 1995, vol 5, pp. 161-173, incorporated herein by reference. Mono-protected diols 43, electrophilic protected alcohols 44, and aldehydes 45 are readily available either commercially (e.g., Aldrich Chemical Co., Milwaukee, Wis.) or can be prepared by well known synthetic procedures.

When $W^{(1)(2)}$ is a beta-lactone group of the formula:

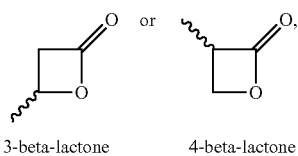

3-beta-lactone    4-beta-lactone protected lactone alcohols 46 can be prepared from aldehydes 45 and electrophilic protected alcohols 44, respectively, by a one-pot-addition-lactonization according to the procedure of Masamune et al., 1976, *J. Am. Chem. Soc.* 98:7874 and Danheiser et al., 1991, *J. Org. Chem.* 56:1176, both of which are incorporated herein by reference. This one-pot-addition-lactonization methodology has been reviewed by Multzer in *Comprehensive Organic Functional Group Transformations*, A. R. Katritzky, O. Meth-Cohn and C. W. Rees, Eds. Pergamon: Oxford, 1995, vol 5, pp. 161, incorporated herein by reference When $W^{(1)(2)}$ is a gamma- or delta-lactone group of the formula:

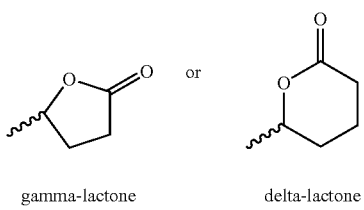

gamma-lactone    delta-lactone protected lactone alcohols 46 can be prepared from aldehydes 45 according to well known synthetic methodology.

For example, the methodology described in Masuyama et al., 2000, *J. Org. Chem.* 65:494; Eisch et al., 1978, *J. Organomet. Chem.* C8 160; Eaton et al., 1947, *J. Org. Chem.* 37:1947; Yunker et al., 1978, *Tetrahedron Lett.* 4651; Bhanot et al., 1977, *J. Org. Chem.* 42:1623; Ehlinger et al., 1980, *J. Am. Chem. Soc.* 102:5004; and Raunio et al., 1957, *J. Org. Chem.* 22:570, all of which citations are incorporated herein by reference. For instance, as described in Masuyama et al., 2000, *J. Org. Chem.* 65:494, aldehydes 45 can be treated with about 1 equivalent of a strong organometallic base, preferably with a $pK_a$ of about 25 or more, more preferably with a $pK_a$ of greater than about 35, in a suitable organic solvent to give a reaction mixture. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. The reaction-mixture temperature is adjusted to within the range of about 0° C. to about 100° C., preferably about room temperature to about 50° C., and a halide of the formula:

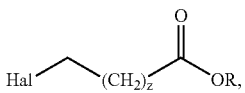

wherein z is 1 or 2 (diluted with a solvent or in undiluted form) is added. The reaction mixture is stirred for a period of about 2 hours to about 48 hours, preferably about 5 to about 10 hours, during which time the reaction's progress can be followed by using an appropriate analytical technique, such as thin layer chromatography or high performance liquid chromatography. When the reaction is deemed substantially complete, protected lactone alcohols 46 can be isolated by workup and purified if desired. When $W^{(1)(2)}$ is a gamma- or delta-lactone group of the formula:

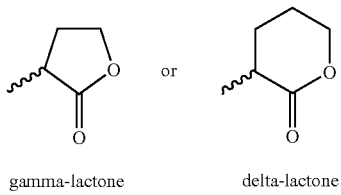

gamma-lactone    delta-lactone protected lactone alcohols 46 can be synthesized by deprotonating the corresponding lactone with a strong base providing the lactone enolate and reacting the enolate with electrophilic protected alcohols 44 (for a detailed discussion of enolate formation of active methylene compounds such as lactones, see House *Modern Synthetic Reactions*; W. A. Benjamin, Inc. Philippines 1972 pp. 492-570, and for a discussion of reaction of lactone enolates with electrophiles such as carbonyl compounds, see March, J. *Advanced Organic Chemistry; Reactions Mechanisms, and Structure*, 4th ed., 1992, pp. 944-945, both of which are incorporated herein by reference). Lactone-enolate formation can be accomplished by adding about 1 equivalent of a strong organometallic base, preferably with a $pK_a$ of about 25 or more, more preferably with a $pK_a$ of greater than about 35, to a mixture comprising a suitable organic solvent and the lactone. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Solvents suitable for lactone-enolate formation include, but are not limited to, diethyl ether and tetrahydrofuran. After enolate formation, the reaction-mixture temperature is adjusted to within the range of about −78° C. to about room temperature, preferably about −50° C. to about 0° C., and electrophilic protected alcohols 44 (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, protected lactone alcohols 46 can be isolated by workup and purified if desired. When $W^{(1)(2)}$ is a lactone group group of the formula:

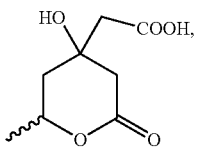

protected lactone alcohols 46 can be prepared from aldehydes 45 according to the procedure described in U.S. Pat. No. 4,622,338, hereby expressly incorporated herein by reference.

When $W^{(1)(2)}$ is a gamma- or delta-lactone group of the formula:

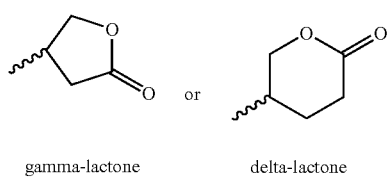

gamma-lactone        delta-lactone protected lactone alcohols 46 can be prepared according to a three step sequence. The first step comprises base-mediated reaction of electrophilic protected alcohols 44 with succinic acid esters (i.e., $R^9O_2CCH_2CH_2CO_2R^9$, wherein $R^9$ is alkyl) or glutaric acid esters (i.e., $R^9O_2CCH_2CH_2CH_2CO_2R^9$, wherein $R^9$ is alkyl) providing a diester intermediate of the formula 44i:

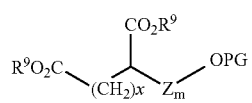

44i wherein x is 1 or 2 depending on whether the gamma or delta lactone group is desired. The reaction can be performed by adding about 1 equivalent of a strong organometallic base, preferably with a $pK_a$ of about 25 or more, more preferably with a $pK_a$ of greater than about 35, to a mixture comprising a suitable organic solvent and the succinic or glutaric acid ester. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride, preferably lithium tetramethylpiperidide. Suitable solvents include, but are not limited to, diethyl ether and tetrahydrofuran. After enolate formation, the reaction-mixture temperature is adjusted to within the range of about −78° C. to about room temperature, preferably about −50° C. to about 0° C., and electrophilic protected alcohols 44 (diluted with a solvent or in undiluted form) are added, preferably at a rate such that the reaction-mixture temperature remains within about one to two degrees of the initial reaction-mixture temperature. The reaction mixture is stirred for a period of about 15 minutes to about 5 hours, during which time the reaction's progress can be followed by using an appropriate analytical technique, such as thin layer chromatography or high performance liquid chromatography. When the reaction is deemed substantially complete, the diester intermediate can be isolated by work-up and purified if desired. In the second step, the intermediate diester can be reduced, with a hydride reducing agent, to yield a diol:

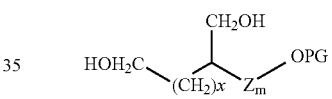

The reduction can be performed according to the procedures referenced in March, J. *Advanced Organic Chemistry; Reactions Mechanisms, and Structure,* 4th ed., 1992, p. 1214, incorporated herein by reference). Suitable reducing agents include, but are not limited to, lithium aluminum hydride, diisobutylaluminum hydride, sodium borohydride, and lithium borohydride). In the third step, the diol can be oxidatively cyclized with $RuH_2(PPh_3)_4$ to the product protected lactone alcohols 46 according to the procedure of Yoshikawa et al., 1986, *J. Org. Chem.* 51:2034 and Yoshikawa et al., 1983, *Tetrahedron Lett.* 26:2677, both of which citations are incorporated herein by reference. When $W^{(1)(2)}$ is a lactone group of the formula:

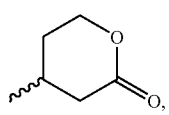

protected lactone alcohols 46 can be synthesized by reacting the Grignard salts of electrophilic protected alcohols 44, where E is a halide, with 5,6-dihydro-2H-pyran-2-one, commercially available (e.g., Aldrich Chemical Co., Milwaukee, Wis.), in the presence of catalytic amounts of a 1-dimethylaminoacetyl)pyrrolidine-2yl)methyl-diarylphosphine-copper(I) iodide complex as described in Tomioka et al., 1995, *Tetrahedron Lett.* 36:4275, incorporated herein by reference.

Scheme 12: Synthesis of Compound of Formula II

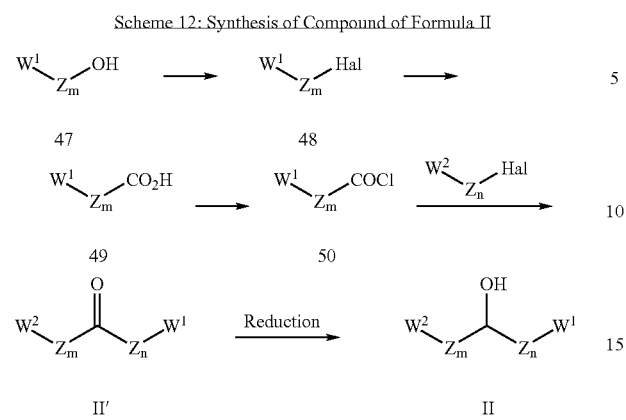

Scheme 12 illustrates the synthesis of alcohol II. The alcohol 47 is intiallly converted to a halogen 48. See Larock, *Comprehensive Organic Transformations*, VCH: New York, 1989, pp. 360-362; all references disclosed therein are incorporated herein by reference. The halide 48 is then converted to a carboxylic acid 49 with subsequent conversion to a acyl halide 50. See Larock, *Comprehensive Organic Transformations*, VCH: New York, 1989, pp. 850-851, 855-856, 859-860, 977, 980, and 985; all references disclosed therein are incorporated herein by reference. The acyl halide 50 is then coupled with the halide to afford compound II'. See Rappoport, *The Chemistry of the Functional Groups, Supp. D*, pt. 2; Wiley: New York, 1983; House, *Modern Synthetic Reactions*, 2$^{nd}$ Ed. Benjamin: New York, 1972, pp. 691-694, 734-765, which are incorporated herein by reference. Finally, compounds II' are reduced using methods known to those of ordinary skill in the art to afford alcohol II. See Larock, *Comprehensive Organic Transformations*; VCH: New York, 1989.

In a typical procedure, the ketone II' is dissolved in an organic solvent such as, but not limited to, toluene, xylene, diethyl ether, t-butyl methyl ether, diglyme, methanol, ethanol, dichloromethane, chloroform, dichloroethane, preferably diethyl ether, and it is then treated with a reducing agent such as, but not limited to, lithium aluminum hydride, sodium borohydride, lithium borohydride, preferably sodium borohydride. When the reaction is complete, as determined by an analytical method such as HPLC, gas chromatography, thin layer chromatography, or NMR, the mixture is subjected to work-up. The compound thus obtained can be purified by various purification methods known in the field, such as chromatography or recrystallization. It is readily recognized that the alcohol compound II can exist as enantiomers. Separation of the stereoisomers (i.e., enantiomers) can be achieved by methods known in the art, for example, conversion to a chiral salt and crystallization, chiral chromatography, or chiral HPLC.

Scheme 13: Synthesis of Compounds III

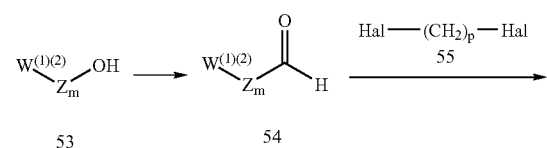

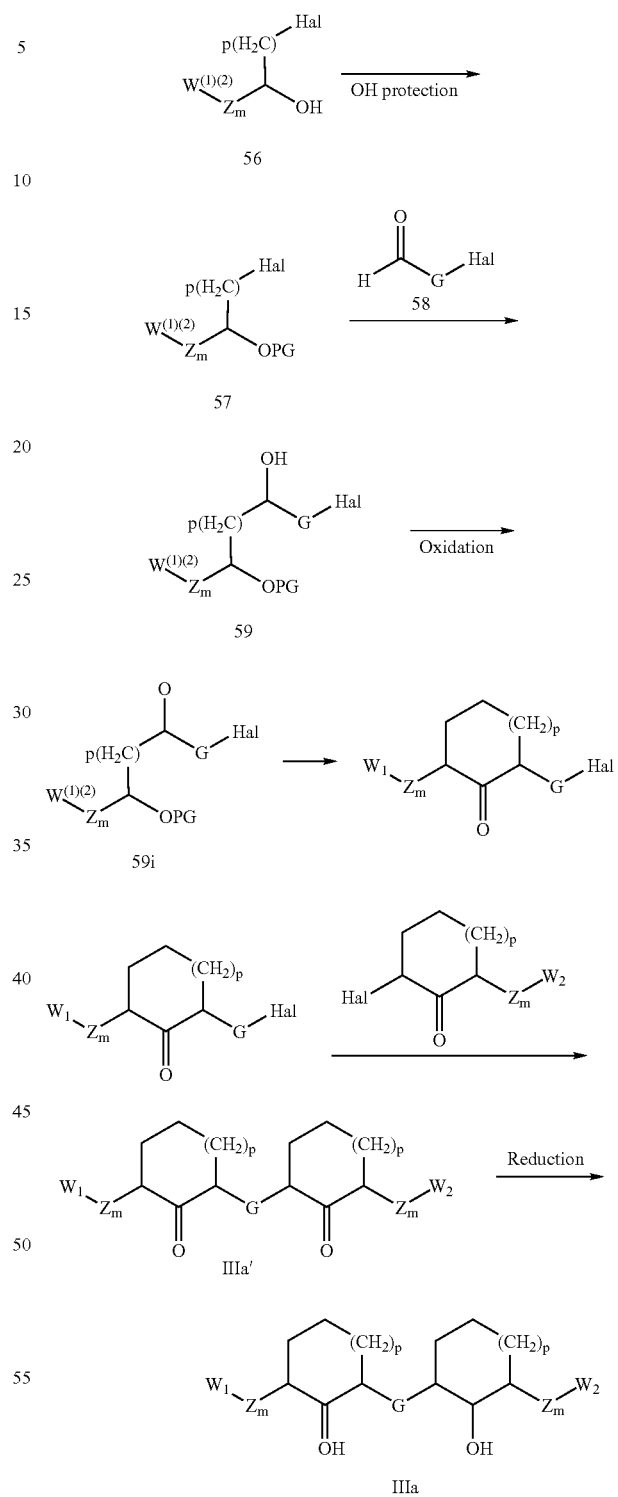

Scheme 13 depicts the synthesis of compounds IIIa, that is, compounds III where a double bond is not present in the ring. In the first step, compounds 53, prepared as discussed in Schemes 1 to 6 above, can be converted to compounds 54 by standard oxidation of the primary alcohol to an aldehyde group. Such oxidations are described in M. Hudlicky, *Oxi-* dations in *Organic Chemistry*, ACS Monograph 186, 1990, pp. 114-127, hereby expressly incorporated herein by reference. In the next step Grignard reaction of 54 with 55 followed by standard OH protection gives 57. Compounds 55 are commercially available (e.g., from Aldrich Chemical Co. Milwakee, Wis.) or can be readily prepared by standard synthetic methodology. For exemplary procedures for Grignard reactions see March, J. *Advanced Organic Chemistry; Reactions Mechanisms, and Structure*, 4th ed., 1992, pp. 920-929, incorporated herein by reference. Similarly, in the next step, the Grignard salt of 57 is condensed with 58 to provide 59. Next 59 is oxidized and then cyclized to 60. When p is one, exemplary cyclization procedures are found in Friedrichsen, W. in *Comprehensive Heterocyclic Chemistry II*; Katritzky, A. R.; Rees, W. C.; Scriven, E. F. V. Eds.; Pergamon Press: Oxford, 1996; Vol. 2, p 351, and *Comprehensive Heterocyclic Chemistry*; Katritzky, A. R.; Rees, W. C. Eds.; Pergamon Press: Oxford, 1986; Vol. 3. When p is 0, cyclization procedures are found in Hepworth, J. D. in *Comprehensive Heterocyclic Chemistry II*; Katritzky, A. R.; Rees, W. C.; Scriven, E. F. V. Eds.; Pergamon Press: Oxford, 1996; Vol. 5, p 351 and *Comprehensive Heterocyclic Chemistry*; Katritzky, A. R.; Rees, W. C. Eds.; Pergamon Press: Oxford, 1986; Vol. 3, all of which citations are hereby expressly incorporated herein by reference.

The hydroxy ketone is subjected to cyclization, as described in the above Hepworth, J. D. in *Comprehensive Heterocyclic Chemistry II*; Katritzky, A. R.; Rees, W. C.; Scriven, E. F. V. Eds.; Pergamon Press: Oxford, 1996; Vol. 5, p 386. For compounds III where $W^{(1)(2)}$ is $HO(CH_2)_n$—$R^1R^2$: The hydroxy group is first deprotected as described in Greene, T. W., *Protective Groups in Organic Synthesis*, 3rd edition (1999). For other structures, where Y is a group such as an acid, aldehydes, etc., protection is needed (acids as esters, preferably pivaloyl, aldehydes as silyl derivatives such as TIPS, stable in both basic and acidic conditions). When $W^{(1)(2)}$ is a lactone it can be introduced as discussed in Scheme 3 above. The compounds are then coupled to afford compound of the formula IIIa.

The reactions are performed under similar conditions for substituted cyclic compounds. After the formation of the monocyclic compounds, they are reacted in situ with electrophiles (e.g., MeI) at temperatures between −40° C. to +60° C., for a reaction time of 1 hr to 5 days. In addition, double bonds can be selectively added or reduced or otherwise manipulated by well known synthetic methods to give compounds III having one or two selectively-placed double bonds (i.e., the double bond(s) can be positioned in the desired location within the ring), for example, the methods disclosed in March, J. *Advanced Organic Chemistry; Reactions Mechanisms, and Structure*, 4th ed., 1992, pp. 771-780, incorporated herein by reference. Finally, compounds IIIa are reduced using methods known to those of ordinary skill in the art to afford alcohol IIIa. See *Comprehensive Organic Transformations*; VCH: New York, 1989. It is readily recognized that the alcohol compound IIIa is stereoisomeric and can therefore exist as enantiomers and diastereomer. Separation of the stereoisomers (i.e., enantiomers or diastereomers) can be achieved by methods known in the art, for example, conversion to a chiral salt and crystallization, chiral chromatography, or chiral HPLC.

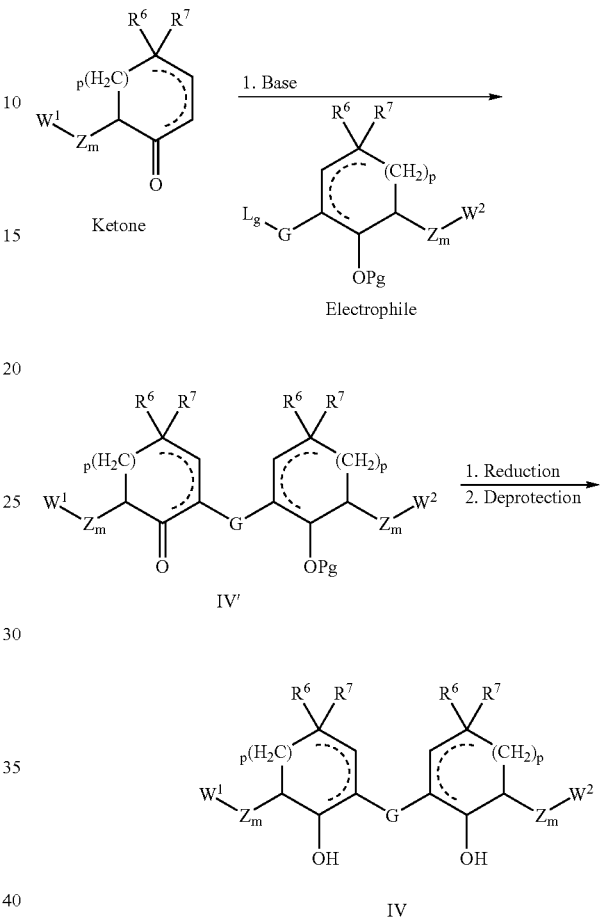

Scheme 14 depicts the synthesis of compounds IV. In the first step, ketone compounds, prepared as discussed in Schemes 1 to 6 above, can be converted to compounds IV' by treating with a strong base (e.g., LiHMDS, LDA) to generate the kinetic enolate followed by addition of the electrophile. In the next step, the ketone moiety of compound IV' is reduced using standard methods known to those of ordinary skill in the art. For exemplary procedures for Grignard reaction see March, J. *Advanced Organic Chemistry; Reactions Mechanisms, and Structure*, 4th ed., 1992, incorporated herein by reference. See also *Comprehensive Heterocyclic Chemistry II*; Katritzky, A. R.; Rees, W. C.; Scriven, E. F. V. Eds.; Pergamon Press: Oxford, 1996; Vol. 2, and *Comprehensive Heterocyclic Chemistry*; Katritzky, A. R.; Rees, W. C. Eds.; Pergamon Press: Oxford, 1986; Vol. 3. Press: Oxford, 1996; Vol. 5.

It is readily recognized that the diol compound IV is stereoisomeric and can therefore exist as enantiomers and diastereomers. Separation of the stereoisomers (i.e., enantiomers or diastereomers) can be achieved by methods known in the art, for example, conversion to a chiral salt and crystallization, chiral chromatography, or chiral HPLC.

Scheme 16 refers to the synthesis of diols of type V (unsymmetrical) and X (symmetrical).

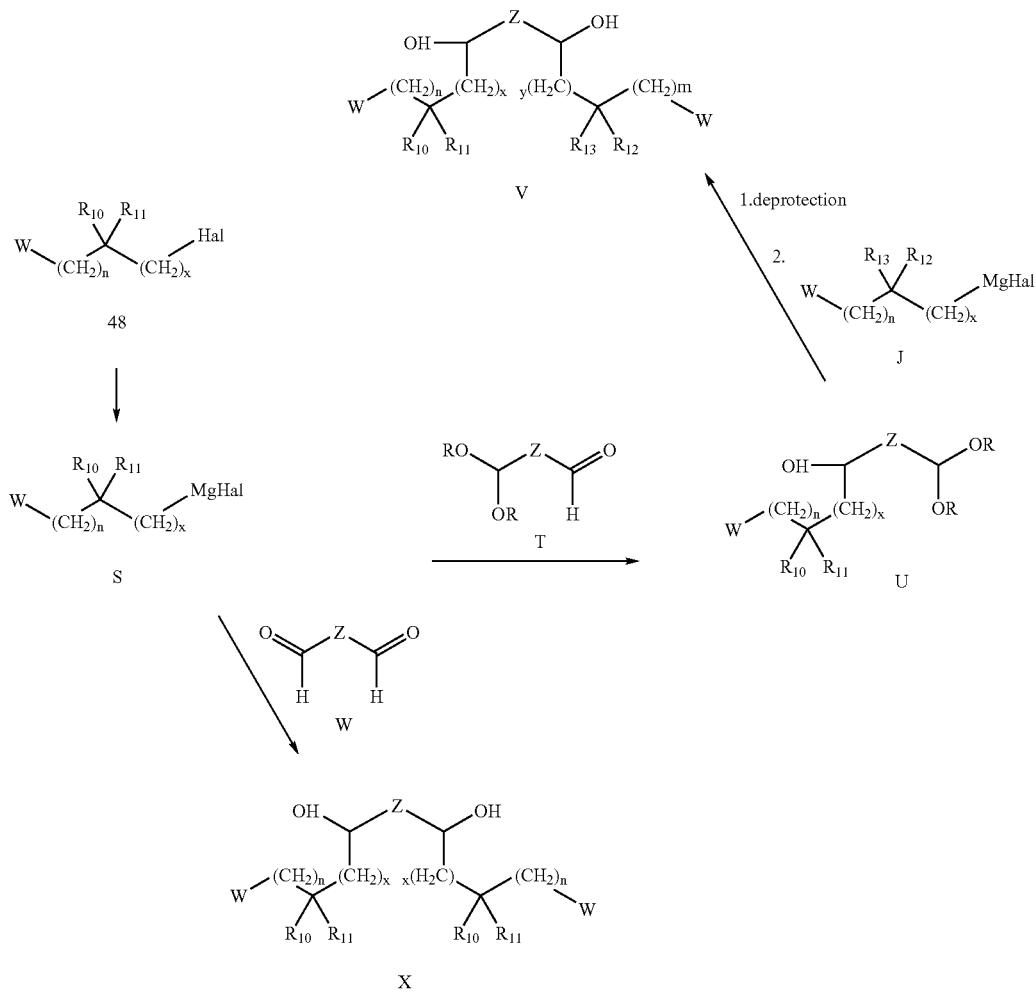

Grignard reagents obtained from halides 48 are treated with an aldehyde in conditions well-known for reactions of organo magnesium derivatives. Aldehydes T and W are commercially available (e.g. Aldrich) or can be obtained by methods described in the literature. The reaction could be performed sequentially to give the non-symmetrical derivatives of type V, with the formation of the intermediate of type U, followed by deprotection of the second aldehyde moiety. Treatment with a second mole of Grignard reagent S of the deprotected intermediate of type U affords the final compound V. If 2 equiv of Grignard reagent are used in the reaction with an aldehyde of type W, the symmetrical diol of type X is obtained.

Scheme 16 describes the synthesis of 2,2,13,13-tetramethyltetradecan-1,6,9,14-tetraol (XD).

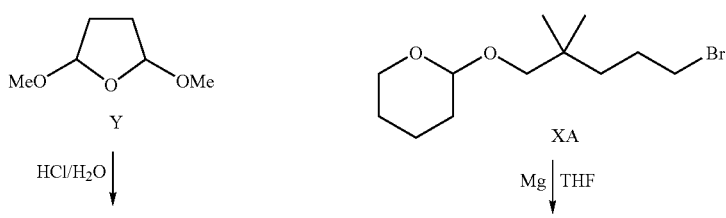

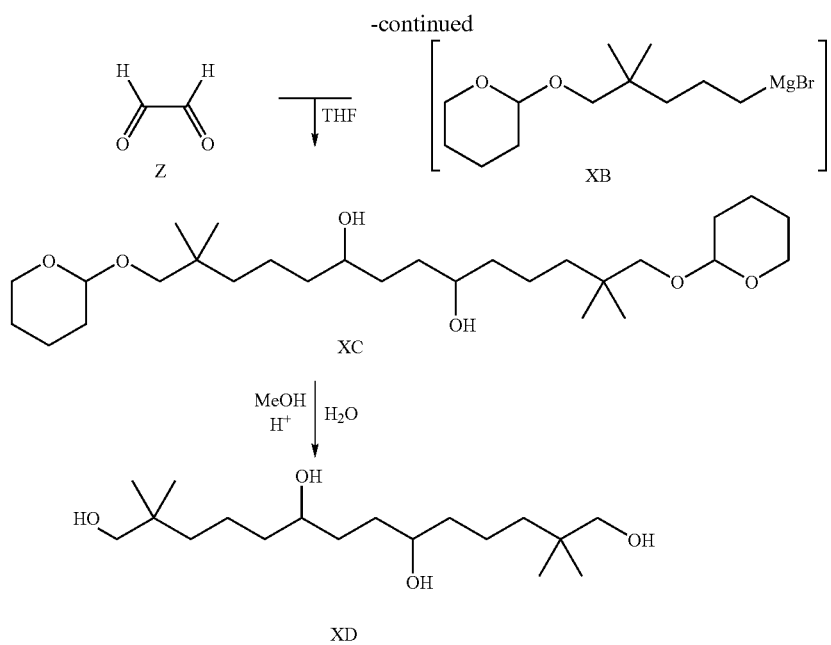

THP-protected bromo alcohol XA was converted into the corresponding Grignard reagent XB following the standard procedure (Vogel, A. I. "Vogel's Textbook of Practical Organic Chemistry", 5th Edition, Longman, England, 1989, p. 535). Further coupling of this Grignard reagent in situ with succinic dialdehyde Z prepared by acid-catalyzed ring-opening of commercially available 2,5-dimethoxytetrahydrofuran Y (Fakstorp, J.; Raleigh, D.; Schniepp, L. E. J. Am. Chem. Soc., 1950, 72, 869, House, H. O.; Cronin, T. H. J. Org. Chem., 1965, 30, 1061) at 0 to 5° C. occurs smoothly to give the bis(THP-protected) tetraol XC in high yield (92% after flash column chromatography purification). Acidic hydrolysis of XC in methanol/aqueous $H_2SO_4$ was completed in two hours to afford tetraol XD. The product is insoluble in dichloromethane and diethyl ether and could be purified by washing with one of these solvents. It is also practically insoluble in chloroform, acetone, acetonitrile, or water, and all can be used for further purifications.

5.2 Therapeutic Uses of Compounds or Compositions of the Invention

In accordance with the invention, a compound of the invention or a composition of the invention, comprising a compound of the invention and a pharmaceutically acceptable vehicle, is administered to a patient, preferably a human, with or at risk of aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. In one embodiment, "treatment" or "treating" refers to an amelioration of a disease or disorder, or at least one discernible symptom thereof. In another embodiment, "treatment" or "treating" refers to inhibiting the progression of a disease or disorder, either physically, e.g., stabilization of a discernible symptom, physiologically, e.g., stabilization of a physical parameter, or both.

In certain embodiments, the compounds of the invention or the compositions of the invention are administered to a patient, preferably a human, as a preventative measure against such diseases. As used herein, "prevention" or "preventing" refers to a reduction of the risk of acquiring a given disease or disorder. In a preferred mode of the embodiment, the compositions of the present invention are administered as a preventative measure to a patient, preferably a human having a genetic predisposition to a aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. Examples of such genetic predispositions include but are not limited to the ε4 allele of apolipoprotein E, which increases the likelihood of Alzheimer's Disease; a loss of function or null mutation in the lipoprotein lipase gene coding region or promoter (e.g., mutations in the coding regions resulting in the substitutions D9N and N291S; for a review of genetic mutations in the lipoprotein lipase gene that increase the risk of cardiovascular diseases, dyslipidemias and dyslipoproteinemias, see Hayden and Ma, 1992, Mol. Cell Biochem. 113:171-176); and familial combined hyperlipidemia and familial hypercholesterolemia.

In another preferred mode of the embodiment, the compounds of the invention or compositions of the invention are administered as a preventative measure to a patient having a non-genetic predisposition to a aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, inflammatory processes and diseases like gastrointestinal disease, irritable bowel syndrome (113S), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. Examples of such non-genetic predispositions include but are not limited to cardiac bypass surgery and percutaneous transluminal coronary angioplasty, which often lead to restenosis, an accelerated form of atherosclerosis; diabetes in women, which often leads to polycystic ovarian disease; and cardiovascular disease, which often leads to impotence. Accordingly, the compositions of the invention may be used for the prevention of one disease or disorder and concurrently treating another (e.g., prevention of polycystic ovarian disease while treating diabetes; prevention of impotence while treating a cardiovascular disease).

5.2.1 Treatment of Cardiovascular Diseases

The present invention provides methods for the treatment or prevention of a cardiovascular disease, comprising administering to a patient a therapeutically effective amount of a compound or a composition comprising a compound of the invention and a pharmaceutically acceptable vehicle. As used herein, the term "cardiovascular diseases" refers to diseases of the heart and circulatory system. These diseases are often associated with dyslipoproteinemias and/or dyslipidemias. Cardiovascular diseases which the compositions of the present invention are useful for preventing or treating include but are not limited to arteriosclerosis; atherosclerosis; stroke; ischemia; endothelium dysfunctions, in particular those dysfunctions affecting blood vessel elasticity; peripheral vascular disease; coronary heart disease; myocardial infarcation; cerebral infarction and restenosis.

5.2.2 Treatment of Dyslipidemias

The present invention provides methods for the treatment or prevention of a dyslipidemia comprising administering to a patient a therapeutically effective amount of a compound or a composition comprising a compound of the invention and a pharmaceutically acceptable vehicle.

As used herein, the term "dyslipidemias" refers to disorders that lead to or are manifested by aberrant levels of circulating lipids. To the extent that levels of lipids in the blood are too high, the compositions of the invention are administered to a patient to restore normal levels. Normal levels of lipids are reported in medical treatises known to those of skill in the art. For example, recommended blood levels of LDL, HDL, free triglycerides and others parameters relating to lipid metabolism can be found at the web site of the American Heart Association and that of the National Cholesterol Education Program of the National Heart, Lung and Blood Institute (http://www.americanheart.org/cholesterol/about_level.html and http://www.nhlbi.nih.gov/health/public/heart/chol/hbc_what.html, respectively). At the present time, the recommended level of HDL cholesterol in the blood is above 35 mg/dL; the recommended level of LDL cholesterol in the blood is below 130 mg/dL; the recommended LDL:HDL cholesterol ratio in the blood is below 5:1, ideally 3.5:1; and the recommended level of free triglycerides in the blood is less than 200 mg/dL.

Dyslipidemias which the compositions of the present invention are useful for preventing or treating include but are not limited to hyperlipidemia and low blood levels of high density lipoprotein (HDL) cholesterol. In certain embodiments, the hyperlipidemia for prevention or treatment by the compounds of the present invention is familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of urea bodies (e.g. β-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a patient, e.g., reducing LDL in the blood of a patient, reducing free triglycerides in the blood of a patient, increasing the ratio of HDL to LDL in the blood of a patient, and inhibiting saponified and/or non-saponified fatty acid synthesis, said methods comprising administering to the patient a compound or a composition comprising a compound of the invention in an amount effective alter lipid metabolism.

5.2.3 Treatment of Dyslipoproteinemias

The present invention provides methods for the treatment or prevention of a dyslipoproteinemia comprising administering to a patient a therapeutically effective amount of a compound or a composition comprising a compound of the invention and a pharmaceutically acceptable vehicle.

As used herein, the term "dyslipoproteinemias" refers to disorders that lead to or are manifested by aberrant levels of circulating lipoproteins. To the extent that levels of lipoproteins in the blood are too high, the compositions of the invention are administered to a patient to restore normal levels. Conversely, to the extent that levels of lipoproteins in the blood are too low, the compositions of the invention are administered to a patient to restore normal levels. Normal levels of lipoproteins are reported in medical treatises known to those of skill in the art.

Dyslipoproteinemias which the compositions of the present invention are useful for preventing or treating include but are not limited to high blood levels of LDL; high blood levels of apolipoprotein B (apo B); high blood levels of Lp(a); high blood levels of apo(a); high blood levels of VLDL; low blood levels of HDL; reduced or deficient lipoprotein lipase levels or activity, including reductions or deficiencies resulting from lipoprotein lipase mutations; hypoalphalipoproteinemia; lipoprotein abnormalities associated with diabetes; lipoprotein abnormalities associated with obesity; lipoprotein abnormalities associated with Alzheimer's Disease; and familial combined hyperlipidemia.

The present invention further provides methods for reducing apo C-II levels in the blood of a patient; reducing apo C-III levels in the blood of a patient; elevating the levels of HDL associated proteins, including but not limited to apo A-I, apo A-II, apo A-IV and apo E in the blood of a patient; elevating the levels of apo E in the blood of a patient, and promoting clearance of triglycerides from the blood of a patient, said methods comprising administering to the patient a compound or a composition comprising a compound of the invention in an amount effective to bring about said reduction, elevation or promotion, respectively.

5.2.4 Treatment of Glucose Metabolism Disorders

The present invention provides methods for the treatment or prevention of a glucose metabolism disorder, comprising administering to a patient a therapeutically effective amount of a compound or a composition comprising a compound of the invention and a pharmaceutically acceptable vehicle. As used herein, the term "glucose metabolism disorders" refers to disorders that lead to or are manifested by aberrant glucose storage and/or utilization. To the extent that indicia of glucose metabolism (i.e., blood insulin, blood glucose) are too high, the compositions of the invention are administered to a patient to restore normal levels. Conversely, to the extent that indicia of glucose metabolism are too low, the compositions of the invention are administered to a patient to restore normal levels. Normal indicia of glucose metabolism are reported in medical treatises known to those of skill in the art.

Glucose metabolism disorders which the compositions of the present invention are useful for preventing or treating include but are not limited to impaired glucose tolerance; insulin resistance; insulin resistance related breast, colon or prostate cancer; diabetes, including but not limited to non-insulin dependent diabetes mellitus (NIDDM), insulin dependent diabetes mellitus (IDDM), gestational diabetes mellitus (GDM), and maturity onset diabetes of the young (MODY); pancreatitis; hypertension; polycystic ovarian disease; and high levels of blood insulin and/or glucose.

The present invention further provides methods for altering glucose metabolism in a patient, for example to increase insulin sensitivity and/or oxygen consumption of a patient, said methods comprising administering to the patient a compound or a composition comprising a compound of the invention in an amount effective to alter glucose metabolism.

5.2.5 Treatment of PPAR-Associated Disorders

The present invention provides methods for the treatment or prevention of a PPAR-associated disorder, comprising administering to a patient a therapeutically effective amount of a compound or a composition comprising a compound of the invention and a pharmaceutically acceptable vehicle. As used herein, "treatment or prevention of PPAR associated disorders" encompasses treatment or prevention of rheumatoid arthritis; multiple sclerosis; psoriasis; inflammatory bowel diseases; breast; colon or prostate cancer; low levels of blood HDL; low levels of blood, lymph and/or cerebrospinal fluid apo E; low blood, lymph and/or cerebrospinal fluid levels of apo A-I; high levels of blood VLDL; high levels of blood LDL; high levels of blood triglyceride; high levels of blood apo B; high levels of blood apo C-III and reduced ratio of post-heparin hepatic lipase to lipoprotein lipase activity. HDL may be elevated in lymph and/or cerebral fluid.

5.2.6 Treatment of Renal Diseases

The present invention provides methods for the treatment or prevention of a renal disease, comprising administering to a patient a therapeutically effective amount of a compound or a composition comprising a compound of the invention and a pharmaceutically acceptable vehicle. Renal diseases that can be treated by the compounds of the present invention include glomerular diseases (including but not limited to acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (including but not limited to acute tubular necrosis and acute renal failure, polycystic renal diseasemedullary sponge kidney, medullary cystic disease, nephrogenic diabetes, and renal tubular acidosis), tubulointerstitial diseases (including but not limited to pyelonephritis, drug and toxin induced tubulointerstitial nephritis, hypercalcemic nephropathy, and hypokalemic nephropathy) acute and rapidly progressive renal failure, chronic renal failure, nephrolithiasis, or tumors (including but not limited to renal cell carcinoma and nephroblastoma). In a most preferred embodiment, renal diseases that are treated by the compounds of the present invention are vascular diseases, including but not limited to hypertension, nephrosclerosis, microangiopathic hemolytic anemia, atheroembolic renal disease, diffuse cortical necrosis, and renal infarcts.

5.2.7 Treatment of Cancer

The present invention provides methods for the treatment or prevention of cancer, comprising administering to a patient a therapeutically effective amount of a compound or a composition comprising a compound of the invention and a pharmaceutically acceptable vehicle. Types of cancer that can be treated using a Compound of the Invention include, but are not limited to, those listed in Table 2.

TABLE 2

Solid tumors, including but not limited to
    fibrosarcoma
    myxosarcoma
    liposarcoma
    chondrosarcoma
    osteogenic sarcoma
    chordoma
    angiosarcoma
    endotheliosarcoma TABLE 2-continued lymphangiosarcoma
lymphangioendotheliosarcoma
synovioma
mesothelioma
Ewing's tumor
leiomyosarcoma
rhabdomyosarcoma
colon cancer
colorectal cancer
kidney cancer
pancreatic cancer
bone cancer
breast cancer
ovarian cancer
prostate cancer
esophogeal cancer
stomach cancer
oral cancer
nasal cancer
throat cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular cancer
small cell lung carcinoma
bladder carcinoma
lung cancer
epithelial carcinoma
glioma
glioblastoma multiforme
astrocytoma
medulloblastoma
craniopharyngioma
ependymoma
pinealoma
hemangioblastoma
acoustic neuroma
oligodendroglioma
meningioma
skin cancer
melanoma
neuroblastoma
retinoblastoma
Blood-borne cancers, including but not limited to:
    acute lymphoblastic B-cell leukemia
    acute lymphoblastic T-cell leukemia
    acute myeloblastic leukemia "AML"
    acute promyelocytic leukemia "APL"
    acute monoblastic leukemia
    acute erythroleukemic leukemia
    acute megakaryoblastic leukemia
    acute myelomonocytic leukemia
    acute nonlymphocyctic leukemia
    acute undifferentiated leukemia
    chronic myelocytic leukemia "CML"
    chronic lymphocytic leukemia "CLL"
    hairy cell leukemia
    multiple myeloma
Acute and chronic leukemias
    Lymphoblastic
    myelogenous
    lymphocytic
    myelocytic leukemias TABLE 2-continued Lymphomas:
    Hodgkin's disease
    non-Hodgkin's Lymphoma
    Multiple myeloma
    Waldenstrom's macroglobulinemia
    Heavy chain disease
    Polycythemia vera Cancer, including, but not limited to, a tumor, metastasis, or any disease or disorder characterized by uncontrolled cell growth, can be treated or prevented by administration of a Compound of the Invention.

5.2.8 Treatment of Other Diseases

The present invention provides methods for the treatment or prevention of Alzheimer's Disease, Syndrome X, septicemia, thrombotic disorders, obesity, pancreatitis, hypertension, inflammation, and impotence, comprising administering to a patient a therapeutically effective amount of a compound or a composition comprising a compound of the invention and a pharmaceutically acceptable vehicle.

As used herein, "treatment or prevention of Alzheimer's Disease" encompasses treatment or prevention of lipoprotein abnormalities associated with Alzheimer's Disease.

As used herein, "treatment or prevention of Syndrome X or Metabolic Syndrome" encompasses treatment or prevention of a symptom thereof, including but not limited to impaired glucose tolerance, hypertension and dyslipidemia/dyslipoproteinemia.

As used herein, "treatment or prevention of septicemia" encompasses treatment or prevention of septic shock.

As used herein, "treatment or prevention of thrombotic disorders" encompasses treatment or prevention of high blood levels of fibrinogen and promotion of fibrinolysis.

In addition to treating or preventing obesity, the compositions of the invention can be administered to an individual to promote weight reduction of the individual.

As used herein, "treatment or prevention of diabetic nephropathy" encompasses treating or preventing kidney disease that develops as a result of diabetes mellitus (DM). Diabetes mellitus is a disorder in which the body is unable to metabolize carbohydrates (e.g., food starches, sugars, cellulose) properly. The disease is characterized by excessive amounts of sugar in the blood (hyperglycemia) and urine; inadequate production and/or utilization of insulin; and by thirst, hunger, and loss of weight. Thus, the compounds of the invention can also be used to treat or prevent diabetes mellitus.

As used herein, "treatment or prevention of diabetic retinopathy" encompasses treating or preventing complications of diabetes that lead to or cause blindness. Diabetic retinopathy occurs when diabetes damages the tiny blood vessels inside the retina, the light-sensitive tissue at the back of the eye.

As used herein, "treatment or prevention of impotence" includes treating or preventing erectile dysfunction, which encompasses the repeated inability to get or keep an erection firm enough for sexual intercourse. The word "impotence" may also be used to describe other problems that interfere with sexual intercourse and reproduction, such as lack of sexual desire and problems with ejaculation or orgasm. The term "treatment or prevention of impotence includes, but is not limited to impotence that results as a result of damage to nerves, arteries, smooth muscles, and fibrous tissues, or as a result of disease, such as, but not limited to, diabetes, kidney disease, chronic alcoholism, multiple sclerosis, atherosclerosis, vascular disease, and neurologic disease.

As used herein, "treatment or prevention of hypertension" encompasses treating or preventing blood flow through the vessels at a greater than normal force, which strains the heart; harms the arteries; and increases the risk of heart attack, stroke, and kidney problems. The term hypertension includes, but is not limited to, cardiovascular disease, essential hypertension, hyperpiesia, hyperpiesis, malignant hypertension, secondary hypertension, or white-coat hypertension.

As used herein, "treatment or prevention of inflammation" encompasses treating or preventing inflammation diseases including, but not limited to, chronic inflammatory disorders of the joints including arthritis, e.g., rheumatoid arthritis and osteoarthritis; respiratory distress syndrome, inflammatory bowel diseases such as ileitis, ulcerative colitis and Crohn's disease; and inflammatory lung disorders such as asthma and chronic obstructive airway disease, inflammatory disorders of the eye such as corneal dystrophy, trachoma, onchocerciasis, uveitis, sympathetic ophthalmitis, and endophthalmitis; inflammatory disorders of the gum, e.g., periodontitis and gingivitis; tuberculosis; leprosy; inflammatory diseases of the kidney including glomerulonephritis and nephrosis; inflammatory disorders of the skin including acne, sclerodermatitis, psoriasis, eczema, photoaging and wrinkles; inflammatory diseases of the central nervous system, including AIDS-related neurodegeneration, stroke, neurotrauma, Alzheimer's disease, encephalomyelitis and viral or autoimmune encephalitis; autoimmune diseases including immune-complex vasculitis, systemic lupus and erythematodes; systemic lupus erythematosus (SLE); and inflammatory diseases of the heart such as cardiomyopathy.

5.3 Combination Therapy

In certain embodiments of the present invention, the compounds and compositions of the invention can be used in combination therapy with at least one other therapeutic agent. The compound of the invention and the therapeutic agent can act additively or, more preferably, synergistically. In a preferred embodiment, a compound or a composition comprising a compound of the invention is administered concurrently with the administration of another therapeutic agent, which can be part of the same composition as the compound of the invention or a different composition. In another embodiment, a compound or a composition comprising a compound of the invention is administered prior or subsequent to administration of another therapeutic agent. As many of the disorders for which the compounds and compositions of the invention are useful in treating are chronic disorders, in one embodiment combination therapy involves alternating between administering a compound or a composition comprising a compound of the invention and a composition comprising another therapeutic agent, e.g., to minimize the toxicity associated with a particular drug. The duration of administration of each drug or therapeutic agent can be, e.g., one month, three months, six months, or a year. In certain embodiments, when a composition of the invention is administered concurrently with another therapeutic agent that potentially produces adverse side effects including but not limited to toxicity, the therapeutic agent can advantageously be administered at a dose that falls below the threshold at which the adverse side is elicited.

The present compositions can be administered together with a statin. Statins for use in combination with the compounds and compositions of the invention include but are not limited to atorvastatin, pravastatin, fluvastatin, lovastatin, simvastatin, and cerivastatin.

The present compositions can also be administered together with a PPAR agonist, for example a thiazolidinedione or a fibrate. Thiazolidinediones for use in combination with the compounds and compositions of the invention include but are not limited to 5((4(2(methyl 2 pyridinylamino)ethoxy)phenyl)methyl) 2,4 thiazolidinedione, troglitazone, pioglitazone, ciglitazone, WAY 120,744, englitazone, AD 5075, darglitazone, and rosiglitazone. Fibrates for use in combination with the compounds and compositions of the invention include but are not limited to gemfibrozil, fenofibrate, clofibrate, or ciprofibrate. As mentioned previously, a therapeutically effective amount of a fibrate or thiazolidinedione often has toxic side effects. Accordingly, in a preferred embodiment of the present invention, when a composition of the invention is administered in combination with a PPAR agonist, the dosage of the PPAR agonist is below that which is accompanied by toxic side effects.

The present compositions can also be administered together with a bile acid binding resin. Bile acid binding resins for use in combination with the compounds and compositions of the invention include but are not limited to cholestyramine and colestipol hydrochloride. The present compositions can also be administered together with niacin or nicotinic acid. The present compositions can also be administered together with a RXR agonist. RXR agonists for use in combination with the compounds of the invention include but are not limited to LG 100268, LGD 1069, 9-cis retinoic acid, 2(1(3,5,5,8,8 pentamethyl 5,6,7,8 tetrahydro 2 naphthyl)cyclopropyl)pyridine 5 carboxylic acid, or 4 ((3, 5,5,8,8 pentamethyl 5,6,7,8 tetrahydro 2 naphthyl)2 carbonyl)benzoic acid. The present compositions can also be administered together with an anti-obesity drug. Anti-obesity drugs for use in combination with the compounds of the invention include but are not limited to β-adrenergic receptor agonists, preferably β-3 receptor agonists, fenfluramine, dexfenfluramine, sibutramine, bupropion, fluoxetine, and phentermine. The present compositions can also be administered together with a hormone. Hormones for use in combination with the compounds of the invention include but are not limited to thyroid hormone, estrogen and insulin. Preferred insulins include but are not limited to injectable insulin, transdermal insulin, inhaled insulin, or any combination thereof. As an alternative to insulin, an insulin derivative, secretagogue, sensitizer or mimetic may be used. Insulin secretagogues for use in combination with the compounds of the invention include but are not limited to forskolin, dibutryl cAMP or isobutylmethylxanthine (IBMX).

The present compositions can also be administered together with a phosphodiesterase type 5 ("PDE5") inhibitor to treat or prevent disorders, such as but not limited to, impotence. In a particular, embodiment the combination is a synergistic combination of a composition of the invention and a PDE5 inhibitor.

The present compositions can also be administered together with a tyrophostine or an analog thereof. Tyrophostines for use in combination with the compounds of the invention include but are not limited to tryophostine 51.

The present compositions can also be administered together with sulfonylurea-based drugs. Sulfonylurea-based drugs for use in combination with the compounds of the invention include, but are not limited to, glisoxepid, glyburide, acetohexamide, chlorpropamide, glibornuride, tolbutamide, tolazamide, glipizide, gliclazide, gliquidone, glyhexamide, phenbutamide, and tolcyclamide. The present compositions can also be administered together with a biguanide. Biguanides for use in combination with the compounds of the invention include but are not limited to metformin, phenformin and buformin.

The present compositions can also be administered together with an α-glucosidase inhibitor. α-glucosidase inhibitors for use in combination with the compounds of the invention include but are not limited to acarbose and miglitol.

The present compositions can also be administered together with an apo A-I agonist. In one embodiment, the apo A-I agonist is the Milano form of apo A-I (apo A-IM). In a preferred mode of the embodiment, the apo A-IM for administration in conjunction with the compounds of the invention is produced by the method of U.S. Pat. No. 5,721,114 to Abrahamsen. In a more preferred embodiment, the apo A-I agonist is a peptide agonist. In a preferred mode of the embodiment, the apo A-I peptide agonist for administration in conjunction with the compounds of the invention is a peptide of U.S. Pat. No. 6,004,925 or 6,037,323 to Dasseux.

The present compositions can also be administered together with apolipoprotein E (apo E). In a preferred mode of the embodiment, the apoE for administration in conjunction with the compounds of the invention is produced by the method of U.S. Pat. No. 5,834,596 to Ageland.

In yet other embodiments, the present compositions can be administered together with an HDL-raising drug; an HDL enhancer; or a regulator of the apolipoprotein A-I, apolipoprotein A-IV and/or apolipoprotein genes.

In one embodiment, the other therapeutic agent can be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethyleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

In another embodiment, the other therapeutic agent can be an hematopoietic colony stimulating factor. Suitable hematopoietic colony stimulating factors include, but are not limited to, filgrastim, sargramostim, molgramostim and erythropoietin alfa.

In still another embodiment, the other therapeutic agent can be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

5.3.1 Combination Therapy of Cardiovascular Diseases

The present compositions can be administered together with a known cardiovascular drug. Cardiovascular drugs for use in combination with the compounds of the invention to prevent or treat cardiovascular diseases include but are not limited to peripheral antiadrenergic drugs, centrally acting antihypertensive drugs (e.g., methyldopa, methyldopa HCl), antihypertensive direct vasodilators (e.g., diazoxide, hydralazine HCl), drugs affecting renin-angiotensin system, peripheral vasodilators, phentolamine, antianginal drugs, cardiac glycosides, inodilators (e.g., amrinone, milrinone, enoximone, fenoximone, imazodan, sulmazole), antidysrhythmic drugs, calcium entry blockers, ranitine, bosentan, and rezulin.

5.3.2 Combination Therapy of Cancer

The present invention includes methods for treating cancer, comprising administering to an animal in need thereof an effective amount of a Compound of the Invention and another therapeutic agent that is an anti-cancer agent. Suitable anticancer agents include, but are not limited to, those listed in Table 3.

TABLE 3

| | |
|---|---|
| Alkylating agents | |
| Nitrogen mustards: | Cyclophosphamide |
| | Ifosfamide |
| | trofosfamide |
| | Chlorambucil |
| | Treos |
| Nitrosoureas: | carbustine (BCNU) |
| | Lomustine (CCNU) |
| Alkylsulphonates | Busulfan |
| | Treosulfan |
| Triazenes: | Dacarbazine |
| Platinum containing compounds: | Cisplatin |
| | carboplatin |
| Plant Alkaloids | |
| Vinca alkaloids: | Vicristine |
| | Vinblastine |
| | Vindesine |
| | Vinorelbine |
| Taxoids: | paclitaxel |
| | Docetaxol |
| DNA Topoisomerase Inhibitors | |
| Epipodophyllins: | Etoposide |
| | Teniposide |
| | Topotecan |
| | 9-aminocamptothecin |
| | camptothecin |
| | crisnatol |
| mitomycins: | Mitomycin C |
| Anti-metabolites | |
| Anti-folates: | |
| DHFR inhibitors: | METHOTREXATE |
| | Trimetrexate |
| IMP dehydrogenase Inhibitors: | Mycophenolic acid |
| | Tiazofurin |
| | Ribavirin |
| | EICAR |
| Ribonucleotide reductase Inhibitors: | Hydroxyurea |
| | deferoxamine |

TABLE 3-continued

Pyrimidine analogs:

| | |
|---|---|
| Uracil analogs | 5-Fluorouracil |
| | Floxuridine |
| | Doxifluridine |
| | Ratitrexed |
| Cytosine analogs | cytarabine (ara C) |
| | Cytosine arabinoside |
| | fludarabine |
| Purine analogs: | mercaptopurine |
| | Thioguanine |
| Hormonal therapies: | |
| Receptor antagonists: | |
| Anti-estrogen | Tamoxifen |
| | Raloxifene |
| | megestrol |
| | goserelin |
| | Leuprolide acetate |
| LHRH agonists: | flutamide |
| | bicalutamide |
| Retinoids/Deltoids | |
| Vitamin D3 analogs: | EB 1089 |
| | CB 1093 |
| | KH 1060 |
| Photodynamic therapies: | vertoporfin (BPD-MA) |
| | Phthalocyanine |
| | photosensitizer Pc4 |
| | Demethoxy-hypocrellin A |
| | (2BA-2-DMHA) |
| Cytokines: | Interferon-α |
| | Interferon-γ |
| | Tumor necrosis factor |
| Others: | |
| Isoprenylation inhibitors: | Lovastatin |
| Dopaminergic neurotoxins: | 1-methyl-4-phenylpyridinium ion |
| Cell cycle inhibitors: | staurosporine |
| Actinomycines: | Actinomycin D |
| | Dactinomycin |
| Bleomycins: | bleomycin A2 |
| | Bleomycin B2 |
| | Peplomycin |
| Anthracyclines: | daunorubicin |
| | Doxorubicin (adriamycin) |
| | Idarubicin |
| | Epirubicin |
| | Pirarubicin |
| | Zorubicin |
| | Mitoxantrone |
| MDR inhibitors | verapamil |
| $Ca^{2+}$ ATPase inhibitors: | thapsigargin |

In a specific embodiment, a composition of the invention further comprises one or more chemotherapeutic agents and/or is administered concurrently with radiation therapy. In another specific embodiment, chemotherapy or radiation therapy is administered prior or subsequent to administration of a present composition, preferably at least an hour, five hours, 12 hours, a day, a week, a month, more preferably several months (e.g., up to three months), subsequent to administration of a composition of the invention.

In other embodiments, the invention provides methods for treating or preventing cancer, comprising administering to an animal in need thereof an effective amount of a Compound of the Invention and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Compounds of the Invention can be administered to an animal that has also undergone surgery as treatment for the cancer.

In one embodiment, the additional method of treatment is radiation therapy.

In a specific embodiment, the Compound of the Invention is administered concurrently with the chemotherapeutic agent or with radiation therapy. In another specific embodiment, the chemotherapeutic agent or radiation therapy is administered prior or subsequent to administration of a Compound of the Invention, preferably at least an hour, five hours, 12 hours, a day, a week, a month, more preferably several months (e.g., up to three months), prior or subsequent to administration of a Compound of the Invention.

A chemotherapeutic agent can be administered over a series of sessions, any one or a combination of the chemotherapeutic agents listed in Table 3 can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, the invention provides methods of treatment of cancer with a Compound of the Invention as an alternative to chemotherapy or radiation therapy where the chemotherapy or the radiation therapy has proven or can prove too toxic, e.g., results in unacceptable or unbearable side effects, for the subject being treated. The animal being treated can, optionally, be treated with another cancer treatment such as surgery, radiation therapy or chemotherapy, depending on which treatment is found to be acceptable or bearable.

The Compounds of the Invention can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the patient's remaining bone-marrow cell population is then eradicated via the administration of a high dose of a Compound of the Invention with or without accompanying high dose radiation therapy, and the stem cell graft is infused back into the animal. Supportive care is then provided while bone marrow function is restored and the animal recovers.

5.4 Surgical Uses

Cardiovascular diseases such as atherosclerosis often require surgical procedures such as angioplasty. Angioplasty is often accompanied by the placement of a reinforcing a metallic tube shaped structure known as a "stent" into a damaged coronary artery. For more serious conditions, open heart surgery such as coronary bypass surgery may be required. These surgical procedures entail using invasive surgical devices and/or implants, and are associated with a high risk of restenosis and thrombosis. Accordingly, the compounds and compositions of the invention may be used as coatings on surgical devices (e.g., catheters) and implants (e.g., stents) to reduce the risk of restenosis and thrombosis associated with invasive procedures used in the treatment of cardiovascular diseases.

5.5 Veterinary and Livestock Uses

A composition of the invention can be administered to a non-human animal for a veterinary use for treating or preventing a disease or disorder disclosed herein.

In a specific embodiment, the non-human animal is a household pet. In another specific embodiment, the non-human animal is a livestock animal. In a preferred embodiment, the non-human animal is a mammal, most preferably a cow, horse, sheep, pig, cat, dog, mouse, rat, rabbit, or guinea pig. In another preferred embodiment, the non-human animal is a fowl species, most preferably a chicken, turkey, duck, goose, or quail.

In addition to veterinary uses, the compounds and compositions of the invention can be used to reduce the fat content of livestock to produce leaner meats. Alternatively, the compounds and compositions of the invention can be used to reduce the cholesterol content of eggs by administering the compounds to a chicken, quail, or duck hen. For non-human animal uses, the compounds and compositions of the invention can be administered via the animals' feed or orally as a drench composition.

5.6 Therapeutic/Prophylactic Administration and Compositions

Due to the activity of the compounds and compositions of the invention, they are useful in veterinary and human medicine. As described above, the compounds and compositions of the invention are useful for the treatment or prevention of aging, Alzheimer's Disease, cancer, cardiovascular disease, diabetic nephropathy, diabetic retinopathy, a disorder of glucose metabolism, dyslipidemia, dyslipoproteinemia, hypertension, impotence, inflammation, insulin resistance, lipid elimination in bile, modulating C reactive protein, obesity, oxysterol elimination in bile, pancreatitis, Parkinson's disease, a perox isome proliferator activated receptor-associated disorder, phospholipid elimination in bile, renal disease, septicemia, metabolic syndrome disorders (e.g., Syndrome X), a thrombotic disorder, enhancing bile production, enhancing reverse lipid transport, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism.

The invention provides methods of treatment and prophylax is by administration to a patient of a therapeutically effective amount of a compound or a composition comprising a compound of the invention. The patient is an animal, including, but not limited to, an animal such a cow, horse, sheep, pig, chicken, turkey, quail, cat, dog, mouse, rat, rabbit, guinea pig, etc., and is more preferably a mammal, and most preferably a human.

The compounds and compositions of the invention, are preferably administered orally. The compounds and compositions of the invention may also be administered by any other convenient route, for example, by intravenous infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

In certain embodiments, for example, for the treatment of Alzheimer's Disease, it may be desirable to introduce one or more compounds of the invention into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds and compositions of the invention can be delivered in a vesicle, in particular a liposome (see Langer, 1990, Science 249:1527 1533; Treat et al., in Liposomes in the Therapy of Infectious Disease and Cancer, Lopez-Berestein and Fidler (eds.), Liss, New York, pp. 353 365 (1989); Lopez Berestein, ibid., pp. 317 327; see generally ibid.).

In yet another embodiment, the compounds and compositions of the invention can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of the target area to be treated, e.g., the liver, thus requiring only a fraction of the systemic dose (see, e.g., Goodson, in Medical Applications of Controlled Release, supra, vol. 2, pp. 115 138 (1984)). Other controlled-release systems discussed in the review by Langer, 1990, Science 249:1527 1533) may be used.

The present compositions will contain a therapeutically effective amount of a compound of the invention, optionally more than one compound of the invention, preferably in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds and compositions of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin.

In a preferred embodiment, the compounds and compositions of the invention are formulated in accordance with routine procedures as a pharmaceutical composition adapted for intravenous administration to human beings. Typically, compounds and compositions of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by intravenous infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

Compounds and compositions of the invention for oral delivery may be in the form of tablets, lozenges, aqueous or oily suspensions, granules, powders, emulsions, capsules, syrups, or elixirs. Compounds and compositions of the invention for oral delivery can also be formulated in foods and food mixes. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds and compositions of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 2000 milligrams of a compound of the invention per kilogram body weight. In specific preferred embodiments of the invention, the oral dose is 0.01 milligram to 1000 milligrams per kilogram body weight, more preferably 0.1 milligram to 100 milligrams per kilogram body weight, more preferably 0.5 milligram to 25 milligrams per kilogram body weight, and yet more preferably 1 milligram to 10 milligrams per kilogram body weight. In a most preferred embodiment, the oral dose is 5 milligrams of a compound of the invention per kilogram body weight. The dosage amounts described herein refer to total amounts administered; that is, if more than one compound of the invention is administered, the preferred dosages correspond to the total amount of the compounds of the invention administered. Oral compositions preferably contain 10% to 95% active ingredient by weight.

Suitable dosage ranges for intravenous (i.v.) administration are 0.01 milligram to 1000 milligrams per kilogram body weight, 0.1 milligram to 350 milligrams per kilogram body weight, and 1 milligram to 100 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention. In another embodiment, the kit comprises a compound of the invention and another lipid-mediating compound, including but not limited to a statin, a thiazolidinedione, or a fibrate.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for lowering fatty acid synthesis. The compounds and compositions of the invention may also be demonstrated to be effective and safe using animal model systems.

Other methods will be known to the skilled artisan and are within the scope of the invention.

The following examples are provided by way of illustration and not limitation.

6. SYNTHETIC EXAMPLES

6.1 Synthesis of 2,2,13,13-Tetramethyltetradecan-1,6,9,14-tetraol

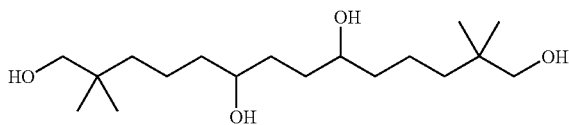

6.1.1 2,2,13,13-Tetramethyl-1,14-bis(tetrahydropyran-2-yloxy)tetradecan-6,9-diol A mixture of 2,5-dimethoxytetrahydrofuran (26.43 g, 0.2 mol) and 0.6 N hydrochloric acid (160 mL) was stirred at room temperature for 1.5 h. The pH was adjusted to 7 by addition of sodium hydrogen carbonate (8.4 g) and the solution was extracted with dichloromethane (3×50 mL). The aqueous phase was acidified with concentrated hydrochloric acid (10 mL) and stirred for another 1.5 h. Basification with sodium hydrogen carbonate (10.1 g) and extraction with dichloromethane was repeated. In total, the acidification—basification—extraction sequence was repeated four times. The combined organic extracts were dried over magnesium sulfate and the dichloromethane was distilled off under atmospheric pressure. The residue was distilled under reduced pressure (b.p.: 75-77° C./15 mm Hg)(House, H. O. et al., *J. Org. Chem.* 1965, 30, 1061. B.p.=55-60° C./12 mm Hg) to give succinaldehyde as a foul smelling, colorless liquid (5.71 g, 33%), which was used immediately after distillation.

Under nitrogen atmosphere, to a stirred suspension of magnesium powder (3.65 g, 0.15 mol) in anhydrous THF (200 mL) was added 2-(5-bromo-2,2-dimethylpentyl)-tetrahydropyran (27.9 g, 0.1 mol) at such a rate as to maintain a gentle reflux. The reaction mixture was heated at reflux for additional 2 h, allowed to cool to room temperature, and then cooled in an ice-water bath. A solution of freshly distilled succinaldehyde (3.44 g, 0.04 mol) in THF (30 mL) was added dropwise. The reaction mixture was left to stir at room temperature overnight. The solution was decanted off the excess magnesium and poured into an aqueous saturated ammonium chloride solution (300 mL). The pH was carefully adjusted to 1-2 with 2 N hydrochloric acid. The reaction mixture was extracted with diethyl ether and the organic extracts were washed with brine and dried over MgSO$_4$. After solvent removal, a light-yellow oil (23.88 g) was obtained which was purified by flash column chromatography (SiO$_2$, ethyl acetate:hexanes=1:3 to 1:1) to afford the pure product as an almost colorless, very viscous oil (18.04 g, 92%). $^1$H NMR (300 MHz, CDCl$_3$/TMS): δ (ppm): 4.54-4.50 (m, 2H), 3.89-3.82 (m, 2H) 3.66 (br. s, 2H), 3.48 (pseudo-t, 4H, J=9.6 Hz), 2.99 (dd, 2H, J=9.1, 3.5 Hz), 2.60 (br. s, 2H), 1.90-1.20 (m, 28H), 0.90-0.88 (m, 12H). $^{13}$C NMR (75 MHz, CDCl$_3$/TMS): δ (ppm): 99.4, 99.2, 76.4, 76.1, 72.1, 71.7, 71.3, 62.4, 62.0, 39.2, 38.8, 38.3, 38.2, 34.1, 33.4, 30.7, 30.6, 25.5, 24.9, 24.6, 24.5, 24.4, 20.0, 19.7, 19.5, 14.2. HRMS (LSIMS, nba): Calcd. for C$_{28}$H$_{55}$O$_6$ (MH$^+$): 487.3998, found: 487.3995.

6.1.2 2,2,13,13-Tetramethyltetradecan-1,6,9,14-tetraol

A solution of 2,2,13,13-tetramethyl-1,14-bis(tetrahydropyran-2-yloxy)tetradecane-6,9-diol (5.07 g, 0.01 mol) in methanol (100 mL) was treated with dilute aqueous sulfuric acid (5 mL of concentrated sulfuric acid in 15 mL of water), and stirred at room temperature overnight. The methanol was removed under reduced pressure and the residue was extracted with ethyl acetate (100 mL). The aqueous phase was saturated with solid sodium chloride and extracted again with ethyl acetate (75 mL). The combined organic extracts were washed with a saturated sodium chloride solution (50 mL) and dried over magnesium sulfate. The solid obtained after solvent removal was washed with diethyl ether (10 mL) to give 2,2,13,13-tetramethyltetradecan-1,6,9,14-tetraol (1.85 g, 58%) as a white powder. M.p.: 96-97° C. $^1$H NMR (300 MHz, DMSO-d$_6$/TMS): δ (ppm): 4.42 (pseudo-t, 2H, J=5.0 Hz), 4.28 (pseudo-t, 2H, J=5.0 Hz), 3.37-3.34 (m, 2H), 3.06 (d, 4H, J=5.0 Hz), 1.47-1.08 (m, 16H), 0.77 (s, 12H). $^{13}$C NMR (75 MHz, DMSO-d$_6$/TMS): δ (ppm): 70.1, 69.9, 38.8, 38.4, 34.9, 33.7, 24.2, 19.7. HRMS (LSIMS, nba): Calcd. for C$_{18}$H$_{39}$O$_4$ (MH$^+$): 319.2843, found: 319.2853.

6.2 Synthesis of 2,2,14,14-Tetramethylpentadecane-1,6,10,15-tetraol

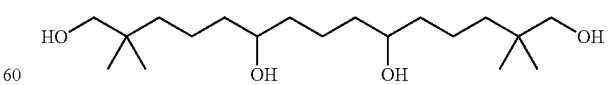

6.2.1 Synthesis of 2,2,14,14-Tetramethyl-1,15-bis(tetrahydropyran-2-yloxy)pentadecan-6,10-diol A solution of glutaric aldehyde (50% wt. aqueous, 25 mL) was extracted with dichloromethane (4×50 mL). The organic extracts were dried over MgSO$_4$ and the dichloromethane was removed by distillation under atmospheric pressure. The residue was distilled under reduced pressure (B.p.: 65-66° C./5 mm Hg) (House, H. O. et al., *J. Org. Chem.* 1965, 30, 1061. B.p.=68-69° C./25 mm Hg) to give glutaric aldehyde as a foul smelling, colorless liquid (7.97 g, 64%), which was used immediately after distillation. Under nitrogen atmosphere, to a stirred suspension of magnesium powder (4.8 g, 0.2 mol) in anhydrous THF (200 mL) was added 2-(5-bromo-2,2-dimethylpentyl)-tetrahydropyran (36.9 g, 0.132 mol) at such a rate as to maintain a gentle reflux. The reaction mixture was heated at reflux for additional 2 h, allowed to cool to room temperature, and cooled in an ice-water bath. A solution of freshly distilled glutaric aldehyde (6.0 g, 0.06 mol) in anhydrous THF (30 mL) was added dropwise. The reaction mixture was left to stir at room temperature overnight. The solution was decanted off the excess magnesium and poured into aqueous saturated ammonium chloride solution (500 mL). The pH was carefully adjusted to 1-2 with 2 N hydrochloric acid and the reaction mixture was extracted with diethyl ether. The organic extracts were washed with brine and dried over MgSO$_4$. After solvent removal, a colorless oil (34.10 g) was obtained which was purified by flash column chromatography (SiO$_2$, ethyl acetate:hexanes=1:5 to 1:1) to afford the pure product as an almost colorless, very viscous oil (16.67 g, 56%). $^1$H NMR (300 MHz, CDCl$_3$/TMS): δ (ppm): 0.89, 0.90 (2×s, 12H), 1.20-1.90 (m, 32H), 2.99 (dd, J=9.1, 3.2 Hz, 2H). 3.48 (pseudo-t, J=8.6 Hz, 4H), 3.63 (br. s, 2H), 3.80-3.88 (m, 2H), 4.51-4.54 (m, 2H). $^{13}$C NMR (75 MHz, CDCl$_3$/TMS): δ (ppm): 19.5, 19.7, 19.8, 20.0, 21.7, 24.4, 24.6, 24.8, 25.5, 30.7, 34.2, 37.4, 38.2, 38.9, 39.2, 62.0, 62.3, 71.5, 71.8, 76.3, 99.2, 99.3. HRMS (LSIMS, nba): Calcd. for C$_{29}$H$_{57}$O$_6$ (MH$^+$): 501.4155, found 501.4152.

6.2.2
2,2,14,14-Tetramethylpentadecane-1,6,10,15-tetraol

To a solution of 2,2,14,14-tetramethyl-1,15-bis(tetrahydropyranyloxy)-pentadecane-6,10-diol (5.75 g, 11.5 mmol) in methanol (100 mL) was added dilute aqueous sulfuric acid (1 mL of concentrated sulfuric acid in 9 mL of water) at room temperature. The reaction mixture was stirred at room temperature for 5 h, diluted with water (20 mL), and the methanol was removed under reduced pressure. The residue was extracted with ethyl acetate. The organic extract was separated and washed with water (30 mL) and saturated sodium chloride solution (30 mL). The combined aqueous extracts were saturated with solid sodium chloride and re-extracted with ethyl acetate (50 mL). The combined organic extracts were dried over magnesium sulfate and concentrated in vacuo to give a colorless oil (4 g) which was dissolved in the minimum amount of dichloromethane and treated with hexanes for 15 min. After 2 h at room temperature, the product crystallized as a white solid. Filtration and additional washing with hexanes (10 mL) gave 2,2,14,14-tetramethylpentadecane-1,6,10,15-tetraol (3.06 g, 80%) as a white solid. M.p.: 85-86° C. $^1$H NMR (300 MHz, DMSO-d$_6$/TMS): δ (ppm): 4.40 (t, 2H, J=5.3 Hz), 4.20 (d, 2H, J=5.5 Hz), 3.40-3.30 (m, 2H), 3.06 (d, 4H, J=5.3 Hz), 1.50-1.05 (m, 18H), 0.77 (s, 12H). $^{13}$C NMR (75 MHz, DMSO-d$_6$/TMS): δ (ppm): 69.9, 69.7, 38.4, 37.5, 34.8, 24.1, 21.7, 19.7. HRMS (LSIMS, nba): Calcd. for C$_{19}$H$_{41}$O$_4$ (MH$^+$): 333.3005, found 333.2997.

7. BIOLOGICAL ASSAYS

7.1 Effects of Illustrative Compounds of the Invention on NonHDL Cholesterol, HDL Cholesterol, Triglyceride Levels, Glycemic Control Indicators and Body Weight Control in Obese Female Zucker Rats In a number of different experiments, illustrative compounds of the invention are administered daily at a dose of up to 100 mg/kg to chow fed obese female Zucker rats for fourteen days in the morning by oral gavage in 1.5% carboxymethylcellulose/0.2% Tween 20 or 20% ethanol/80% polyethylene glycol (dosing vehicles). Animals are weighed daily. Animals are allowed free access to rodent chow and water throughout the study except on days of blood sampling where food is restricted for six hours prior to blood sampling. Blood glucose is determined after the 6 hour fast in the afternoon without anesthesia from a tail vein. Serum is also prepared from pretreatment blood samples subsequently obtained from the orbital venous plexus (with O$_2$/CO$_2$ anesthesia) and following the fourteenth dose at sacrifice from the heart following O$_2$/CO$_2$ anesthesia. Serums are assayed for lipoprotein cholesterol profiles, triglycerides, total cholesterol, Non-HDL cholesterol, HDL cholesterol, the ratio of HDL cholesterol to that of Non-HDL cholesterol, insulin, non-esterified fatty acids, and beta-hydroxy butyric acid. The percent body weight gain and the ratio of liver to body weight is also determined. These are shown as absolute values or as a percent change of the pretreatment values in Table 1

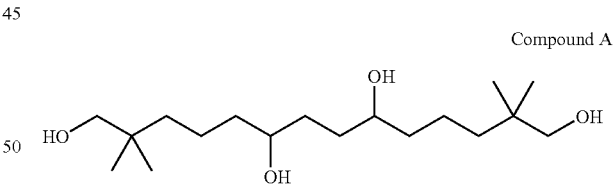

Compound A

TABLE 1

Examples of effects of oral da daily treatment of obese female Zucker rats with compounds of the invention for fourteen days
Percent of Pre-treatment

| Compound | Expt. # | n | Dose (mg/kg/day) | % wt. gain | HDL-C/non-HDL-C | TG | TC | Non-HDL-C | HDL-C | Glucose | Insulin | NEFA | BHA |
|---|---|---|---|---|---|---|---|---|---|---|---|---|---|
| Vehicle | LR90 | 4 | 0 | 12 | 1 | 27 | 1 | 15 | −11 | 7 | 26 | 79 | 9 |
| A | | 4 | 100 | 13 | 1 | 43 | 4 | 30 | −19 | 11 | 70 | 143 | 73 | n is number of animals per experiment

7.2 Effects of Illustrative Compounds of the Invention on the In Vitro Lipid Synthesis in Isolated Hepatocytes Compounds were tested for inhibition of lipid synthesis in primary cultures of rat hepatocytes. Male Sprague-Dawley rats were anesthetized with intraperitoneal injection of sodium pentobarbital (80 mg/kg). Rat hepatocytes were isolated essentially as described by the method of Seglen (Seglen, P. O. Hepatocyte suspensions and cultures as tools in experimental carcinogenesis. *J. Toxicol. Environ. Health* 1979, 5, 551-560). Hepatocytes were suspended in Dulbecco's Modified Eagles Medium containing 25 mM D-glucose, 14 mM HEPES, 5 mM L-glutamine, 5 mM leucine, 5 mM alanine, 10 mM lactate, 1 mM pyruvate, 0.2% bovine serum albumin, 17.4 mM non-essential amino acids, 20% fetal bovine serum, 100 nM insulin and 20 μg/mL gentamycin) and plated at a density of $1.5 \times 10^5$ cells/cm$^2$ on collagen-coated 96-well plates. Four hours after plating, media was replaced with the same media without serum. Cells were grown overnight to allow formation of monolayer cultures. Lipid synthesis incubation conditions were initially assessed to ensure the linearity of [1-$^{14}$C]-acetate incorporation into hepatocyte lipids for up to 4 hours. Hepatocyte lipid synthesis inhibitory activity was assessed during incubations in the presence of 0.25 μCi [1-$^{14}$C]-acetate/well (final radiospecific activity in assay is 1 Ci/mol) and 0, 1, 3, 10, 30, 100 or 300 μM of compounds for 4 hours. At the end of the 4-hour incubation period, medium was discarded and cells were washed twice with ice-cold phosphate buffered saline and stored frozen prior to analysis. To determine total lipid synthesis, 170 μl of MicroScint-E® and 50 μl water was added to each well to extract and partition the lipid soluble products to the upper organic phase containing the scintillant. Lipid radioactivity was assessed by scintillation spectroscopy in a Packard TopCount NXT. Lipid synthesis rates were used to determine the IC$_{50}$S of the compounds that are presented in Table 2.

TABLE 2

Effect of Compounds on Lipid Synthesis in Primary Rat Hepatocytes.

| Compound | IC$_{50}$ (μM) | 95% Confidence Interval | | r$^2$ |
| --- | --- | --- | --- | --- |
| | | Lower | Upper | |
| A | 1.1 | 1.0 | 1.2 | 0.99 |

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

What is claimed:

1. A compound of the formula I:

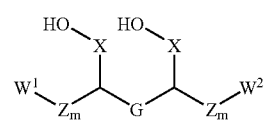

or a pharmaceutically acceptable salt, hydrate, solvate, or a mixture thereof, wherein
   (a) each occurrence of Z is independently CH$_2$, CH=CH, or phenyl, where each occurrence of m is independently an integer ranging from 1 to 9, but when Z is phenyl then m is 1;
   (b) G is (CH$_2$)$_x$, where x is 1-7, CH$_2$CH=CHCH$_2$, CH=CH, CH$_2$-phenyl-CH$_2$, or phenyl;
   (c) W$^1$ and W$^2$ are independently L, V, C(R$^1$)(R$^2$)—(CH$_2$)$_c$—C(R$^3$)(R$^4$)—(CH$_2$)$_n$—Y or C(R$^1$)(R$^2$)—(CH$_2$)$_c$—V where c is 1 or 2 and n is an integer ranging from 0 to 7;
   (d) each occurrence of R$^1$ or R$^2$ is independently (C$_1$-C$_6$)alkyl, (C$_2$-C$_6$)alkenyl, (C$_2$-C$_6$)alkynyl, phenyl, or benzyl or when one or both of W$^1$ and W$^2$ is C(R$^1$)(R$^2$)—(CH$_2$)$_c$—C(R$^3$)(R$^4$)—(CH$_2$)$_n$—Y, then R$^1$ and R$^2$ can both be H to form a methylene group; or R$^1$ and R$^2$ and the carbon to which they are both attached are taken together to form a (C$_3$-C$_7$)cycloakyl group;
   (e) R$^3$ is H, (C$_1$-C$_6$)alkyl, (C$_2$-C$_6$)alkenyl, (C$_2$-C$_6$)alkynyl, (C$_1$-C$_6$)alkoxyl, phenyl, benzyl, Cl, Br, CN, NO$_2$, or CF$_3$;
   (f) R$^4$ is OH, (C$_1$-C$_6$)alkyl, (C$_2$-C$_6$)alkenyl, (C$_2$-C$_6$)alkynyl, (C$_1$-C$_6$)alkoxyl, phenyl, benzyl, Cl, Br, CN, NO$_2$, or CF$_3$;
   (g) L is C(R$^1$)(R$^2$)—(CH$_2$)$_n$—Y, wherein n is an integer from 1 to 5;
   (h) V is:

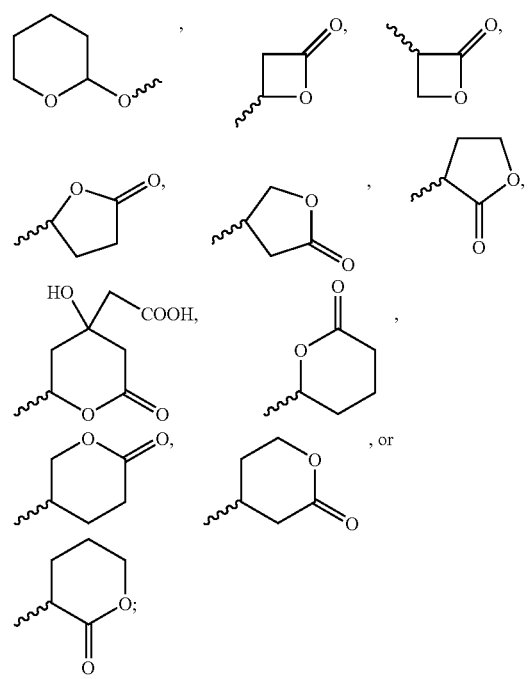

(i) each occurrence of Y is independently (C$_1$-C$_6$)alkyl, OH, COOH, COOR$^5$, SO$_3$H,

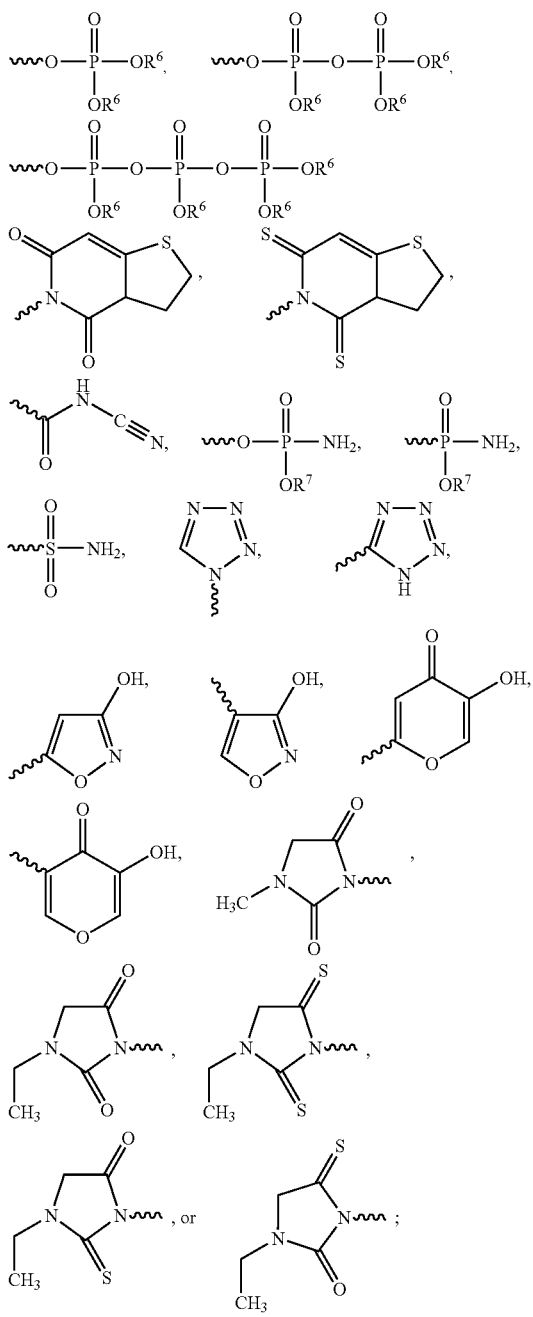

wherein:
(i) $R^5$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of $R^6$ is independently H, $(C_1-C_6)$alkyl, $(C_2-C_6)$alkenyl, or $(C_2-C_6)$alkynyl and is unsubstituted or substituted with one or two halo, OH, $(C_1-C_6)$alkoxy, or phenyl groups;
(iii) each occurrence of $R^7$ is independently H, $(C_1-C_6)$alkyl, $(C_2-C_6)$alkenyl, or $(C_2-C_6)$alkynyl; and
(j) X is $(CH_2)_z$ or Ph, wherein z is an integer from 0 to 4.

2. The compound of claim 1, wherein G is $(CH_2)_2$.

3. The compound of claim 1, wherein each occurrence of $Z_m$ is independently $(CH_2)$ and m is 1-4.

4. The compound of claim 1, wherein each occurrence of $W^1$ and $W^2$ is independently L.

5. The compound of claim 2, wherein L is $C(CH_3)_2$—$(CH_2)$—OH.

6. The compound of claim 1, wherein each occurrence of $W^1$ and $W^2$ is independently V.

7. The compound of claim 6, wherein V is

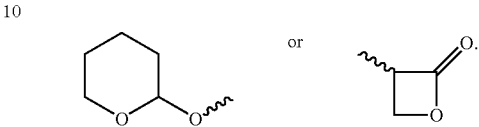

8. A compound of the formula II:

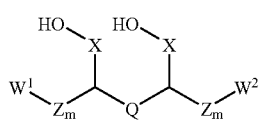

II or a pharmaceutically acceptable salt, hydrate, solvate, or a mixture thereof, wherein:
(a) each occurrence of Z is independently $CH_2$ or $CH=CH$, wherein each occurrence of m is independently an integer ranging from 1 to 9;
(b) Q is $(CH_2)_x$, $CH_2CH=CHCH_2$, or $CH=CH$, where x is 2, 3, or 4;
(c) $W^1$ and $W^2$ are independently L, V, or $C(R^1)(R^2)$—$(CH_2)_c$—V, where c is 1 or 2;
(d) each occurrence of $R^1$ and $R^2$ is independently $(C_1-C_6)$alkyl, $(C_2-C_6)$alkenyl, $(C_2-C_6)$alkynyl, phenyl, benzyl, or $R^1$ and $R^2$ and the carbon to which they are both attached are taken together to form a $(C_3-C_7)$cycloalkyl group;
(e) L is $C(R^1)(R^2)(CH_2)_n$—Y, where n is an integer ranging from 0 to 5;
(f) V is:

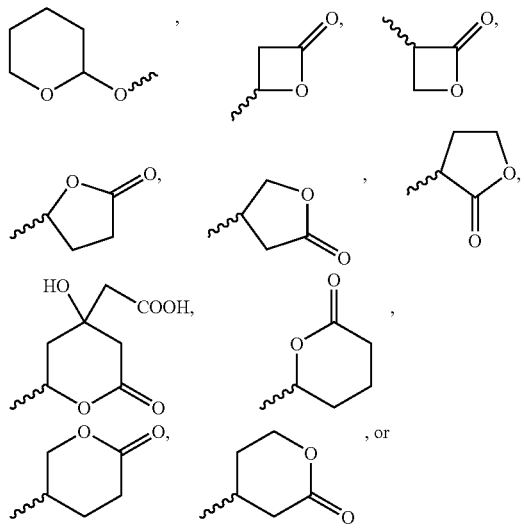

-continued

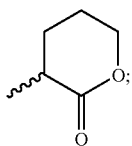

(g) each occurrence of Y is independently (C₁-C₆)alkyl, OH, COOH, COOR³, SO₃H,

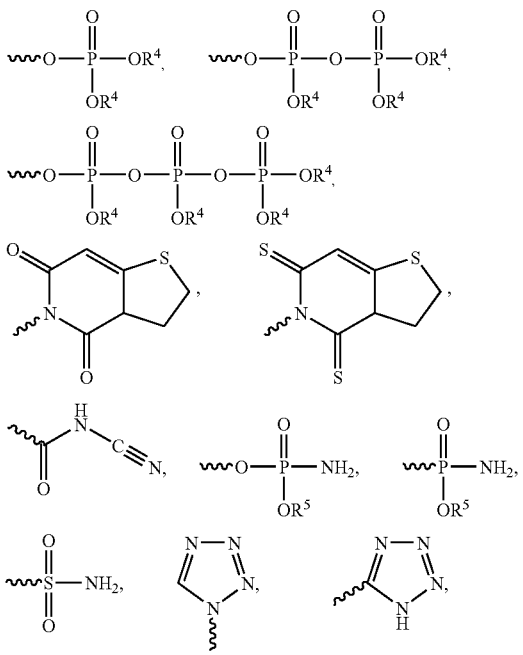

wherein:
(i) R³ is (C₁-C₆)alkyl, (C₂-C₆)alkenyl, (C₂-C₆)alkynyl, phenyl, or benzyl and is unsubstituted or substituted with one or more halo, OH, (C₁-C₆)alkoxy, or phenyl groups,
(ii) each occurrence of R⁴ is independently H, (C₁-C₆)alkyl, (C₂-C₆)alkenyl, or (C₂-C₆)alkynyl and is unsubstituted or substituted with one or two halo, OH, (C₁-C₆)alkoxy, or phenyl groups; and
(iii) each occurrence of R⁵ is independently H, (C₁-C₆)alkyl, (C₂-C₆)alkenyl, or (C₂-C₆)alkynyl; and
(h) X is (CH₂)_z or Ph, wherein z is an integer from 0 to 4.

9. The compound of claim 8, wherein each occurrence of W¹ and W² is independently L.

10. The compound of claim 9, wherein L is C(CH₃)₂—(CH₂)_n—Y.

11. The compound of claim 10, wherein each occurrence of Y is independently OH, COOR⁷, or COOH.

12. The compound of claim 8, wherein Q is CH=CH.

13. The compound of claim 8, wherein Z_m is CH₂ and m is 1-3.

14. The compound of claim 8, wherein each of W₁ and W₂ is independently C(R¹)(R²)—(CH₂)_x—V.

15. The compound of claim 14, wherein R¹ and R² are each independently (C₁-C₆)alkyl.

16. The compound of claim 15, wherein R¹ and R² are each methyl.

17. A compound of the formula III

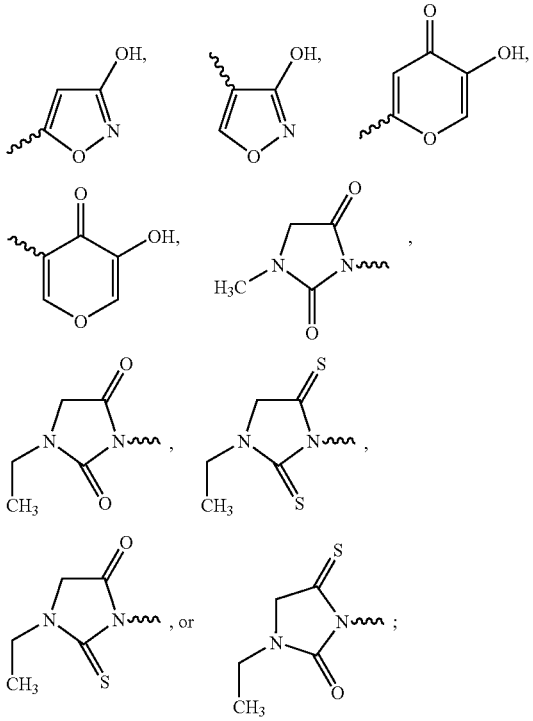

or a pharmaceutically acceptable salt, hydrate, solvate, or a mixture thereof, wherein:
(a) each occurrence of m is independently an integer ranging from 1 to 9;
(b) r is 2, 3, or 4;
(c) each occurrence of n is independently an integer ranging from 0 to 7;
(d) each occurrence of R¹, R², R¹¹, and R¹² is independently (C₁-C₆)alkyl, (C₂-C₆)alkenyl, (C₂-C₆)alkynyl, phenyl, benzyl, or R¹ and R² and the carbon to which they are both attached are taken together to form a (C₃-C₇)cycloakyl group, or R¹¹ and R¹² and the carbon to which they are both attached are taken together to form a (C₃-C₇)cycloakyl group; and
(e) each occurrence of Y is independently (C₁-C₆)alkyl, OH, COOH, COOR³, SO₃H,

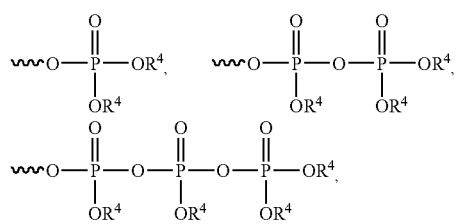

-continued

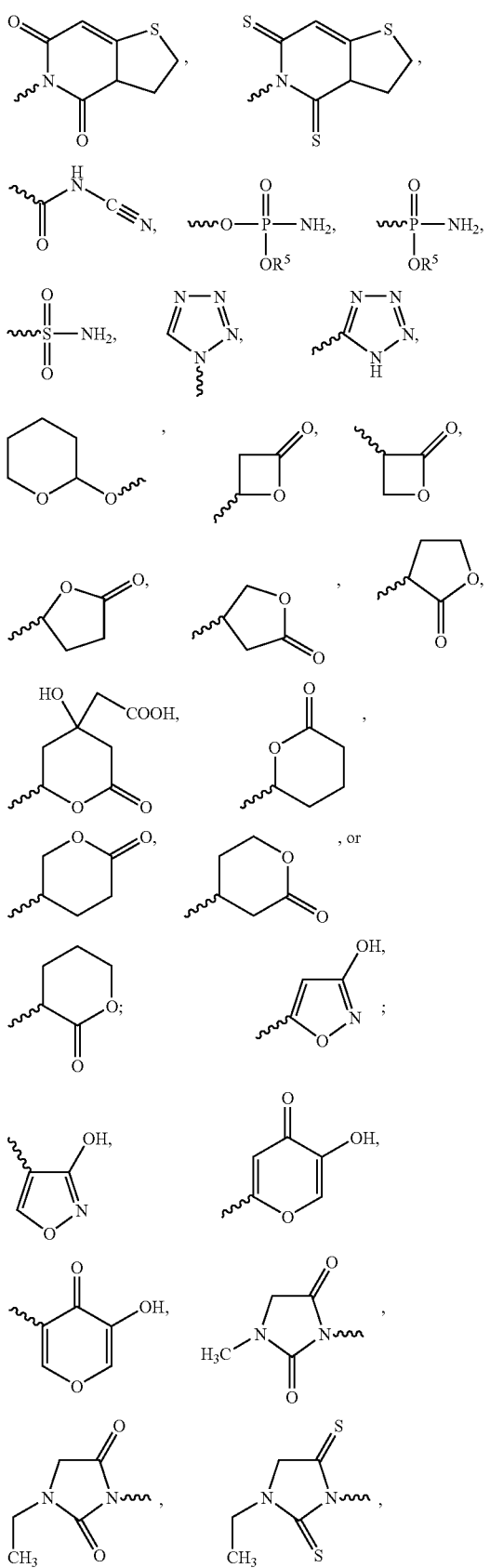

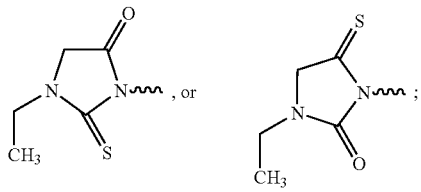

wherein:

(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups, (ii) each occurrence of $R^4$ is independently H, $(C_1-C_6)$ alkyl, $(C_2-C_6)$alkenyl, or $(C_2-C_6)$alkynyl and is unsubstituted or substituted with one or two halo, OH, $C_1-C_6$ alkoxy, or phenyl groups;

(iii) each occurrence of $R^5$ is independently H, $(C_1-C_6)$ alkyl, $(C_2-C_6)$alkenyl, or $(C_2-C_6)$alkynyl; and (f) X is $(CH_2)_z$ or Ph, wherein z is an integer from 0 to 4.

18. The compound of claim 17, wherein each occurrence of $Y^1$ and $Y^2$ is independently OH, $COOR^3$, or COOH.

19. A compound of the formula IV

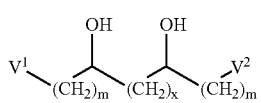

IV or a pharmaceutically acceptable salt, hydrate, solvate, or a mixture thereof, wherein:

(a) each occurrence of m is an independent integer ranging from 1 to 9;

(b) x is 2, 3, or 4;

(c) each of $V^1$ and $V^2$ is independently:

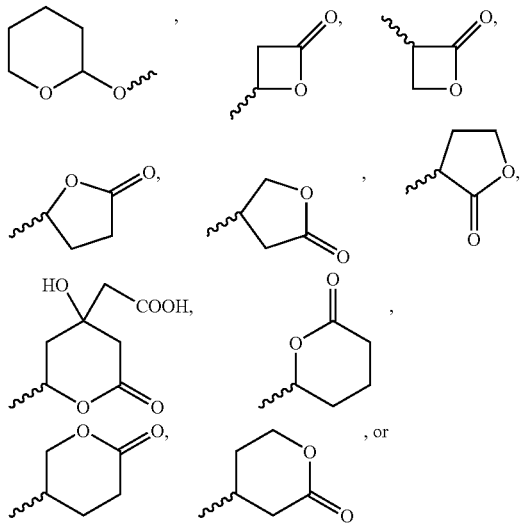

-continued

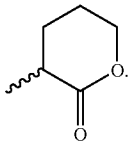

20. A compound of the formula V:

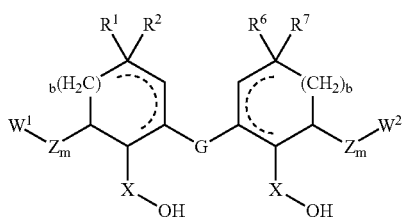

or a pharmaceutically acceptable salt, hydrate, solvate, or a mixture thereof, wherein:

(a) each occurrence of Z is independently $CH_2$, CH=CH, or phenyl, where each occurrence of m is independently an integer ranging from 1 to 5, but when Z is phenyl then its associated m is 1;

(b) G is $(CH_2)_x$, $CH_2CH=CHCH_2$, CH=CH, $CH_2$-phenyl-$CH_2$, or phenyl, where x is an integer ranging from 1 to 7;

(c) $W^1$ and $W^2$ are independently $C(R^8)(R^9)$—$(CH_2)_n$-Y, where n is an integer ranging from 0 to 7;

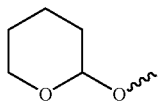 , 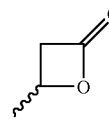 , 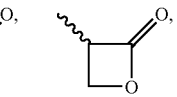

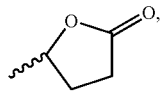 , 

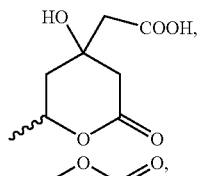 , 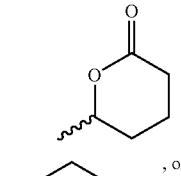

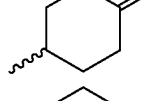 , 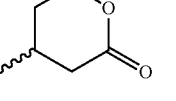 , or

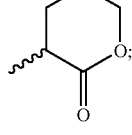 ;

(d) each occurrence of $R^8$ and $R^9$ is independently H, $(C_1-C_6)$alkyl, $(C_2-C_6)$alkenyl, $(C_2-C_6)$alkynyl, phenyl, or benzyl or $R^8$ and $R^9$ can be taken together to form a carbonyl group;

(e) each occurrence of $R^1$ and $R^2$ is independently H, $(C_1-C_6)$alkyl, $(C_2-C_6)$alkenyl, $(C_2-C_6)$alkynyl, phenyl, or benzyl or $R^1$ and $R^2$ can be taken together to form a carbonyl group or $R^1$ and $R^2$ and the carbon to which they are both attached are taken together to form a $(C_3-C_7)$cycloakyl group;

(f) each occurrence of $R^6$ and $R^7$ is independently H, $(C_1-C_6)$alkyl, or $R^6$ and $R^7$ can be taken together to form a carbonyl group or $R^6$ and $R^7$ and the carbon to which they are both attached are taken together to form a $(C_3-C_7)$cycloakyl group;

(g) Y is $(C_1-C_6)$alkyl, OH, COOH, $COOR^3$, $SO_3H$,

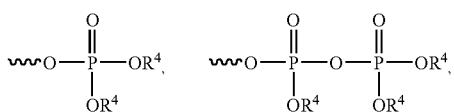

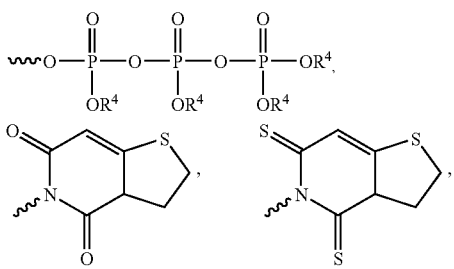

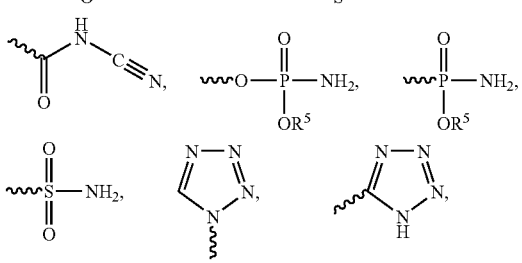

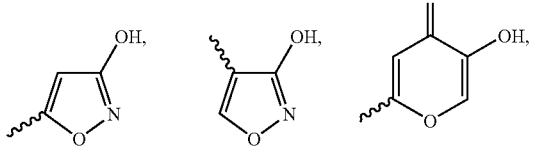

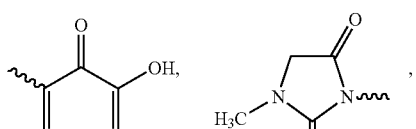

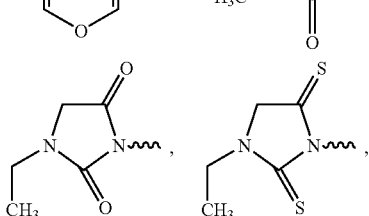

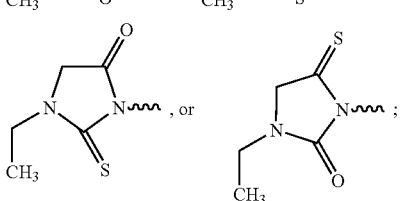

wherein:
(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of $R^4$ is independently H, $(C_1-C_6)$ alkyl, $(C_2-C_6)$alkenyl, or $(C_2-C_6)$alkynyl and is unsubstituted or substituted with one or two halo, OH, $C_1-C_6$ alkoxy, or phenyl groups;
(iii) each occurrence of $R^5$ is independently H, $(C_1-C_6)$ alkyl, $(C_2-C_6)$alkenyl, or $(C_2-C_6)$alkynyl;
(h) each occurrence of b is independently 0 or 1 or optionally the presence of one or more additional carbon-carbon bonds that when present complete one or more carbon-carbon double bonds; and
(i) X is $(CH_2)_z$ or Ph, wherein z is an integer from 0 to 4.

21. The compound of claim 20, wherein each occurrence of $W^1$ and $W^2$ is an independent $C(R^1)(R^2)-(CH_2)_n-Y$ group and each occurrence of Y is independently OH, $COOR^3$, or COOH.

22. A compound of the formula VI:

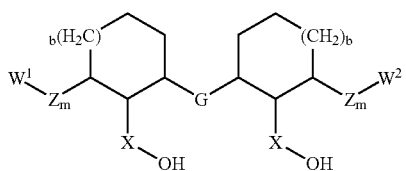

VI or a pharmaceutically acceptable salt, hydrate, solvate, or a mixture thereof, wherein
(a) each occurrence of m is independently an integer ranging from 1 to 5;
(b) X is $(CH_2)_z$ or Ph, wherein z is an integer from 0 to 4;
(c) $W^1$ and $W^2$ are independently $C(R^1)(R^2)-(CH_2)_n-Y$, where n is an integer ranging from 0 to 7;

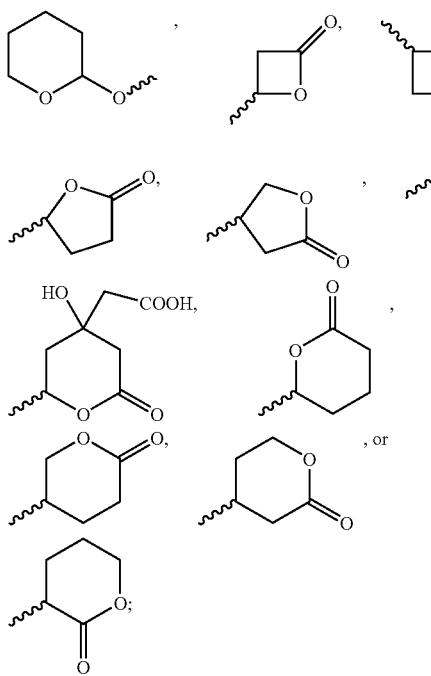

(d) each occurrence of $R^1$ or $R^2$ is independently $(C_1-C_6)$ alkyl, $(C_2-C_6)$alkenyl, $(C_2-C_6)$alkynyl, or $R^1$ and $R^2$ and the carbon to which they are both attached are taken together to form a $(C_3-C_7)$cycloakyl group;
(e) Y is $(C_1-C_6)$alkyl, $(CH_2)_n$OH, $(CH_2)_n$COOH, $(CH_2)_n$ $COOR^3$, $SO_3H$,

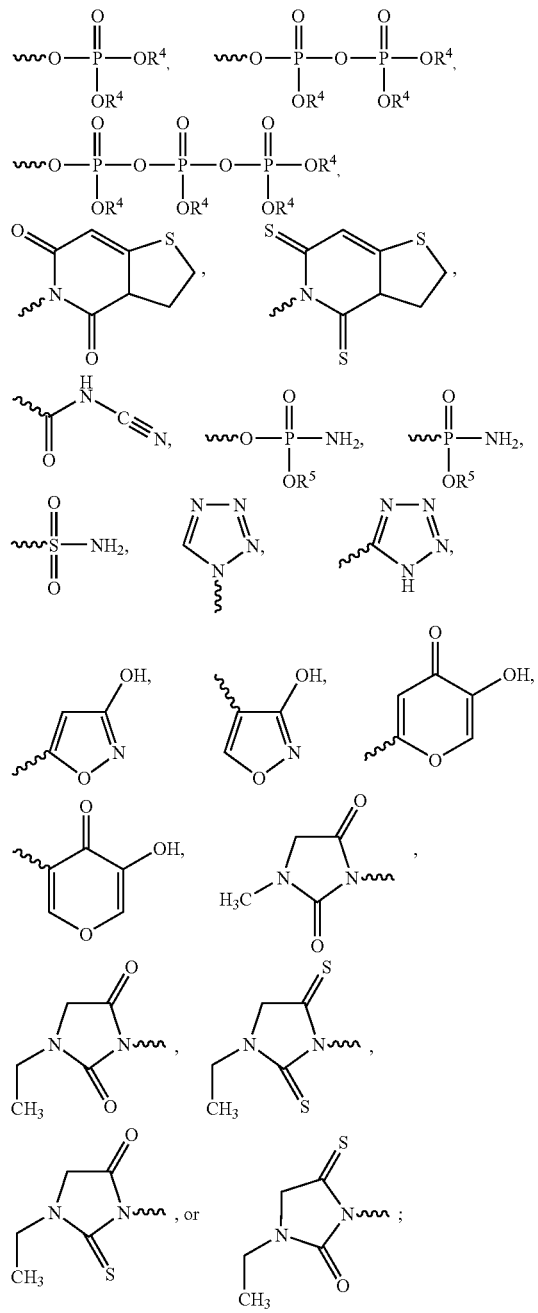

wherein:
(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of $R^4$ is independently H, $(C_1-C_6)$ alkyl, $(C_2-C_6)$alkenyl, or $(C_2-C_6)$alkynyl and is unsubstituted or substituted with one or two halo, OH, $C_1$-$C_6$ alkoxy, or phenyl groups, (iii) each occurrence of $R^5$ is independently H, ($C_1$-$C_6$) alkyl, ($C_2$-$C_6$)alkenyl, or ($C_2$-$C_6$)alkynyl;

(f) each occurrence of b is independently 0 or 1; and (g) X is $(CH_2)_z$ or Ph, wherein z is an integer from 0 to 4.

23. The compound of claim 22, wherein each occurrence of $W^1$ and $W^2$ independently $C(R^1)(R^2)$—$(CH_2)_n$—Y and each occurrence of Y is independently OH, $COOR^3$, or COOH.

24. A compound of structure:

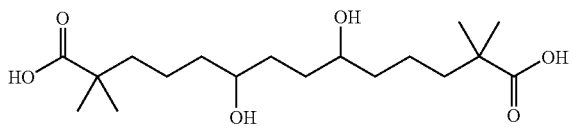

6,9-Dihydroxy-2,2,13,13-tetramethyl-tetradecanedioic acid;

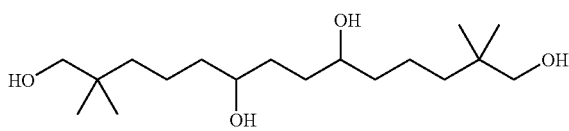

2,2,13,13-Tetramethyl-tetradecane-1,6,9,14-tetraol;

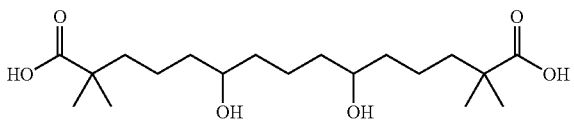

6,10-Dihydroxy-2,2,14,14-tetramethyl-pentadecanedioic acid; and

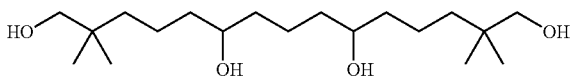

2,2,14,14-Tetramethyl-pentadecane-1,6,10,15-tetraol, or a pharmaceutically acceptable salt, hydrate, or solvate thereof.

25. A pharmaceutical composition comprising a compound of claim 1, 8, 17, 19, 20, 22, or 24 and a pharmaceutically acceptable vehicle, excipient, or diluent.

26. A pharmaceutical composition comprising a compound of claim 1, 8, 17, 19, 20, 22, or 24 and further comprising a second therapeutic agent.

27. A pharmaceutical composition comprising a compound of claim 1, 8, 17, 19, 20, 22, 24, or 26 and a pharmaceutically acceptable vehicle, excipient, or diluent which is administered in combination with a statin.

28. A compound according to claim 1 wherein said compound has the structure:

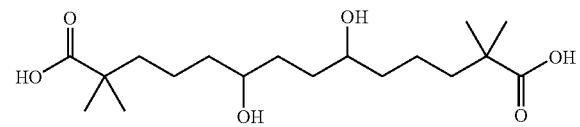

6,9-Dihydroxy-2,2,13,13-tetramethyl-tetradecanedioic acid; or a pharmaceutically acceptable salt, hydrate, or solvate thereof.

29. A compound according to claim 1 wherein said compound has the structure:

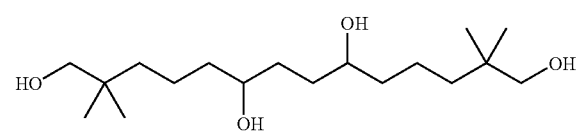

2,2,13,13-Tetramethyl-tetradecane-1,6,9,14-tetraol; or a pharmaceutically acceptable salt, hydrate, or solvate thereof.

30. A compound according to claim 1 wherein said compound has the structure:

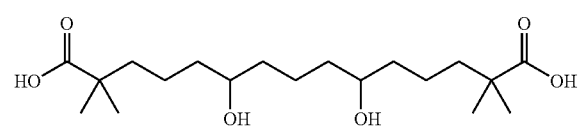

6,10-Dihydroxy-2,2,14,14-tetramethyl-pentadecanedioic acid; or a pharmaceutically acceptable salt, hydrate, or solvate thereof.

31. A compound according to claim 1 wherein said compound has the structure:

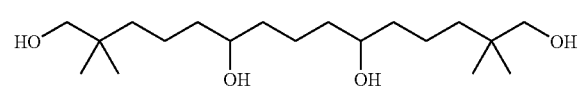

2,2,14,14-Tetramethyl-pentadecano-1,6,10,15-tetraol; or a pharmaceutically acceptable salt, hydrate, or solvate thereof.

* * * * *